(12) United States Patent
Yen et al.

(10) Patent No.: US 11,192,881 B2
(45) Date of Patent: Dec. 7, 2021

(54) COMPOUND FOR ORGANIC ELECTROLUMINESCENCE DEVICE USING THE SAME

(71) Applicants: Feng-Wen Yen, Taipei (TW); Wen-Feng Hsiao, Hsinchu (TW)

(72) Inventors: Feng-Wen Yen, Taipei (TW); Wen-Feng Hsiao, Hsinchu (TW)

(73) Assignee: LUMINESCENCE TECHNOLOGY CORP., Hsin-Chu (TW)

( * ) Notice: Subject to any disclaimer, the term of this patent is extended or adjusted under 35 U.S.C. 154(b) by 297 days.

(21) Appl. No.: 16/551,724

(22) Filed: Aug. 27, 2019

(65) Prior Publication Data

US 2021/0061787 A1    Mar. 4, 2021

(51) Int. Cl.

| | | |
|---|---|---|
| *H01L 51/50* | (2006.01) | |
| *C07D 403/04* | (2006.01) | |
| *H01L 51/52* | (2006.01) | |
| *C07D 409/14* | (2006.01) | |
| *C07D 413/04* | (2006.01) | |
| *C07D 417/14* | (2006.01) | |
| *C07D 401/04* | (2006.01) | |
| *C07F 7/08* | (2006.01) | |
| *H01L 51/00* | (2006.01) | |
| *C07D 401/14* | (2006.01) | |

(Continued)

(52) U.S. Cl.
CPC ......... *C07D 403/04* (2013.01); *C07D 401/04* (2013.01); *C07D 401/14* (2013.01); *C07D 409/14* (2013.01); *C07D 413/04* (2013.01); *C07D 417/14* (2013.01); *C07F 7/0816* (2013.01); *H01L 51/0054* (2013.01); *H01L 51/0055* (2013.01); *H01L 51/0056* (2013.01); *H01L 51/0067* (2013.01); *H01L 51/0069* (2013.01); *H01L 51/0072* (2013.01); *H01L 51/0094* (2013.01); *H01L 51/5024* (2013.01); *H01L 51/5056* (2013.01); *H01L 51/5072* (2013.01); *H01L 51/5096* (2013.01); *H01L 51/5206* (2013.01); *H01L 51/5221* (2013.01)

(58) Field of Classification Search
None
See application file for complete search history.

(56) References Cited

U.S. PATENT DOCUMENTS

2018/0277767 A1* 9/2018 Cha .................... H01L 51/0073

FOREIGN PATENT DOCUMENTS

KR        2015/004009        *    1/2015    ............. H01L 51/54

* cited by examiner

*Primary Examiner* — Gregory D Clark

(57) ABSTRACT

An organic compound is described. An organic electroluminescence device comprises the organic compound as a host or a hole blocking layer. The organic compound of the following formula may lower a driving voltage or increases a current efficiency or a half-life of the organic electroluminescence device.

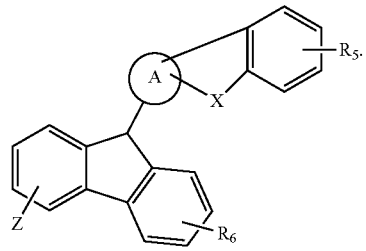

The same definition as described in the present invention.

15 Claims, 3 Drawing Sheets

COMPOUND FOR ORGANIC ELECTROLUMINESCENCE DEVICE USING THE SAME

FIELD

The present invention relates generally to a compound, and, more specifically, to an organic electroluminescence (hereinafter referred to as organic EL) device using the compound.

BACKGROUND

Organic electroluminescence (organic EL) devices, i.e., organic light-emitting diodes (OLEDs) that make use of organic compounds, are becoming increasingly desirable than before. One of the organic compounds has the following formula:

H1

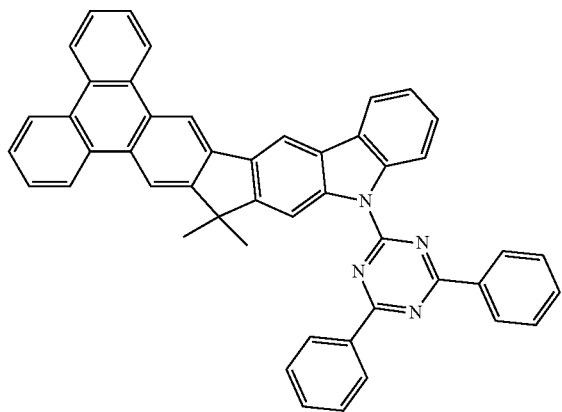

An organic EL device is a light-emitting diode (LED) in which the light emitting layer is a film made from organic compounds, which emits light in response to an electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

However, there is still a need for improvement in the case of use of those organic materials in an organic EL device of some prior art displays, for example, in relation to the lift time, current efficiency or driving voltage of the organic EL device.

SUMMARY

According to the reasons described above, an object of the present invention is to resolve the problems of prior arts and to offer a novel compound.

Another object of the invention is to provide an organic EL device using the compound. The organic EL device of the present invention may operate under reduced voltage, or may exhibit higher current efficiency or longer life time.

formula (1)

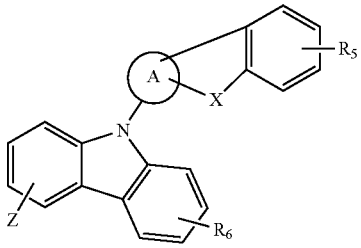

wherein X represents a divalent bridge selected from the group consisting of O, S, $NAr_1$, $CR_1R_2$ and $SiR_3R_4$; ring A represents a fused ring hydrocarbon unit with two to four rings; $R_1$ to $R_6$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms; An represents a substituted or unsubstituted aryl group having 6 to 30 carbon atoms; Z is represented by the following formula (2):

formula (2)

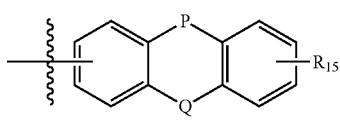

wherein Q represents a divalent bridge selected from the group consisting of O, S, $NAr_2$, $CR_7R_8$ and $SiR_9R_{10}$; P is a single bond or a divalent bridge selected from the group consisting of O, S, $NAr_3$, $CR_{11}R_{12}$, $SiR_{13}R_{14}$; wherein at least one of P and Q is $NAr_3$ if P is not a single bond; $Ar_2$ and $Ar_3$ independently represent a substituted or unsubstituted aryl group having 6 to 30 carbon atoms; $R_7$ to $R_{15}$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

The present invention further discloses an organic EL device. The organic EL device may comprise an anode, a cathode and one or more organic layers formed between the anode and the cathode. At least one of the organic layers comprises the organic compound of formula (1).

DETAILED DESCRIPTION

Figure 1:
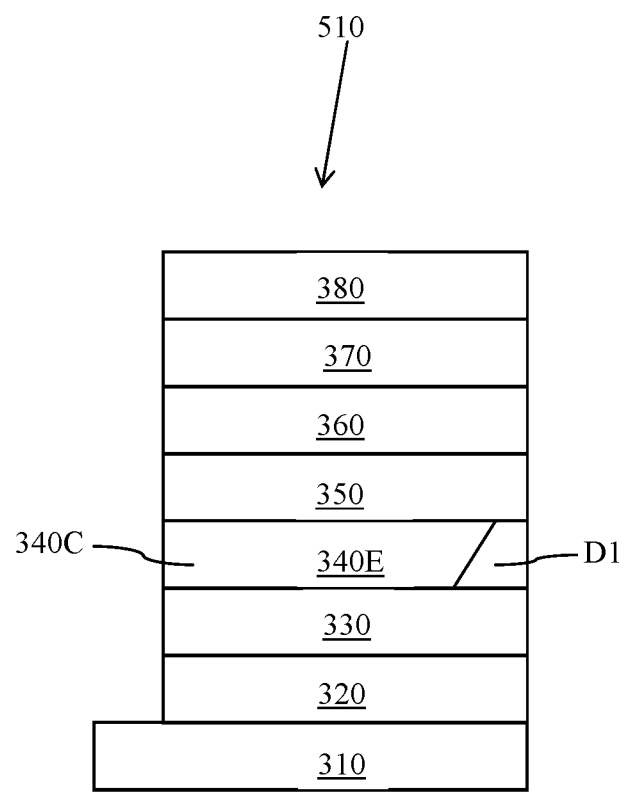
FIG. 1 is a cross-sectional view of a first organic EL device according to a second embodiment of the present invention.

Generally, an organic EL device comprises at least one organic layer disposed between and electrically connected to an anode and a cathode. When an external voltage is applied across the organic EL device, electrons and holes are injected from the cathode and the anode, respectively. Electrons will be injected from a cathode into a LUMO (lowest unoccupied molecular orbital) and holes will be injected from an anode into a HOMO (highest occupied molecular orbital). Subsequently, the electrons recombine with holes in the light emitting layer to form excitons and then emit light. When luminescent molecules absorb energy to achieve an excited state, the exciton may either be in a singlet state or a triplet state, depending on how the spins of the electrons and holes have been combined.

The terms "halogen" and "halide" are used interchangeably and refer to fluorine, chlorine, bromine, and iodine.

The term "alkyl" refers to and includes both straight and branched chain alkyl radicals. Preferred alkyl groups are those containing from 1 to 20 carbon atoms, more preferably 1 to 15 carbon atoms. Suitable alkyl groups include methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group is optionally substituted.

The term "aryl" refers to and includes both single-ring aromatic hydrocarbyl groups and polycyclic aromatic ring systems. The polycyclic rings may have two, three, four or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing 6 to 30 carbon atoms, preferably 6 to 20 carbon atoms, more preferably 6 to 12 carbon atoms. Especially preferred is an aryl group having 6 carbons, 10 carbons or 12 carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group is optionally substituted.

The terms "aralkyl" or "arylalkyl" are used interchangeably and refer to an alkyl group that is substituted with an aryl group. Preferred aralkyl groups are those containing 6 to 30 carbon atoms. Additionally, the aralkyl group is optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing 3 to 30 carbon atoms, preferably 3 to 20 carbon atoms, more preferably 3 to 12 carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group is optionally substituted.

The terms "$R_1$" to "$R_{16}$" may independently be hydrogen or a substituent selected from the group consisting of deuterium, halogen, alkyl, cycloalkyl, heteroalkyl, heterocycloalkyl, aralkyl, alkoxy, aryloxy, amino, silyl, alkenyl, cycloalkenyl, heteroalkenyl, alkynyl, aryl, heteroaryl, and combination thereof. $R_1$ to $R_{16}$ may preferably and independently be hydrogen or a substituent selected from the group consisting of hydrogen, alkyl, aryl, aralkyl, heteroaryl, and combination thereof.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group is optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group is optionally substituted.

The term 'alkenyl' refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group is optionally substituted.

The term "alkynyl" refers to and includes both straight and branched chain alkyne radicals. Preferred alkynyl groups are those containing two to fifteen carbon atoms. Additionally, the alkynyl group is optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[fh]quinoxaline and dibenzo[fh]quinoline. One of ordinary skill in the art can readily envision other nitrogen analogs of the aza-derivatives described above, and all such analogs are intended to be encompassed by the terms as set forth herein.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R_1$ represents mono-substitution, then one $R_1$ must be other than H (i.e., a substitution). Similarly, when $R_1$ represents di-substitution, then two of $R_1$ must be other than H. Similarly, when $R^1$ represents no substitution, $R_1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

As used herein, "deuterium" refers to an isotope of hydrogen. Deuterated compounds can be readily prepared using methods known in the art.

It is to be understood that when a molecular fragment is described as being a substituent or otherwise attached to another moiety, its name may be written as if it were a fragment (e.g., phenyl, phenylene, naphthyl, dibenzofuryl) or as if it were the whole molecule (e.g., benzene, naphthalene, dibenzofuran). As used herein, these different ways of designating a substituent or attached fragment are considered to be equivalent.

Each of the terms $Ar_1$, $Ar_2$ and $Ar_3$ may be selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof. The aryl group may have 6 to 30 carbon atoms.

In a first embodiment of the present invention, an organic compound which may be a host of an organic EL device is disclosed. The organic compound may be represented by the following formula (1):

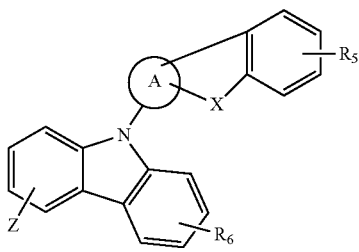

formula (1)

wherein X represents a divalent bridge selected from the group consisting of O, S, $NAr_1$, $CR_1R_2$ and $SiR_3R_4$; ring A represents a fused ring hydrocarbon unit with two to four rings; $R_1$ to $R_6$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms; $Ar_1$ represents a substituted or unsubstituted aryl group having 6 to 30 carbon atoms; Z is represented by the following formula (2):

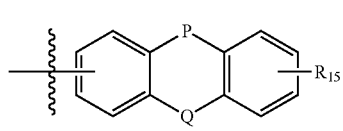

formula (2)

wherein Q represents a divalent bridge selected from the group consisting of O, S, $NAr_2$, $CR_7R_8$ and $SiR_9R_{10}$; P is a single bond or a divalent bridge selected from the group consisting of O, S, $NAr_3$, $CR_{11}R_{12}$, $SiR_{13}R_{14}$; wherein at least one of P and Q is $NAr_3$ if P is not a single bond; $Ar_2$ and $Ar_3$ independently represent a substituted or unsubstituted aryl group having 6 to 30 carbon atoms; $R_7$ to $R_{15}$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

When P is a single bond, Z may be represented by the following formula (3):

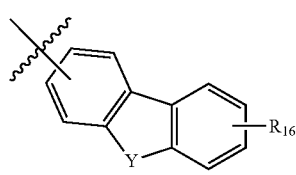

formula (3)

wherein Y represents a divalent bridge selected from the group consisting of O, S, $NAr_2$, $CR_7R_8$ and $SiR_9R_{10}$. $R_{16}$ may be selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

Figure 2:
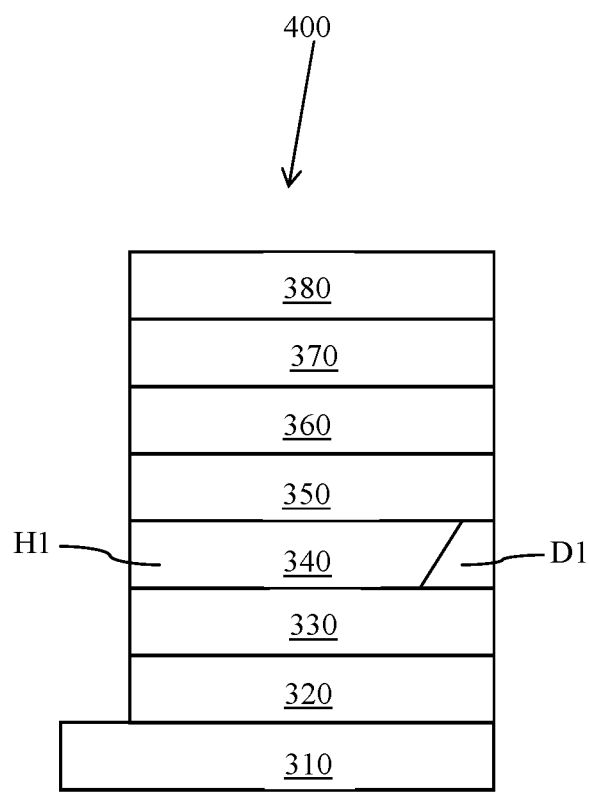
FIG. 2 is a cross-sectional view of an organic EL device without the host 340C of FIG. 1.

FIG. 2 is a cross-sectional view of an organic EL device without the organic compound of formula (1) (without 340C of FIG. 1). Referring to FIG. 2, the organic EL device 400 may have a driving voltage of about 5.1 V, a current efficiency of about 18 cd/A, or a half-life of about 350 hours.

Referring to FIG. 1, by comprising the organic compound of formula (1) as the host 340C, the first organic EL device 510 may have a driving voltage lower than that of the organic EL device 400 (FIG. 2). Moreover, by comprising the organic compound of formula (1) as the host 340C, the first organic EL device 510 of FIG. 1 may have a current efficiency higher than that of the organic EL device 400 (FIG. 2). Furthermore, by comprising the organic compound of formula (1) as the host 340C, the first organic EL device 510 of FIG. 1 may have a half-life longer than that of the organic EL device 400 (FIG. 2).

As the host 340C of the first organic EL device 510 of FIG. 1, the organic compound of formula (1) may lower the driving voltage to be about 2.8 V to about 4.5 V. Moreover, the organic compound of formula (1) may increase the current efficiency to be about 26 cd/A to about 45 cd/A. Furthermore, the organic compound of formula (1) may increase the half-life to be about 420 hours to about 1100 hours.

Figure 3:
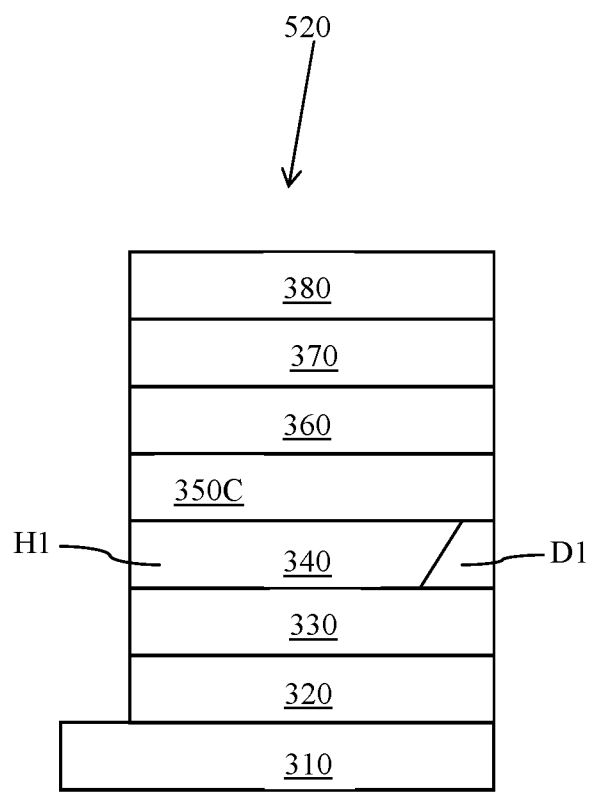
FIG. 3 is a cross-sectional view of a second organic EL device according to a third embodiment of the present invention.

In a third embodiment of the present invention, a second organic EL device using the organic compound of formula (1) is disclosed. FIG. 3 is a cross-sectional view of the second organic EL device. Referring to FIG. 3, the second organic EL device 520 may comprise the organic compound of formula (1) as a hole blocking layer 350C.

FIG. 2 is a cross-sectional view of an organic EL device without the organic compound of formula (1) (without 350C of FIG. 3). Referring to FIG. 2, the organic EL device 400 may have a driving voltage of about 5.1 V, a current efficiency of about 18 cd/A, or a half-life of about 350 hours.

Referring to FIG. 3, by comprising the organic compound of formula (1) as the hole blocking layer 350C, the second organic EL device 520 may have a driving voltage lower than that of the organic EL device 400 (FIG. 2). Moreover, by comprising the organic compound of formula (1) as the hole blocking layer 350C, the second organic EL device 520 of FIG. 3 may have a current efficiency higher than that of the organic EL device 400 (FIG. 2). Furthermore, by comprising the organic compound of formula (1) as the hole blocking layer 350C, the second organic EL device 520 of FIG. 3 may have a half-life longer than that of the organic EL device 400 (FIG. 2).

Referring to FIG. 3, as the hole blocking layer 350C of the second organic EL device 520, the organic compound of formula (1) may lower the driving voltage to be about 4.0 V to about 4.8 V. Moreover, the organic compound of formula (1) may increase the current efficiency to be about 20 cd/A to about 28 cd/A. Furthermore, the organic compound of formula (1) may increase the half-life to be about 370 hours to about 520 hours.

The organic compound according to claim 1, wherein the organic compound is represented by one of the following formula (4) to formula (9):

formula (4)
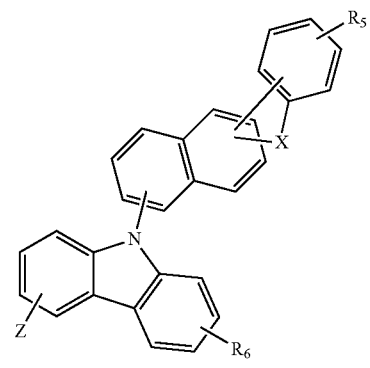
formula (5)
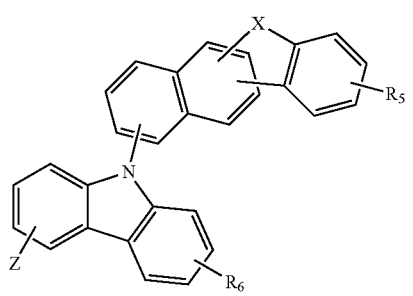
(formula 6)
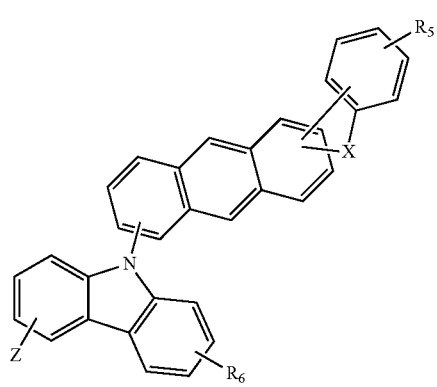
formula (7)
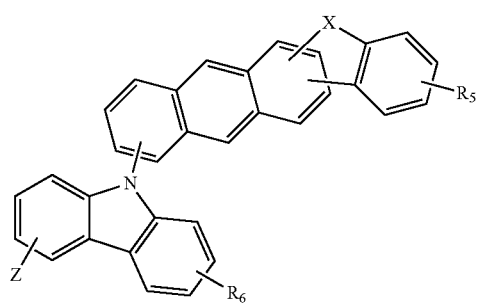
formula (8)
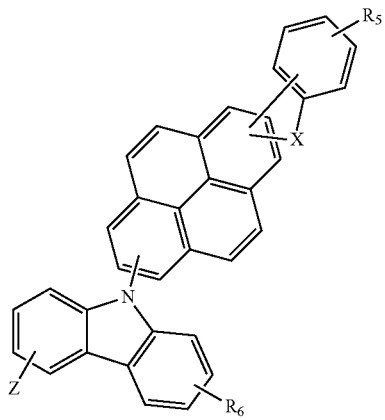
(formula 9)
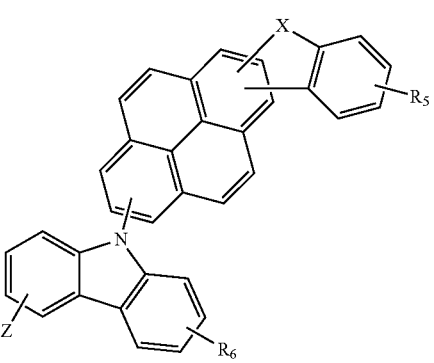
The organic compound according to claim 1, wherein the organic compound is represented by one of the following formula (10) to formula (29):
formula (10)
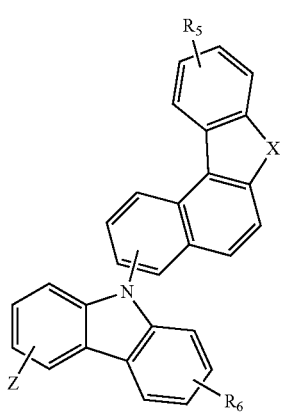

formula (11)
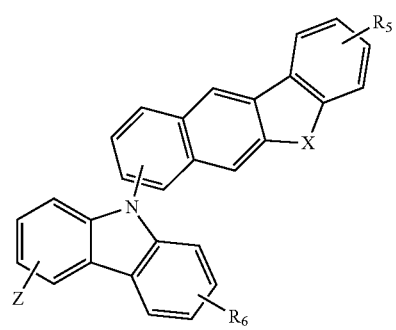
formula (12)
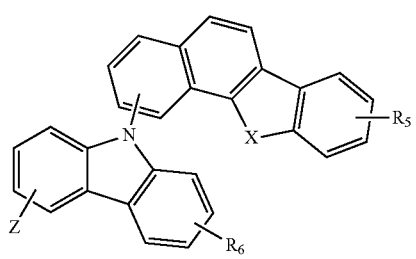
formula (13)
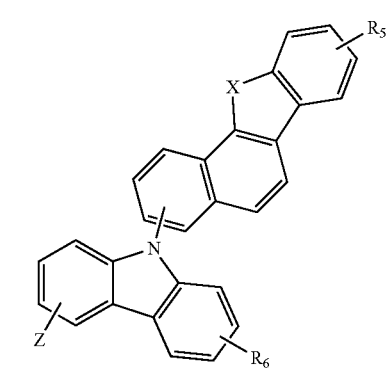
formula (14)
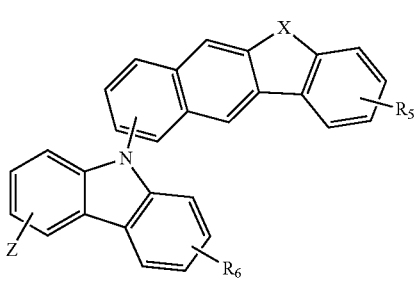
formula (15)
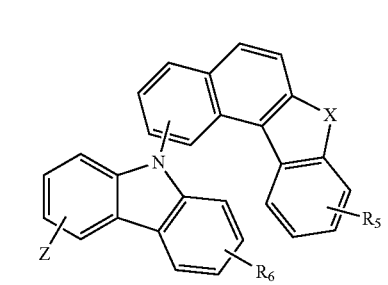
formula (16)
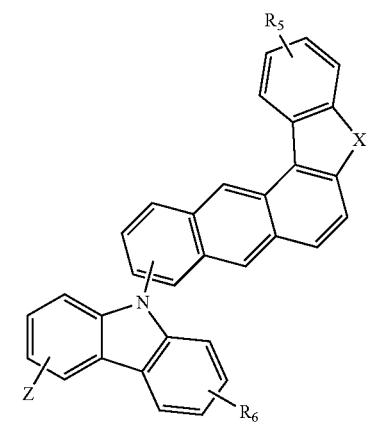
formula (17)
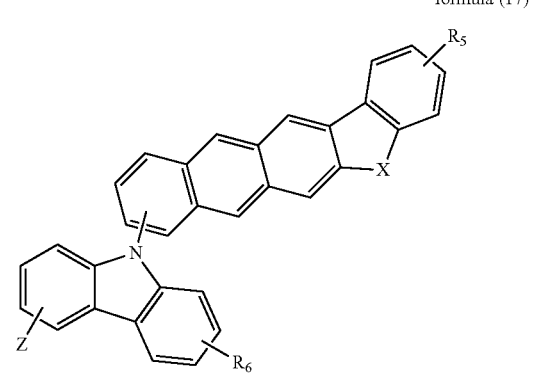
formula (18)
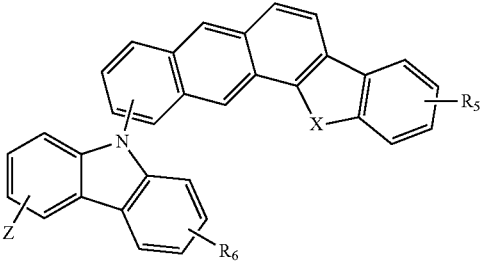
formula (19)
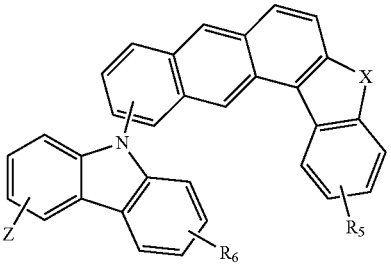

formula (20)
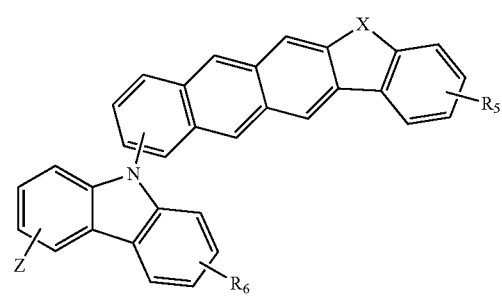
formula (21)
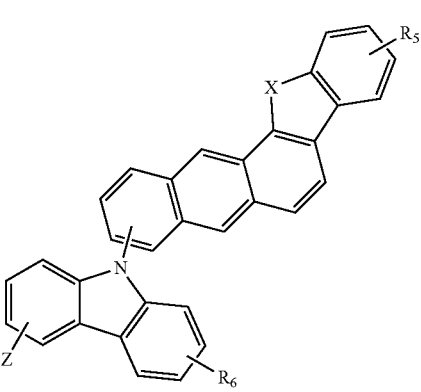
formula (22)
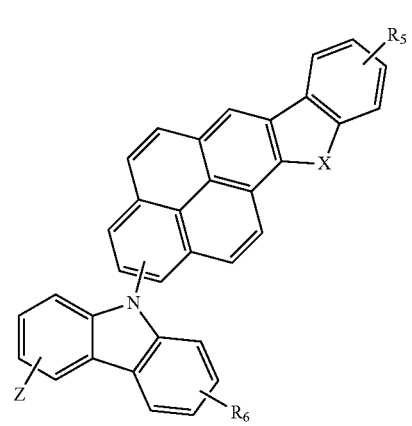
formula (23)
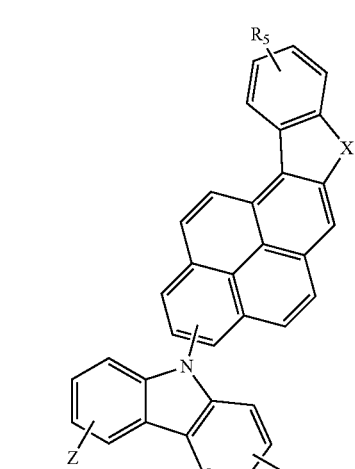
formula (24)
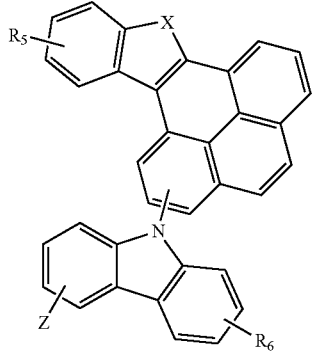
formula (25)
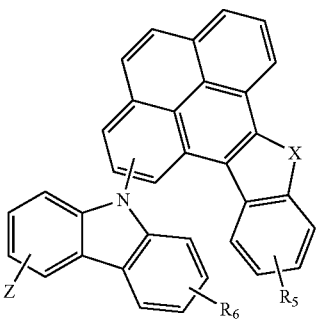
formula (26)
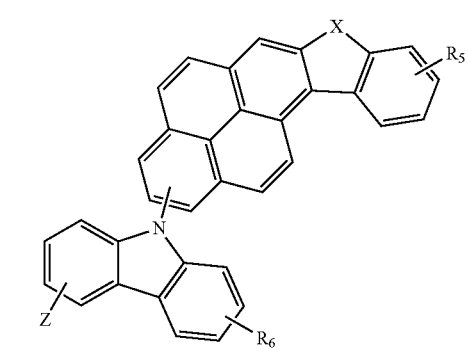
formula (27)
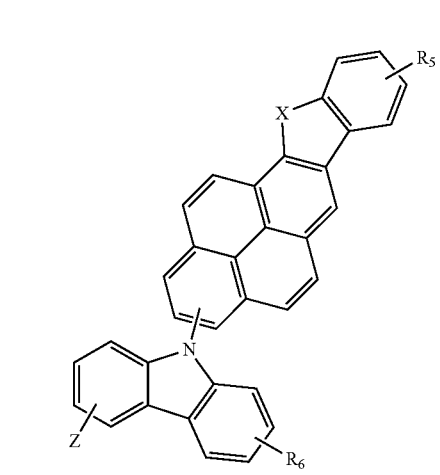

formula (28)

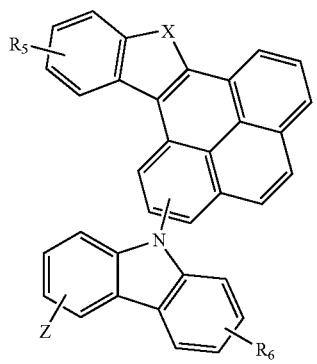

formula (29)

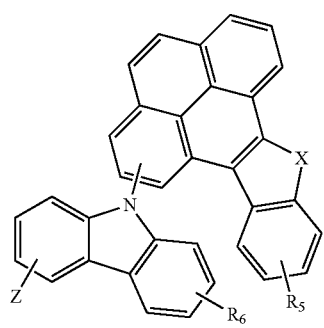

The organic compound according to claim 1, wherein the alkyl group, aralkyl group, aryl group, heteroaryl group, arylamine group, or heteroarylamine group is substituted by a halogen, an alkyl group, an aryl group, or a heteroaryl group.

The organic compound according to claim 1, wherein $Ar_1$ represents a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted triphenylenyl group.

The organic compound according to claim 1, wherein $Ar_1$ represents one of the following substituents:

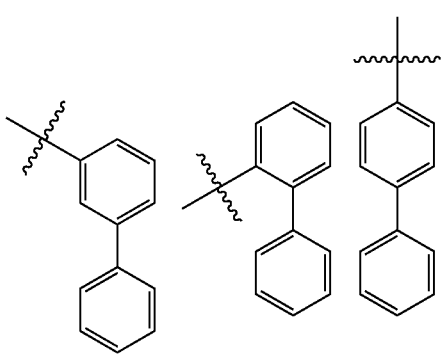

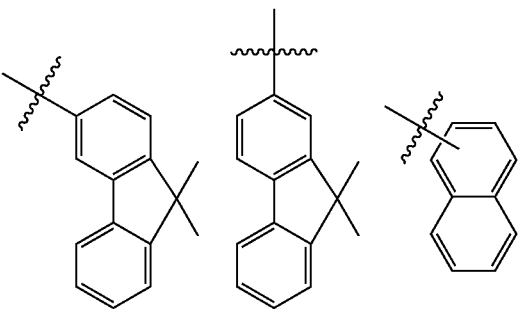

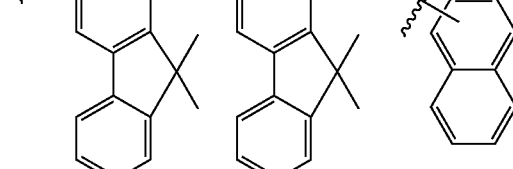

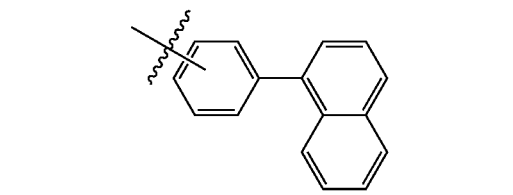

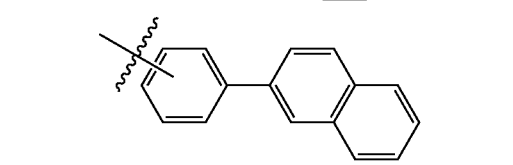

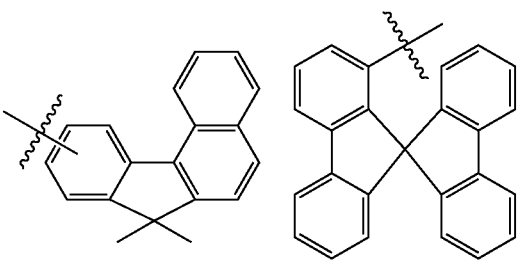

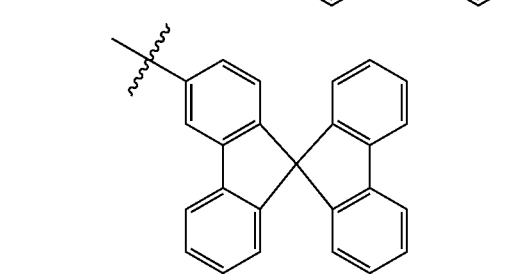

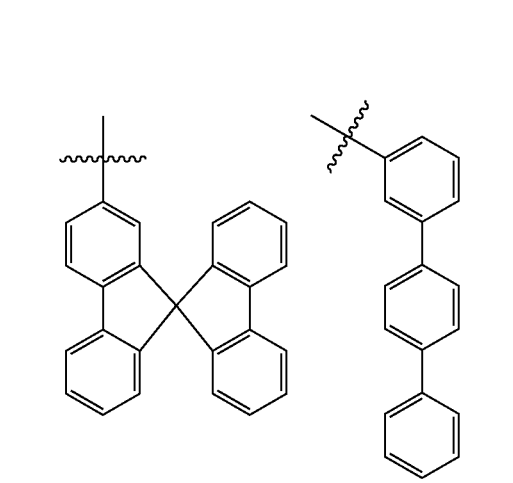

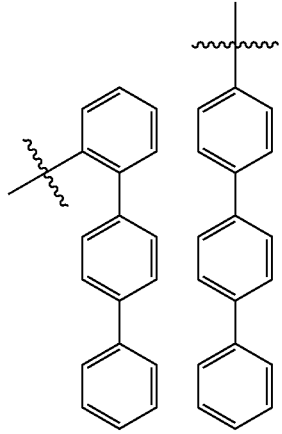
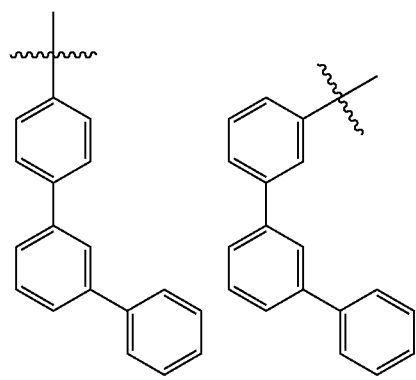
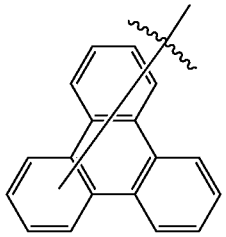
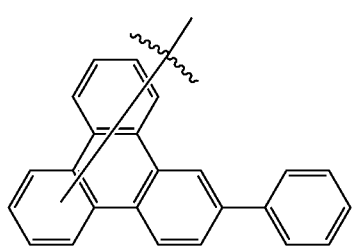
The organic compound of the present invention may be one of the following compounds:
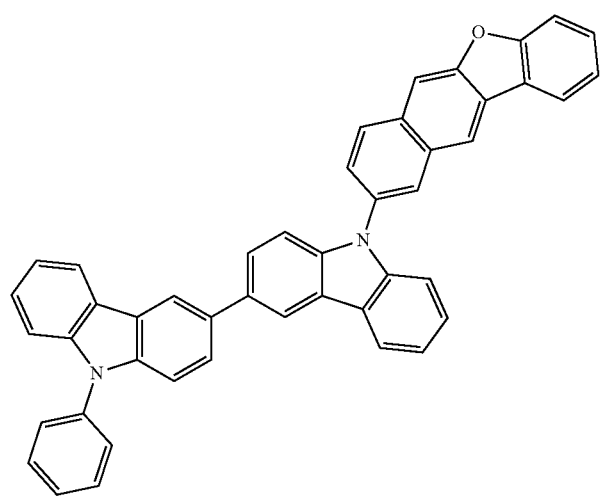
C1

-continued
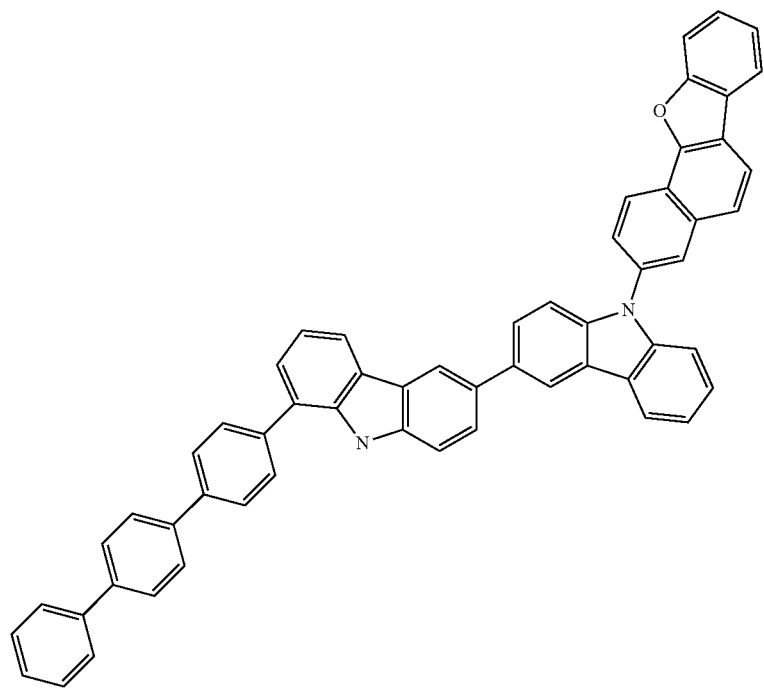
C2
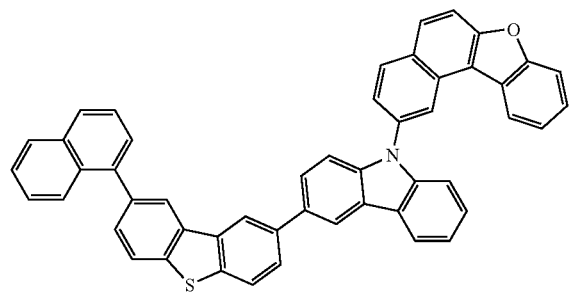
C3
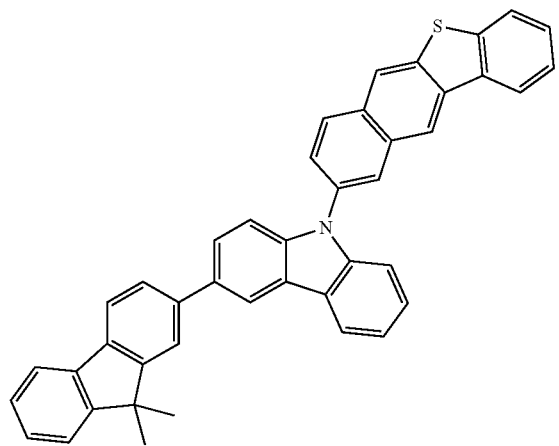
C4
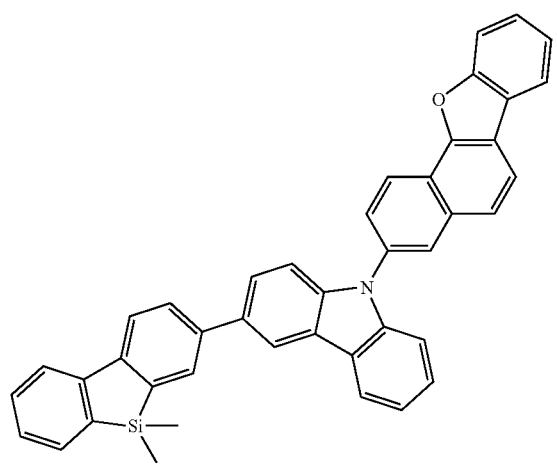
C5
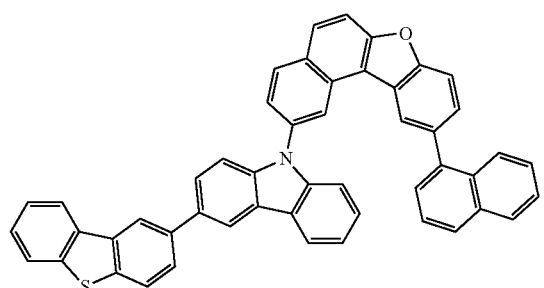
C6

-continued
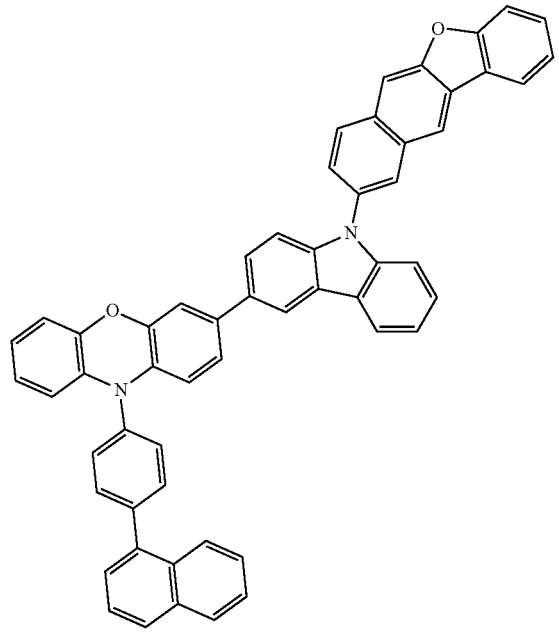
C7
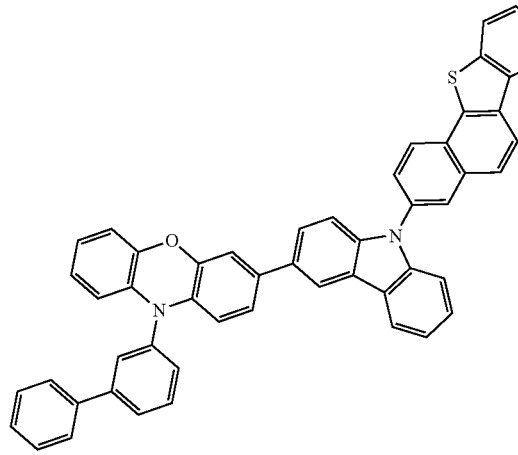
C8
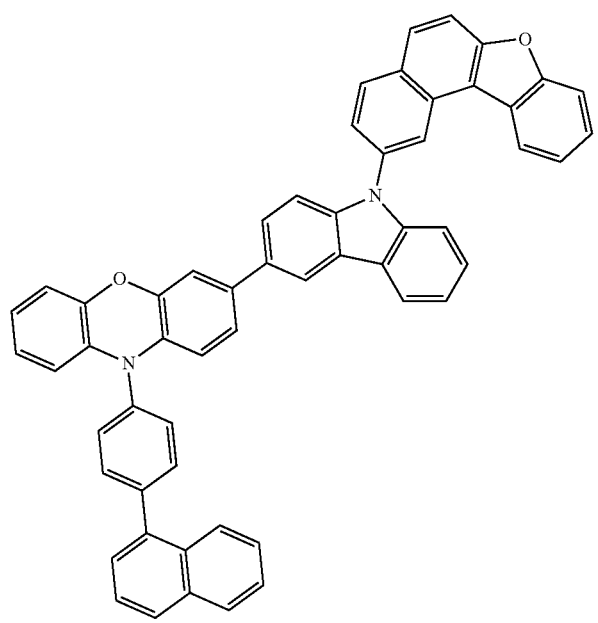
C9

-continued
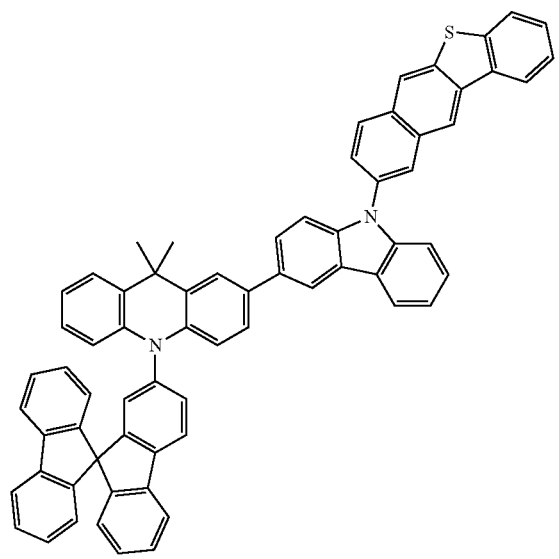
C10
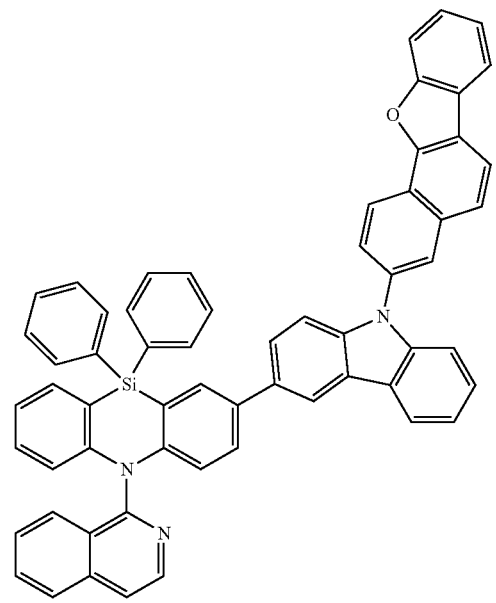
C11
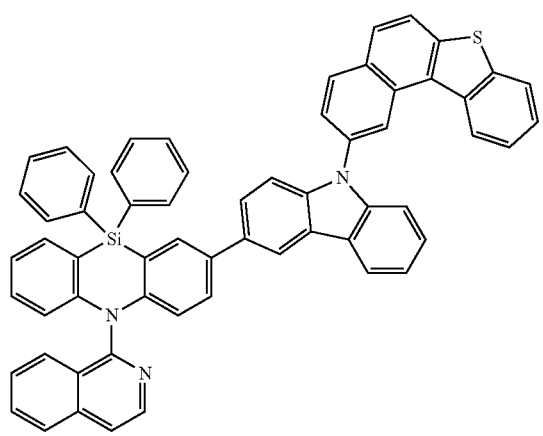
C12
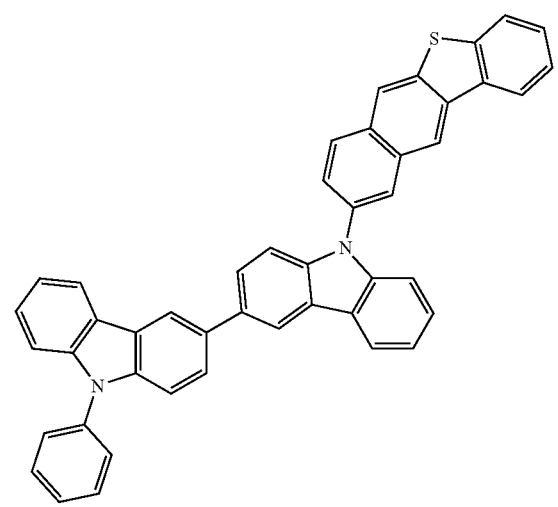
C13

-continued
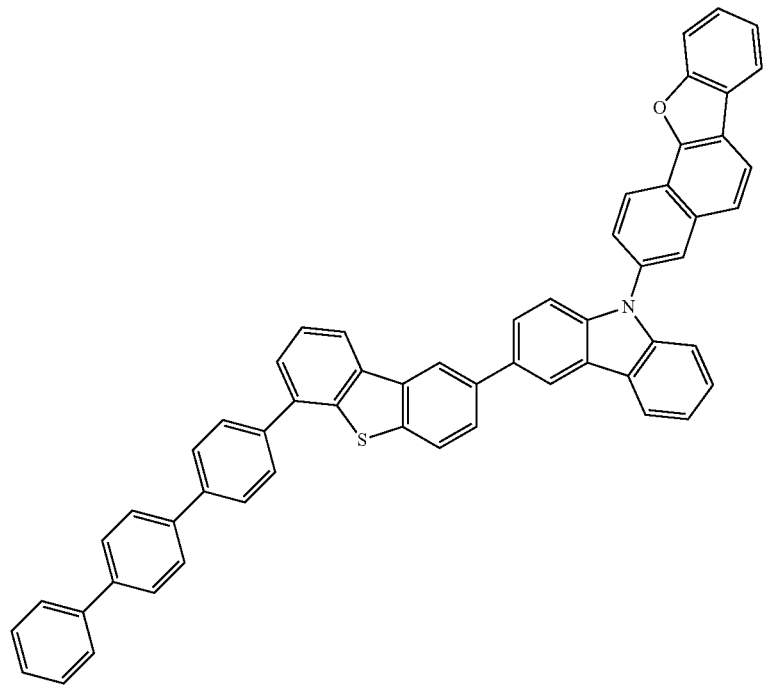
C14
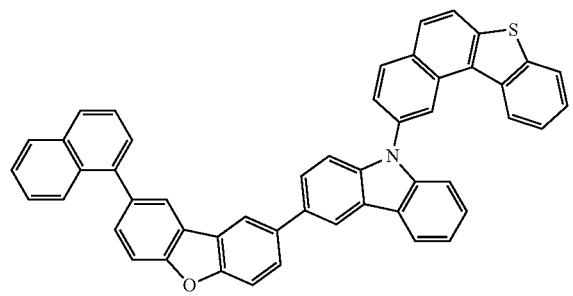
C15
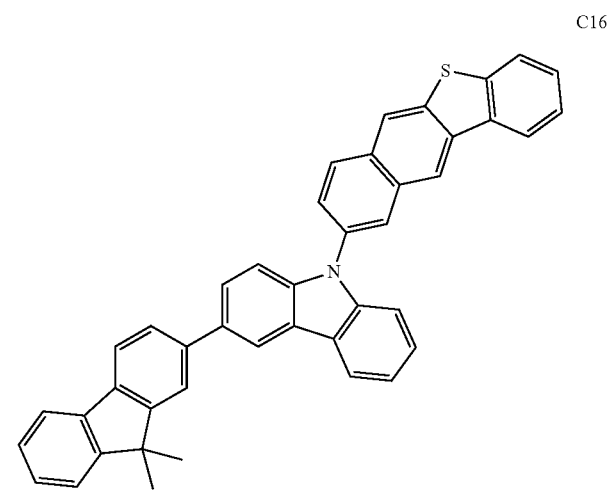
C16
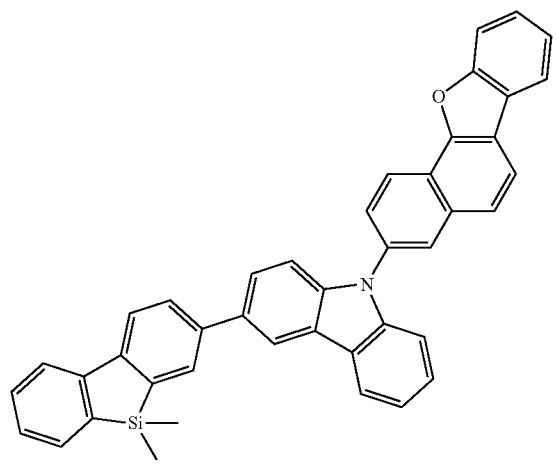
C17
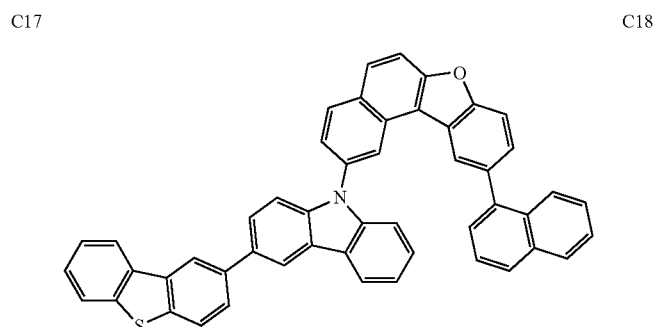
C18

C19
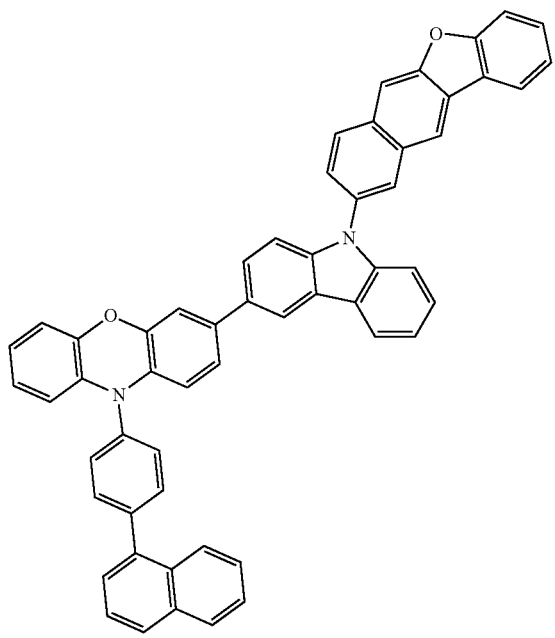
C20
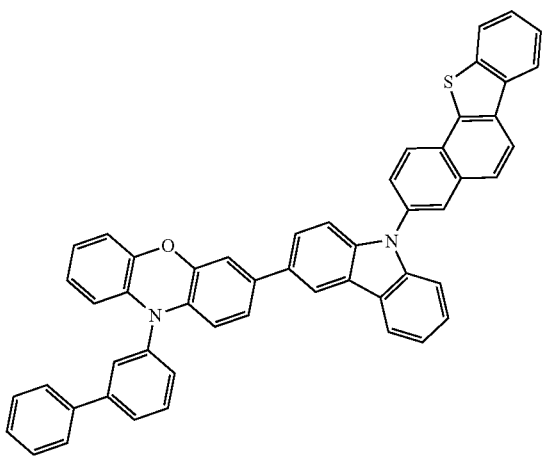
C21
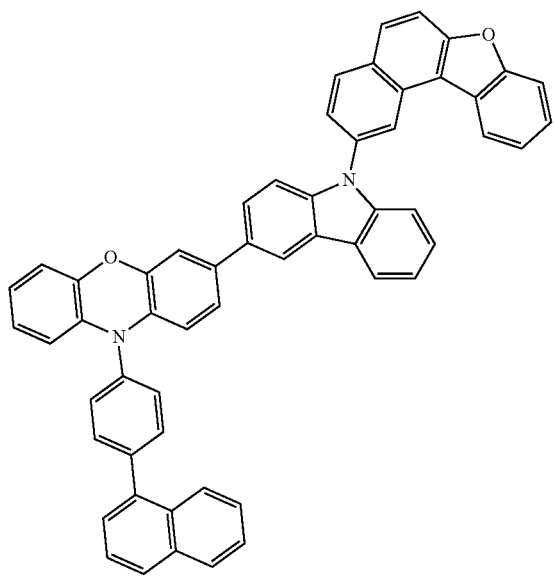
C22
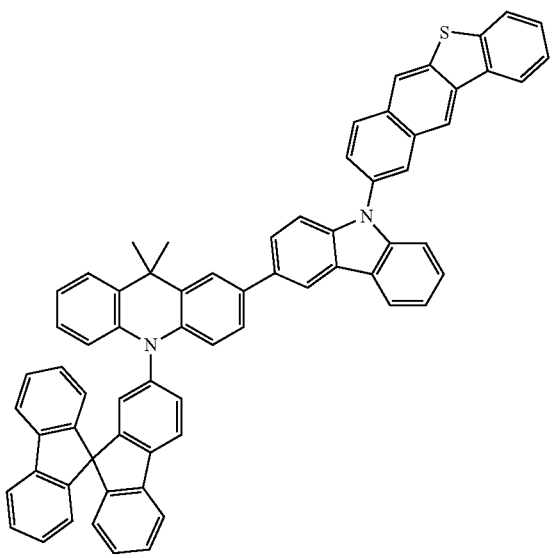

-continued
C23
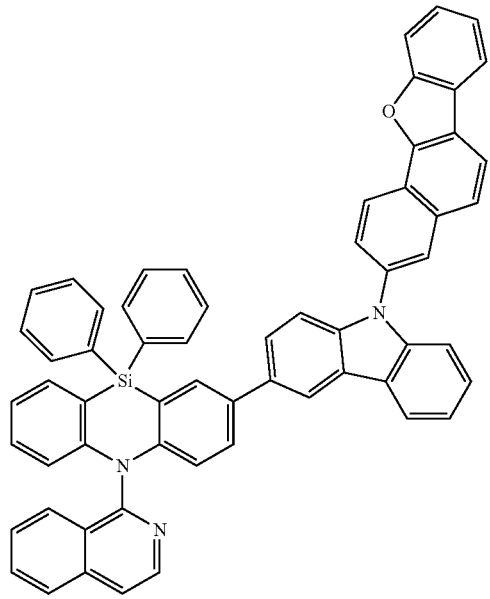
C24
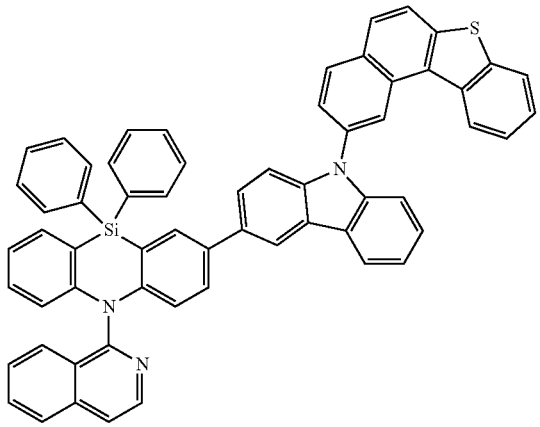
C25
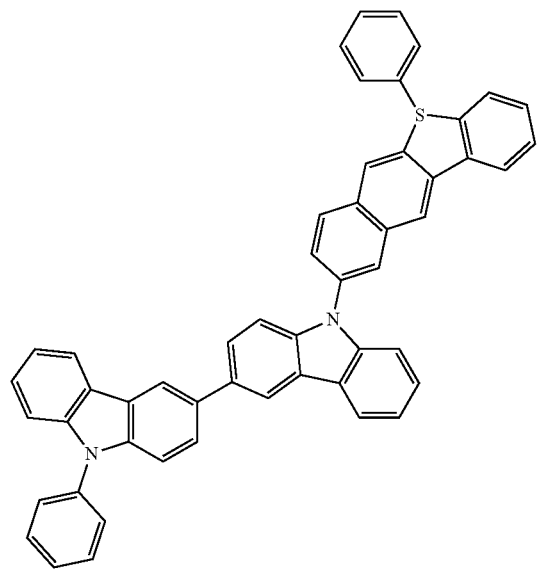
C26
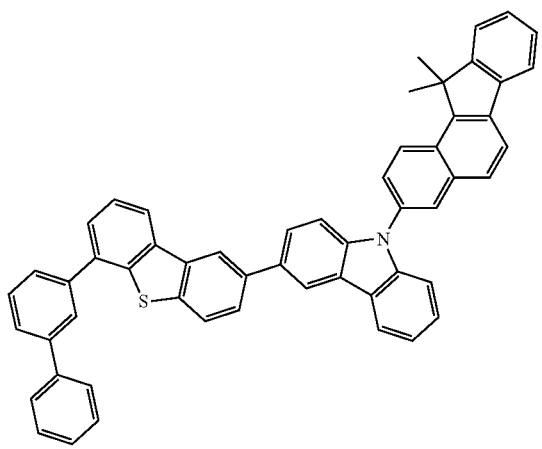

-continued
C27
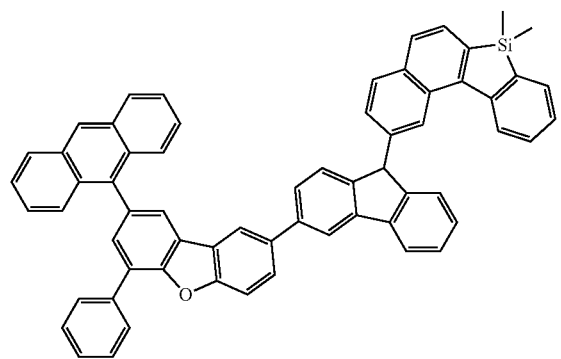
C28
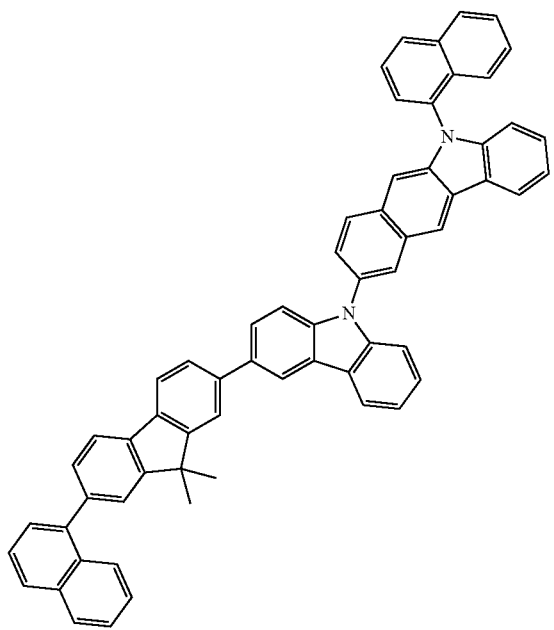
C29
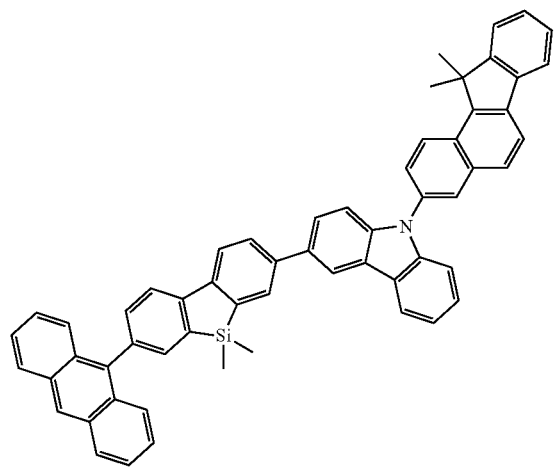
C30
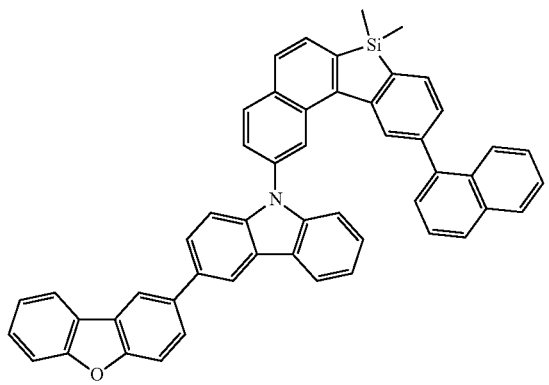

-continued
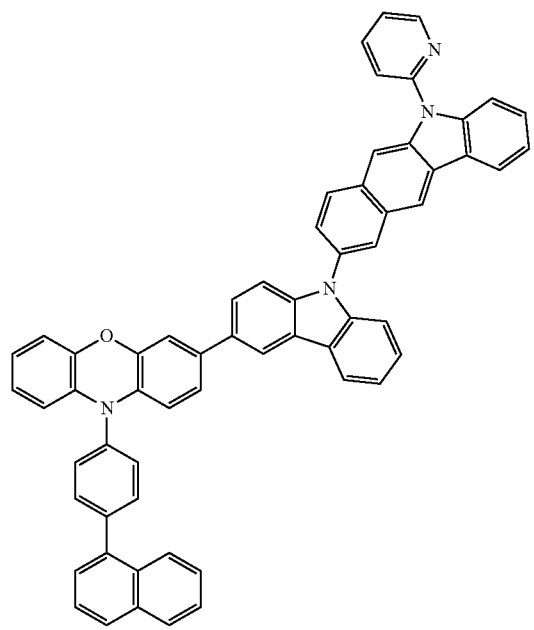
C31
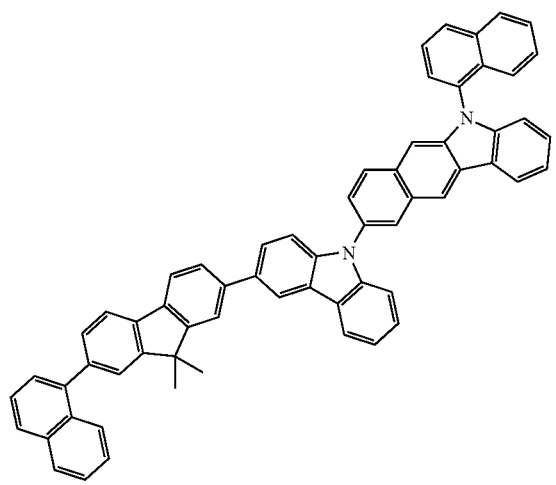
C32
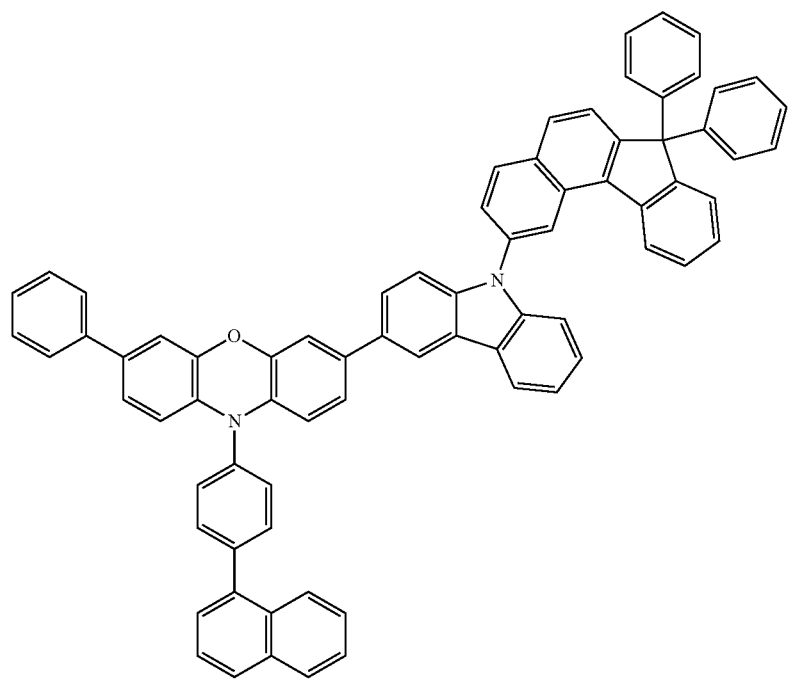
C33

C34
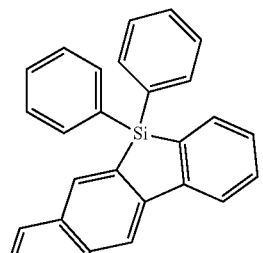
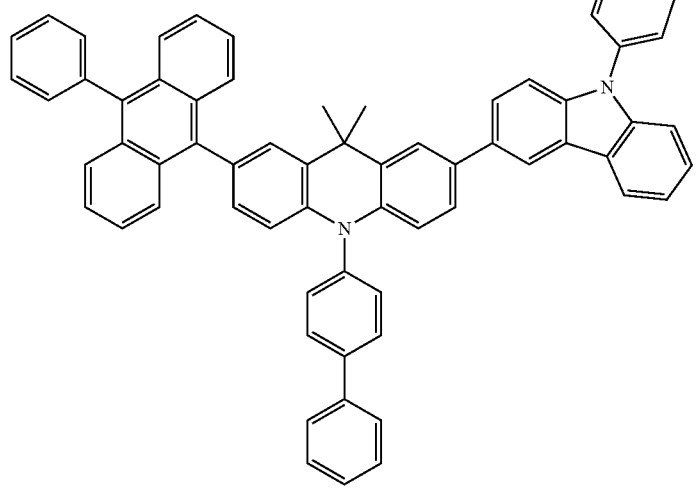
C35
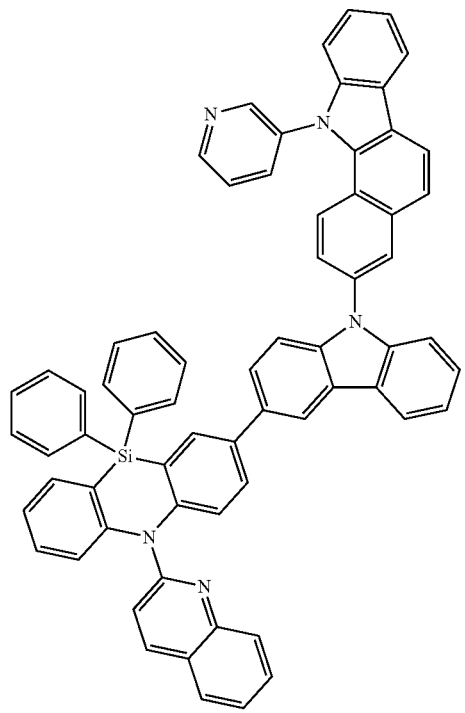
C36
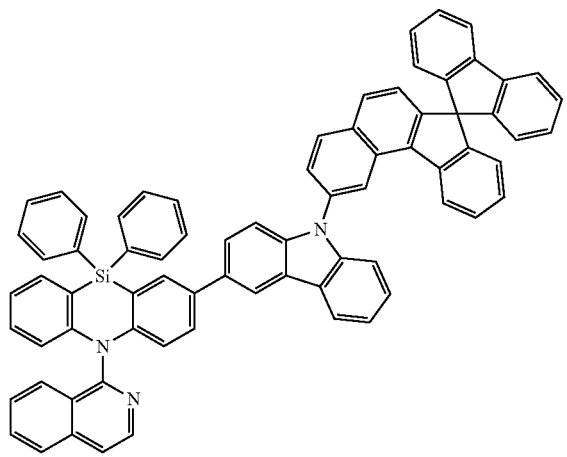

-continued
C37
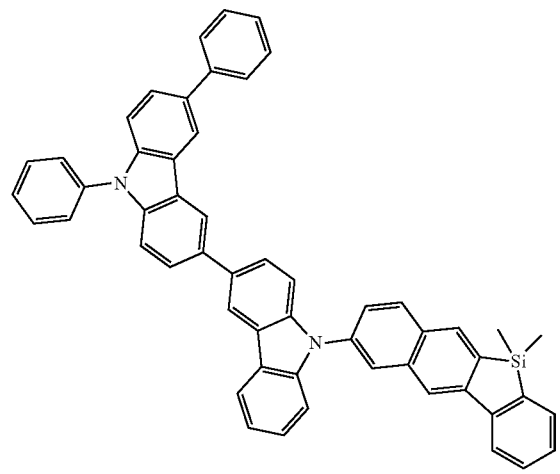
C38
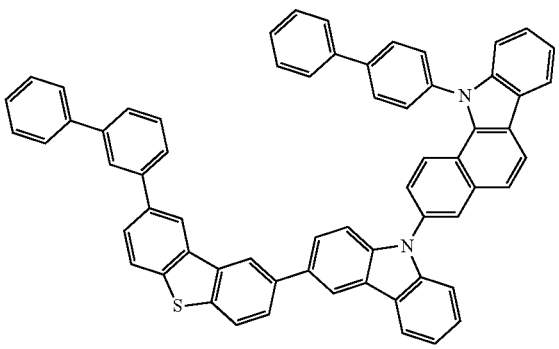
C39
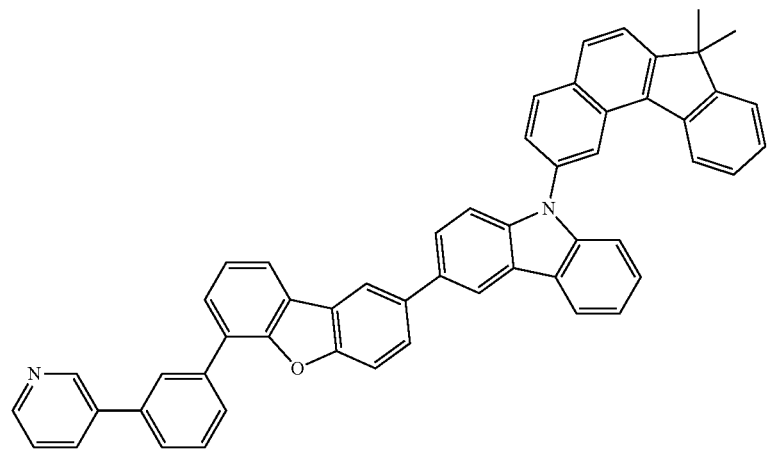
C40
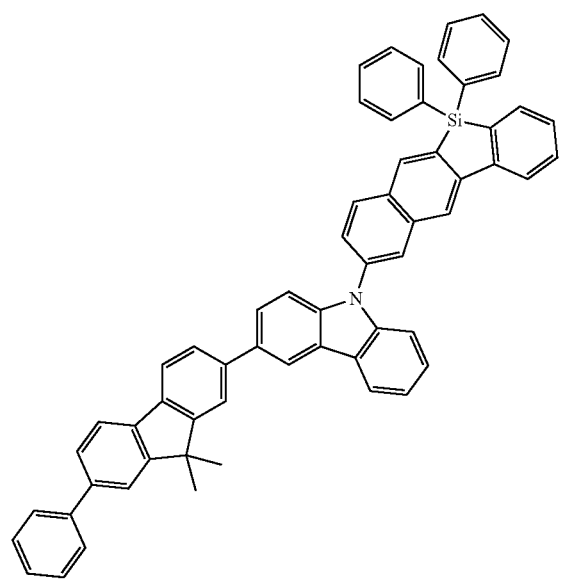
C41
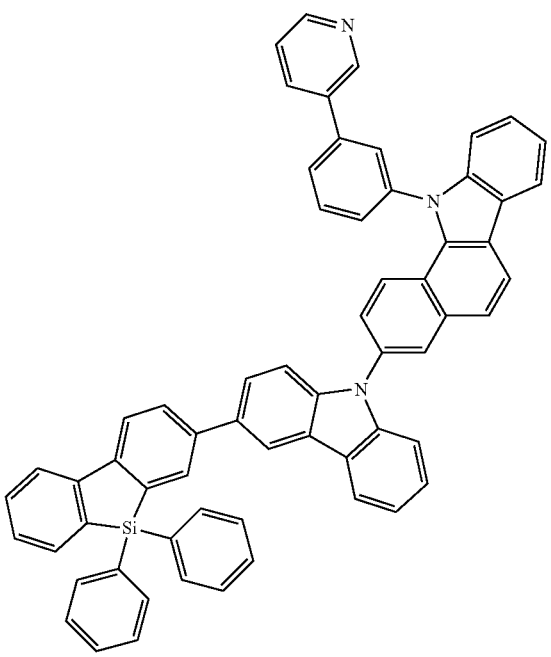

-continued
C42
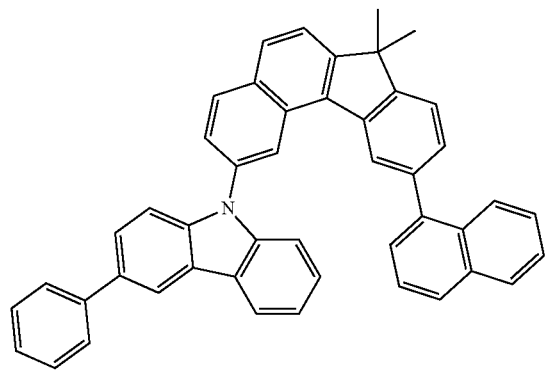
C43
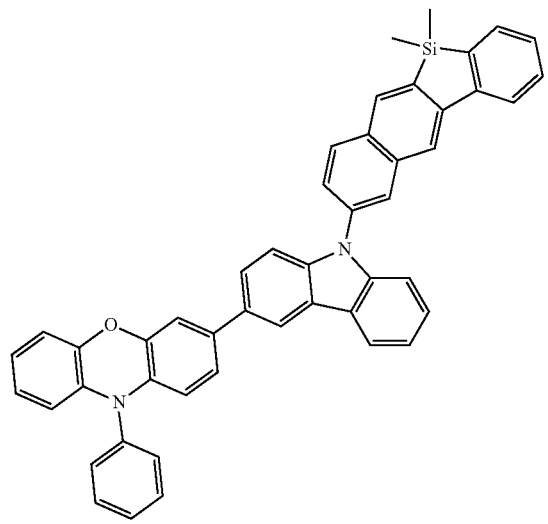
C44
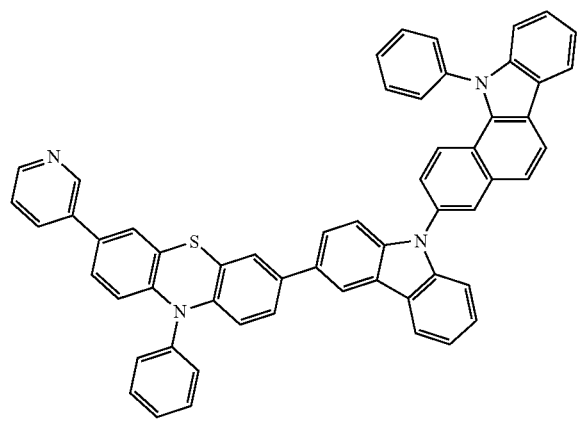
C45
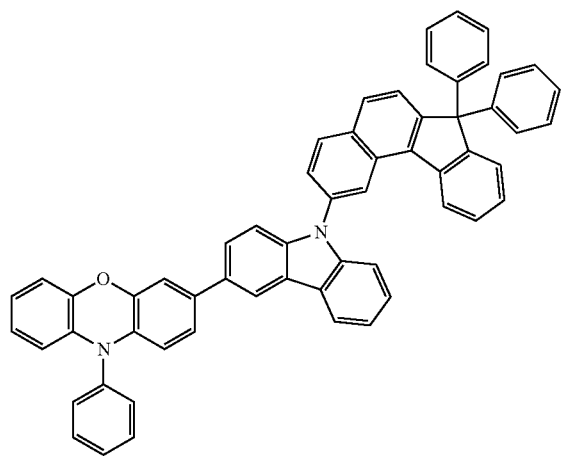
C46
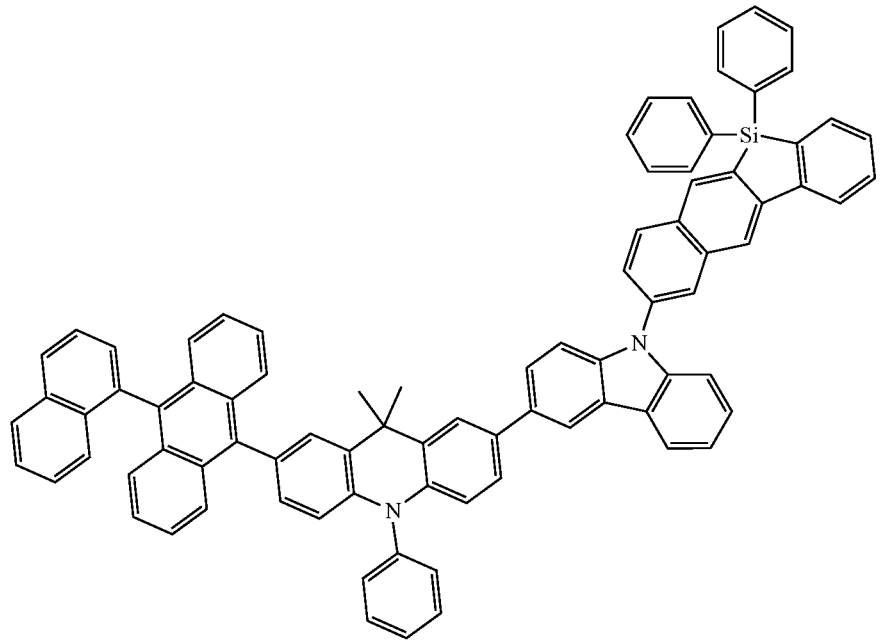

-continued
C47
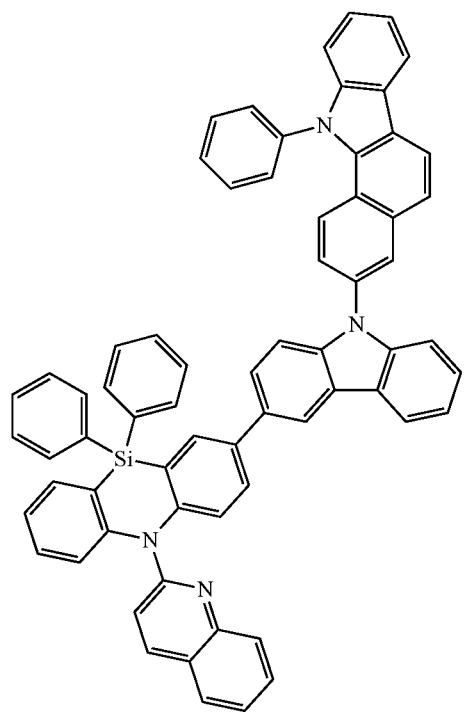
C48
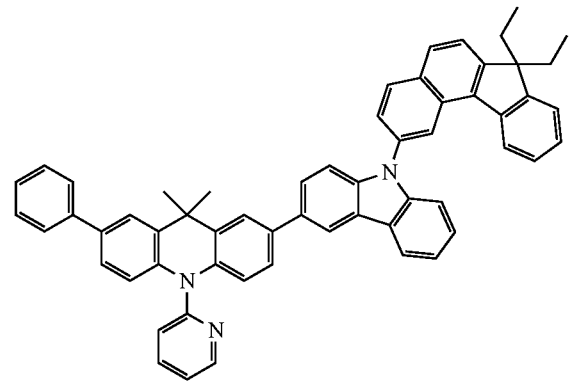
C49
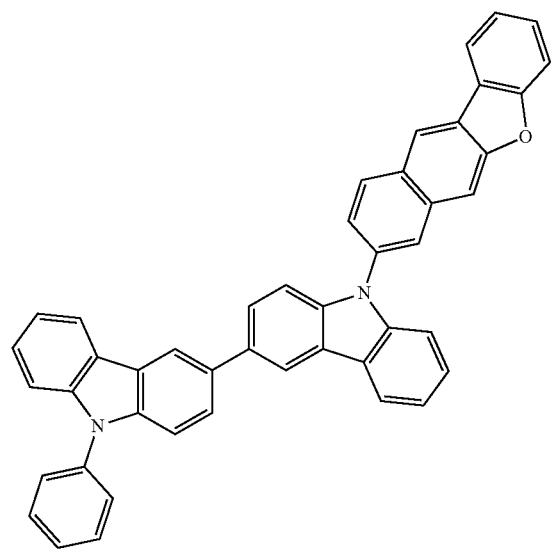
C50
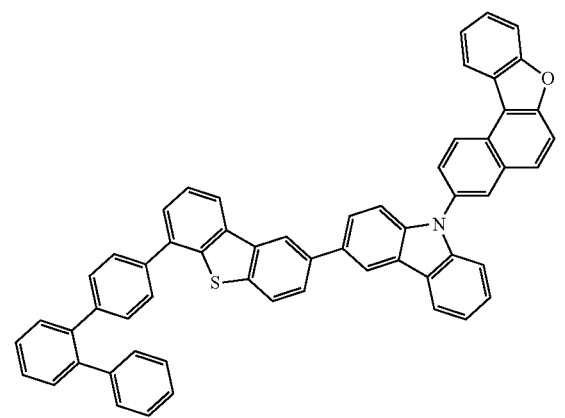

C51
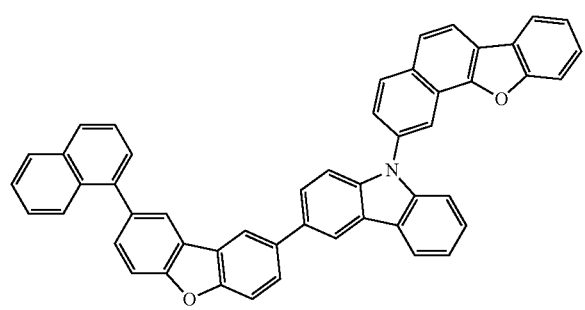
C52
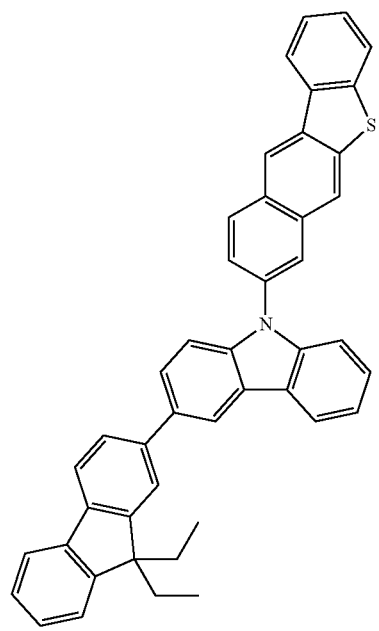
C53
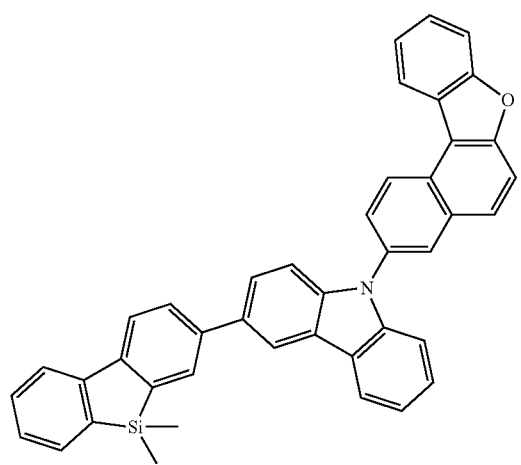
C54
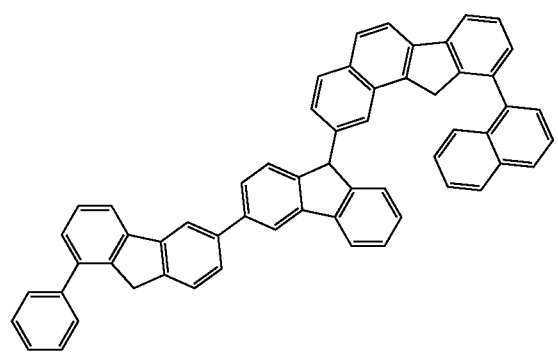

-continued
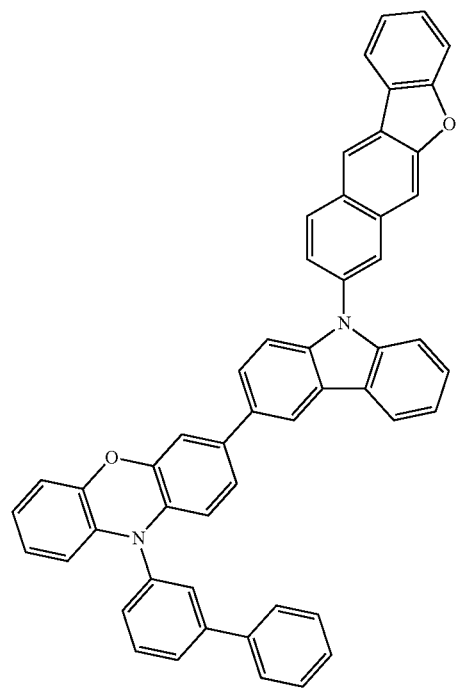
C55
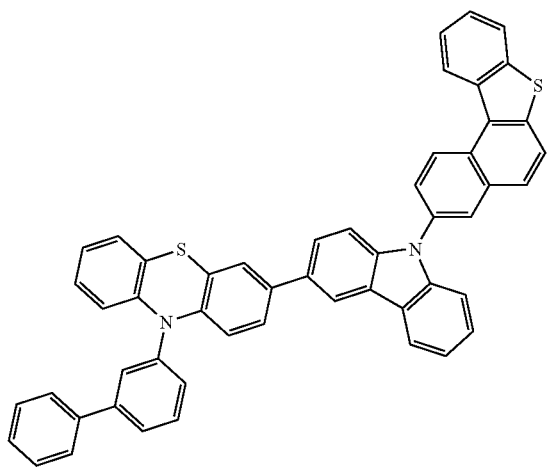
C56
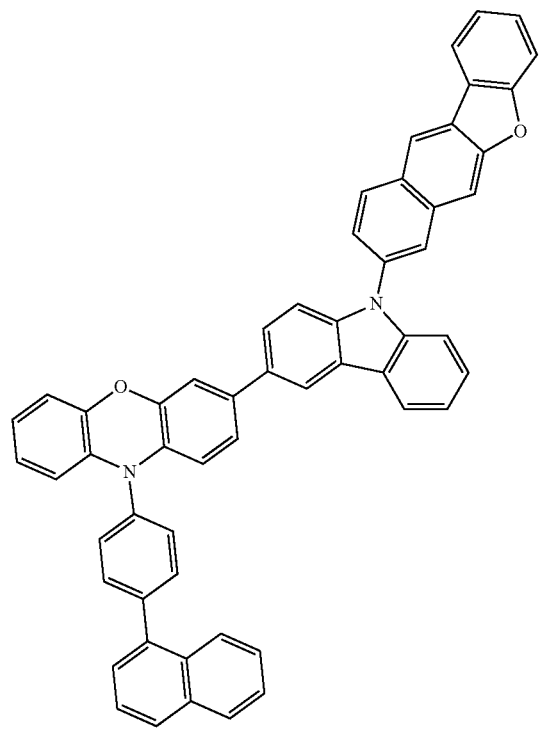
C57
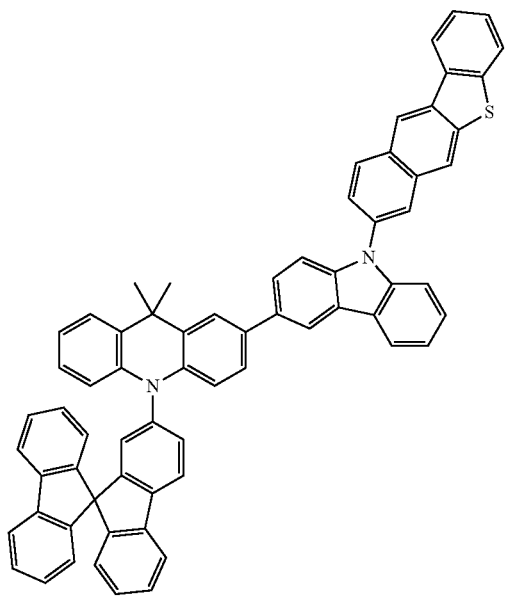
C58

-continued
C59
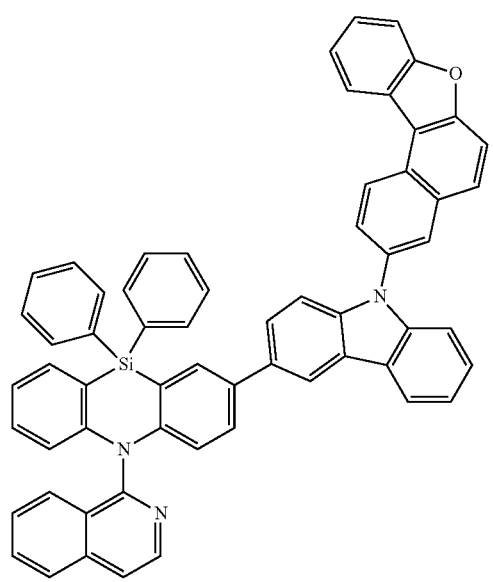
C60
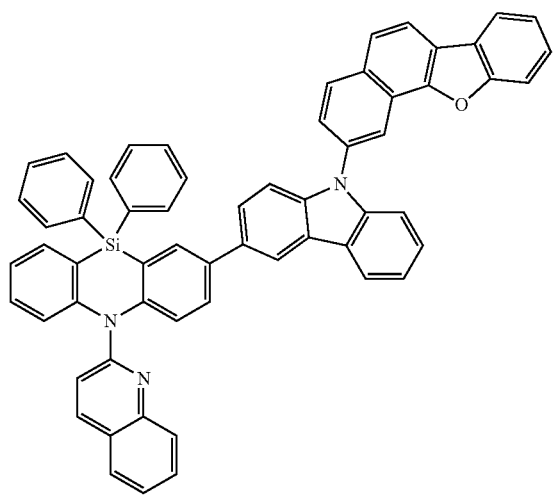
C61
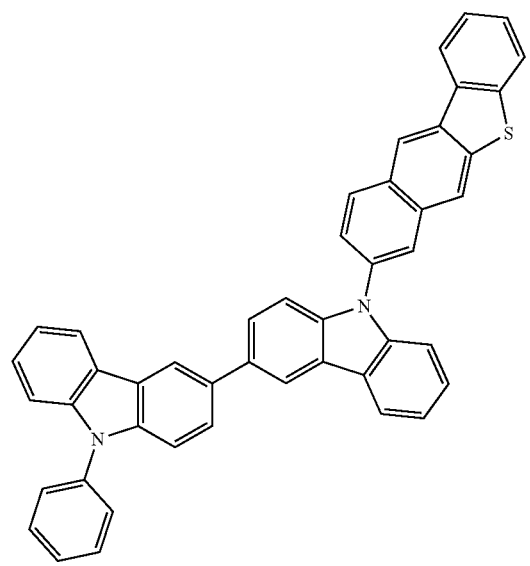
C62
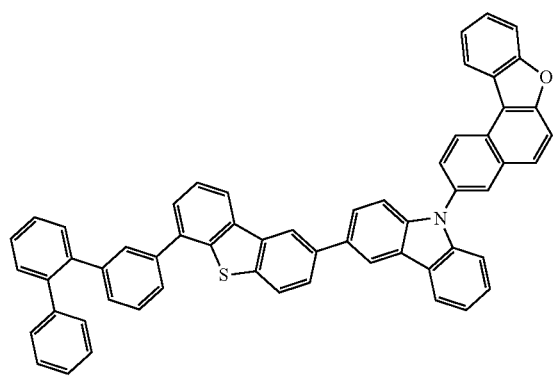
C63
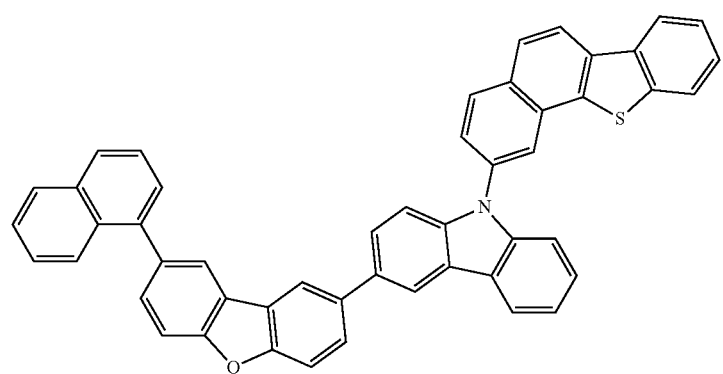

-continued
C64
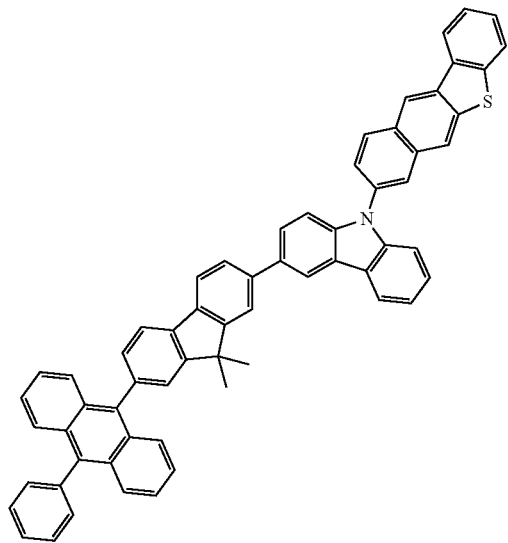
C65
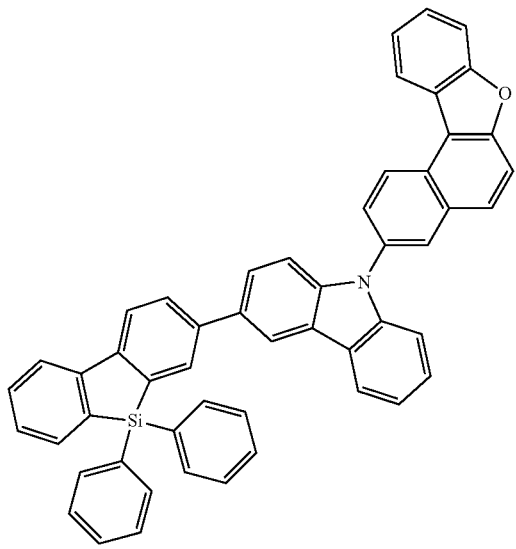
C66
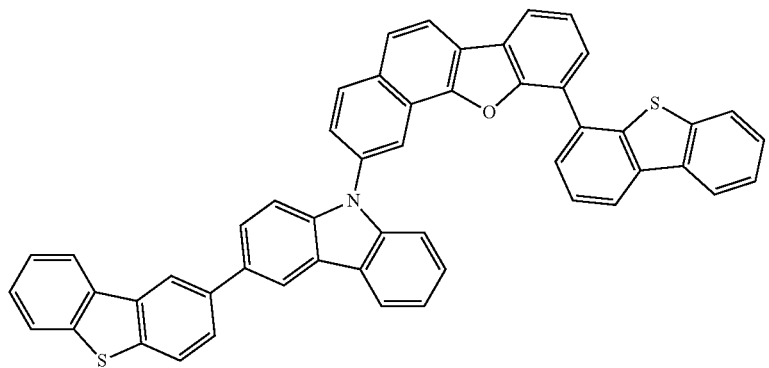
C67
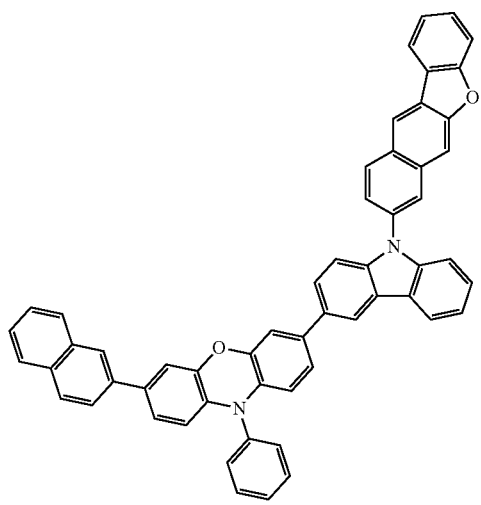
C68
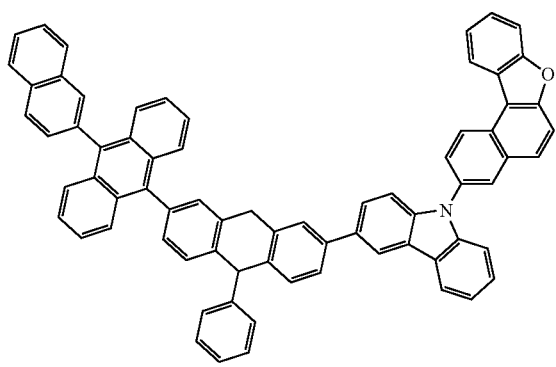

-continued
C69
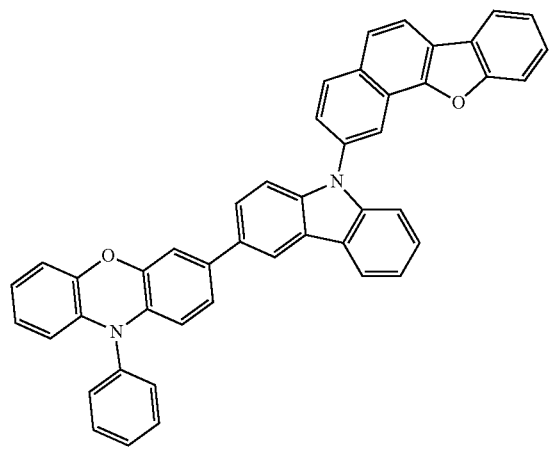
C70
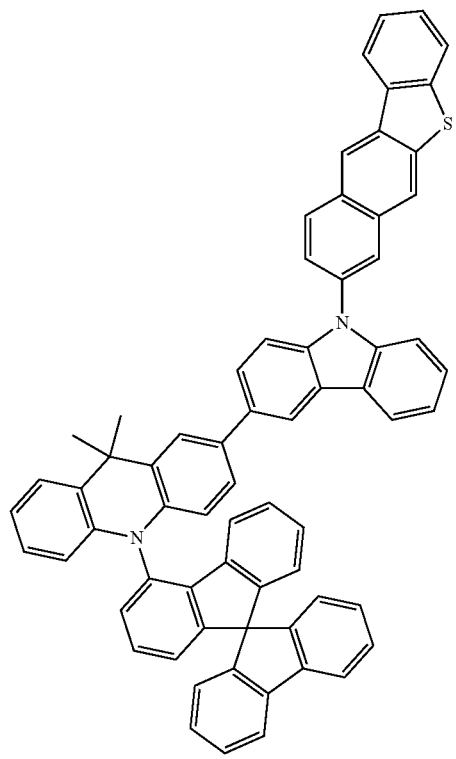
C71
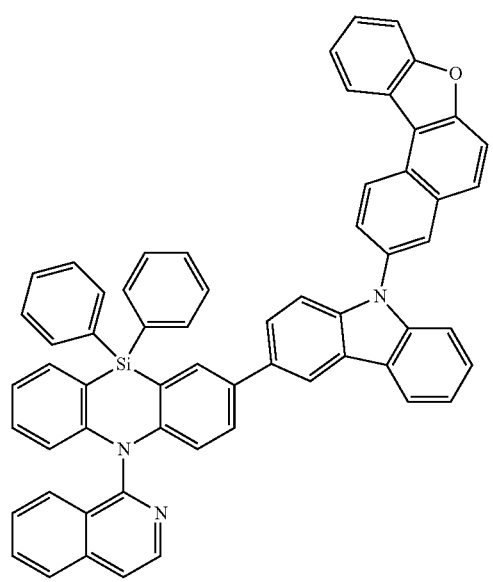
C72
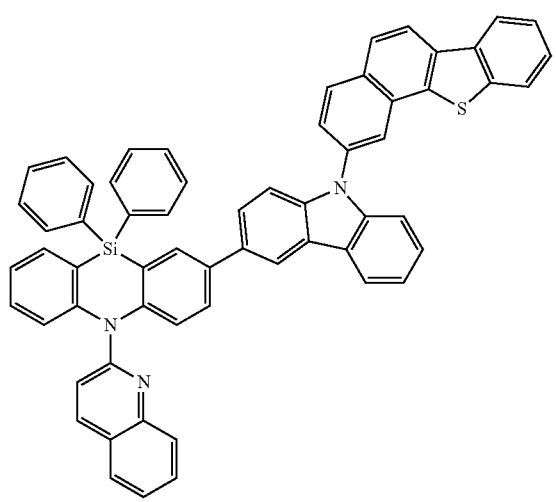

-continued
C73
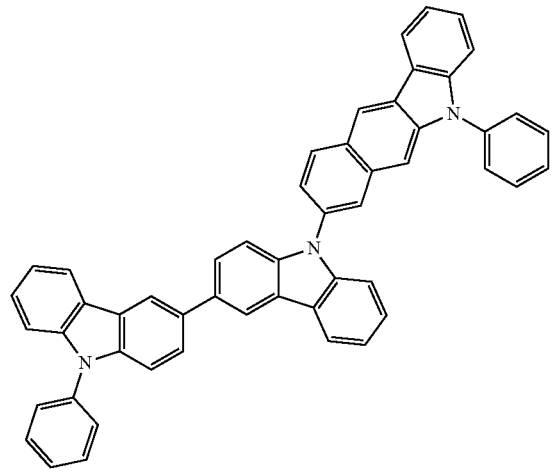
C74
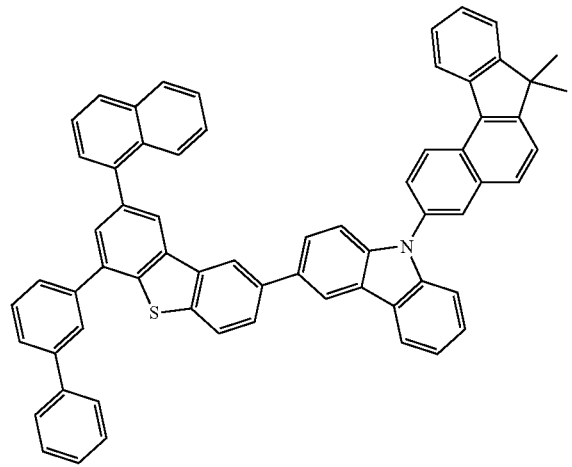
C75
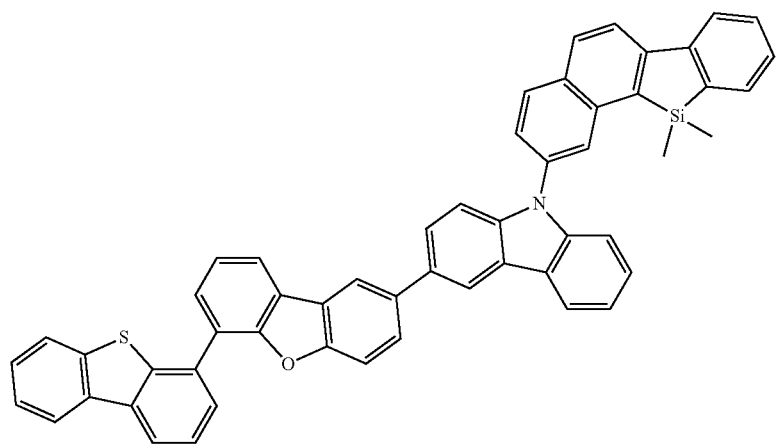
C76
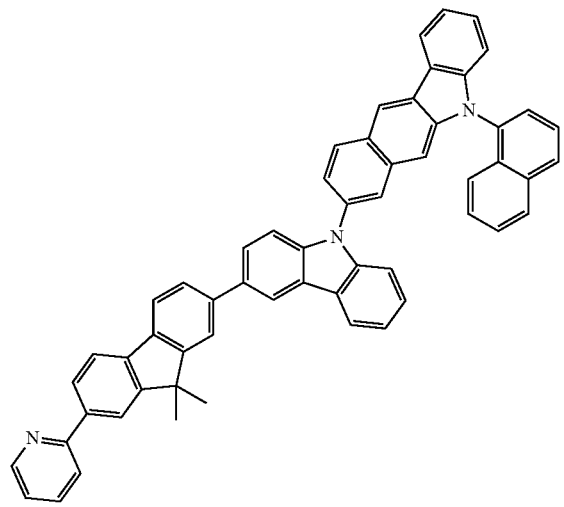
C77
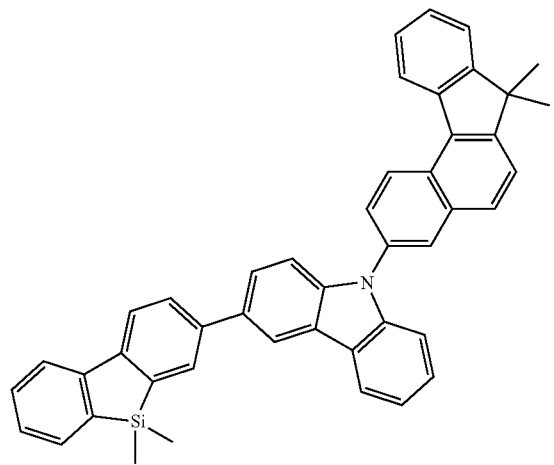

C78
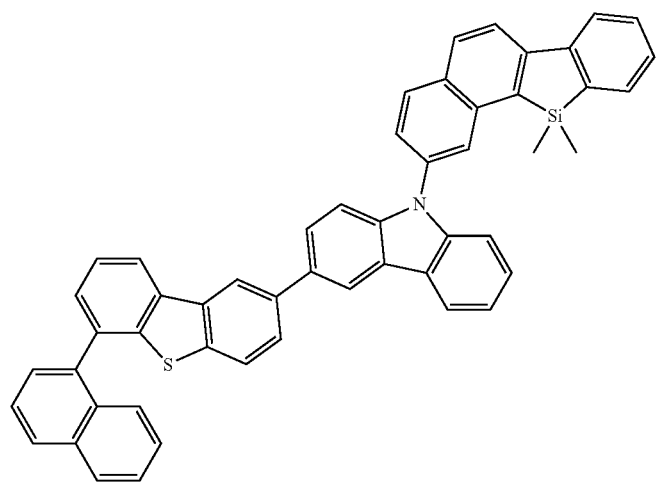
C79
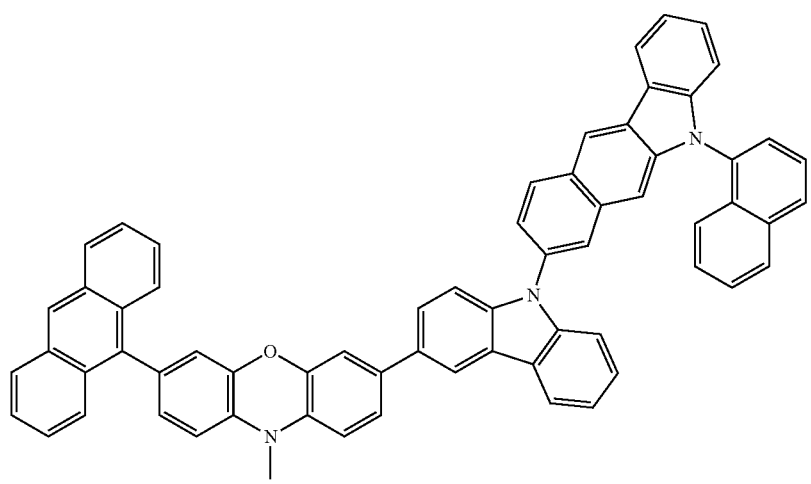
C80
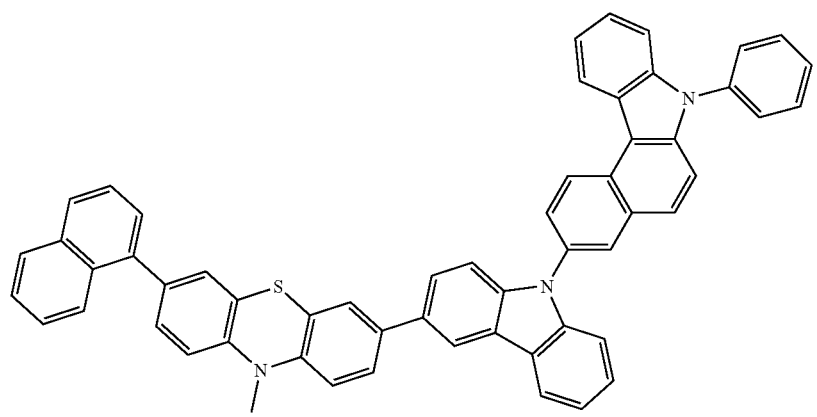

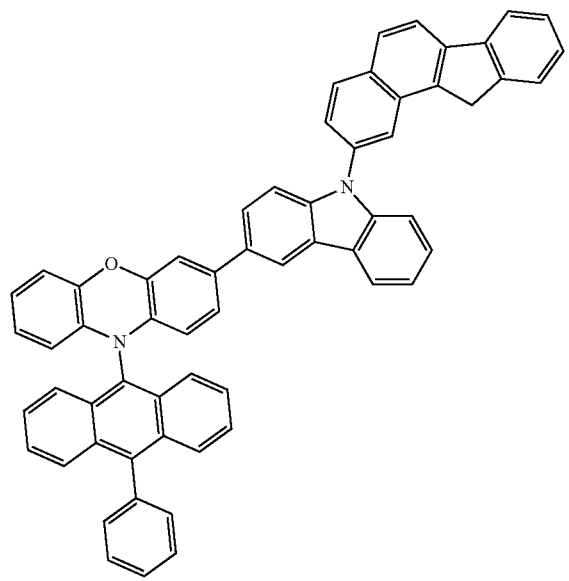
C81
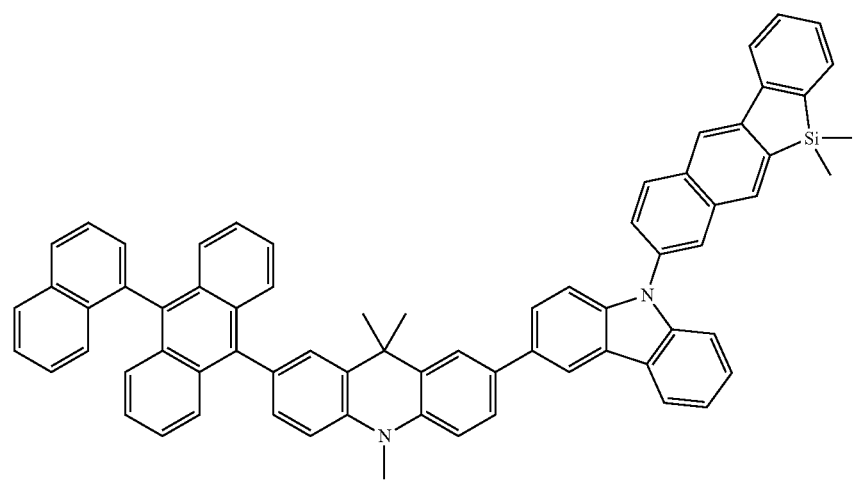
C82

C83
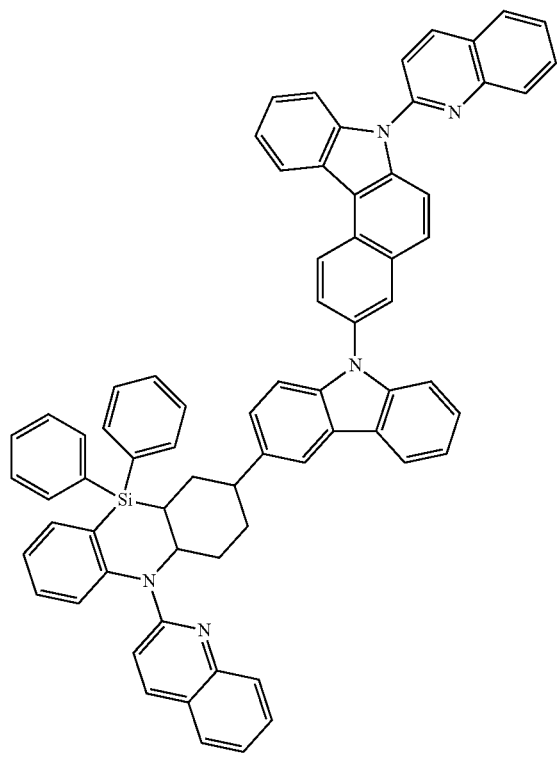
C84
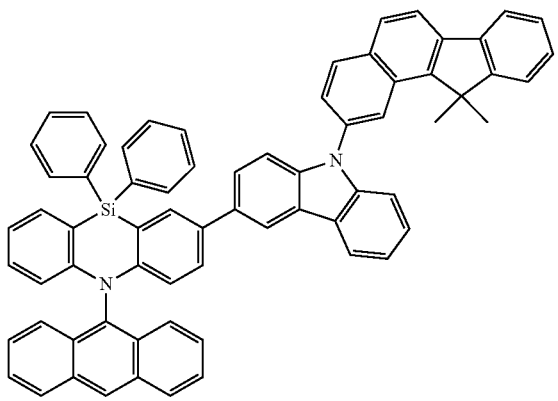
C85
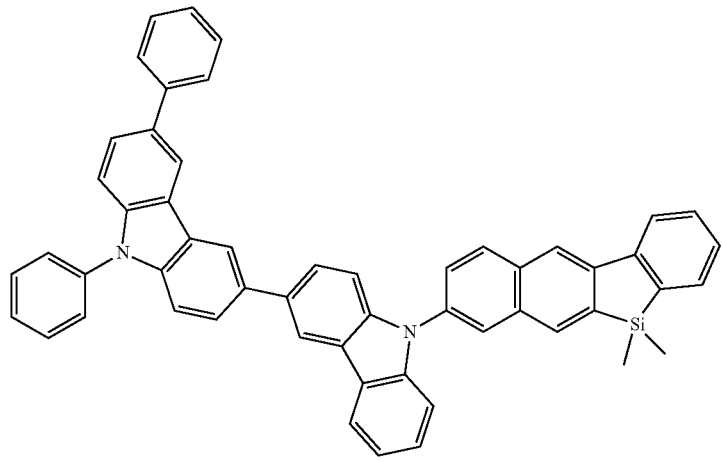
C86
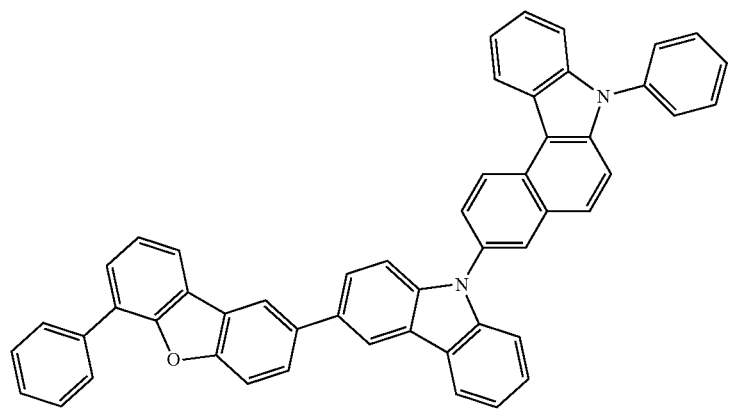

-continued
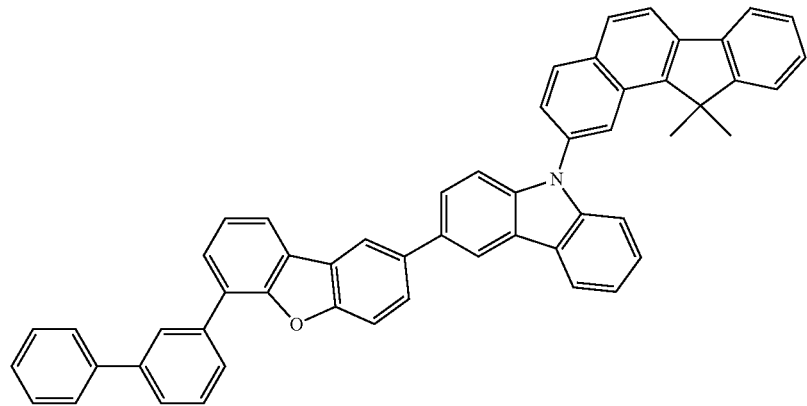
C87
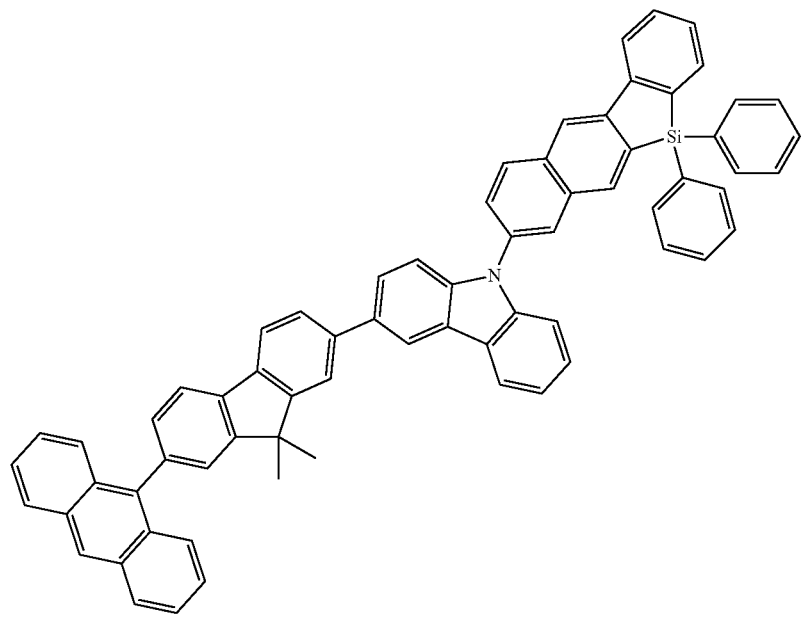
C88
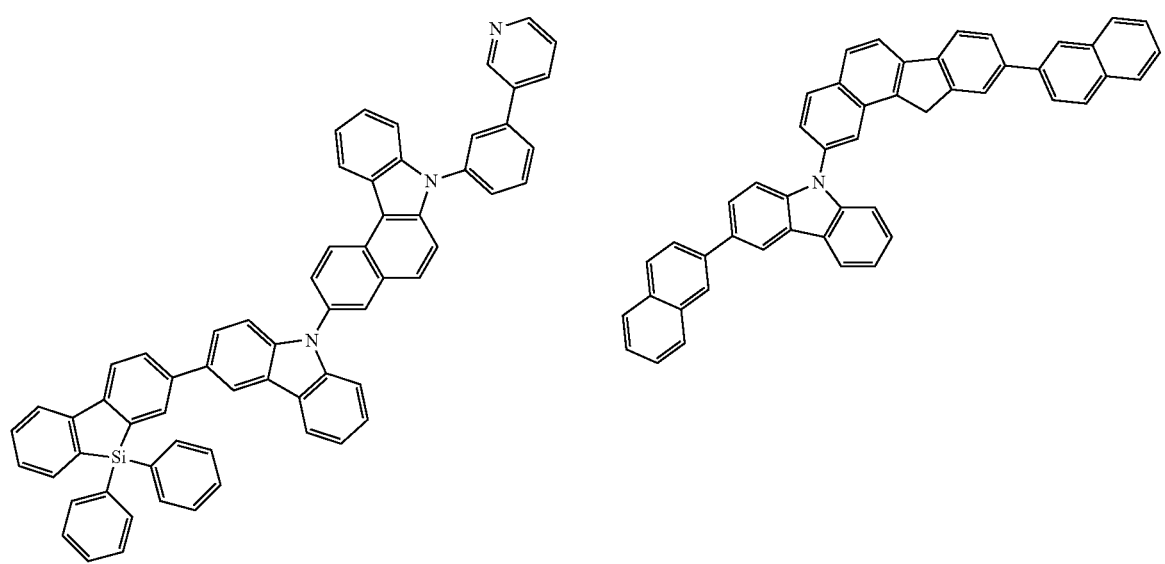
C89 C90

-continued
C91
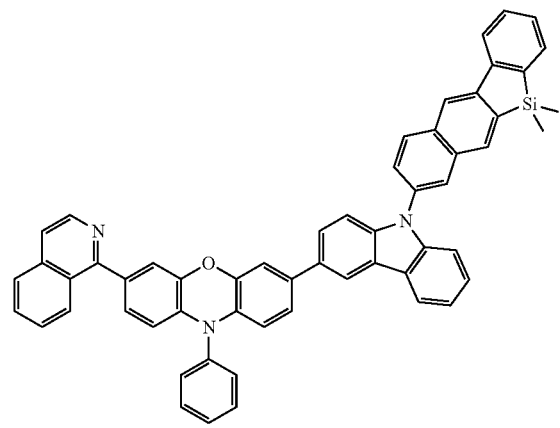
C92
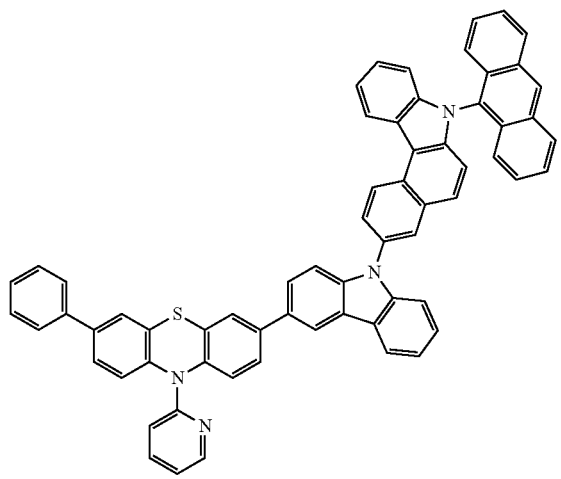
C93
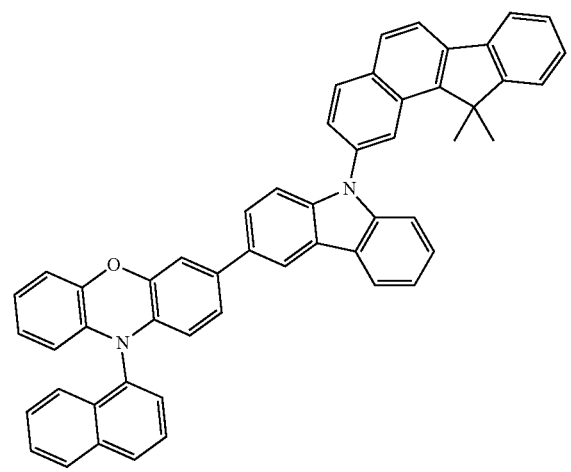
C94
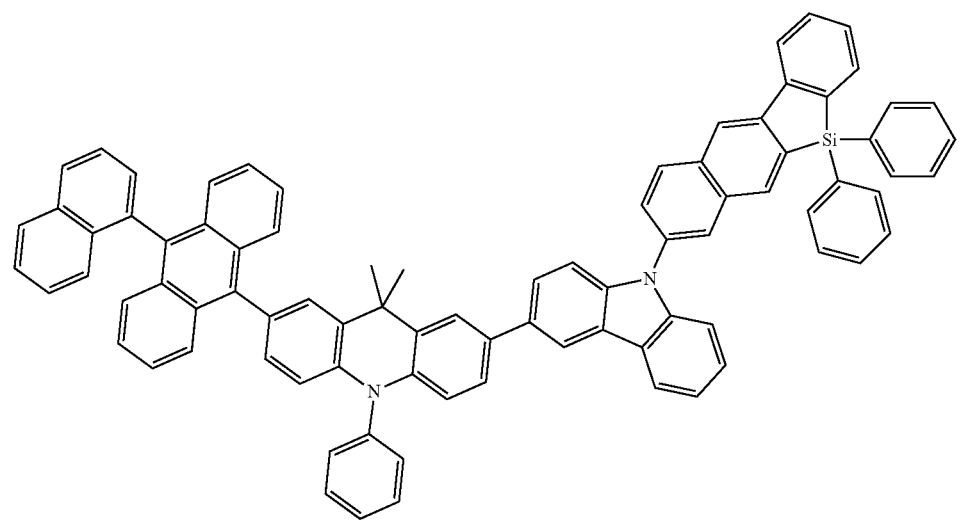

-continued
C95
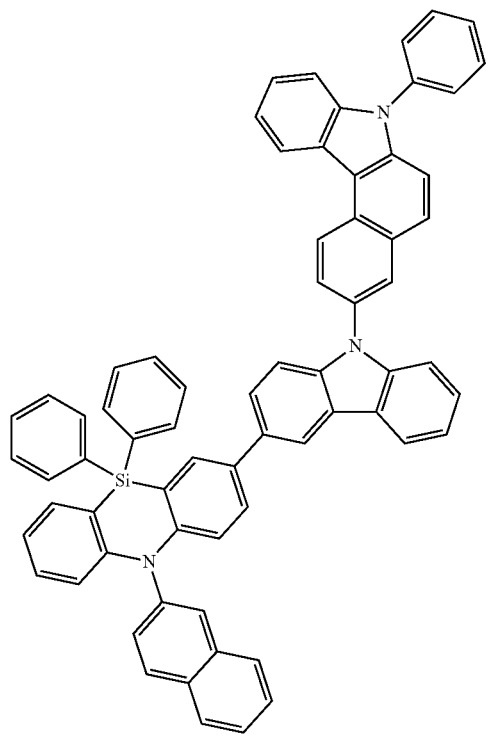
C96
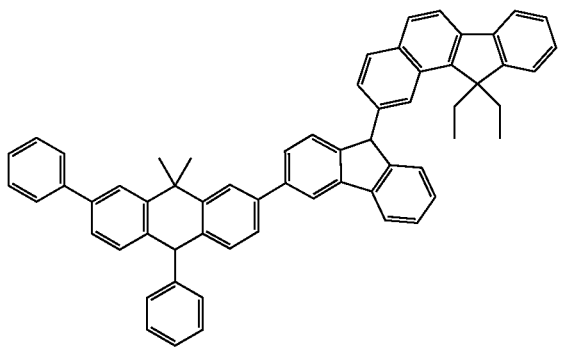
C97
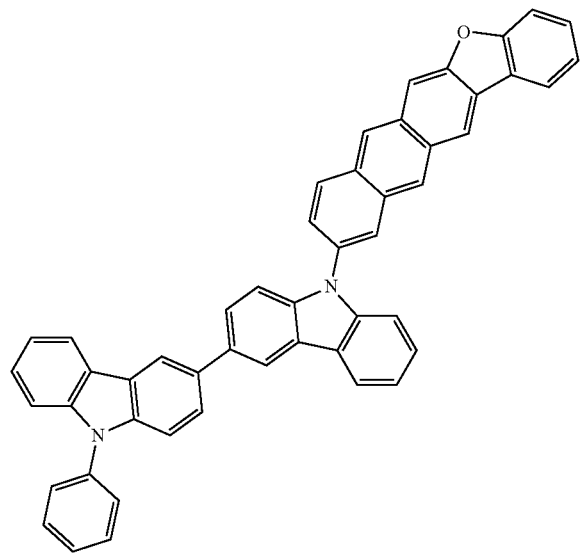
C98
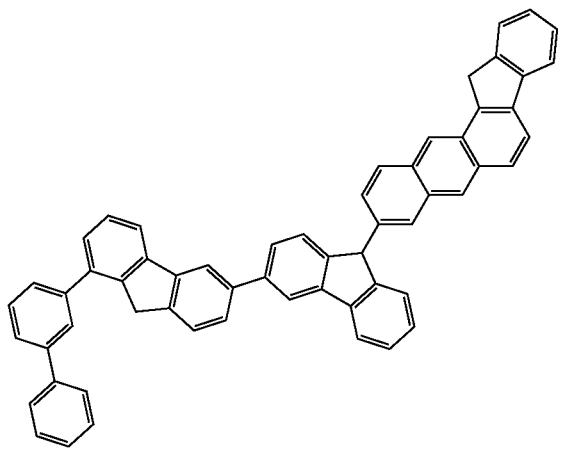

-continued
C99
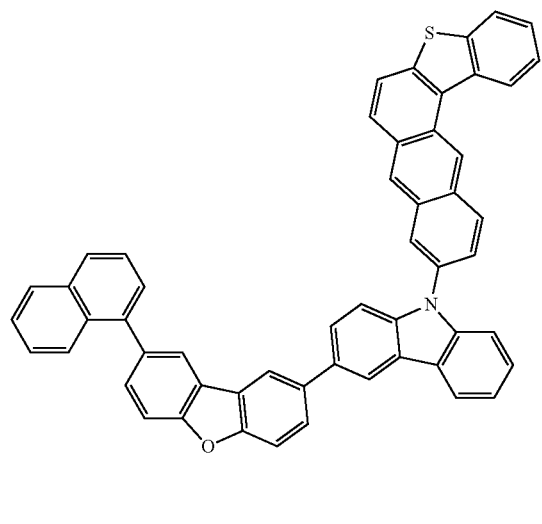
C100
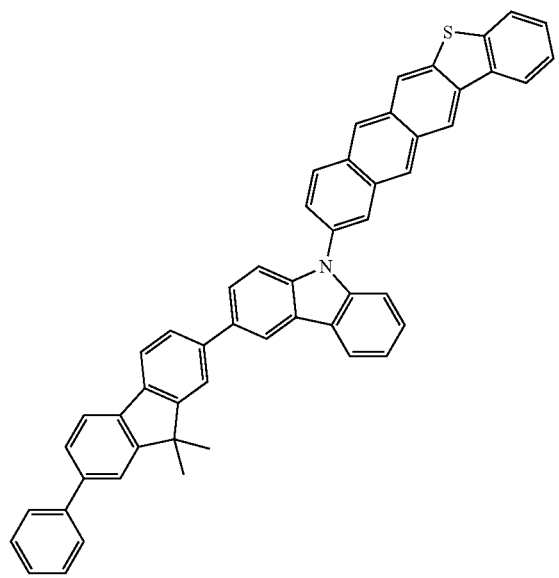
C101
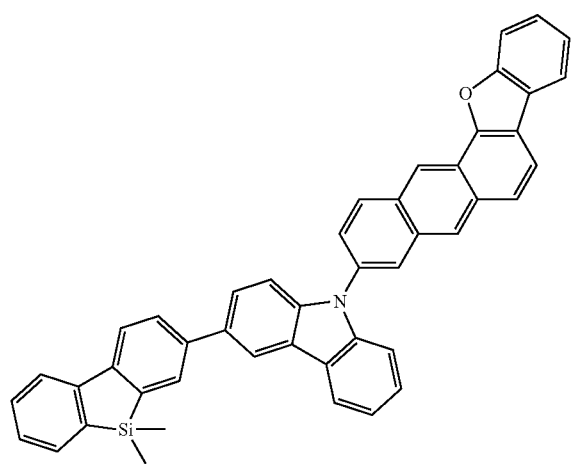
C102
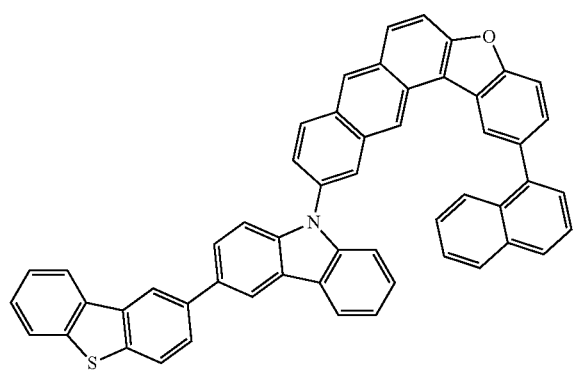

-continued
C103
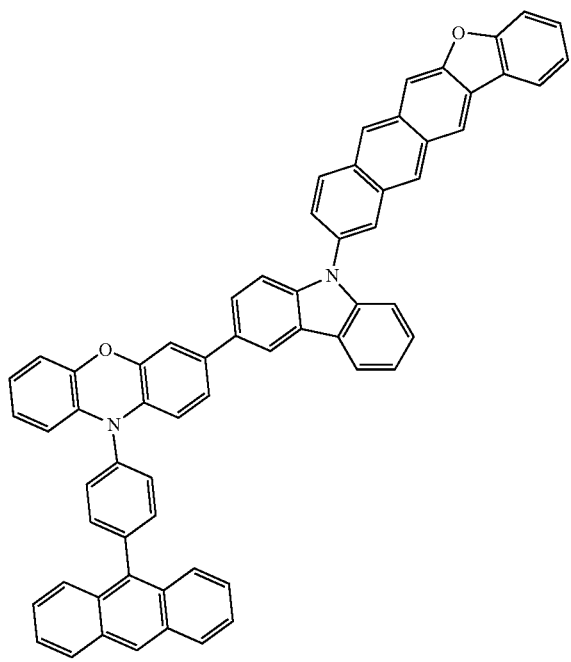
C104
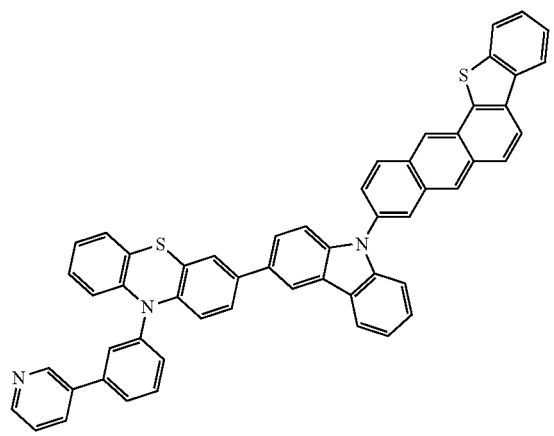
C105
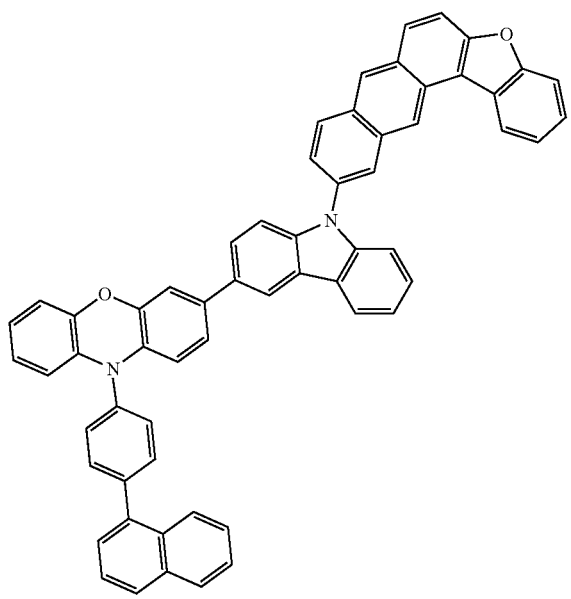
C106
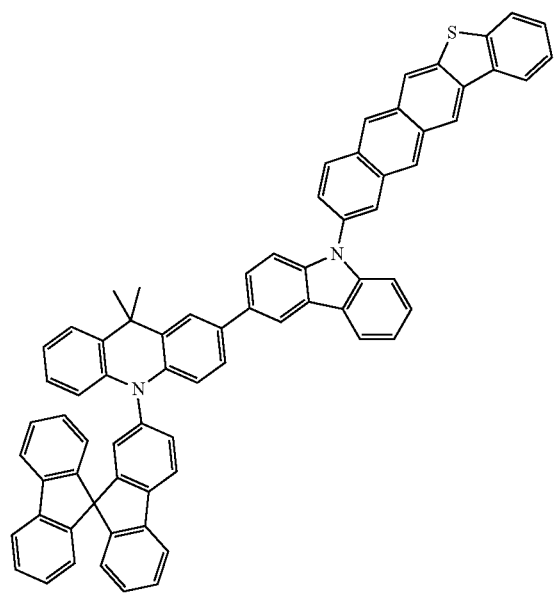

-continued
C107
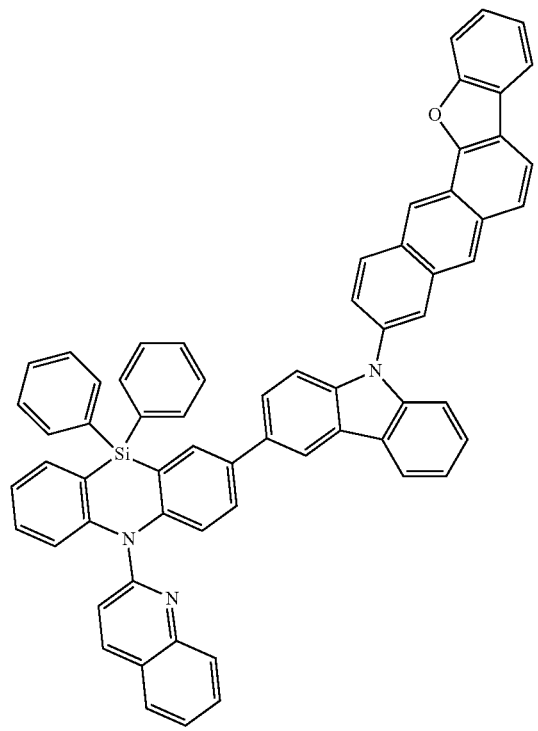
C108
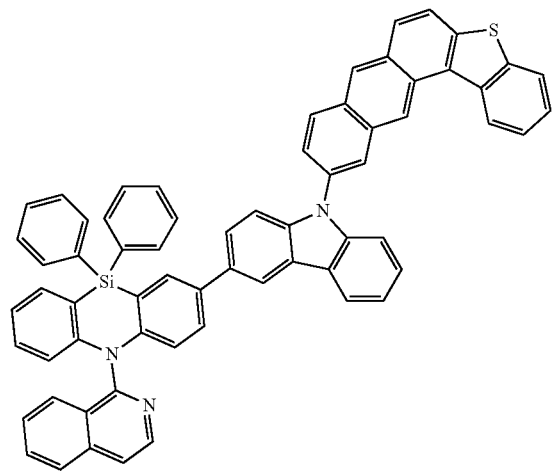
C109
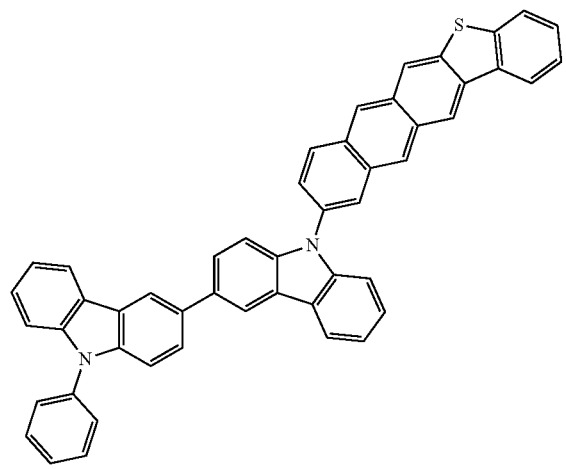
C110
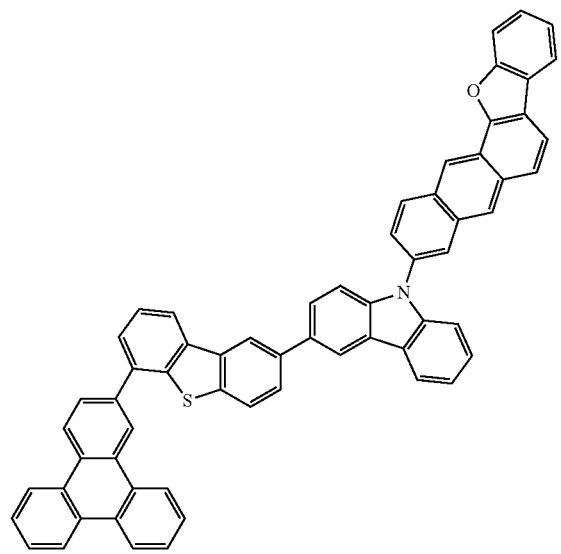

-continued
C111
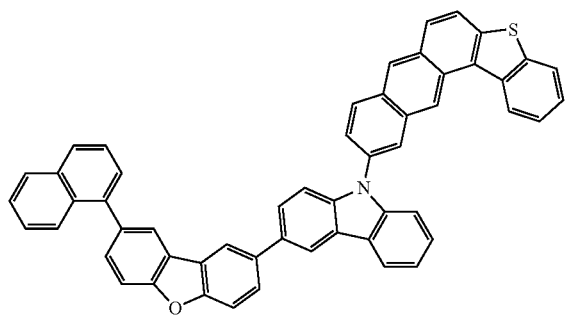
C112
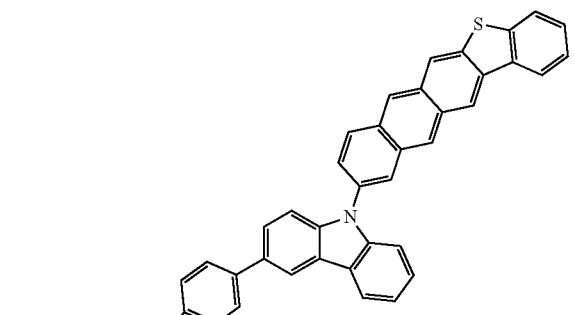
C113
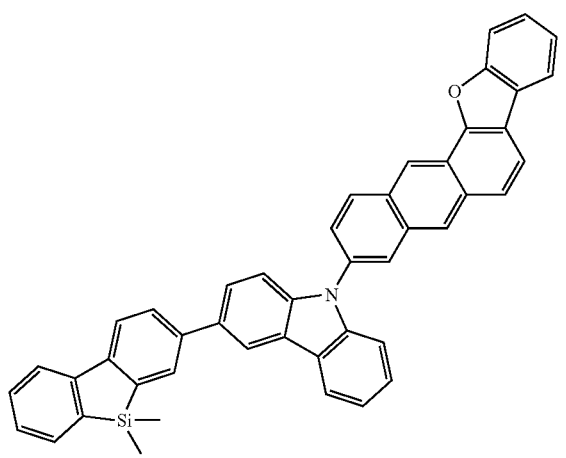
C114
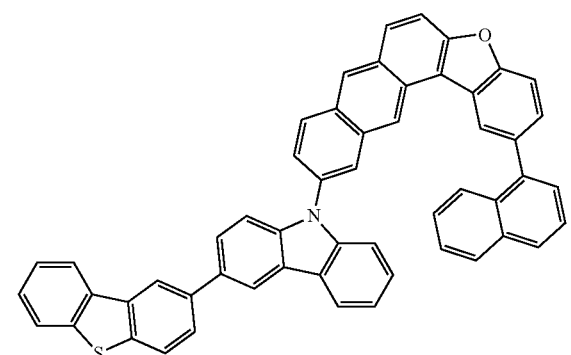
C115
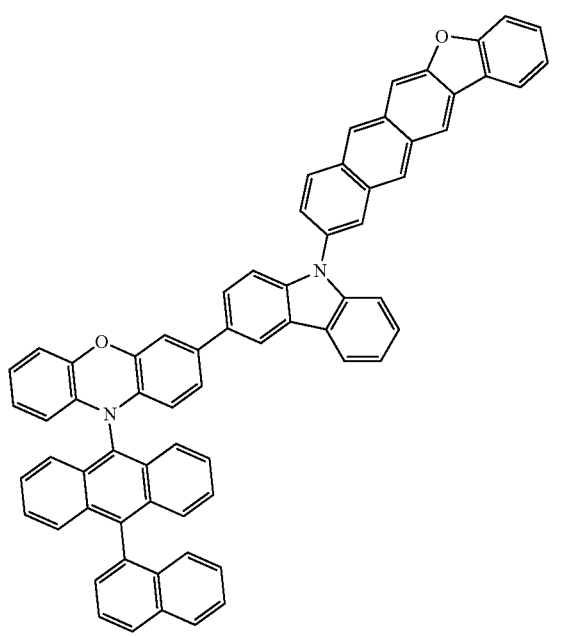
C116
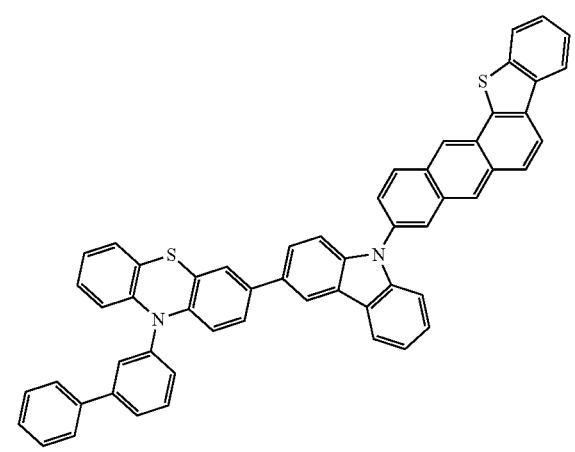

-continued
C117
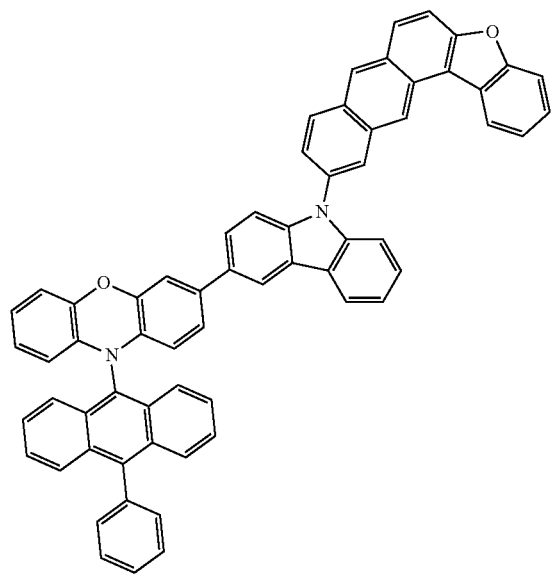
C118
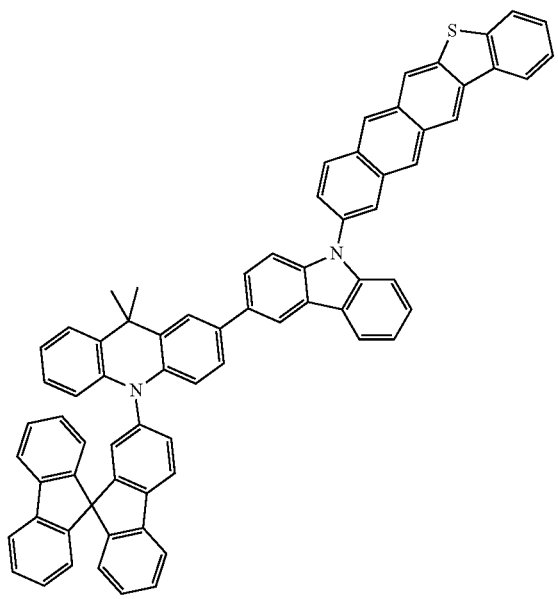
C119
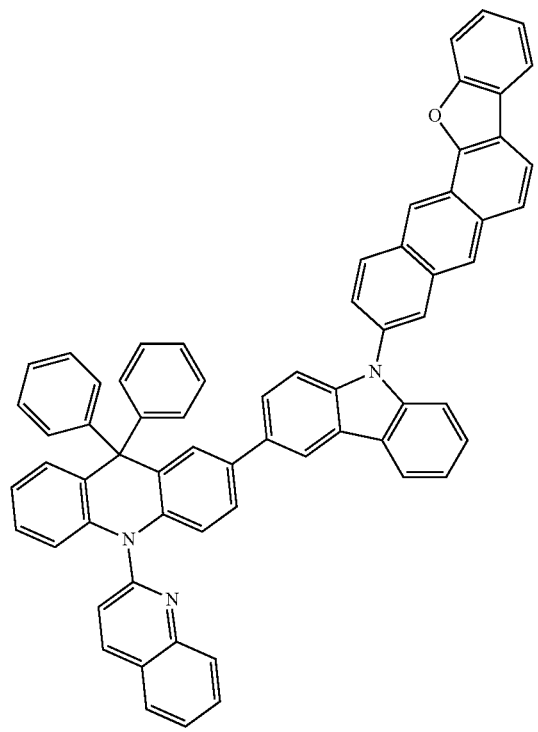
C120
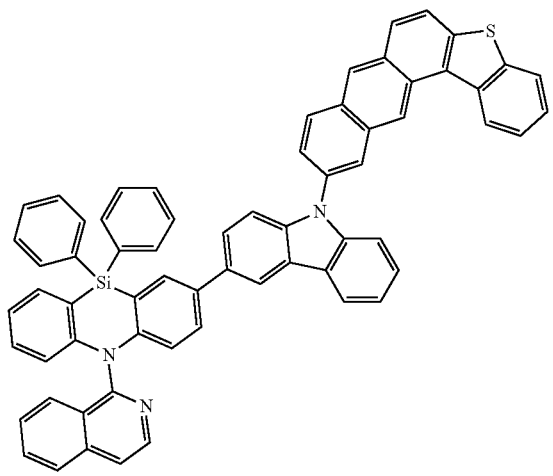

C121
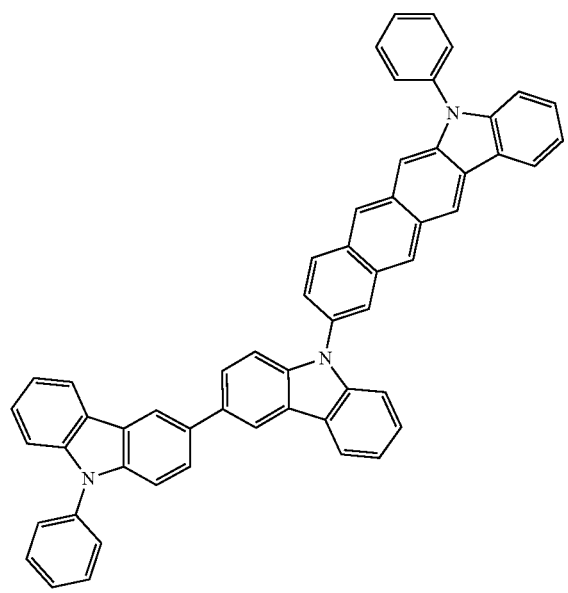
C122
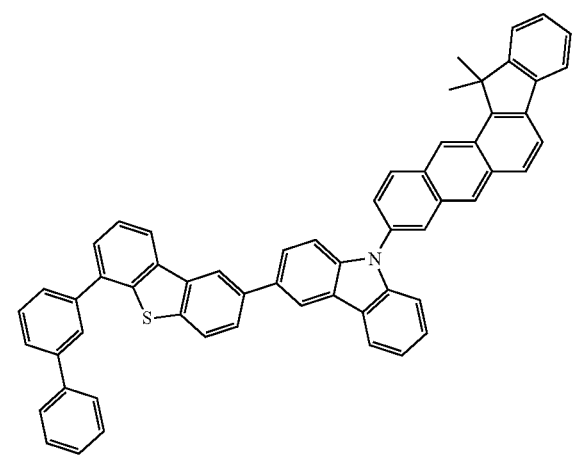
C123
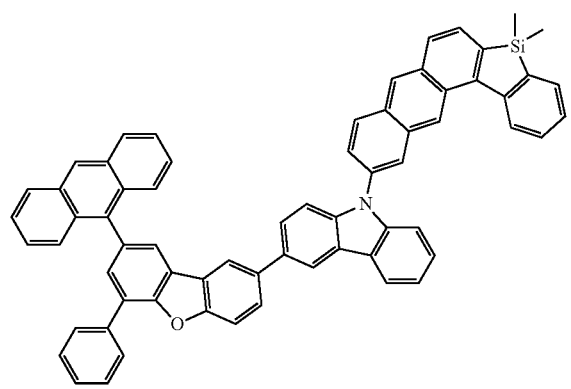
C124
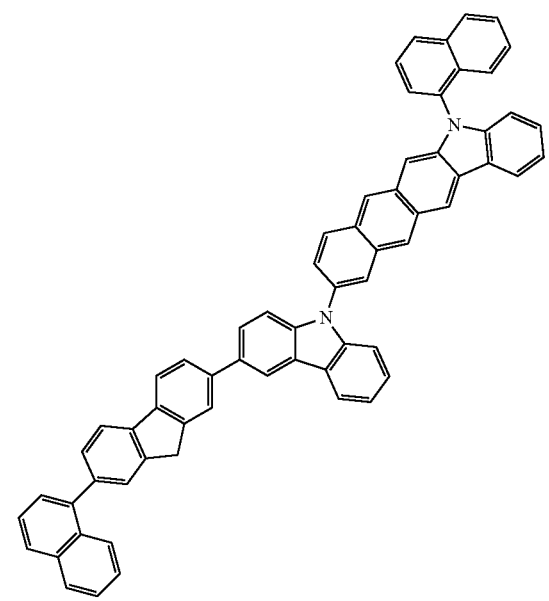

-continued
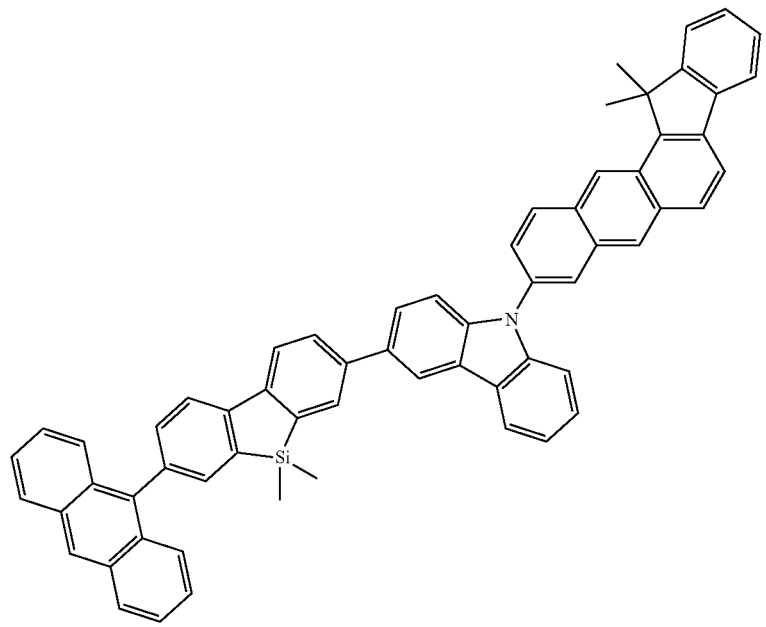
C125
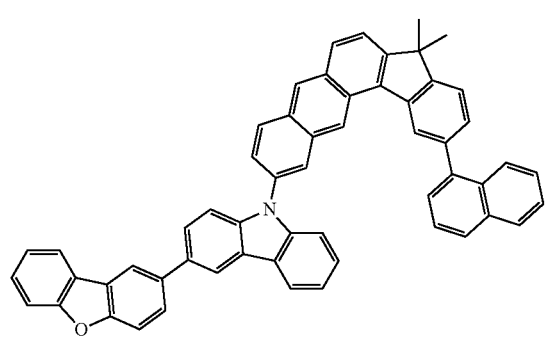
C126
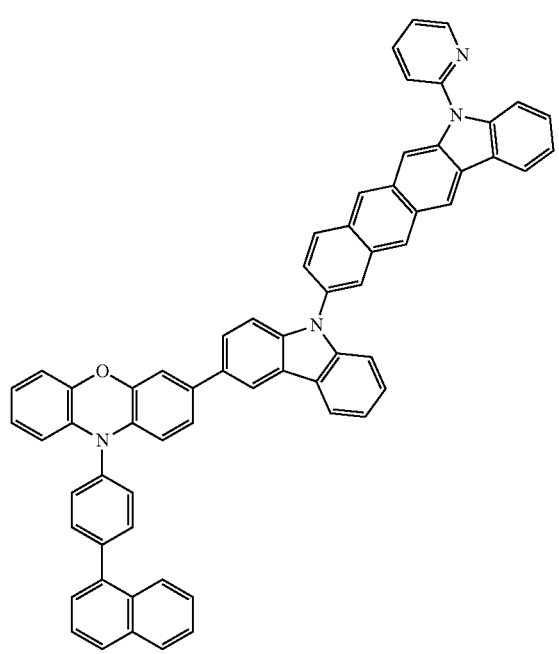
C127

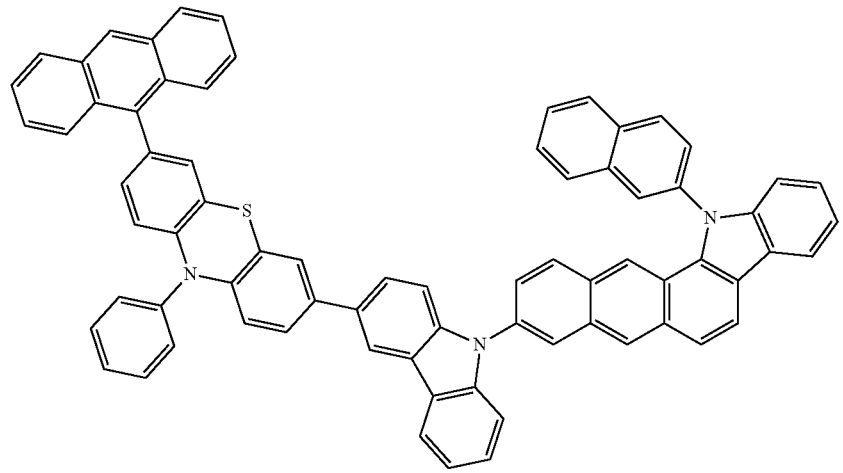
C128
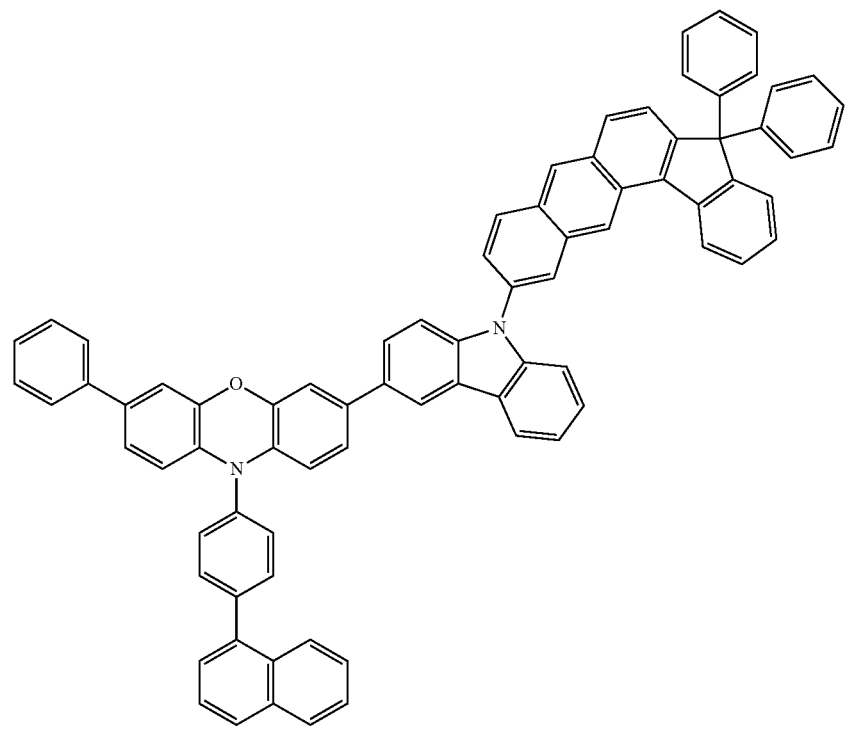
C129

-continued
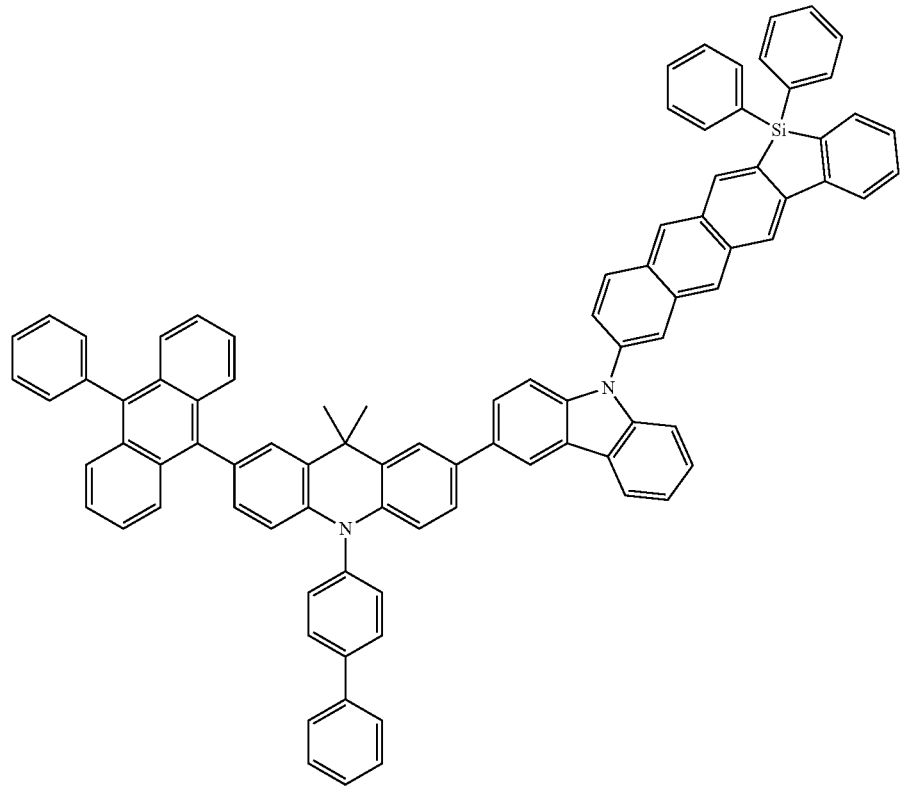
C130
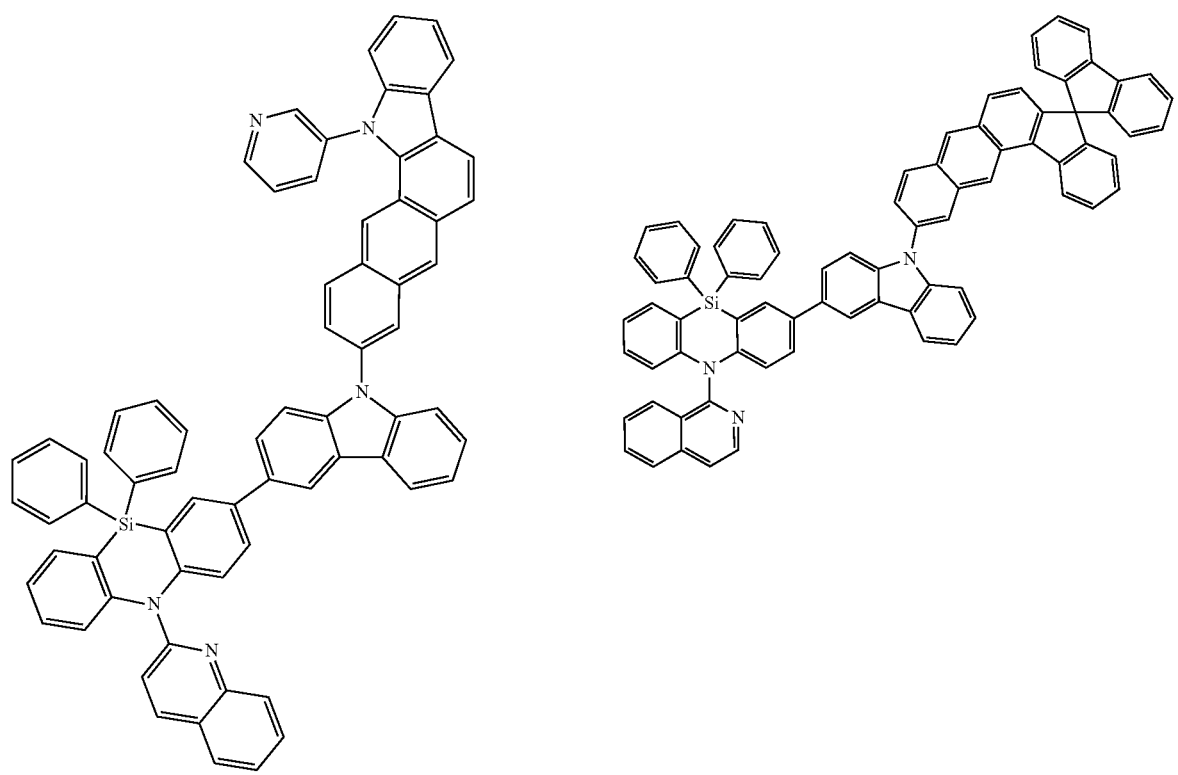
C131
C132

-continued
C133
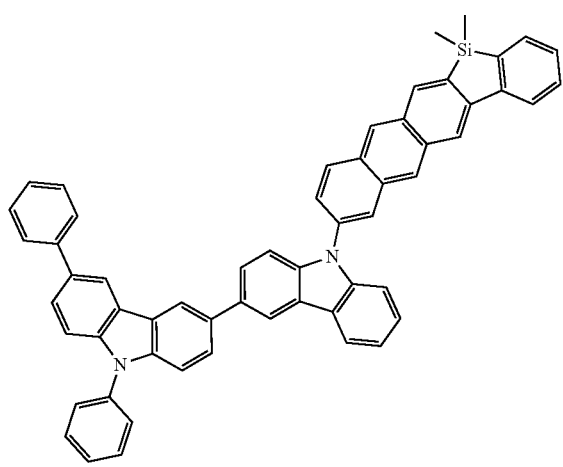
C134
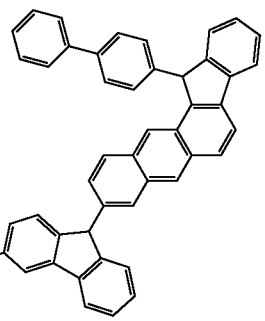
C135
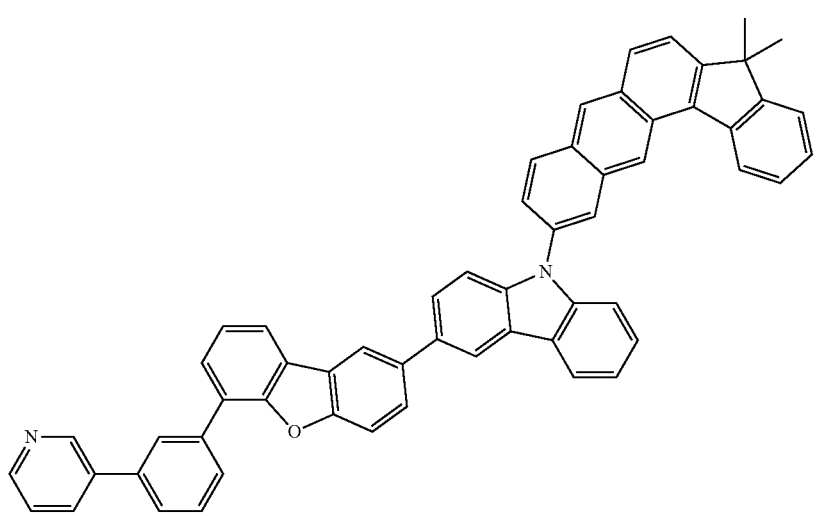
C136
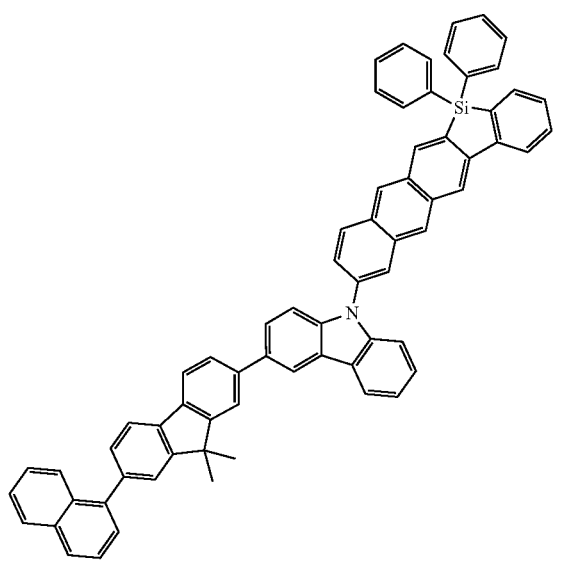
C137
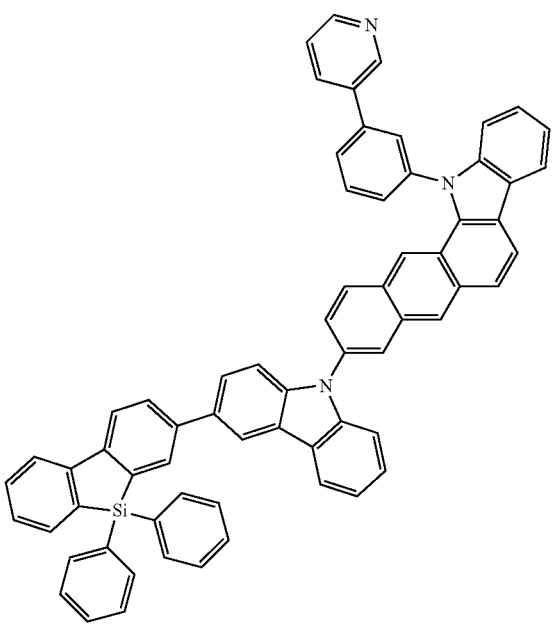

-continued
C138
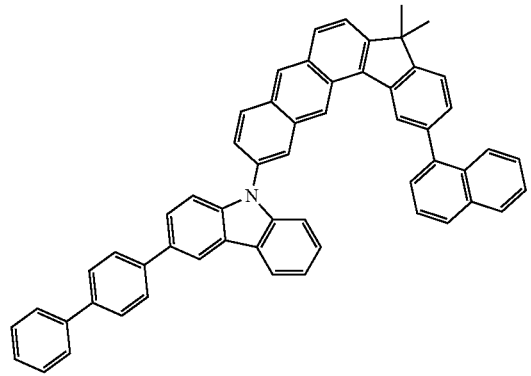
C139
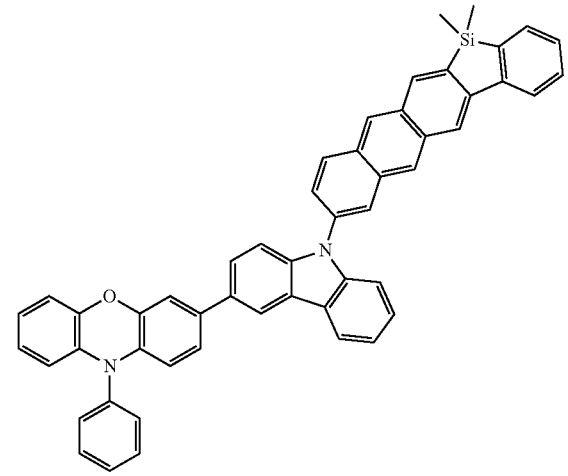
C140
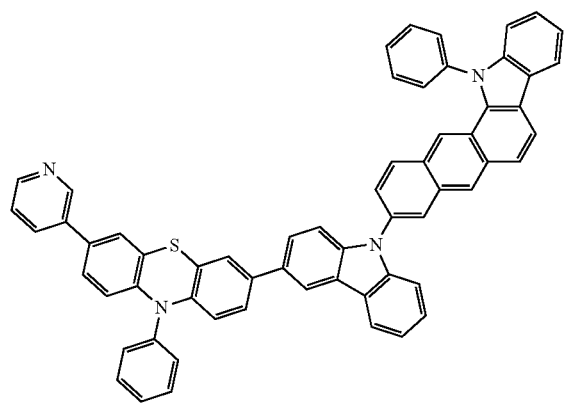
C141
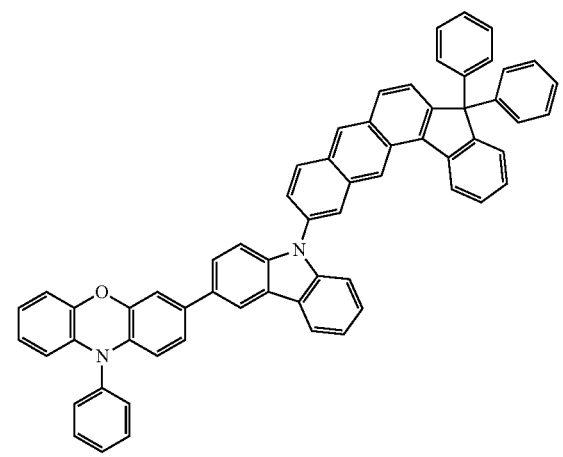
C142
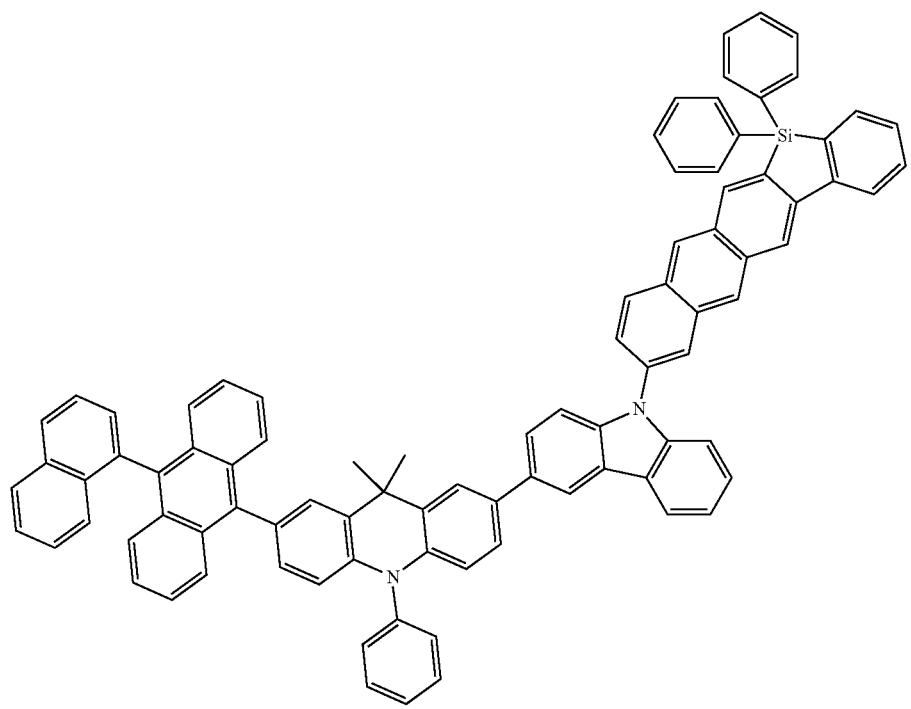

C143
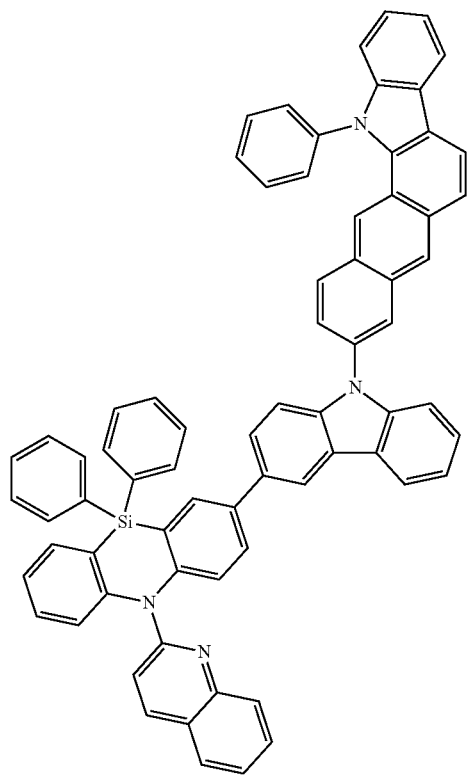
C144
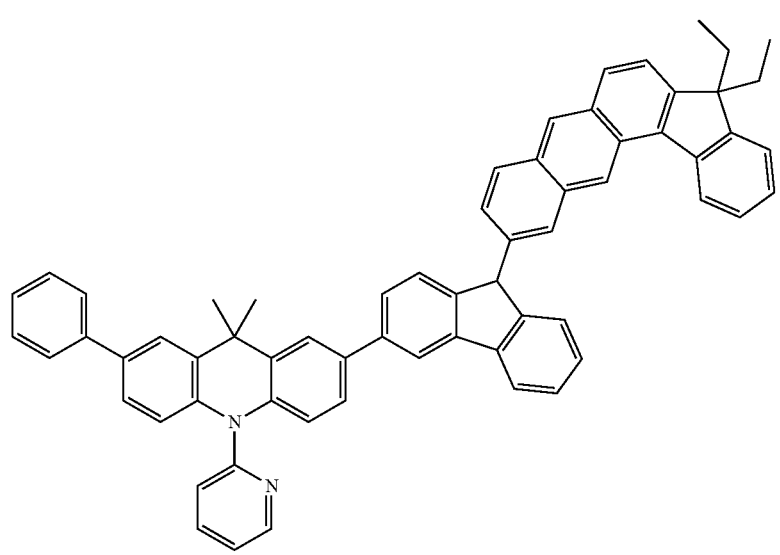

-continued
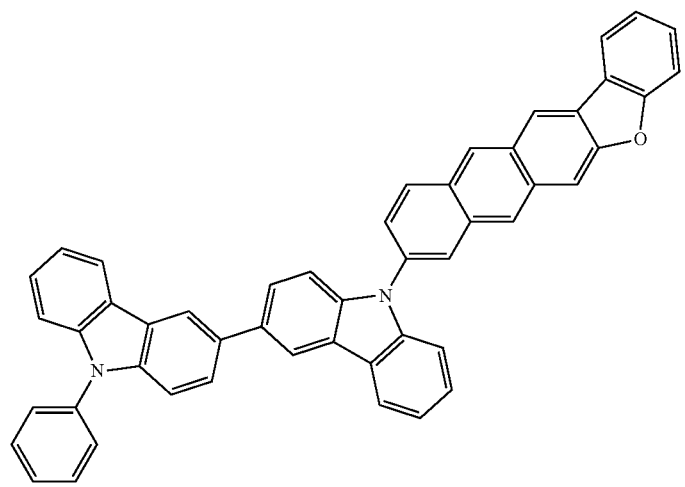
C145
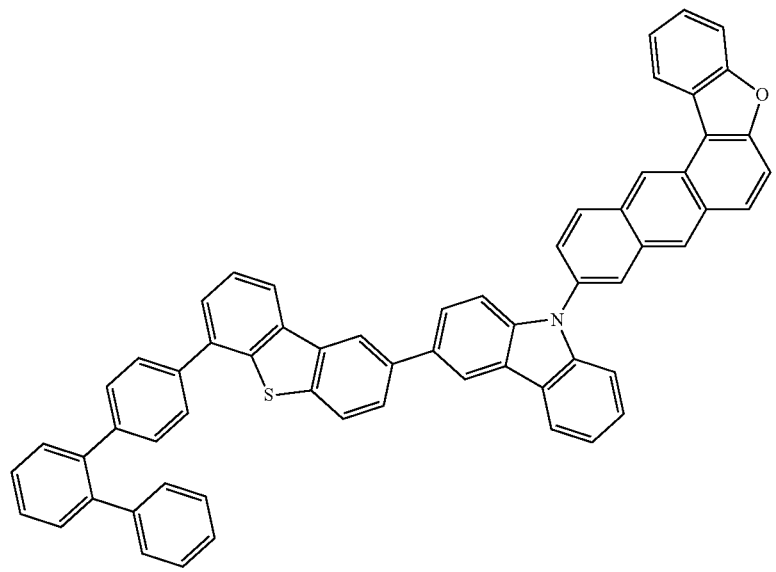
C146
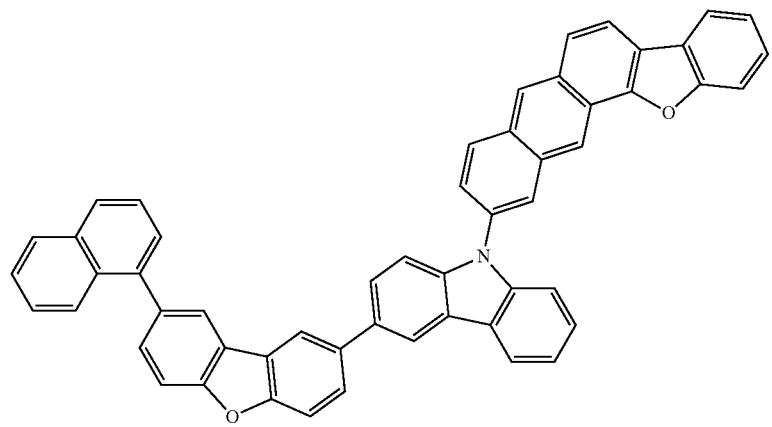
C147

-continued
C148
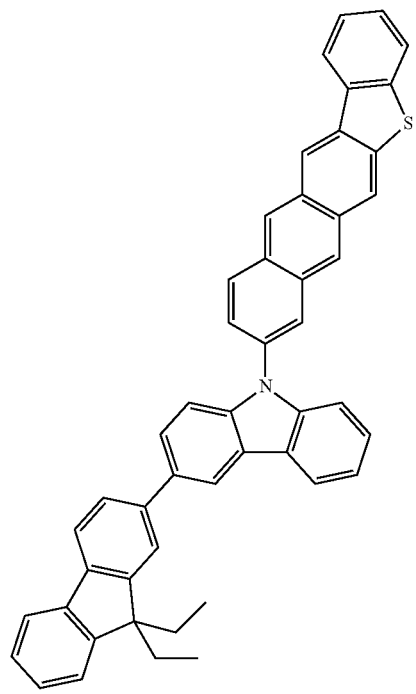
C149
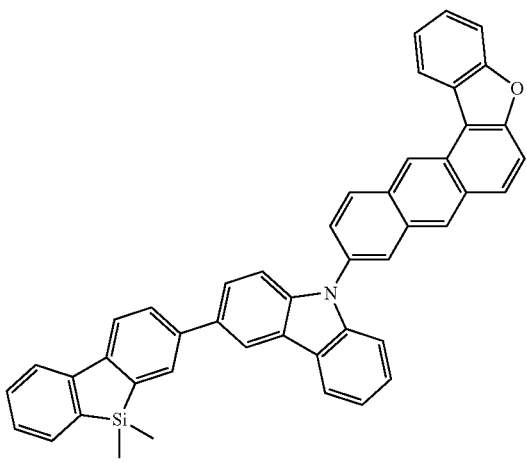
C150
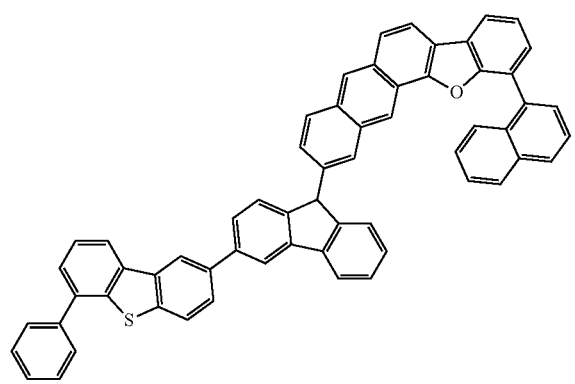
C151
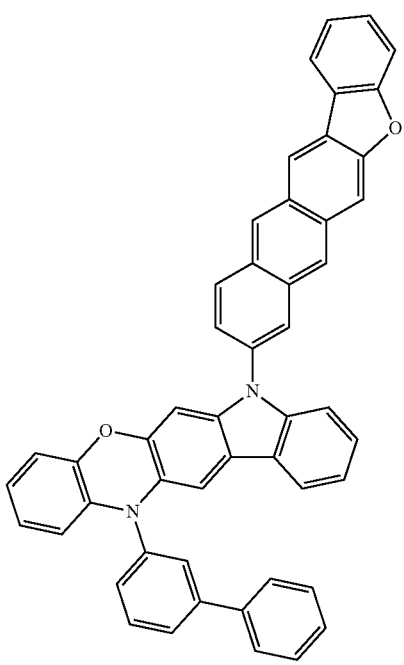

-continued
C152
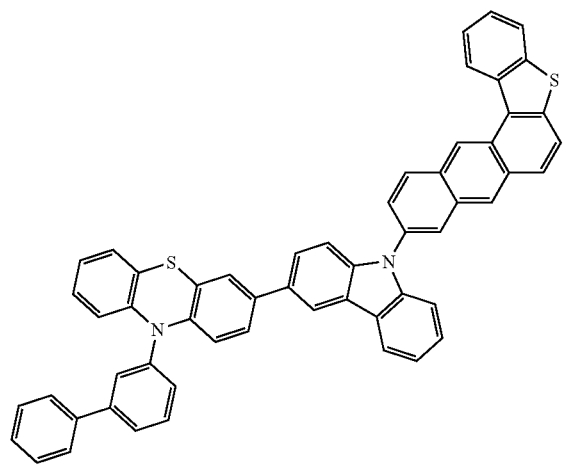
C153
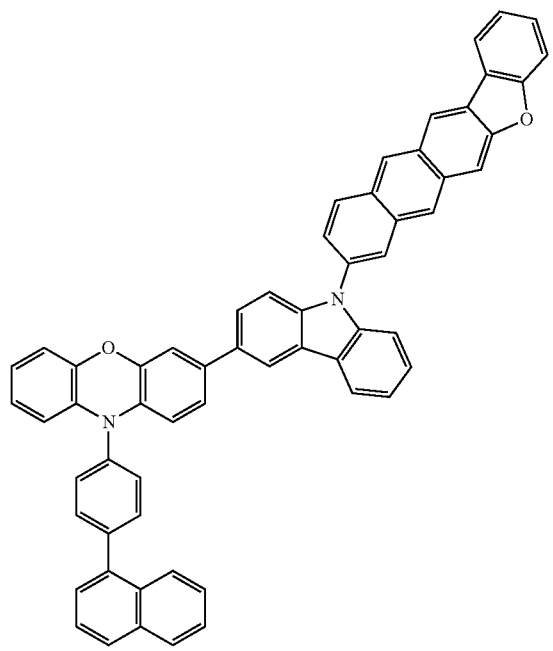
C154
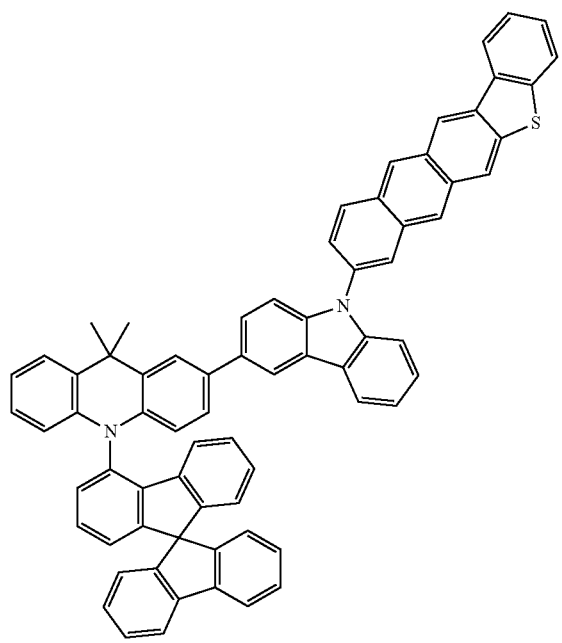
C155
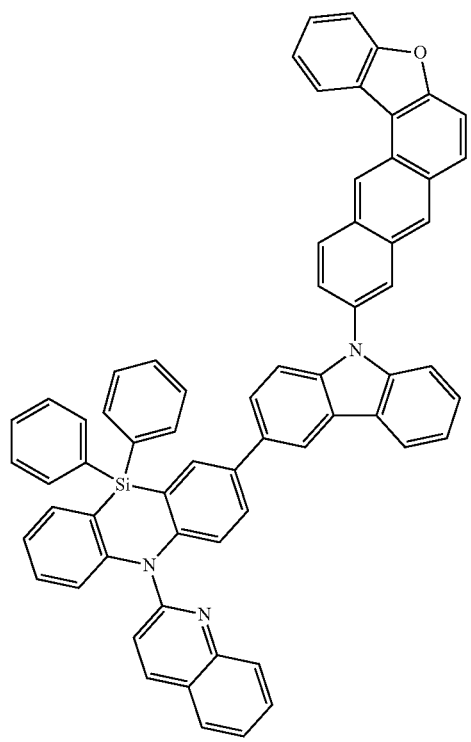

-continued
C156
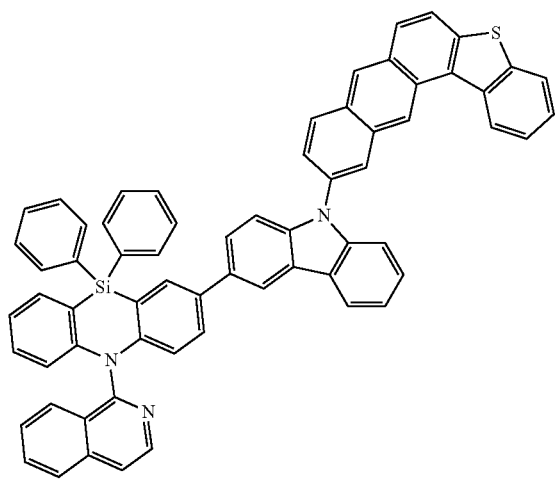
C157
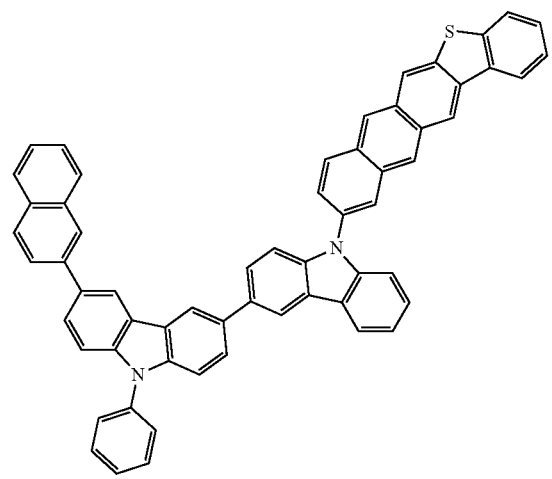
C158
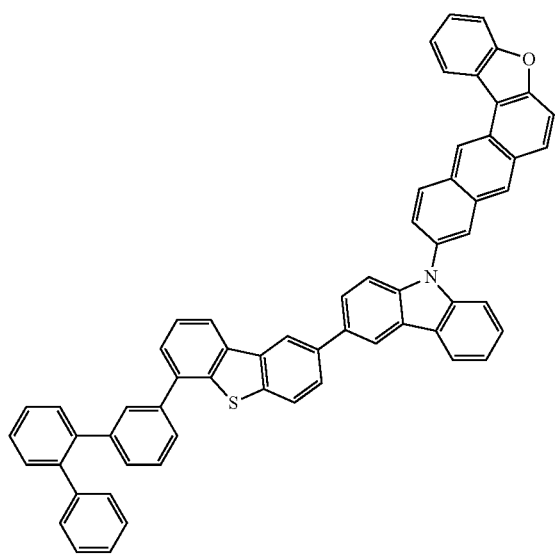
C159
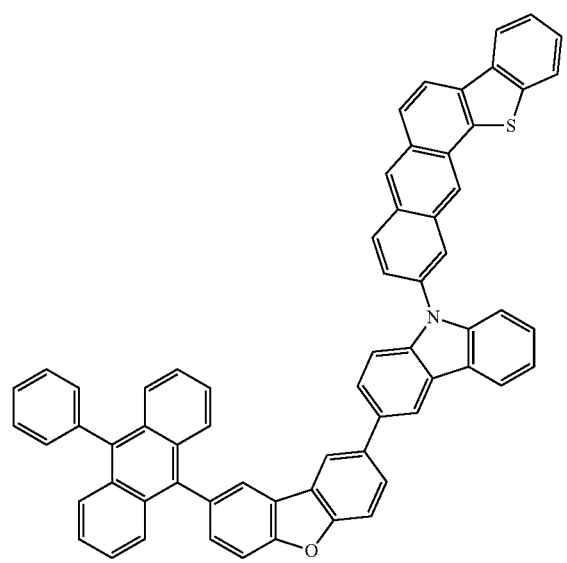

-continued
C160
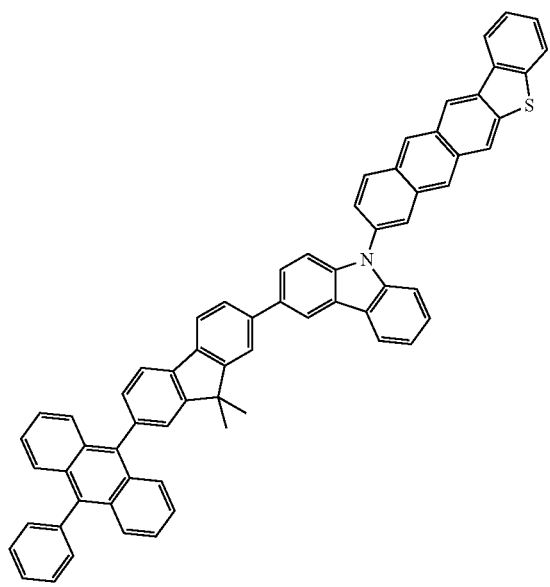
C161
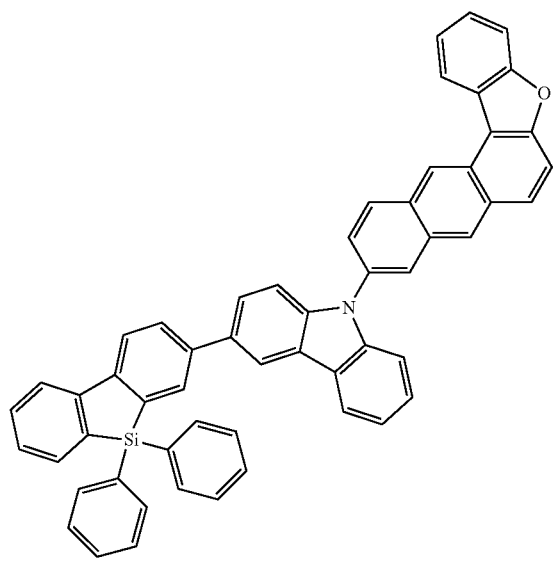
C162
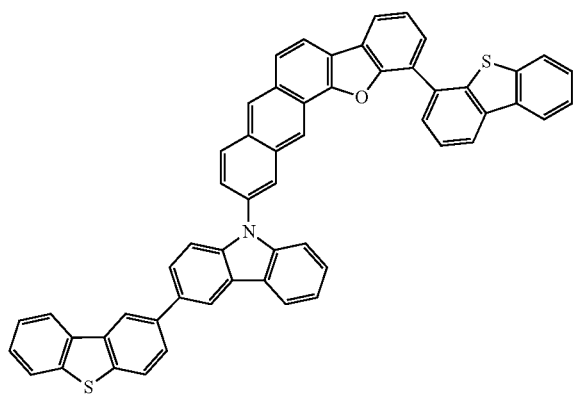
C163
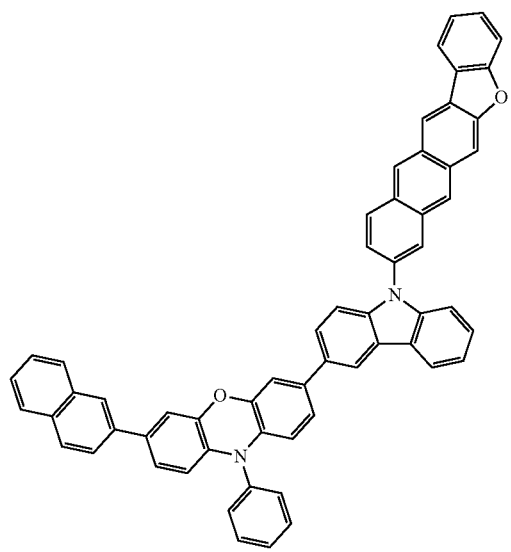

-continued
C164
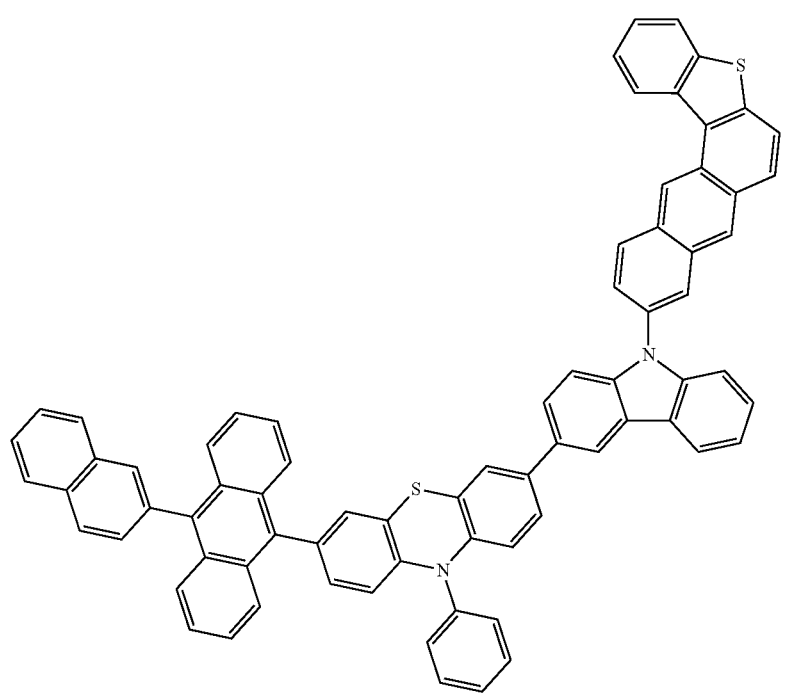
C165
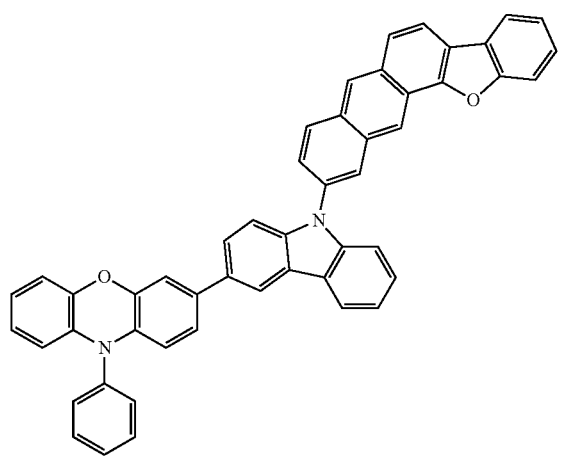
C166
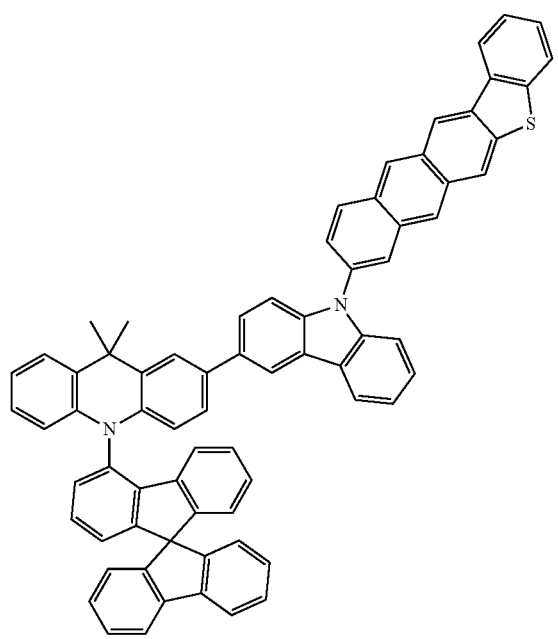

-continued
C167
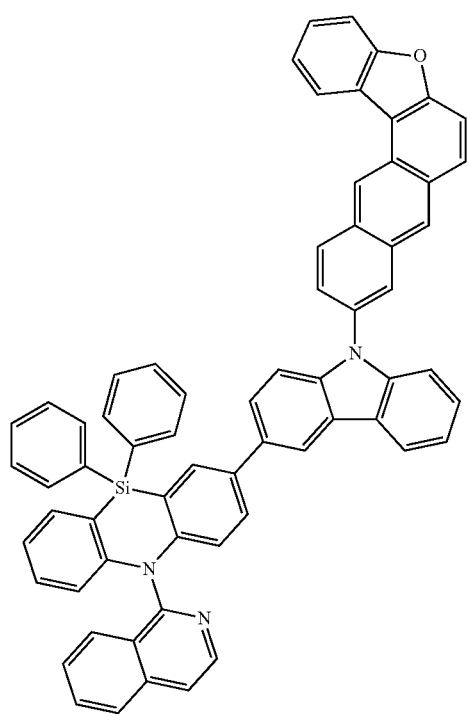
C168
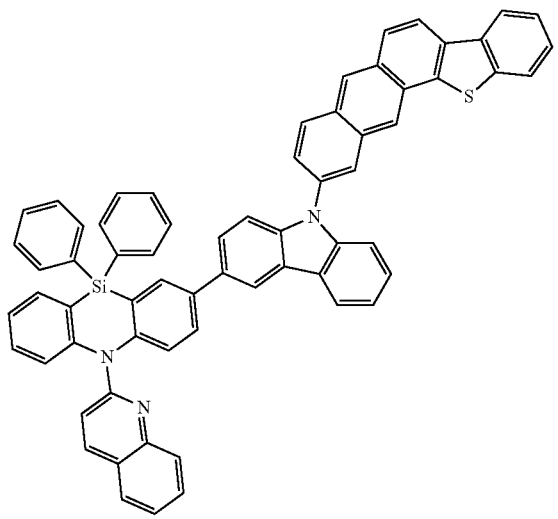
C169
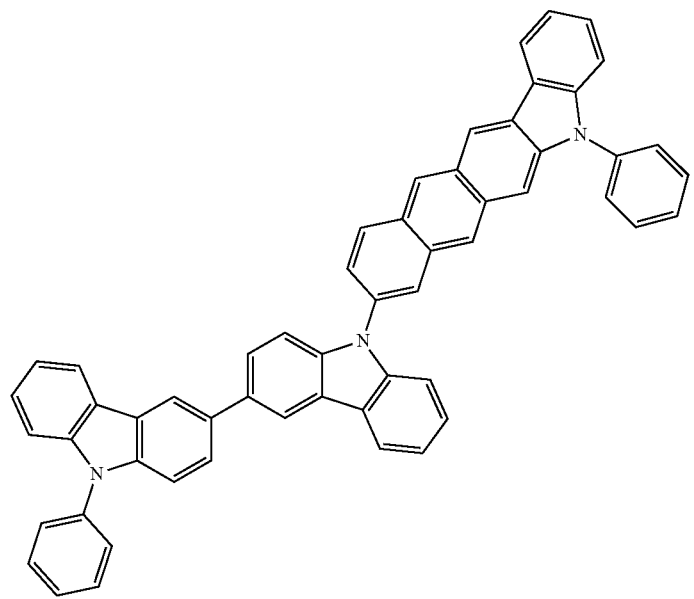

-continued
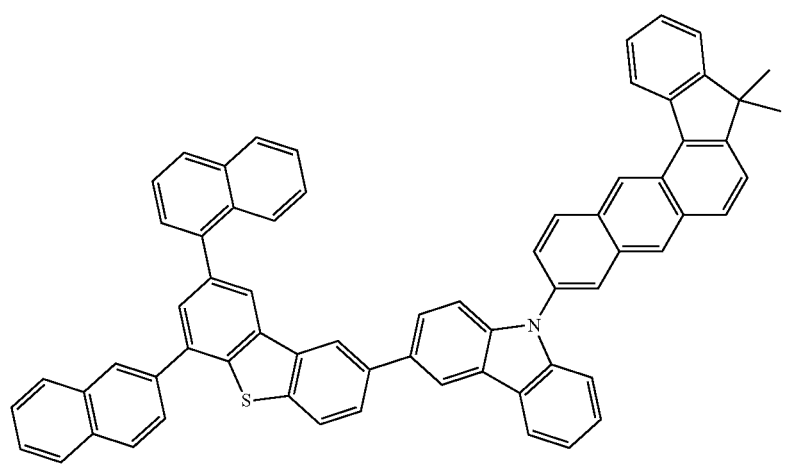
C170
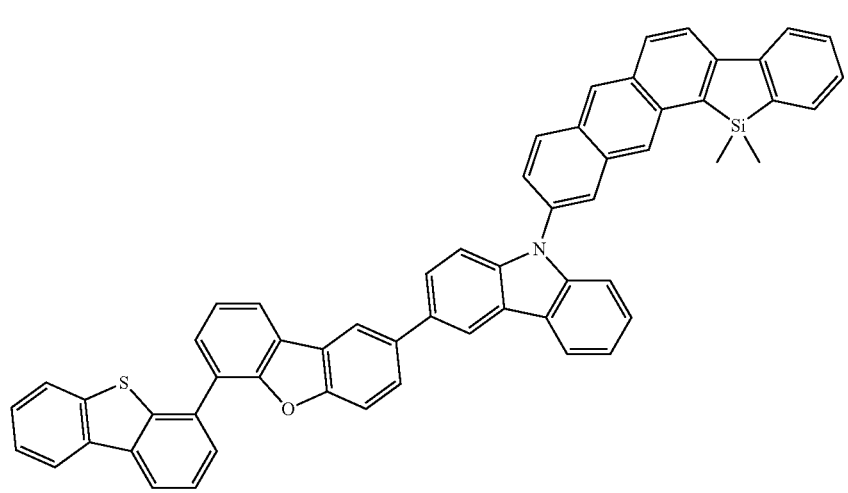
C171
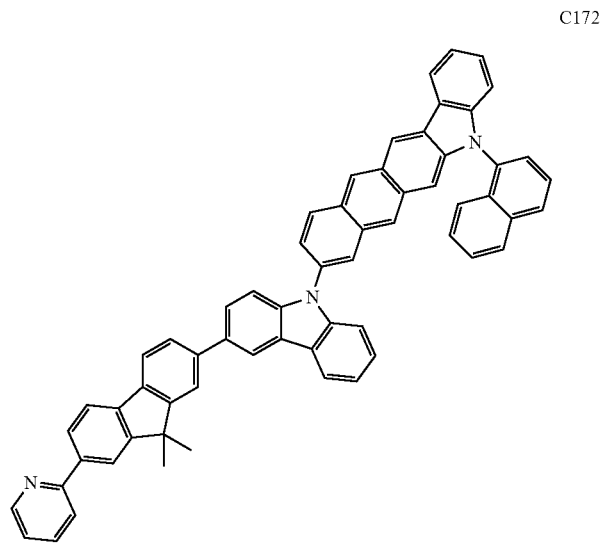
C172
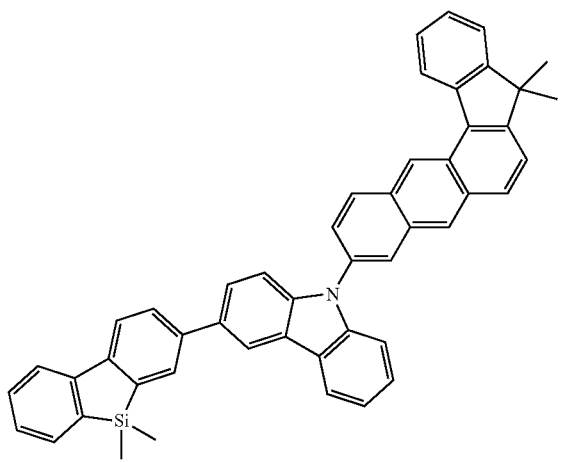
C173

-continued
C174
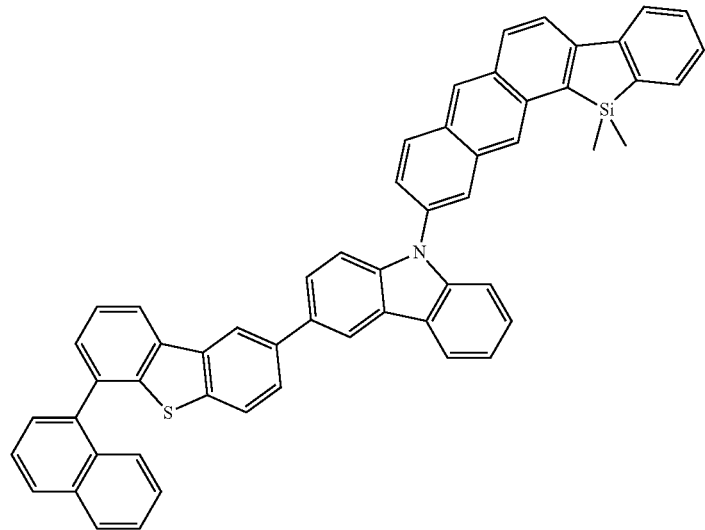
C175
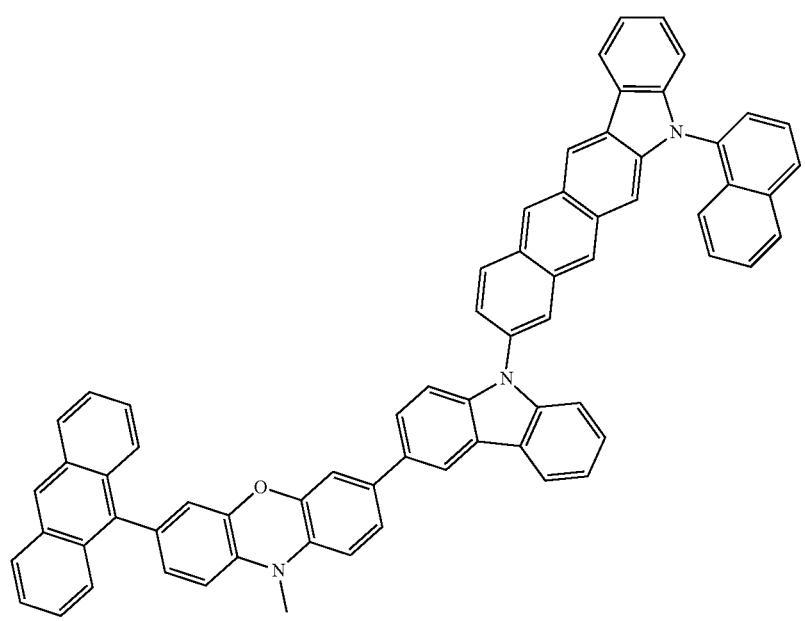

-continued
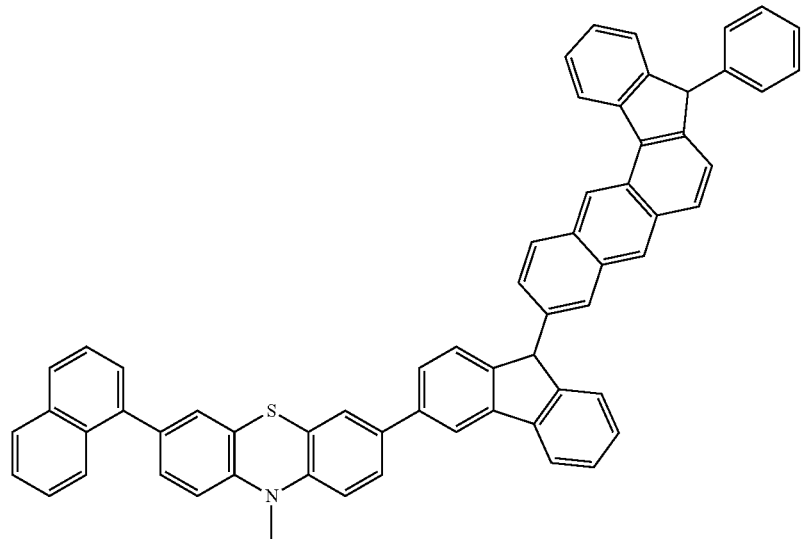
C176
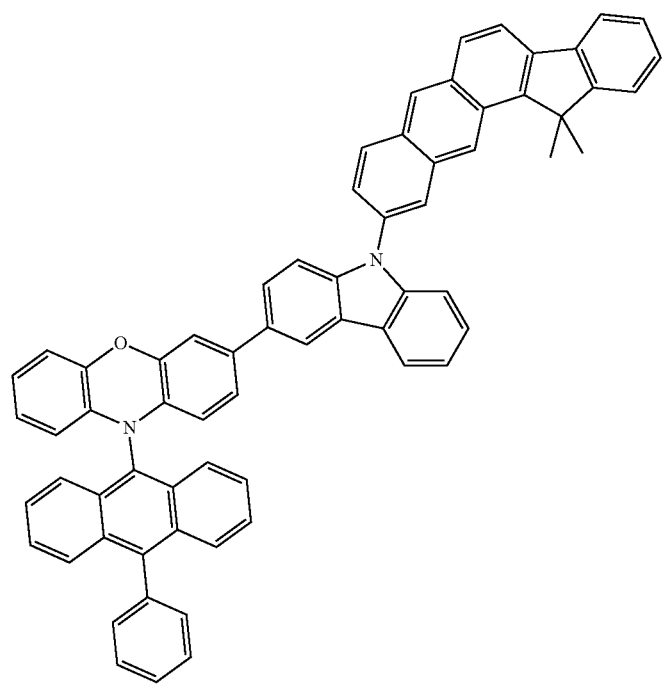
C177

-continued
C178
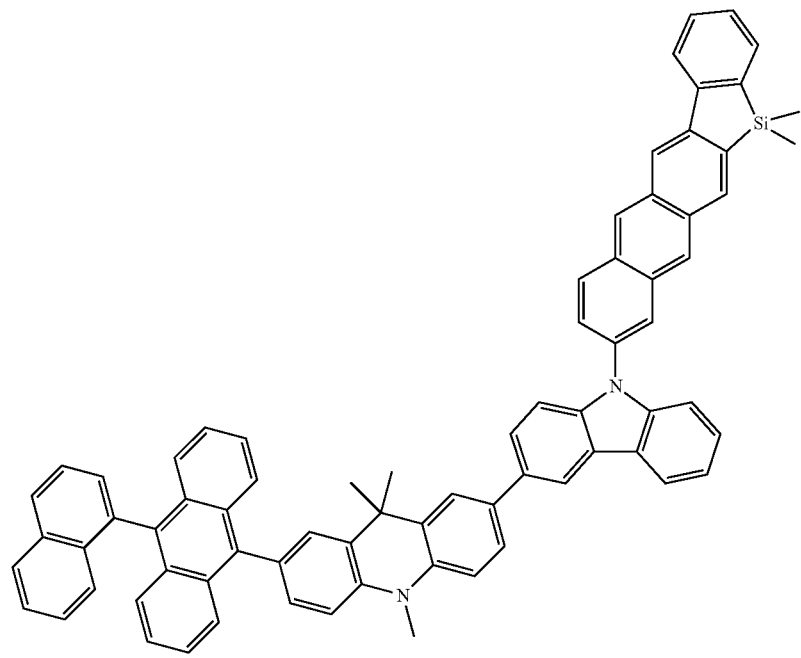
C179
C180
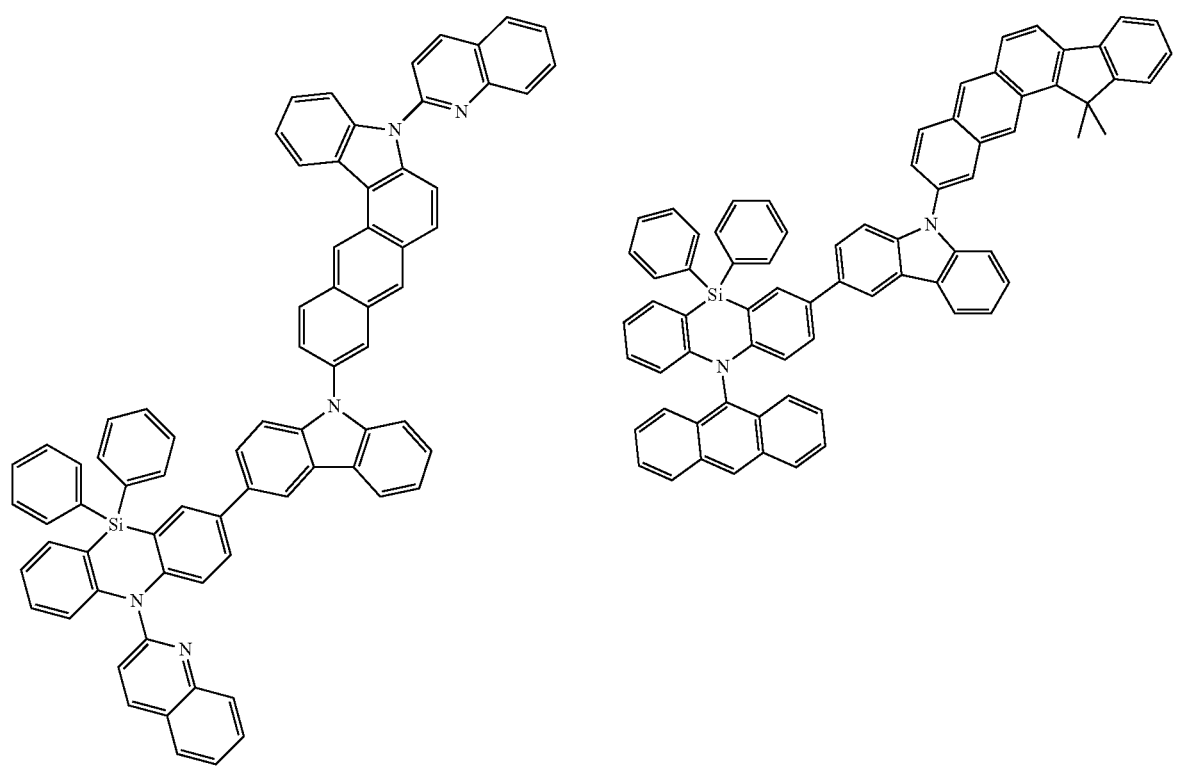

-continued
C181
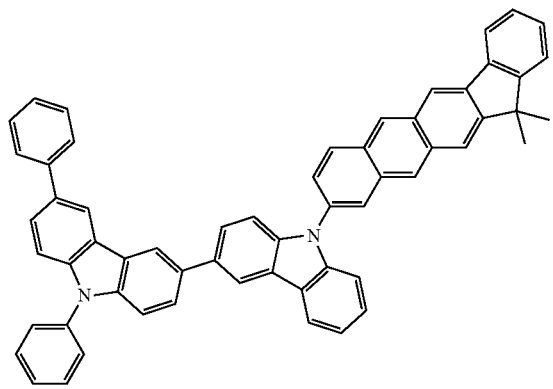
C182
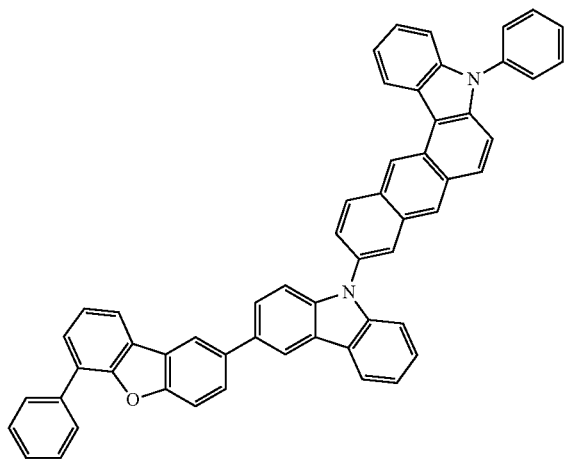
C183
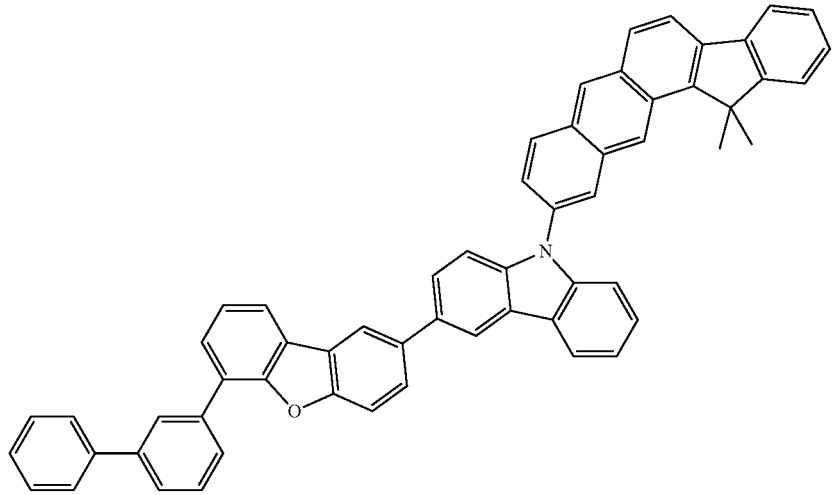
C184
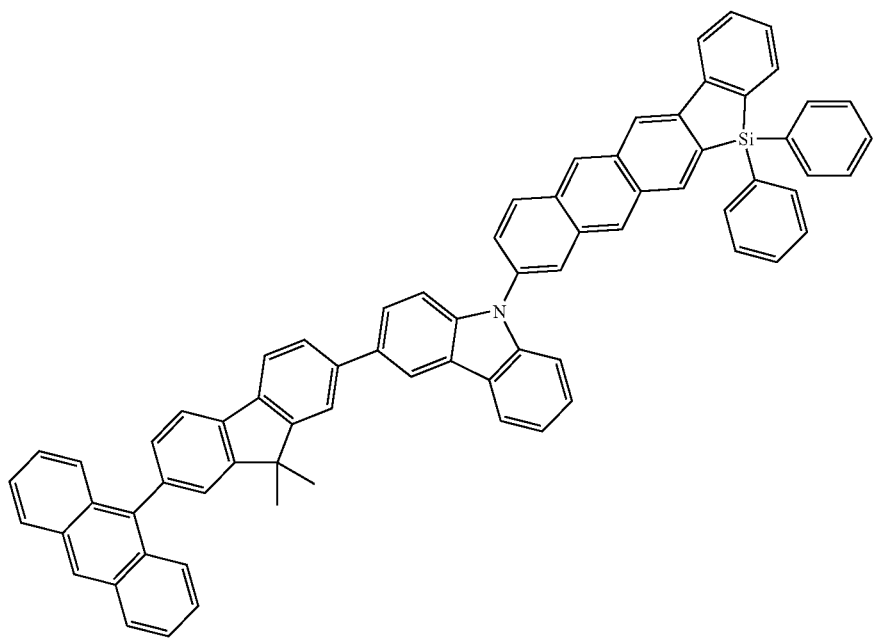

-continued
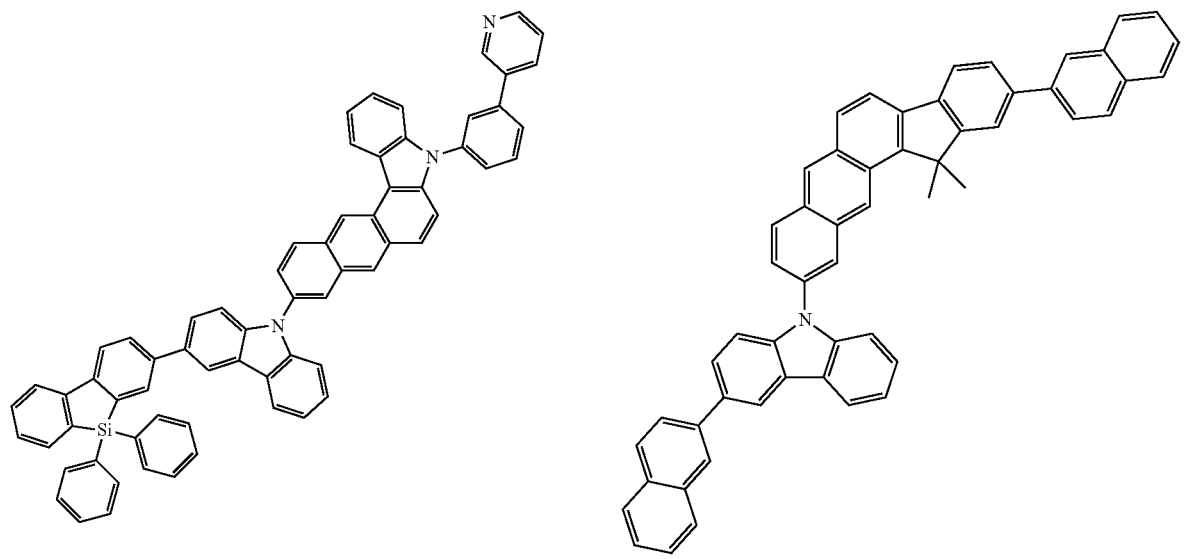
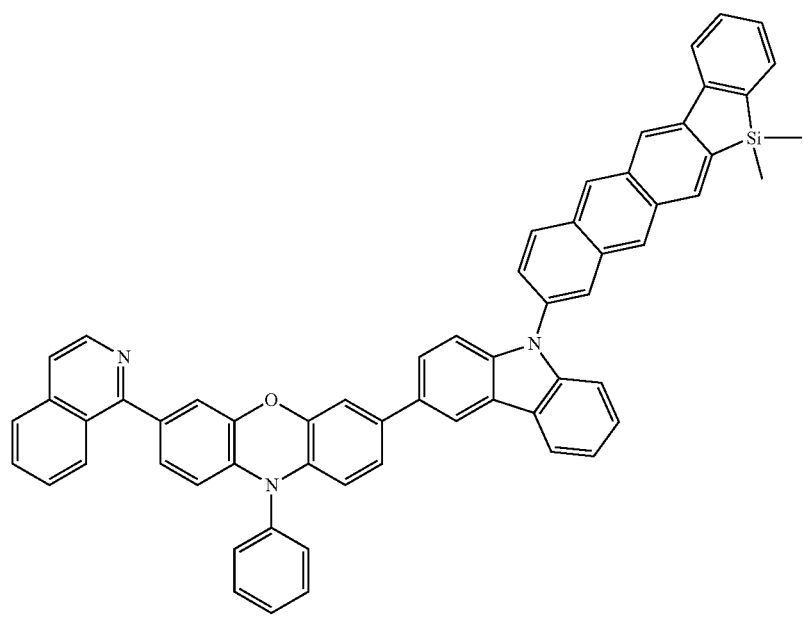

-continued
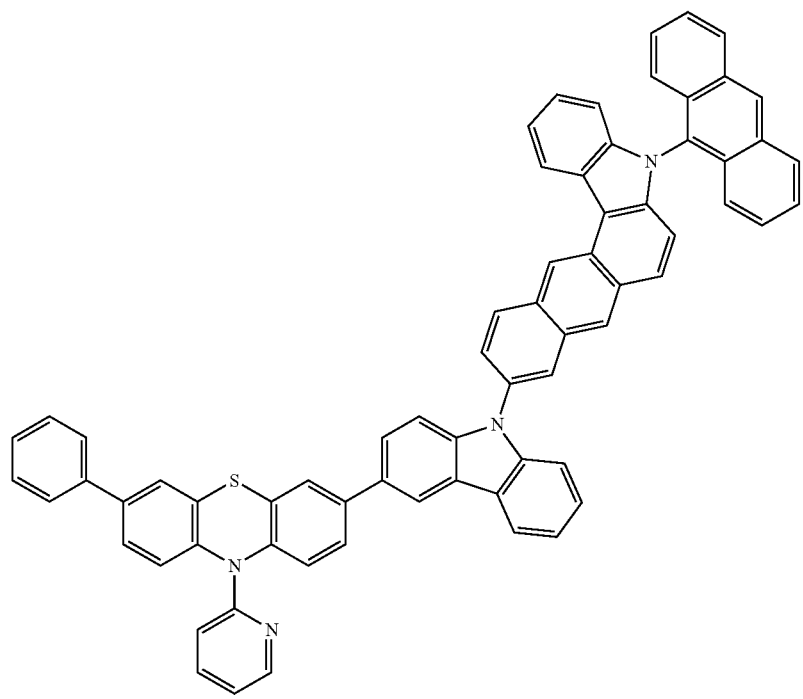
C188
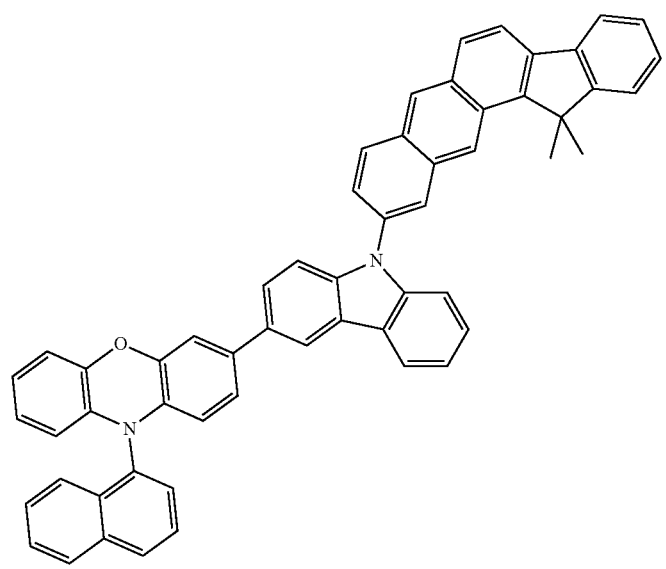
C189

C190
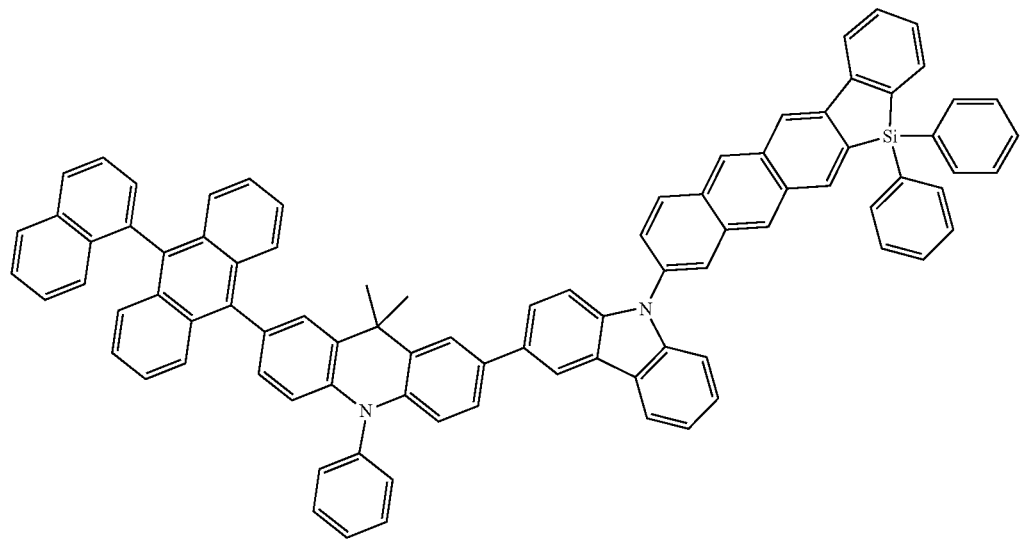
C191
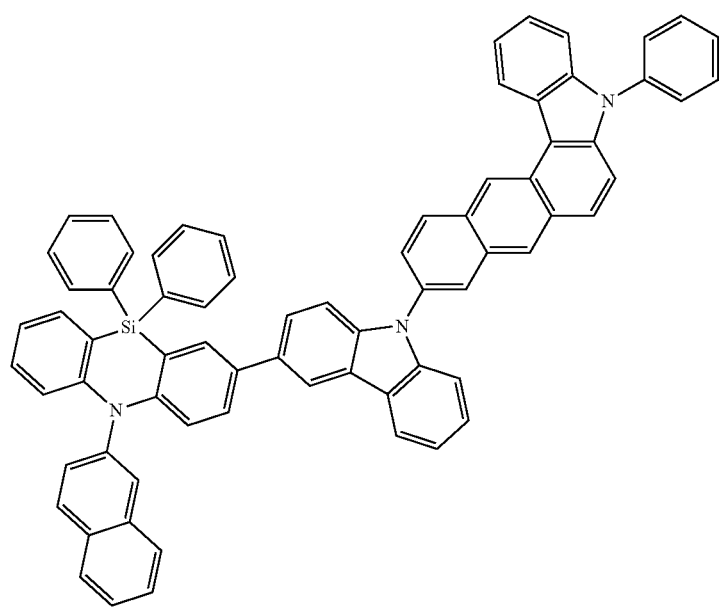
C192
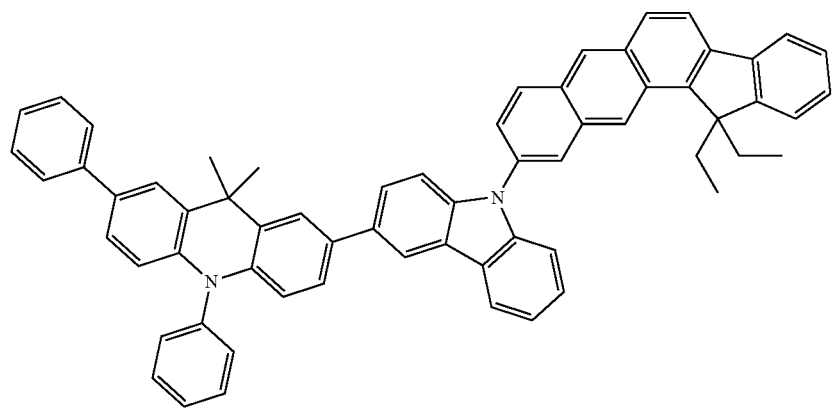

-continued
C193
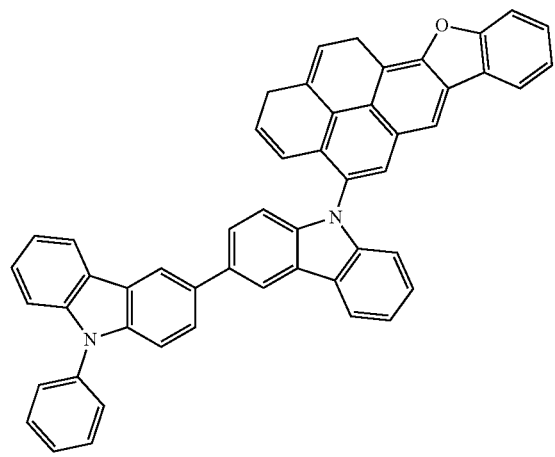
C194
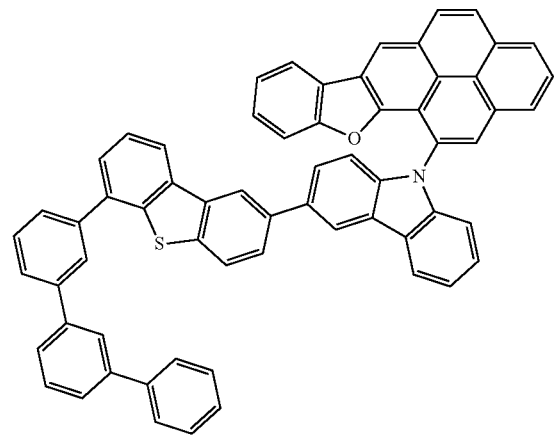
C195
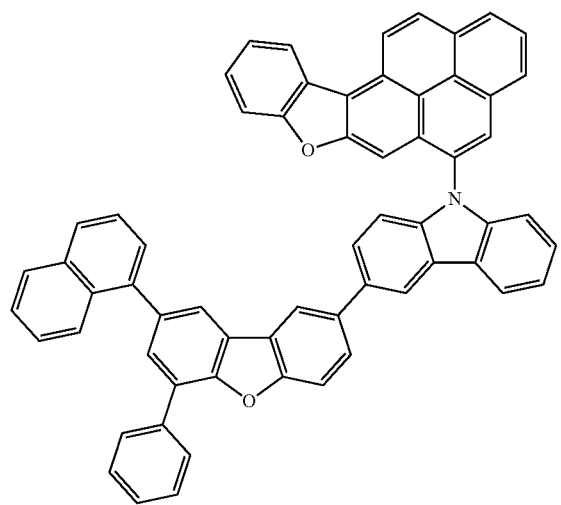
C196
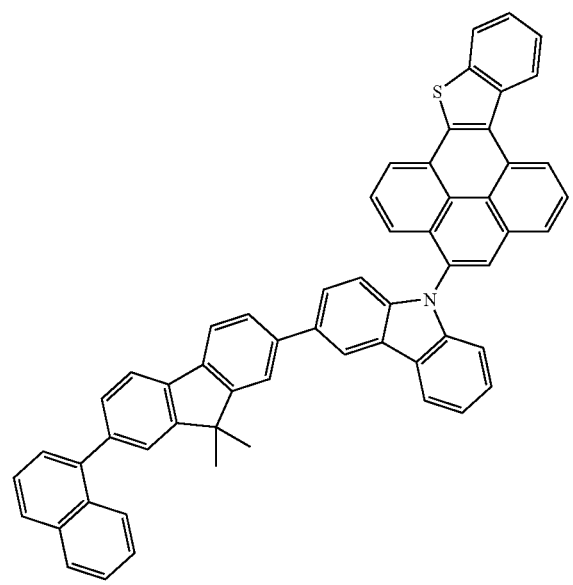
C197
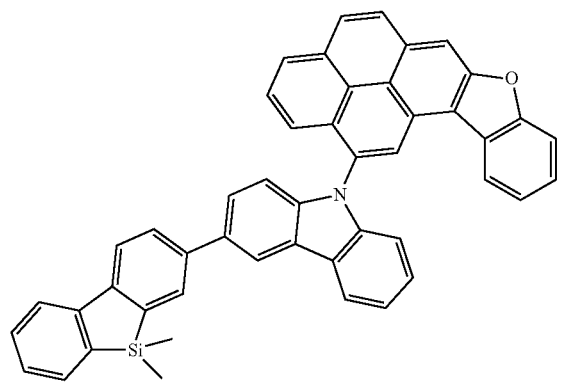
C198
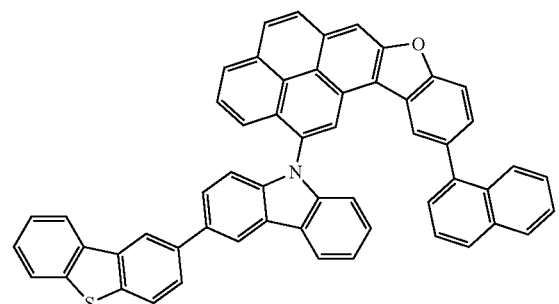

-continued
C199
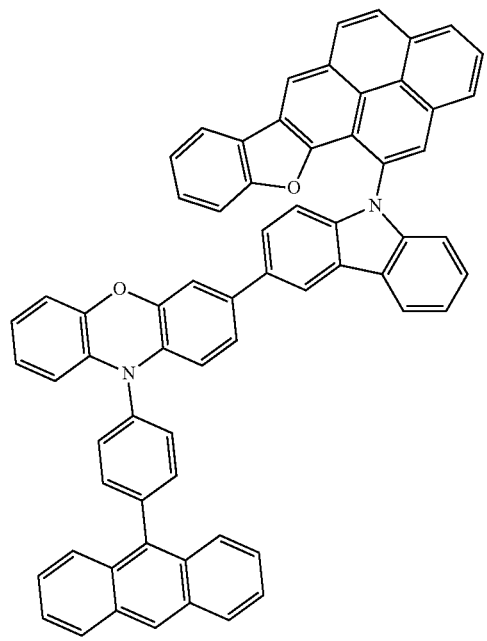
C200
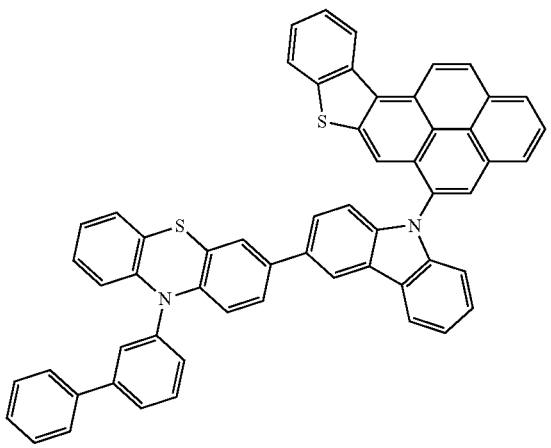
C201
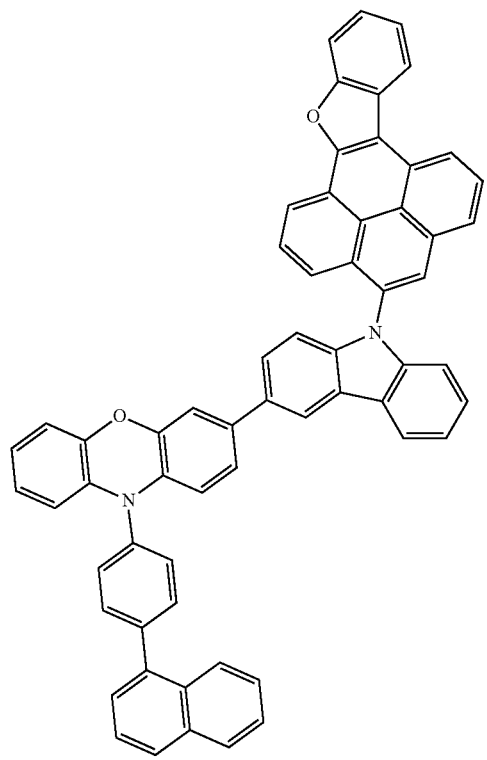
C202
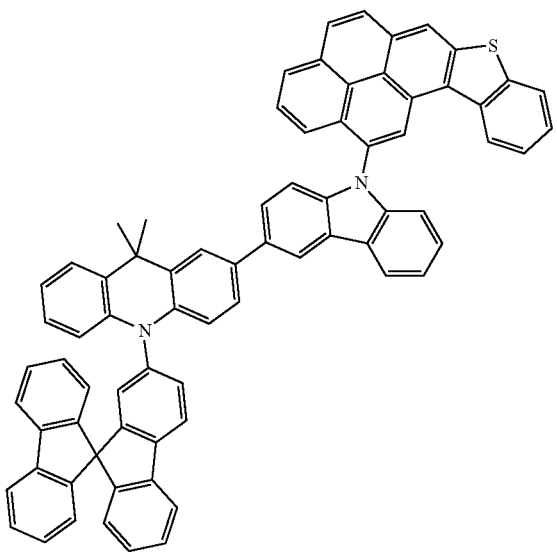

-continued
C203
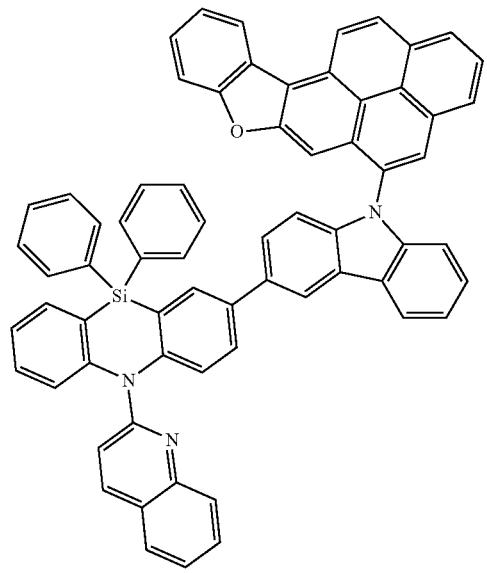
C204
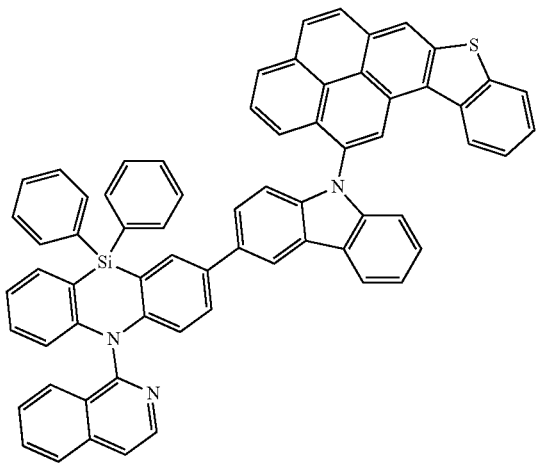
C205
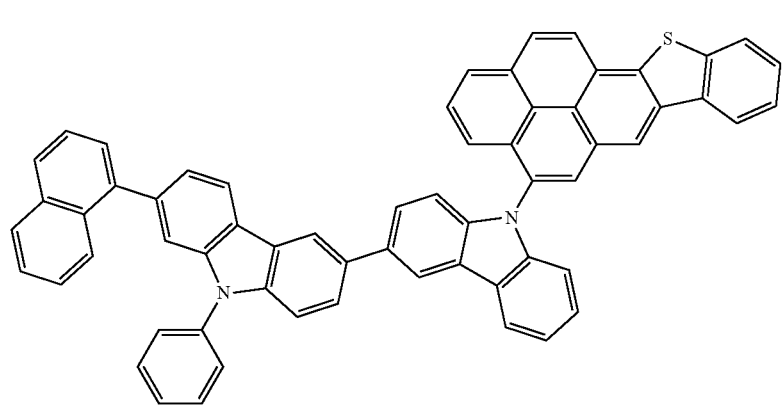
C206
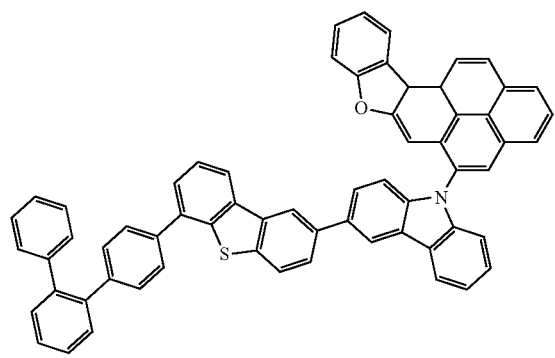
C207
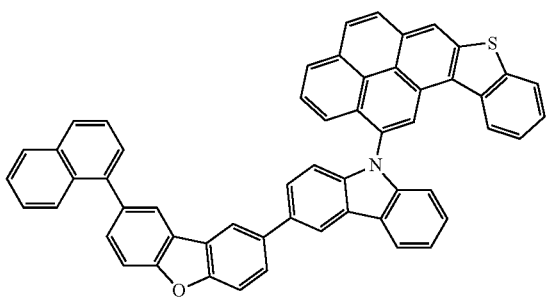

-continued
C208
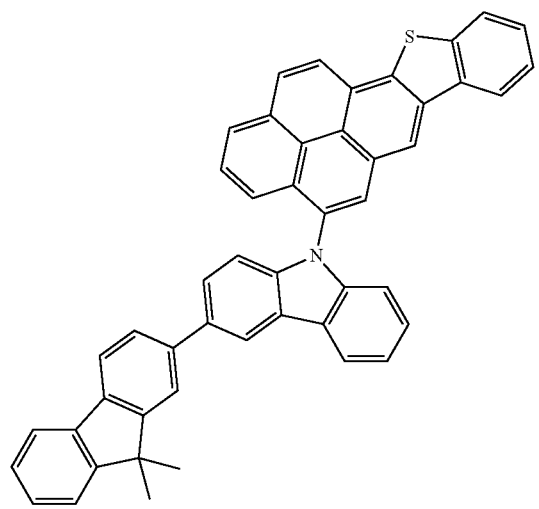
C209
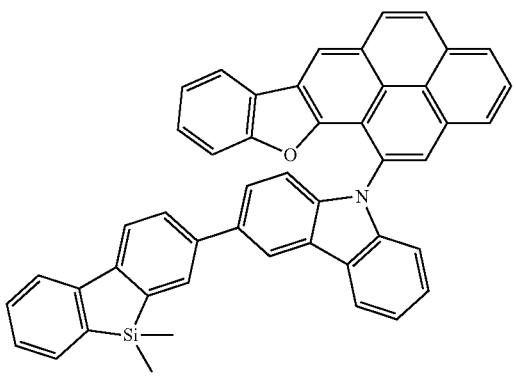
C210
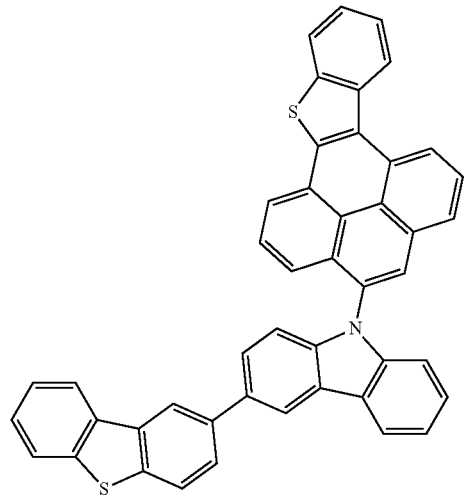
C211
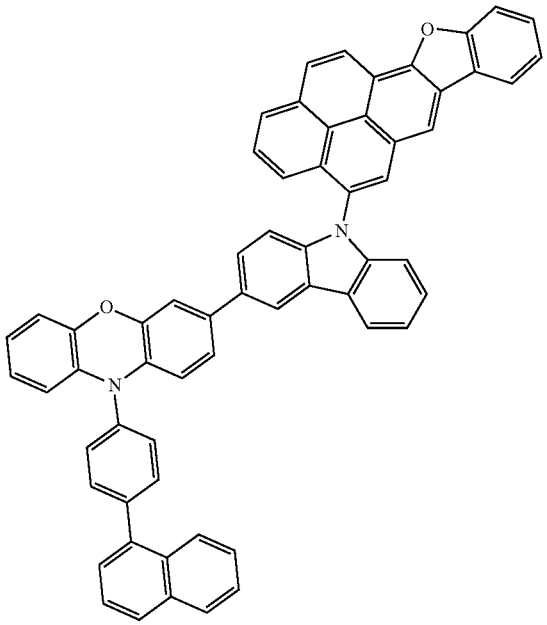

-continued
C212
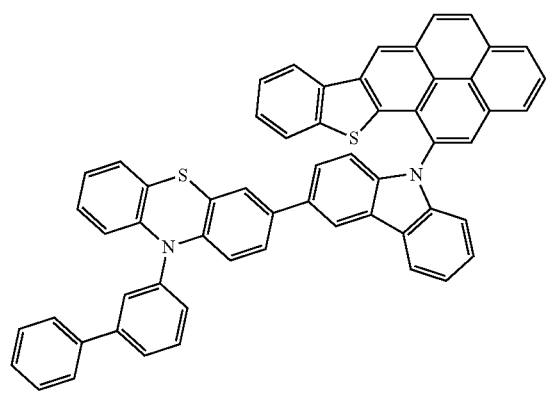
C213
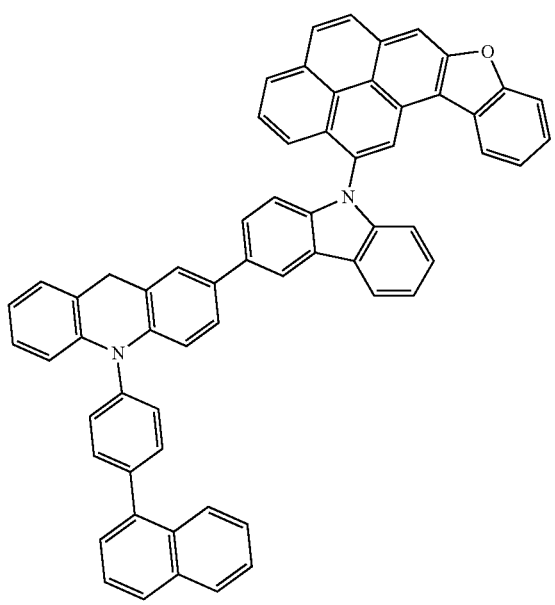
C214
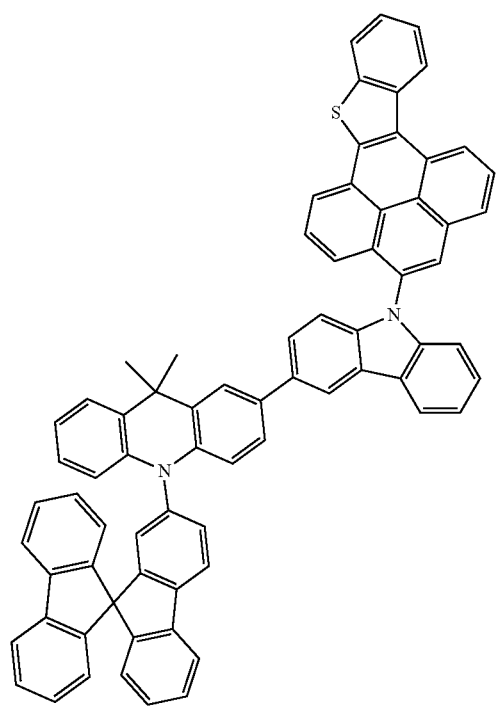
C215
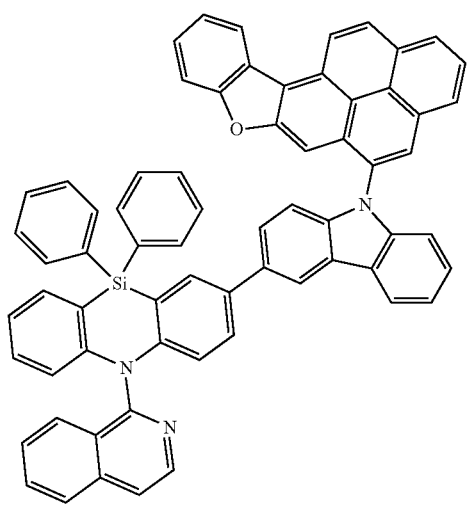

-continued
C216
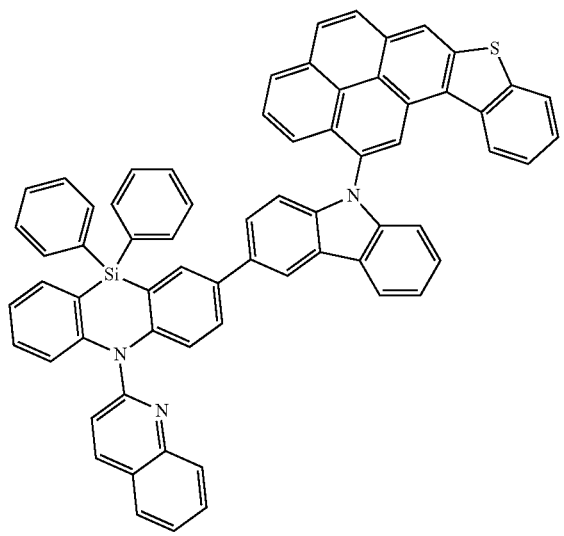
C217
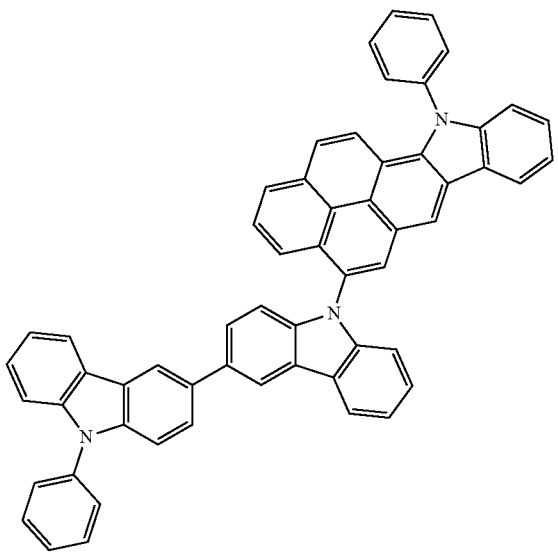
C218
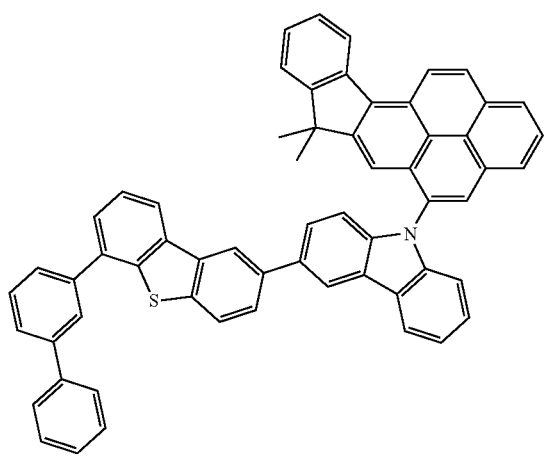
C219
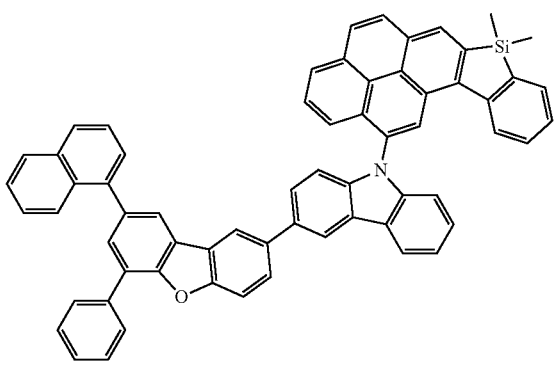

-continued
C220
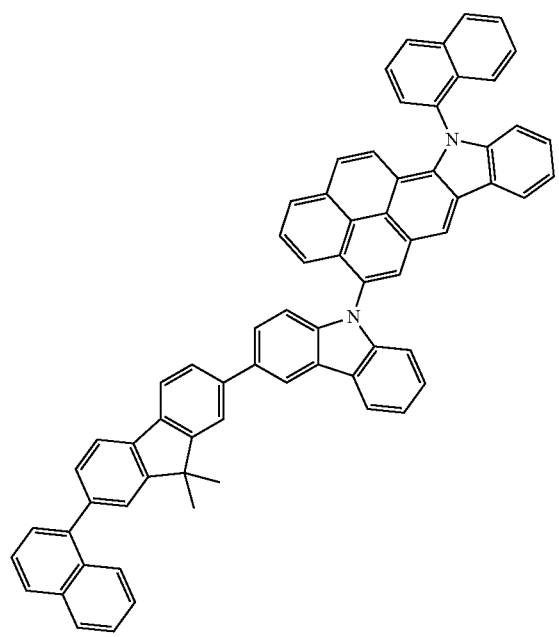
C221
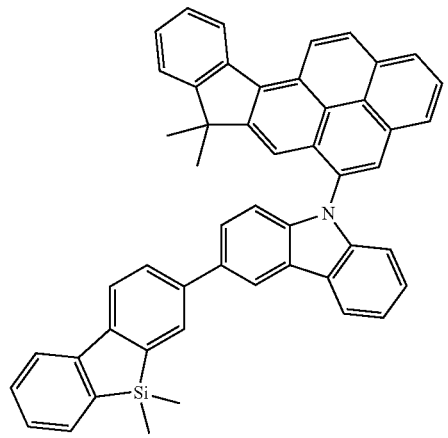
C222
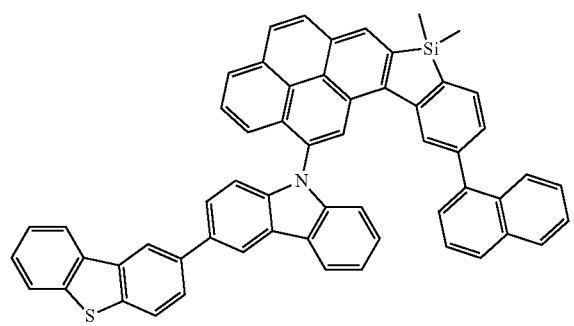
C223
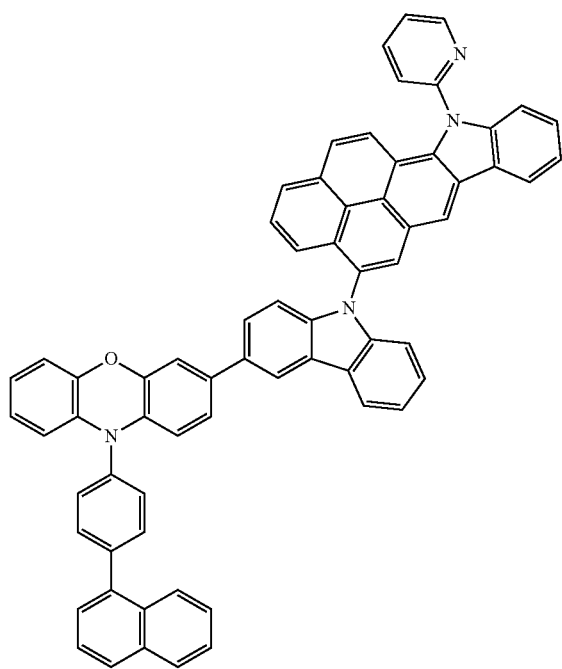

-continued
C224
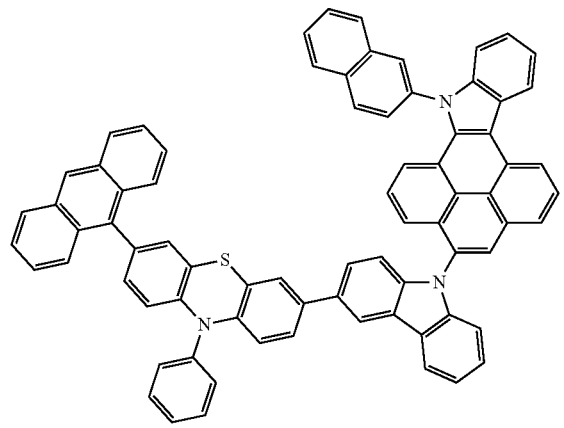
C225
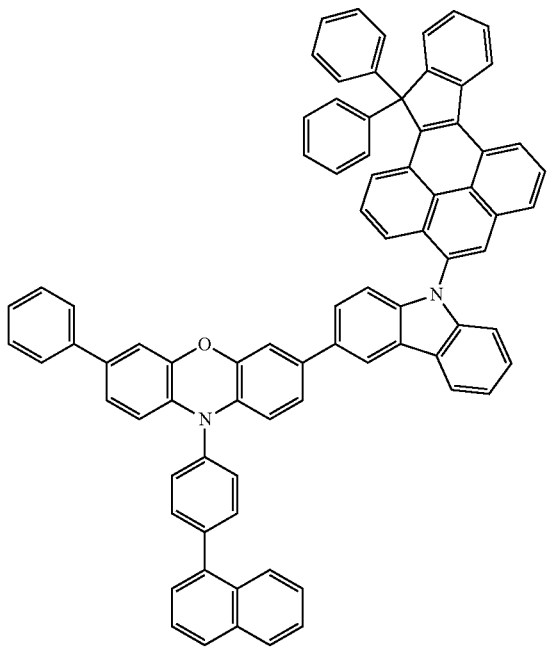
C226
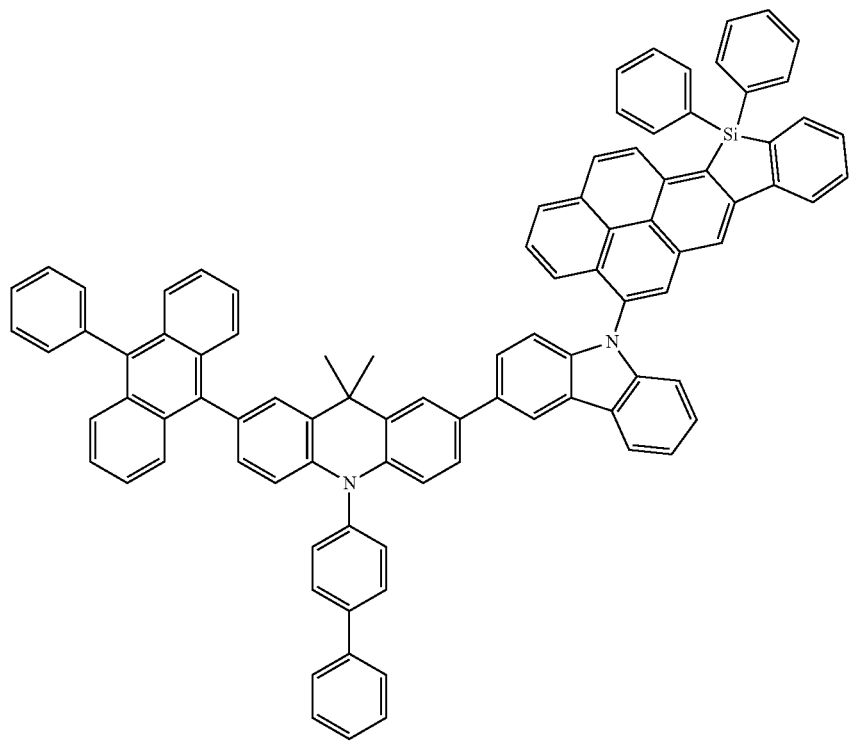

-continued
C227
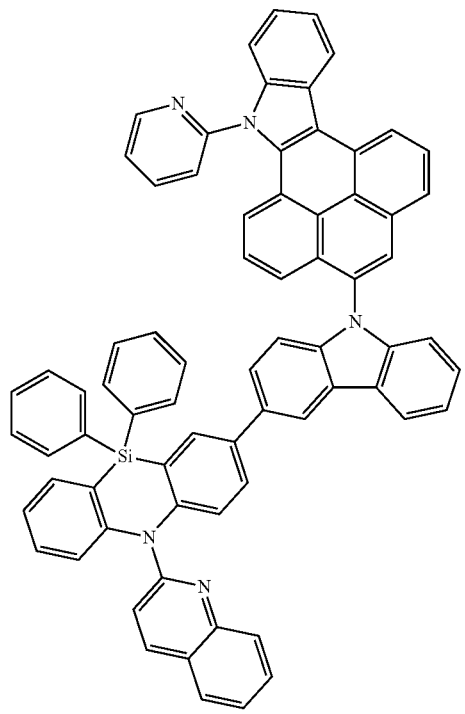
C228
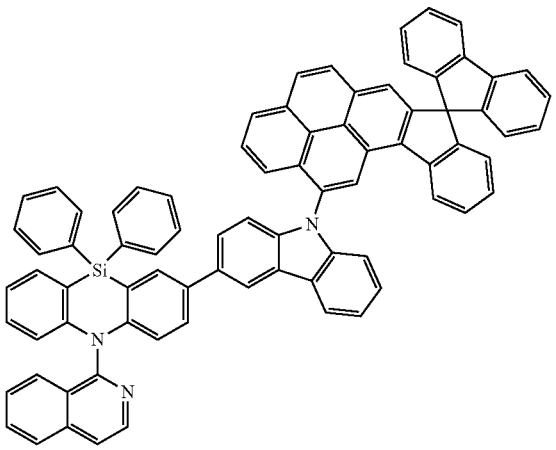
C229
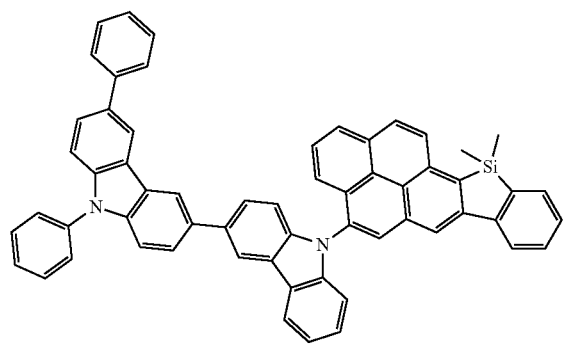
C230
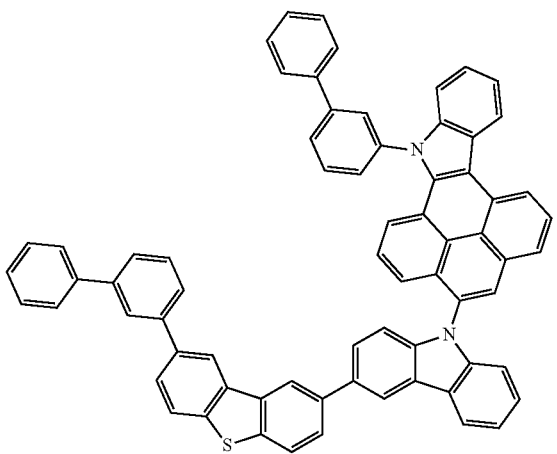

-continued
C231
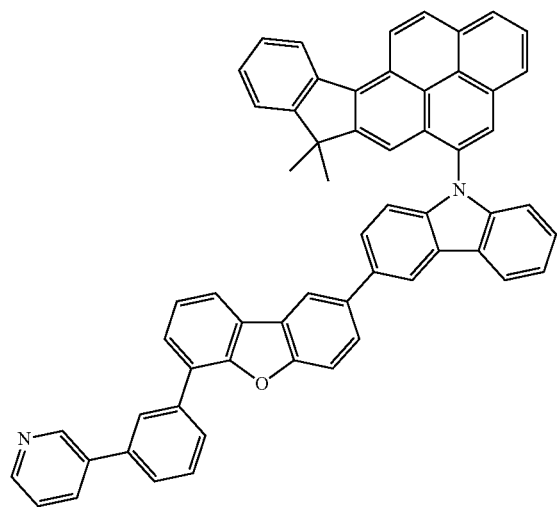
C232
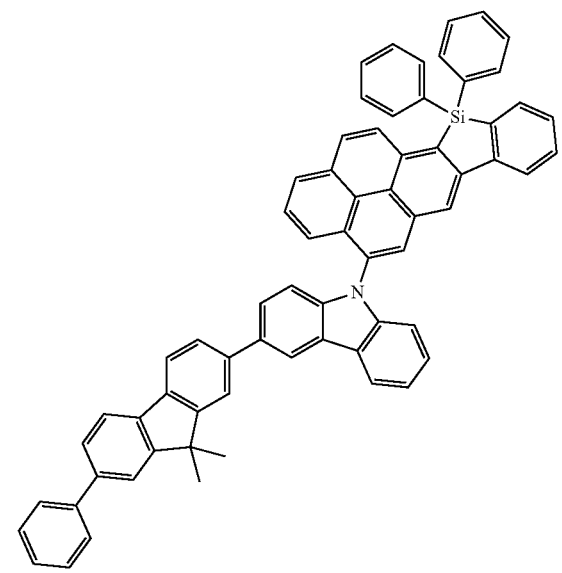
C233
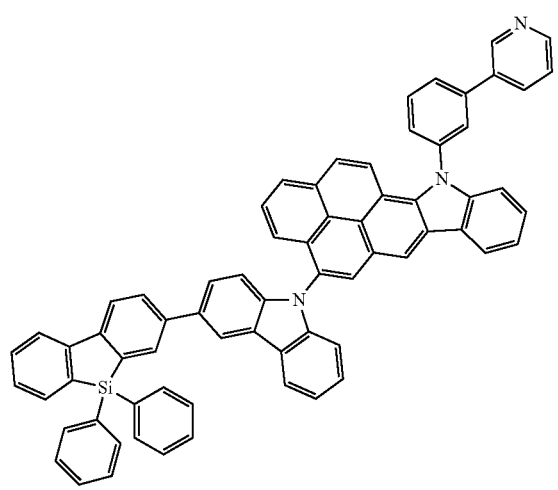
C234
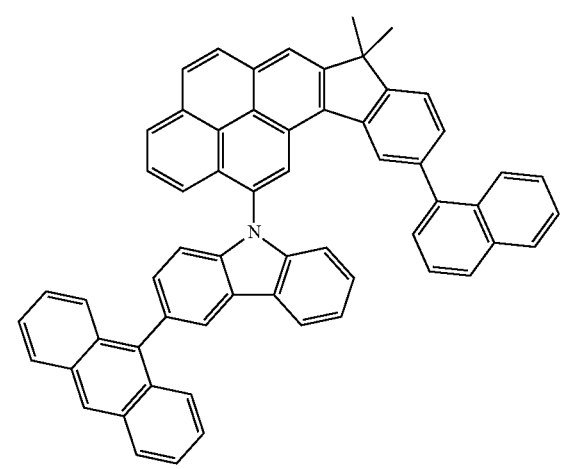
C235
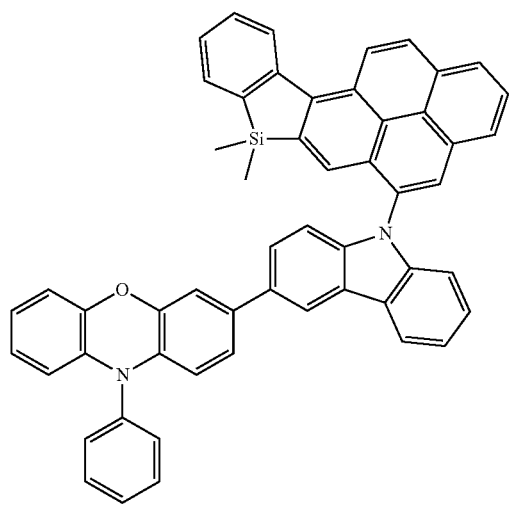
C236
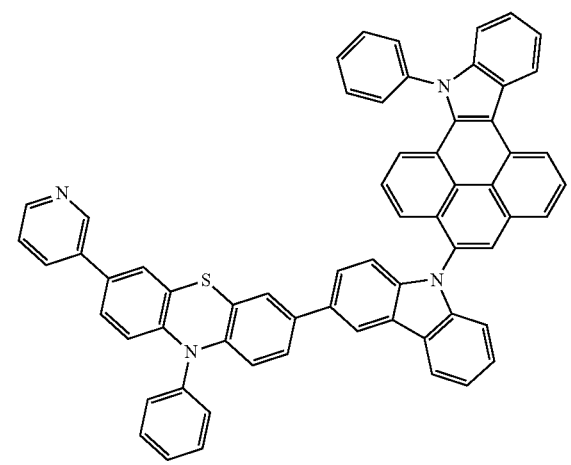

C237
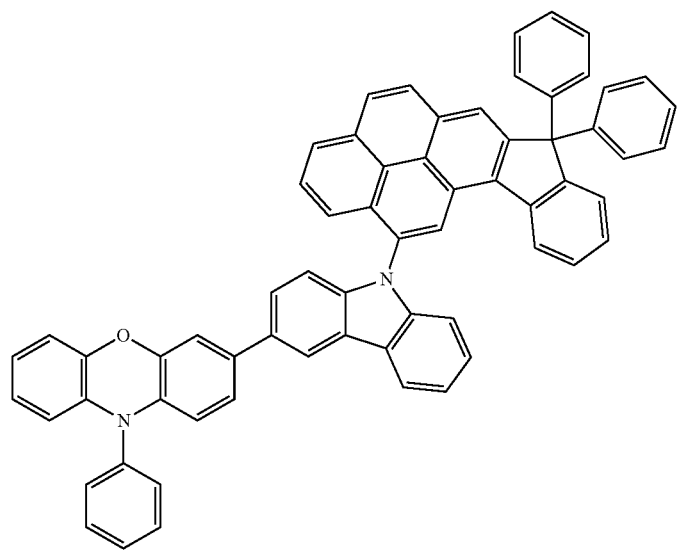
C238

-continued
C239
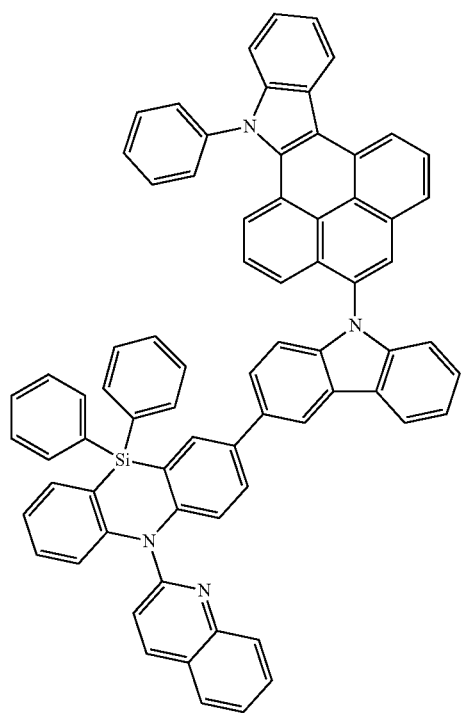
C240
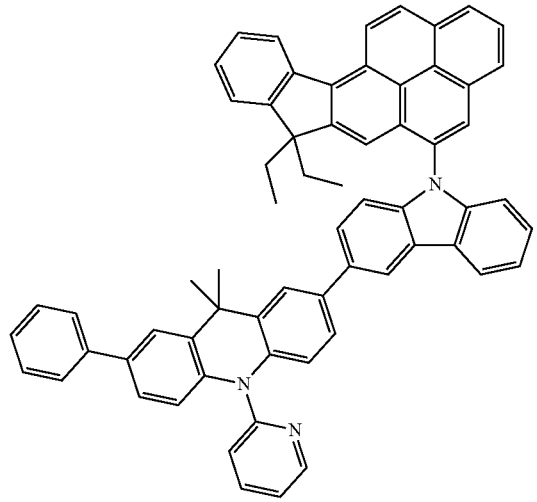
C241
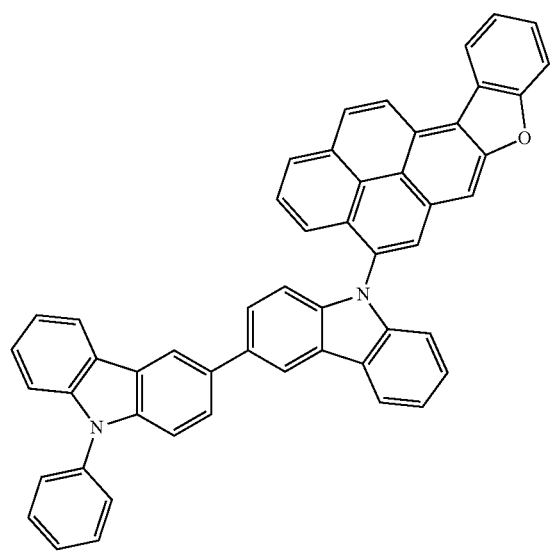
C242
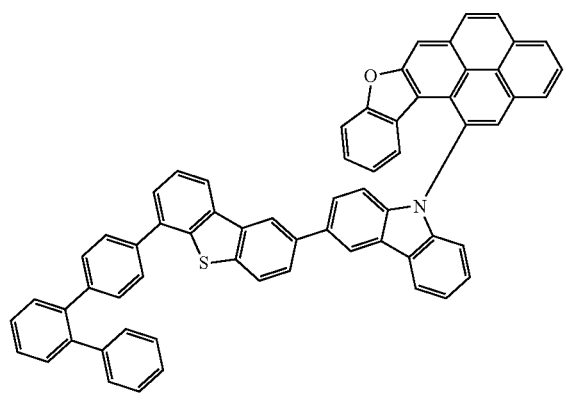

-continued
C243
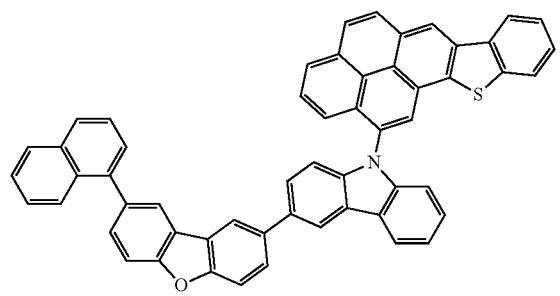
C244
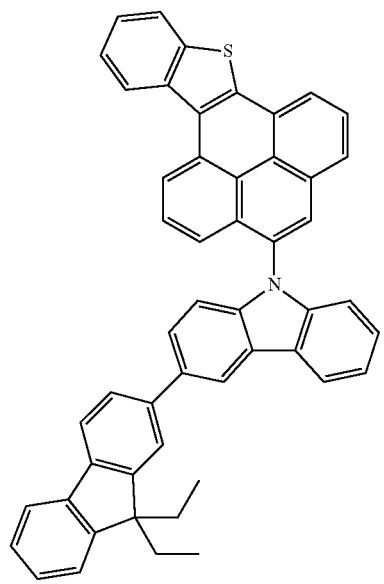
C245
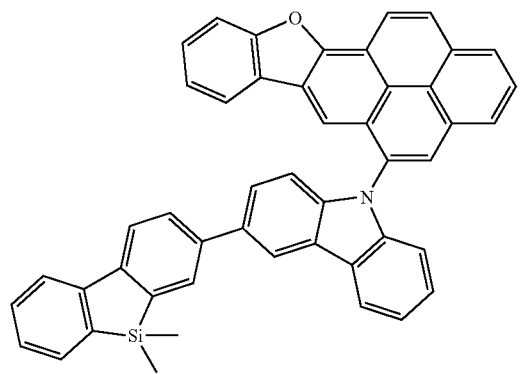
C246
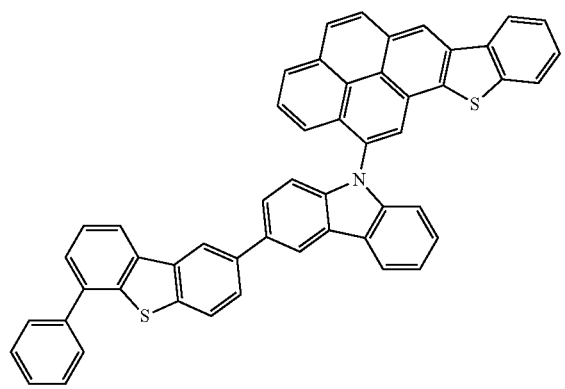

-continued
C247
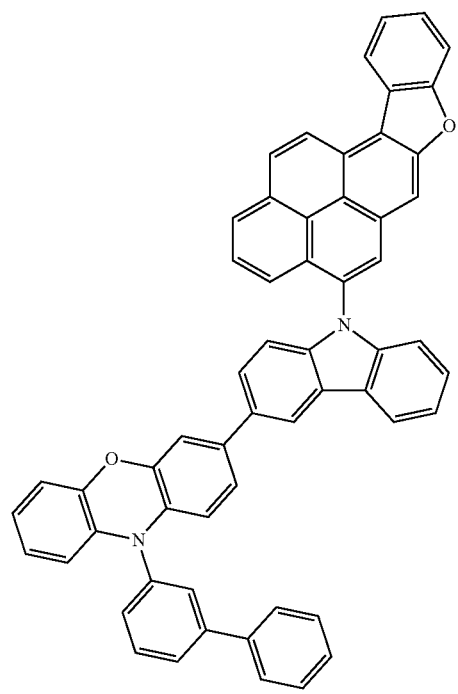
C248
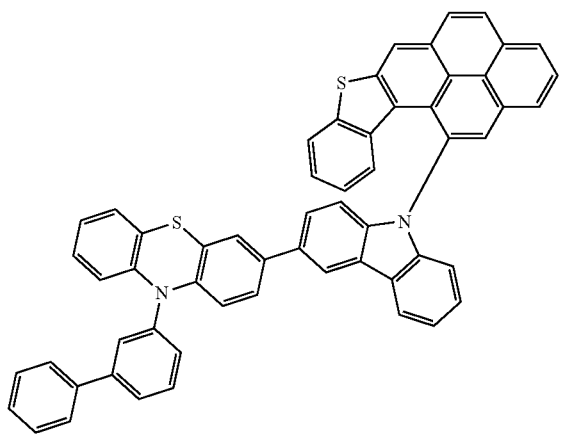
C249
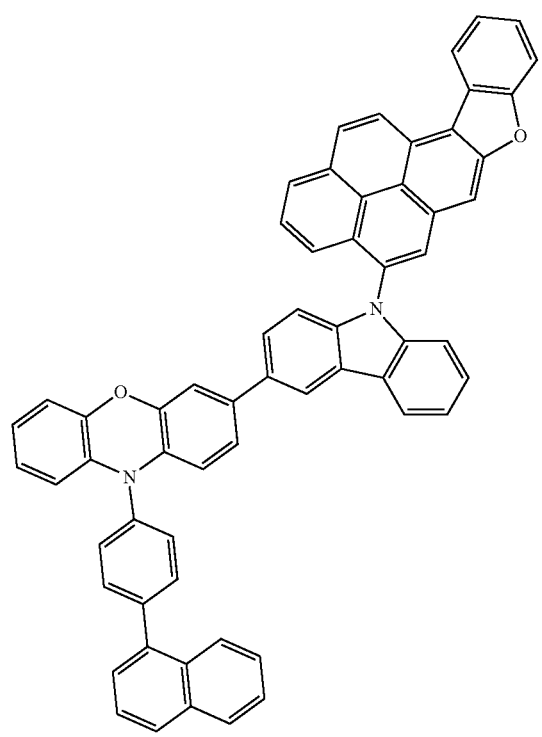
C250
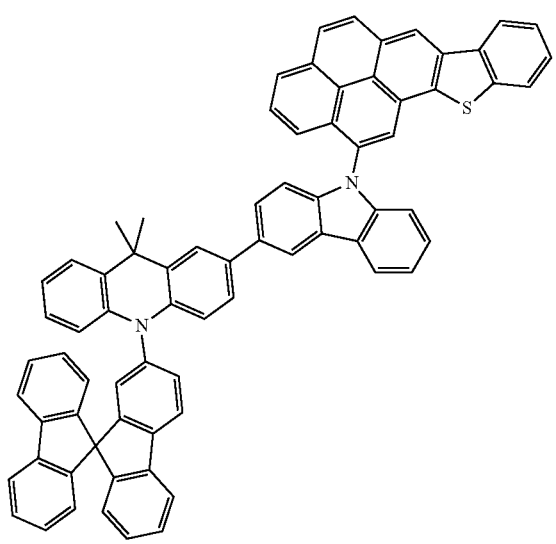

-continued
C251
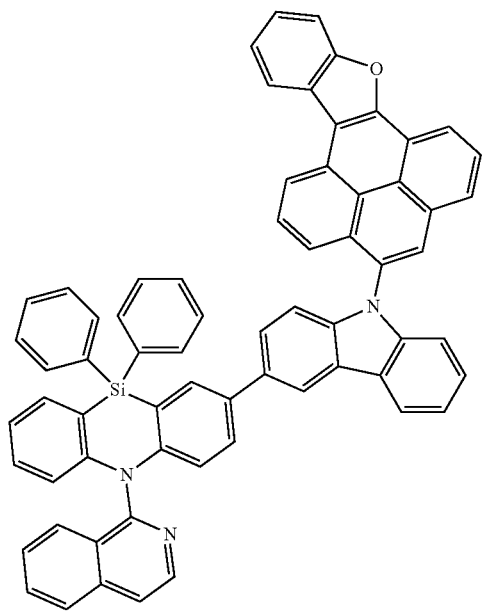
C252
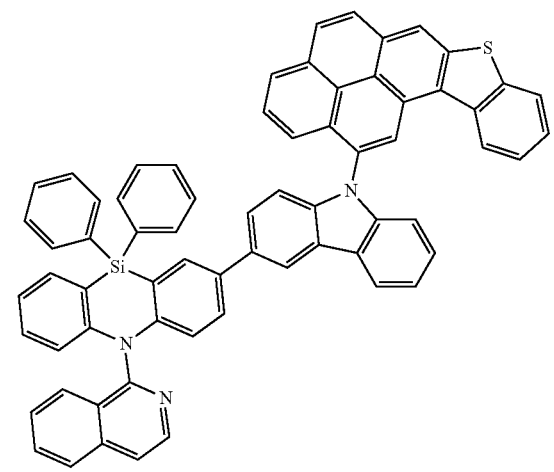
C253
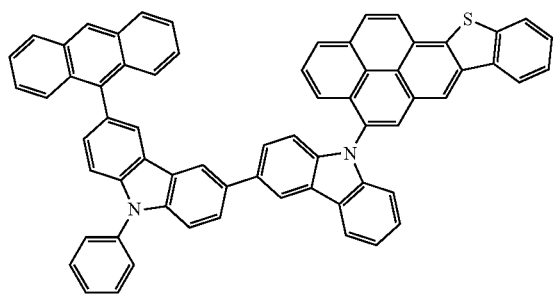
C254
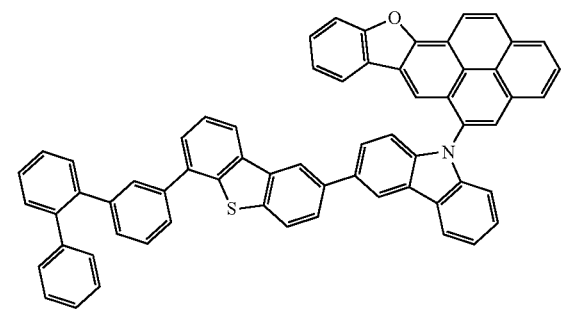
C255
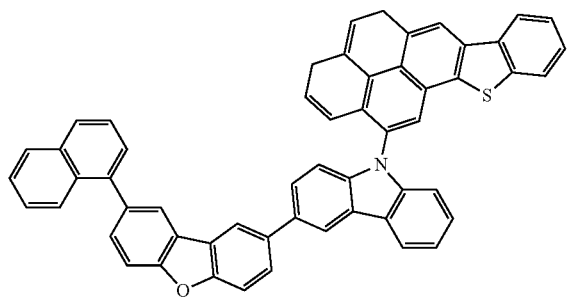
C256
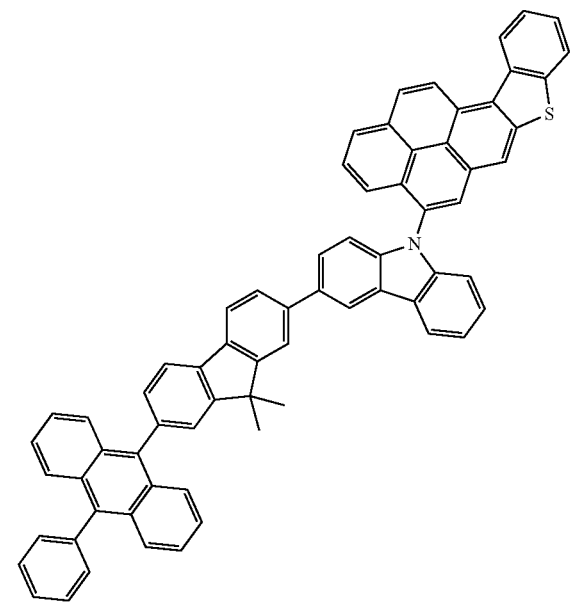

-continued
C257
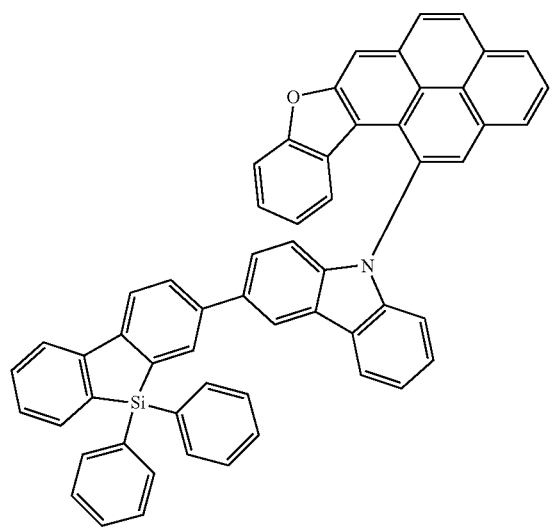
C258
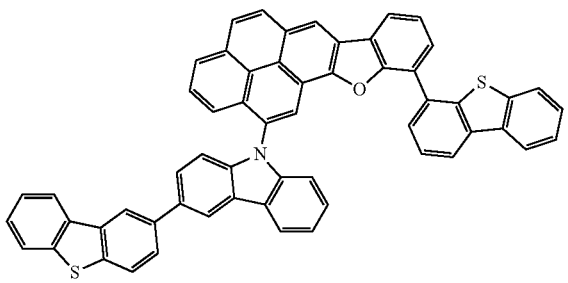
C259
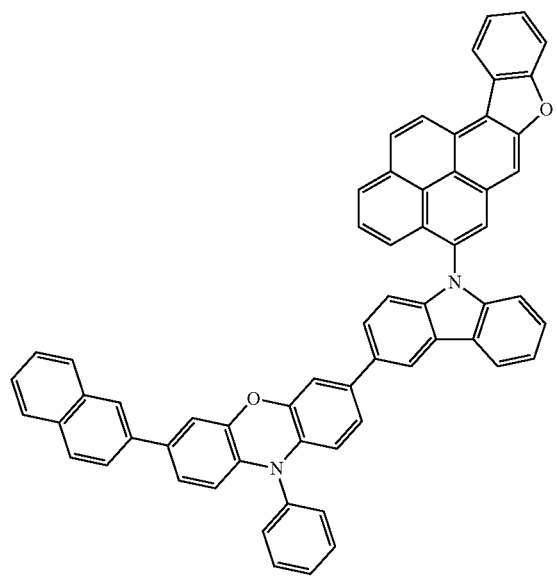
C260
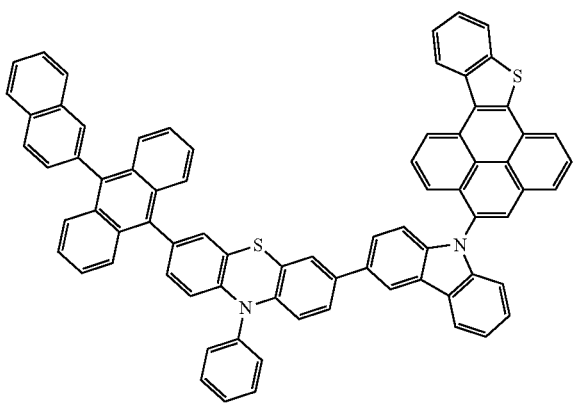

C261
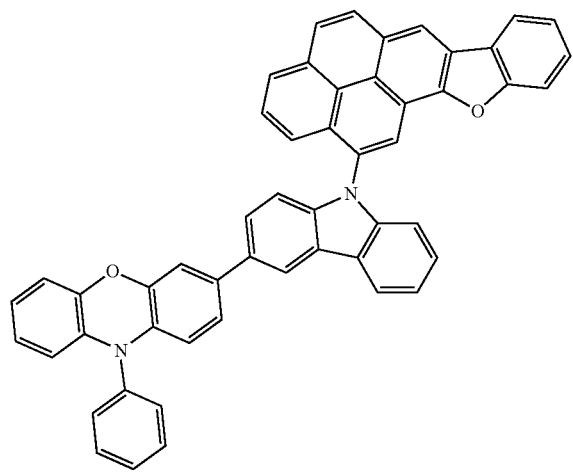
C262
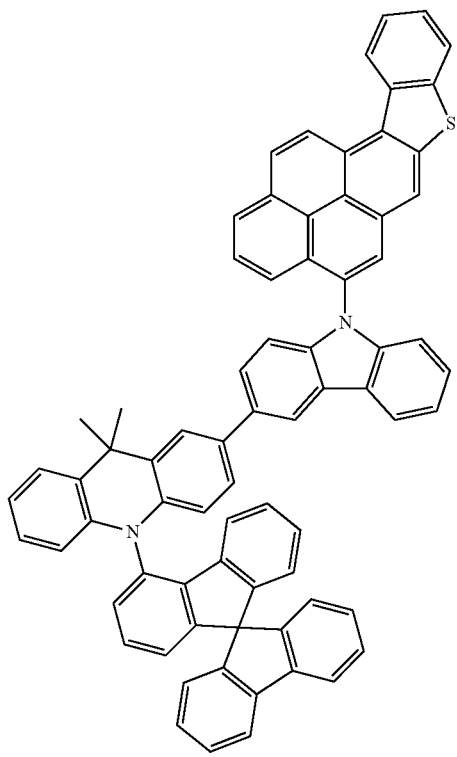
C263
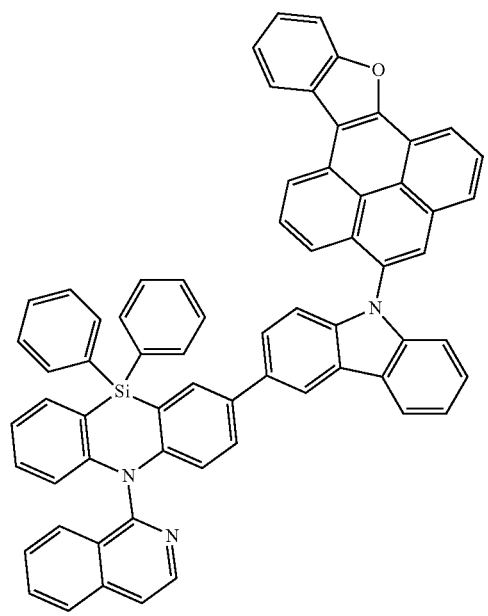
C264
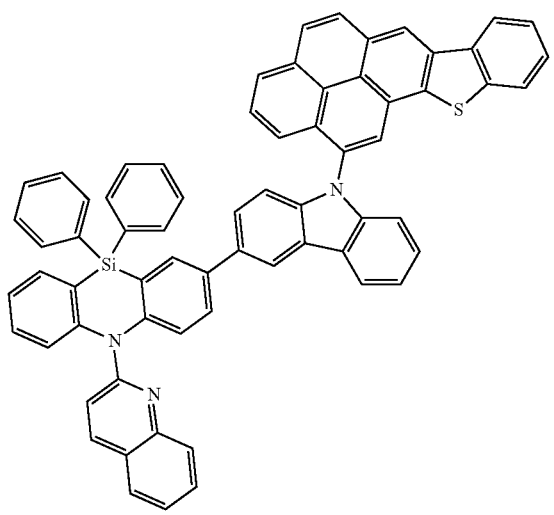

-continued
C265
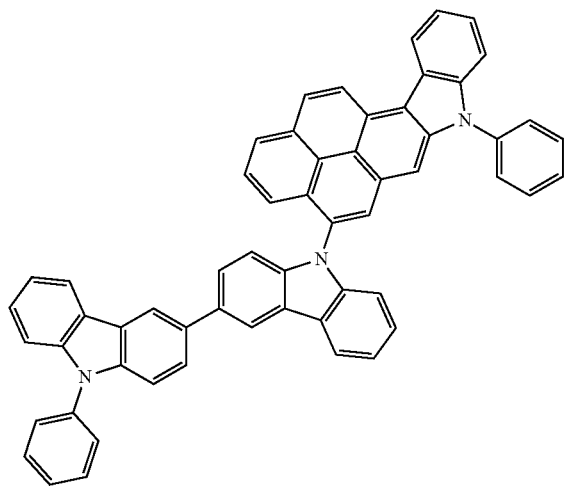
C266
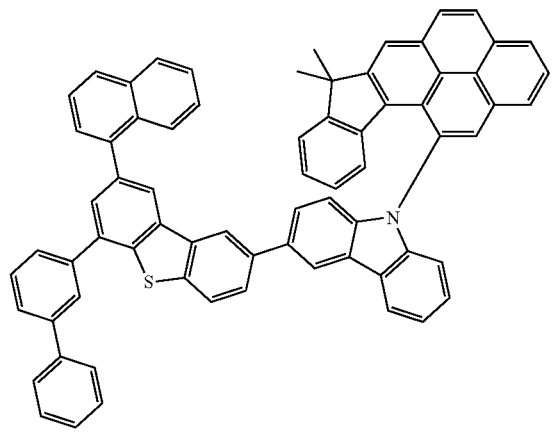
C267
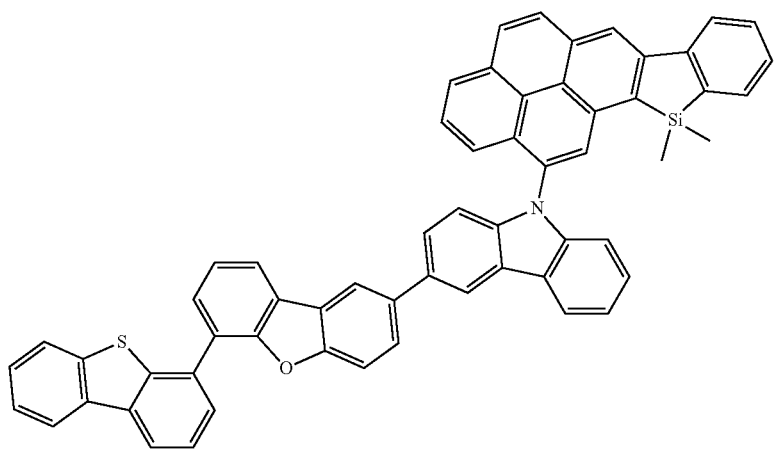
C268
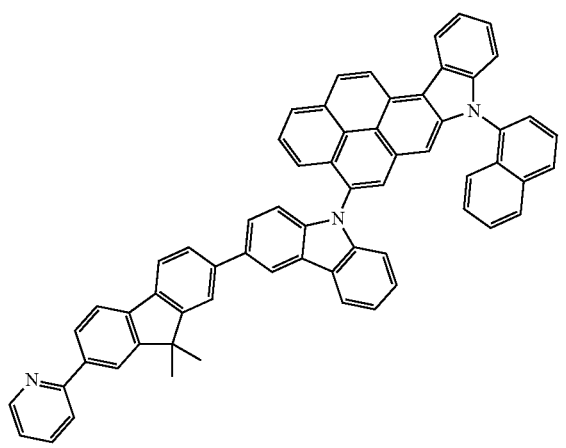
C269
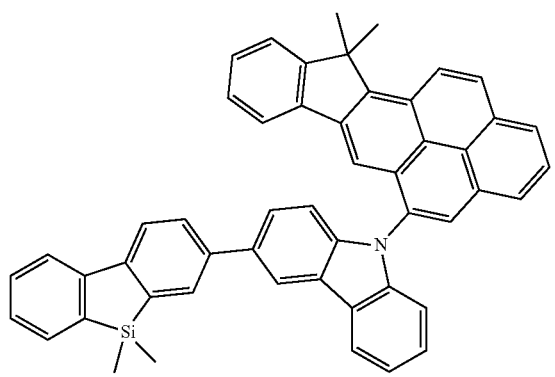

-continued
C270
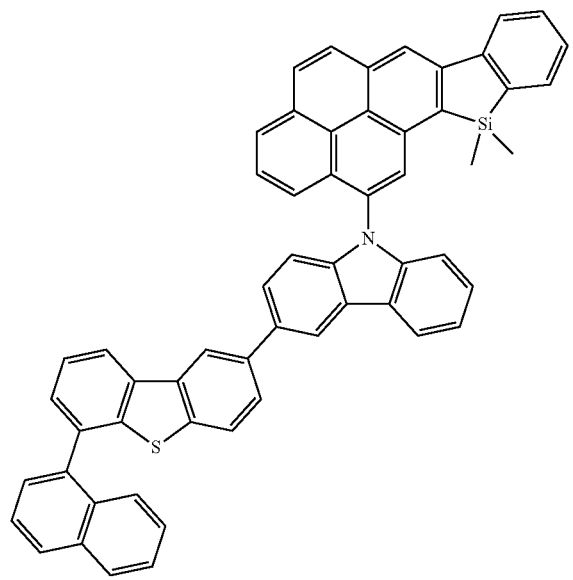
C271
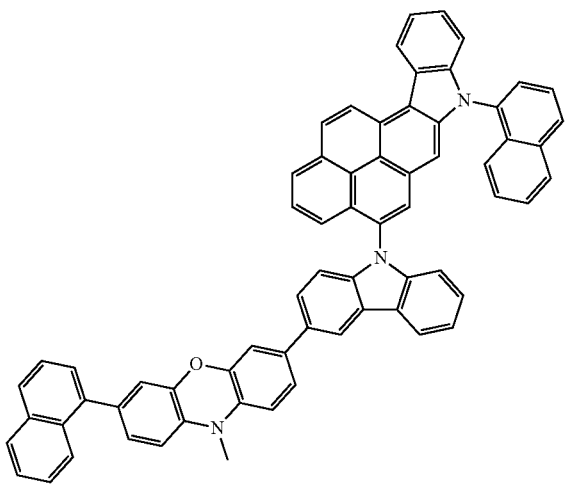
C272
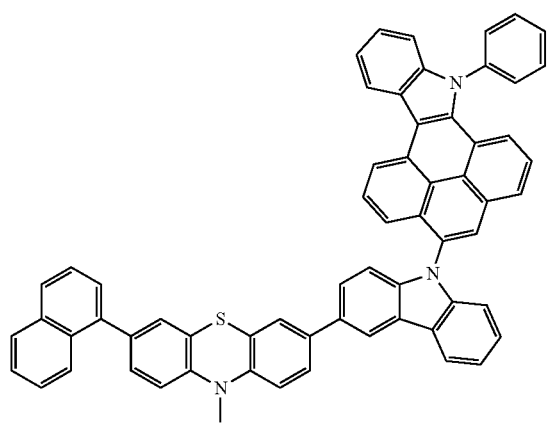
C273
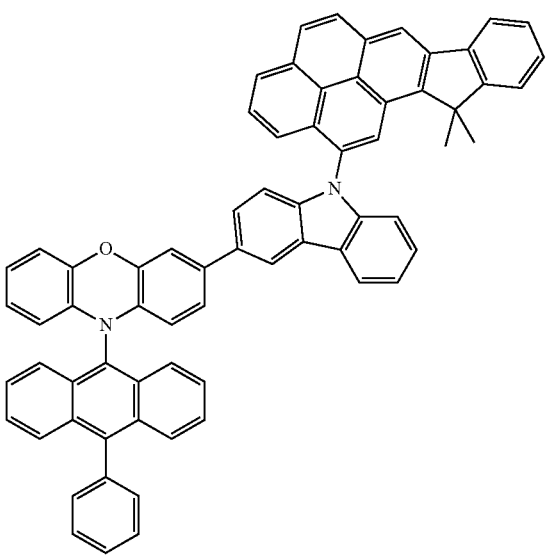

-continued
C274
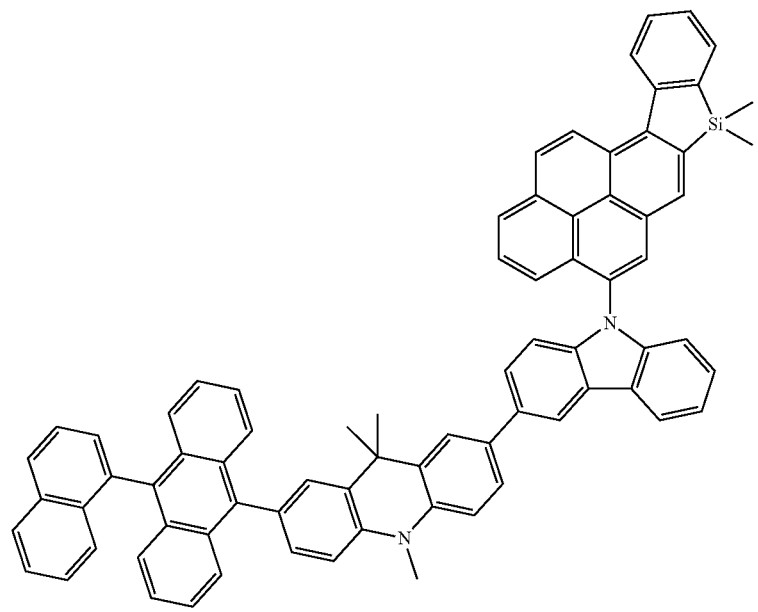
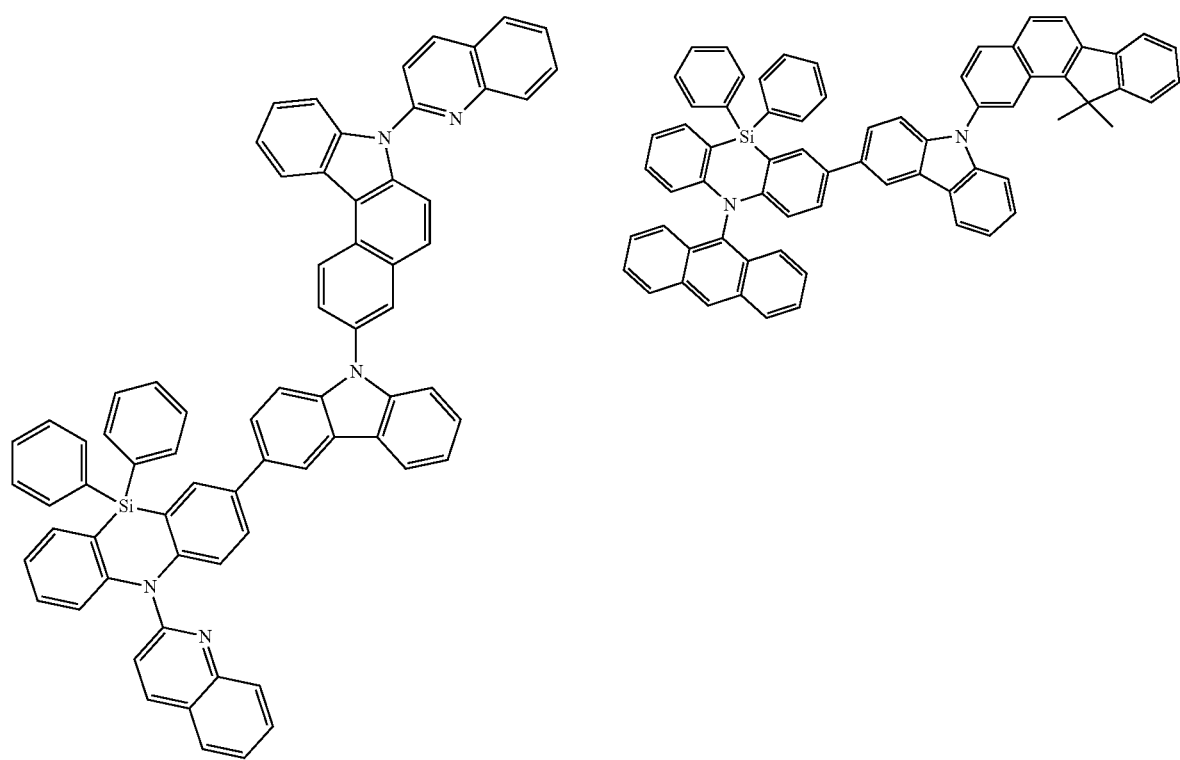
C275
C276

-continued
C275
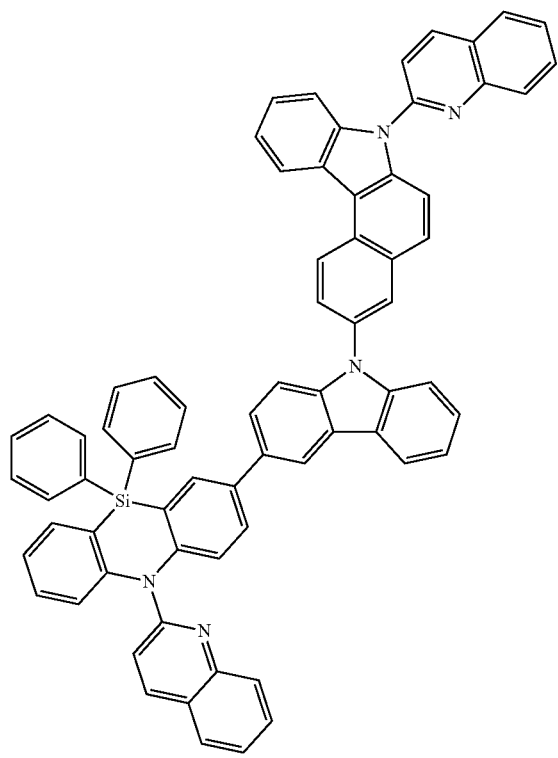
C276
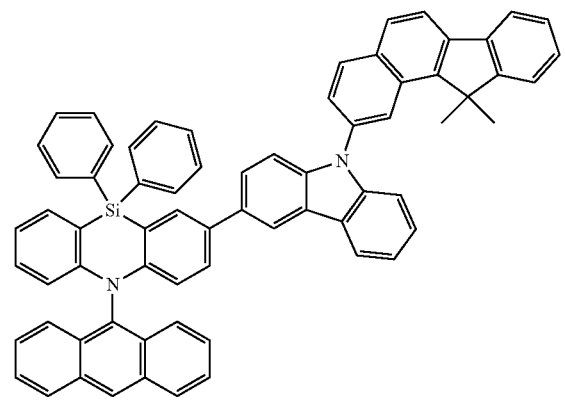
C277
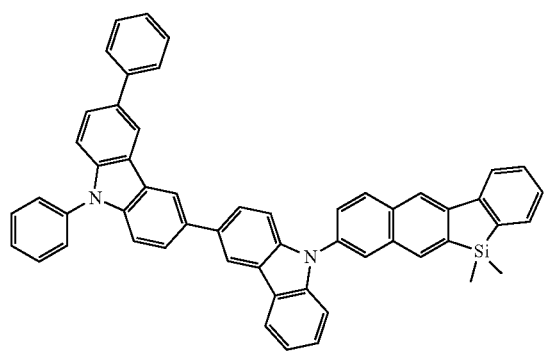
C278
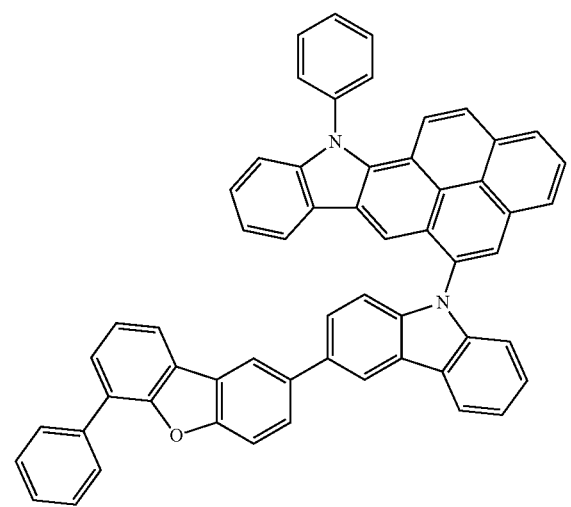

-continued
C279
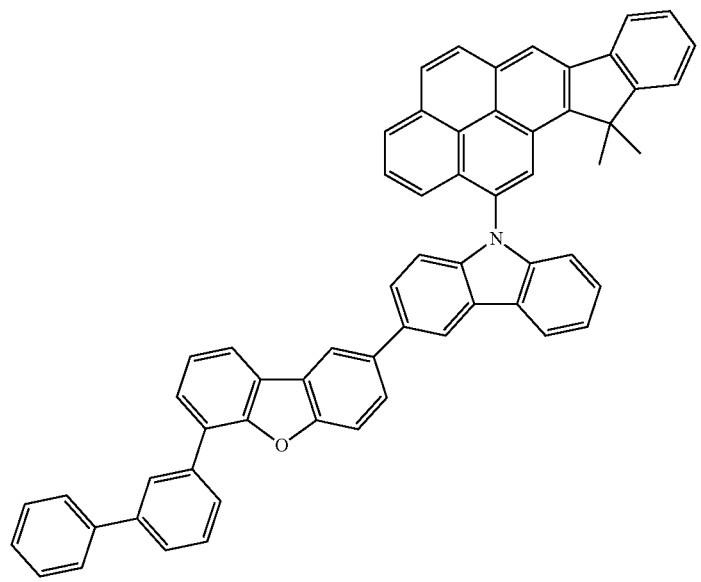
C280
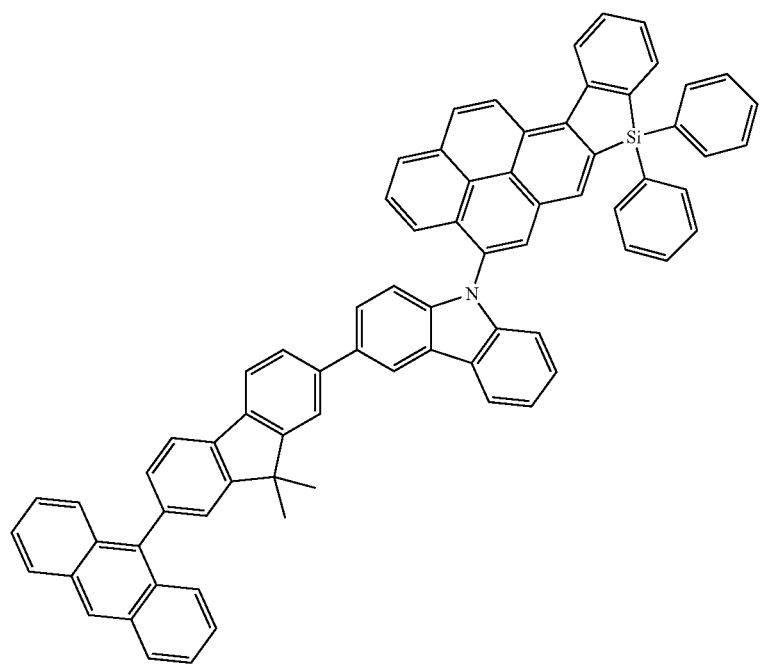
C281
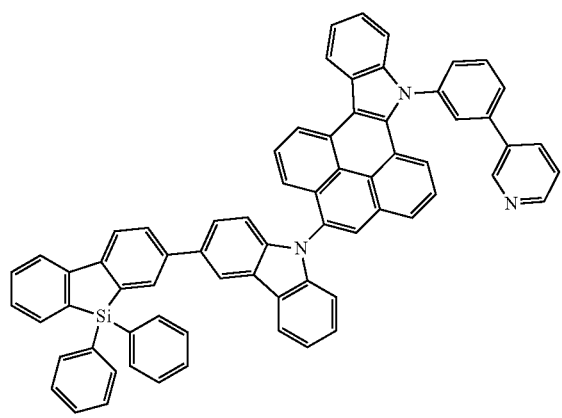
C282
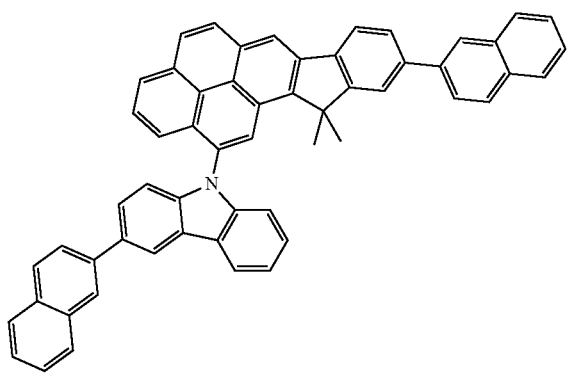

-continued
C283
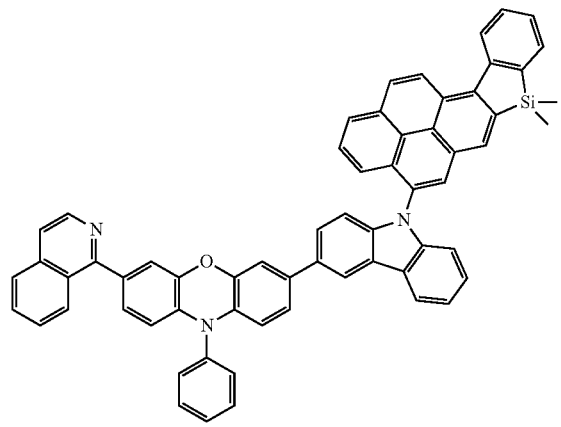
C284
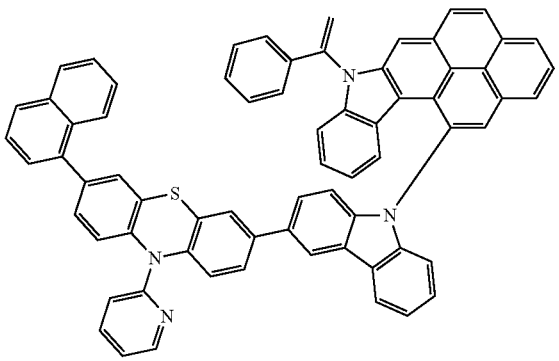
C285
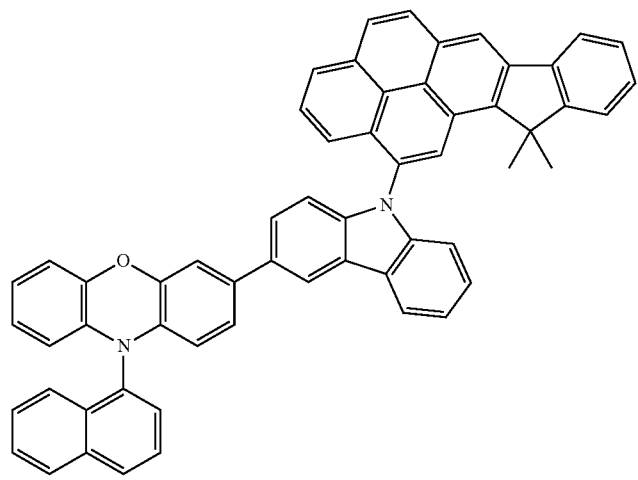
C286
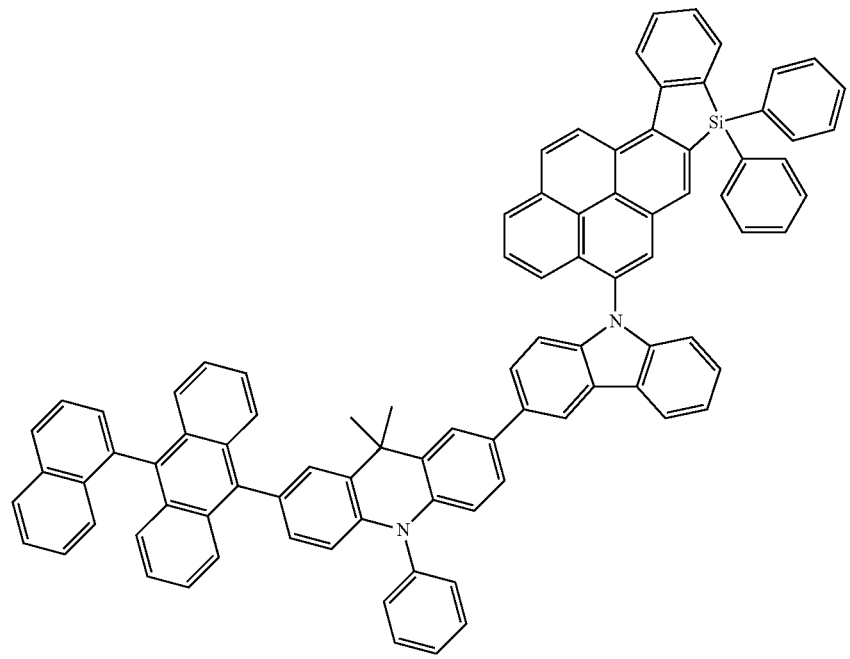

-continued

C287

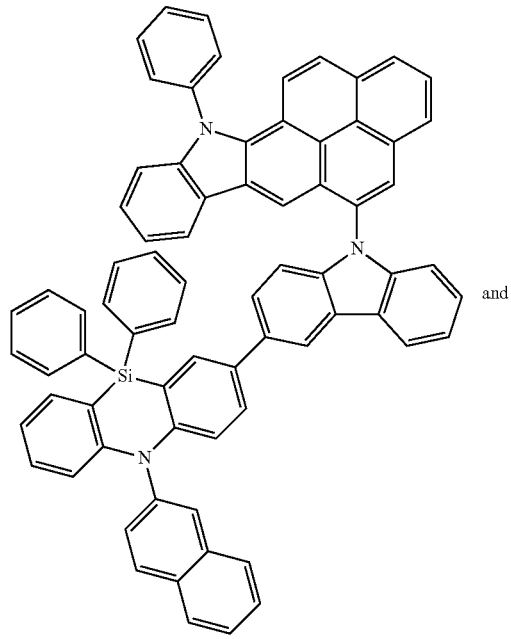

and

C288

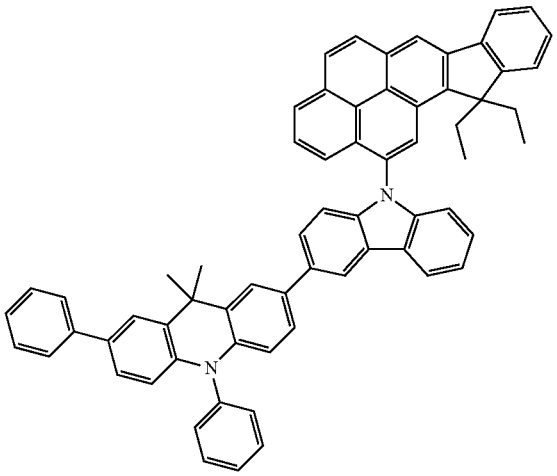

An organic electroluminescence device comprising a pair of electrodes having a cathode and an anode, and between the pair of electrodes comprising one or more organic layers. At least one of the organic layers comprises the organic compound of the present invention.

The light emitting layer may comprise the compound of formula (1) as a host material.

The light emitting layer may comprise the compound of formula (1) as a hole transporting layer.

The light emitting layer may comprise the compound of formula (1) as a electron transporting layer.

The light emitting layer may comprise the compound of formula (1) as a electron blocking layer.

The light emitting layer may comprise the compound of formula (1) as a hole blocking layer.

The organic electroluminescence device may be a lighting panel.

The organic electroluminescence device may be a backlight panel.

Referring to FIG. 1, the first organic EL device 510 may comprise an anode 310, a cathode 380 and one or more organic layers 320, 330, 340E, 350, 360, 370 formed between the anode 310 and the cathode 380. From the bottom to the top, the one or more organic layers may comprise a hole injection layer 320, a hole transport layer 330, an emissive layer 340E, a hole blocking layer 350, an electron transport layer 360 and an electron injection layer 370.

The emissive layer 340E may comprise a 15% dopant D1 and the organic compound of formula (1) 340C doped with the dopant D1. The dopant D1 may be a green guest material for tuning the wavelength at which the emissive layer 340E emits light, so that the color of emitted light may be green. The organic compound of formula (1) may be a host 340C of the emissive layer 340E.

FIG. 2 is a cross-sectional view of an organic EL device without the organic compound of formula (1). Referring to FIG. 2, the organic EL device 400 may comprise an anode 310, a cathode 380 and one or more organic layers 320, 330, 340, 350, 360, 370 formed between the anode 310 and the cathode 380. From the bottom to the top, the one or more organic layers may comprise a hole injection layer 320, a hole transport layer 330, an emissive layer 340, a hole blocking layer 350, an electron transport layer 360 and an electron injection layer 370. The emissive layer 340 may comprise a 15% dopant D1 and an organic compound H1 doped with the dopant D1. The dopant D1 may be a green guest material. The organic compound H1 is a host of the emissive layer 340.

To those organic EL devices of FIG. 1 and FIG. 2, EL spectra and CIE coordination are measured by using a PR650 spectra scan spectrometer.

Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of FIG. 1 and FIG. 2 may be summarized in Table 1 below. The half-life is defined as the time that the initial luminance of 1000 cd/m$^2$ has dropped to half.

TABLE 1

| Host (H1 or 340C) | Dopant | Driving Voltage (V) | Current Efficiency (cd/A) | CIE (y) | Half-life (hours) |
|---|---|---|---|---|---|
| H1 | D1 | 5.1 | 18 | 0.53 | 350 |
| C1 | D1 | 3.8 | 35 | 0.55 | 660 |
| C2 | D1 | 3.8 | 37 | 0.54 | 700 |
| C3 | D1 | 3.7 | 39 | 0.53 | 720 |
| C7 | D1 | 4.0 | 28 | 0.52 | 490 |
| C9 | D1 | 3.8 | 34 | 0.55 | 630 |
| C17 | D1 | 4.3 | 26 | 0.54 | 440 |
| C49 | D1 | 3.6 | 35 | 0.54 | 680 |
| C51 | D1 | 3.2 | 44 | 0.54 | 930 |
| C53 | D1 | 3.6 | 34 | 0.53 | 700 |
| C57 | D1 | 4.4 | 26 | 0.56 | 420 |
| C59 | D1 | 3.1 | 42 | 0.55 | 950 |
| C60 | D1 | 3.0 | 45 | 0.53 | 1100 |
| C97 | D1 | 3.1 | 43 | 0.56 | 960 |

TABLE 1-continued

| Host (H1 or 340C) | Dopant | Driving Voltage (V) | Current Efficiency (cd/A) | CIE (y) | Half-life (hours) |
|---|---|---|---|---|---|
| C98 | D1 | 3.7 | 35 | 0.54 | 660 |
| C105 | D1 | 4.3 | 27 | 0.54 | 450 |
| C145 | D1 | 4.2 | 29 | 0.52 | 500 |
| C147 | D1 | 4.5 | 27 | 0.56 | 430 |
| C149 | D1 | 4.3 | 25 | 0.54 | 420 |
| C193 | D1 | 2.8 | 45 | 0.53 | 980 |
| C195 | D1 | 3.0 | 42 | 0.52 | 900 |
| C197 | D1 | 3.1 | 44 | 0.54 | 920 |
| C201 | D1 | 3.0 | 43 | 0.53 | 920 |
| C241 | D1 | 3.9 | 36 | 0.55 | 670 |
| C245 | D1 | 4.0 | 36 | 0.53 | 660 |
| C246 | D1 | 3.8 | 34 | 0.55 | 680 |
| C251 | D1 | 3.7 | 30 | 0.56 | 520 |

According to Table 1, in the first organic EL device 510, the organic M compound of formula (1) comprised as a host 340C of FIG. 1 exhibits performance better than a prior art organic EL material (H1).

A method of producing the first organic EL device 510 of FIG. 1 and the organic EL device 400 of FIG. 2 is described. ITO-coated glasses with 9-12 ohm/square in resistance and 120-160 nm in thickness are provided (hereinafter ITO substrate) and cleaned in a number of cleaning steps in an ultrasonic bath (e.g., detergent, deionized water).

Before vapor deposition of the organic layers, cleaned ITO substrates may be further treated by UV and ozone. All pre-treatment processes for ITO substrate are under clean room (class 100), so that an anode 310 may be formed.

One or more organic layers 320, 330, 340 (FIG. 2), 340E (FIG. 1), 350, 360, 370 are applied onto the anode 310 in order by vapor deposition in a high-vacuum unit (10-7 Torr), such as resistively heated quartz boats. The thickness of the respective layer and the vapor deposition rate (0.1-0.3 nm/sec) are precisely monitored or set with the aid of a quartz-crystal monitor.

It is also possible, as described above, each of the organic layers may comprise more than one organic compound. For example, an emissive layer 340E or 340 may be formed of a dopant and a host doped with the dopant. An emissive layer 340E or 340 may also be formed of a co-host and a host co-deposited with the co-host. This may be successfully achieved by co-vaporization from two or more sources. Accordingly, the compounds for the organic layers of the present invention are thermally stable.

Referring to FIG. 1 and FIG. 2, onto the anode 310, Dipyrazino[2,3-f:2,3-]quinoxaline-2,3,6,7,10,11-hexacarbonitrile (HAT-CN) may be applied to form a hole injection layer (HIL) 320 having a thickness of about 20 nm in the organic EL device 510 or 400. N,N-Bis(naphthalene-1-yl)-N,N-bis(phenyl)-benzidine (NPB) may be applied to form a hole transporting layer (HTL) 330 having a thickness of about 110 nm. Referring to FIG. 1 and FIG. 2, in the organic EL device 510 (FIG. 1) or 400 (FIG. 2), an emissive layer (EML) 340E or 340 may be formed to have a thickness of about 30 nm.

Referring to FIG. 2, in the organic EL device 400, 12-(4,6-diphenyl-1,3,5-triazin-2-yl)-10,10-dimethyl-10,12-dihydrophenanthro[9',10':5,6]indeno[2,1-b]carbazole (i.e., H1 of paragraph [0002]) may be applied to form a host H1 of an emissive layer 340 of FIG. 2. The emissive layer 340 may further comprise bis(2-phenylpyridinato)(2,4-diphenylpyridinato)-iridium(III) as a dopant D1, also a green guest of the emissive layer 340.

On the emissive layer 340 having a thickness of about 30 nm, a compound HB1 may be a hole blocking material (HBM) to form a hole blocking layer (HBL) 350 having a thickness of about 10 nm. 2-(naphthalen-1-yl)-9-(4-(1-(4-(10-(naphthalene-2-yl)anthracen-9-yl)-phenyl)-1H-benzo[d]imidazol-2-yl)phenyl)-1,10-phenanthroline (ET1) may be applied as an electron transporting material to co-deposit with 8-hydroxyquinolato-lithium (LiQ) at a ratio of 1:1, thereby forming an electron transporting layer 360 of the organic EL device 510 or 400. The electron transporting layer (ETL) 360 may have a thickness of about 35 nm. Table 2 shows the layer thickness and materials of the organic EL device 510 (FIG. 1) or 400 (FIG. 2).

TABLE 2

| Layer | Material | Thickness (nm) |
|---|---|---|
| Cathode | Al | 160 |
| EIL | LiQ | 1 |
| ETL | LiQ:ET1 (50%) | 35 |
| HBL | HB1 | 10 |
| EML | 340C or H1:D1 (15%) | 30 |
| HTL | NPB | 110 |
| HIL | HAT-CN | 20 |
| Anode | ITO substrate | 120~160 |

The organic compounds ET1, HB1, D1, NPB and HAT-CN for producing the organic EL device 400 or 510 in this invention may have the formulas as follows:

ET1

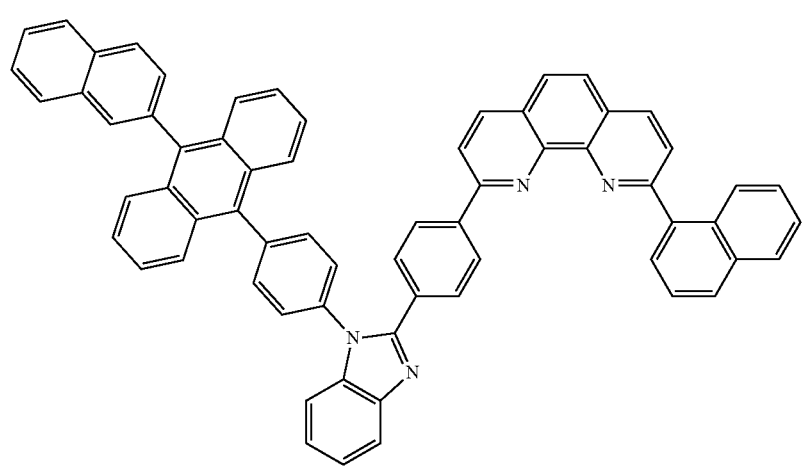

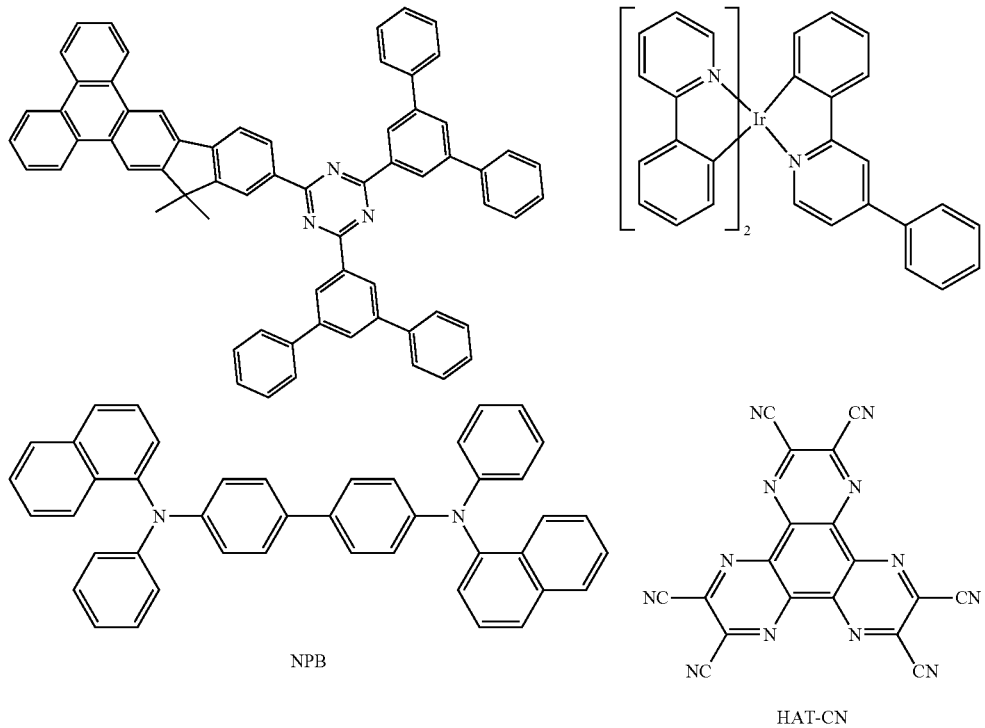

Referring to FIG. 1 and FIG. 2, the organic EL device 510 or 400 may further comprise a low work function metal, such as Al, Mg, Ca, Li or K, as a cathode 380 by thermal evaporation. The cathode 380 having a thickness of about 160 nm may help electrons injecting the electron transporting layer 360 from cathode 380. Between the cathode 380 (e.g., Al in Table 2) and the electron transporting layer 360, a thin electron injecting layer (EIL) 370 of LiQ is introduced. The electron injecting layer (EIL) 370 has a thickness of about 1 nm is to reduce the electron injection barrier and to improve the performance of the organic EL device 510 or 400. The material of the electron injecting layer 370 may alternatively be metal halide or metal oxide with low work function, such as LiF, MgO, or $Li_2O$.

In a third embodiment of the present invention, a second organic EL device using the organic compound of formula (1) is disclosed. The method of producing the second organic EL device 520 of FIG. 3 is substantially the same as the method of producing the organic EL device 400 of FIG. 2. The difference is that the hole blocking layer (HBL) 350C of FIG. 3 is made by using the organic compound of formula (1), rather than HB1.

Table 3 shows the layer thickness and materials of the organic EL device 520 (FIG. 3) or 400 (FIG. 2).

TABLE 3

| Layer | Material | Thickness (nm) |
|---|---|---|
| Cathode | Al | 160 |
| EIL | LiQ | 1 |
| ETL | LiQ:ET1 (50%) | 35 |
| HBL | 350C or HB1 | 10 |
| EML | H1:D1 (15%) | 30 |
| HTL | NPB | 110 |

TABLE 3-continued

| Layer | Material | Thickness (nm) |
|---|---|---|
| HIL | HAT-CN | 20 |
| Anode | ITO substrate | 120~160 |

To those organic EL devices of FIG. 3 and FIG. 2, EL spectra and CIE coordination are measured by using a PR650 spectra scans pectrometer.

Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 units) test reports of those organic EL devices of FIG. 3 and FIG. 2 may be summarized in Table below. The half-lif eof the fluorescent green-emitting organic EL device 520 or 400 is defined as the time that the initial luminance of 1000 $cd/m^2$ has dropped to half.

TABLE 4

| Material for HBL 350 or 350C | ETM for ETL 360 | Driving Voltage (V) | Current Efficiency (cd/A) | CIE(y) | Half-life (hours) |
|---|---|---|---|---|---|
| HB1 | ET1 | 5.1 | 18 | 0.53 | 350 |
| C1 | ET1 | 4.4 | 23 | 0.52 | 420 |
| C2 | ET1 | 4.5 | 24 | 0.55 | 430 |
| C7 | ET1 | 4.1 | 27 | 0.56 | 520 |
| C9 | ET1 | 4.0 | 26 | 0.54 | 510 |
| C49 | ET1 | 4.4 | 24 | 0.55 | 430 |
| C51 | ET1 | 4.4 | 23 | 0.52 | 420 |
| C57 | ET1 | 4.2 | 25 | 0.55 | 480 |
| C59 | ET1 | 4.7 | 21 | 0.54 | 390 |
| C97 | ET1 | 4.3 | 25 | 0.53 | 470 |

TABLE 4-continued

| Material for HBL 350 or 350C | ETM for ETL 360 | Driving Voltage (V) | Current Efficiency (cd/A) | CIE(y) | Half-life (hours) |
|---|---|---|---|---|---|
| C98 | ET1 | 4.5 | 22 | 0.52 | 410 |
| C145 | ET1 | 4.7 | 22 | 0.54 | 390 |
| C147 | ET1 | 4.8 | 20 | 0.52 | 370 |
| C193 | ET1 | 4.7 | 21 | 0.54 | 380 |
| C195 | ET1 | 4.0 | 27 | 0.53 | 520 |
| C241 | ET1 | 4.1 | 26 | 0.55 | 500 |
| C254 | ET1 | 4.0 | 28 | 0.54 | 520 |

According to Table 4, in the second organic EL device 520, the organic compound of formula (1) comprised as a hole blocking layer 350C of FIG. 3 exhibits performance better than a prior art hole blocking material (HB1 as a HBL 350 of FIG. 2).

Referring to FIG. 1 or FIG. 3, the organic EL device 510 or 520 of the present invention may alternatively be a lighting panel or a backlight panel.

Detailed preparation of the organic compounds of the present invention will be clarified by exemplary embodiments below, but the present invention is not limited thereto. EXAMPLES 1 to 19 show the preparation of the organic compounds of the present invention.

Example 1

Synthesis of C1

Synthesis of Intermediate 1a

A mixture of 3-bromo-6-fluoro-2-methoxynaphthalene (5 g, 19.6 mmol), (2-aminophenyl)boronic acid (2.95 g, 21.6 mmol), 30 ml of 2M $Na_2CO_{3(aq)}$, 30 ml of ethanol and 60 ml of toluene was degassed and placed under nitrogen condition, and then $Pd(PPh_3)_4$ (0.45 g, 0.4 mmol) was added and heated at 100° C. for 12 hours. After the reaction was finished, the mixture was cooled to room temperature, and then extracted with ethyl acetate and water. The organic layer dried with anhydrous $MgSO_4$, and then evaporated under reduced pressure. The residue was purified by column chromatography on silica to give Intermediate 1a (3.5 g, 67%) as a white solid.

Synthesis of Intermediate 1b to 1f

Synthesis of Intermediate 1b to 1f was prepared according to the synthesis method of Intermediate 1a.

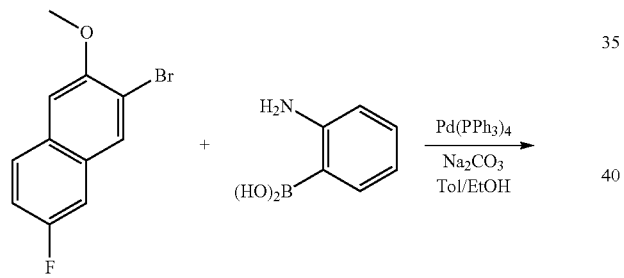

| Reactant structure | | Product structure | Weight Yield |
|---|---|---|---|
| (5 g, 19.6 mmol) | (2.95 g, 21.6 mmol) | 1b | 3.3 g 63% |

-continued
| Reactant structure | Product structure | Weight Yield |
|---|---|---|
| 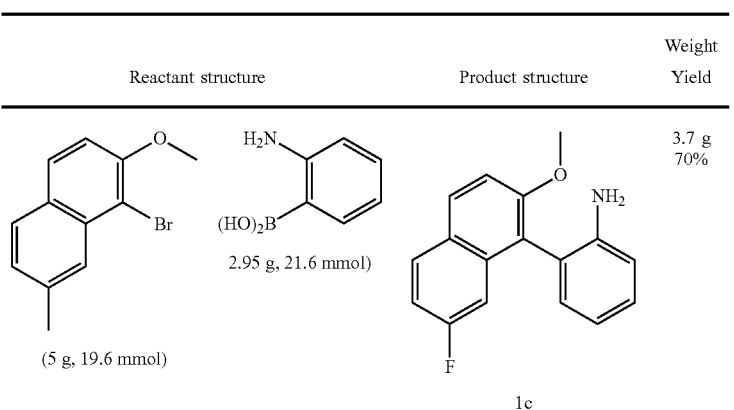 | | 3.7 g 70% |
| 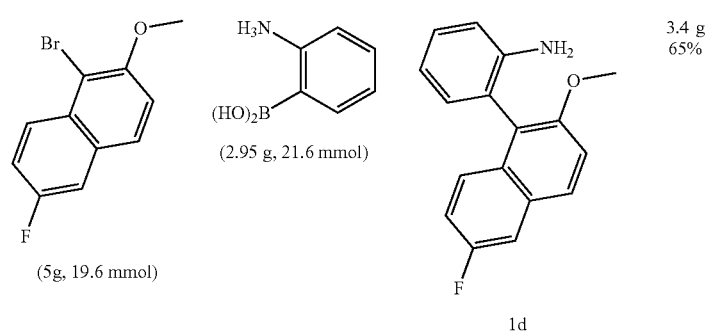 | | 3.4 g 65% |
| 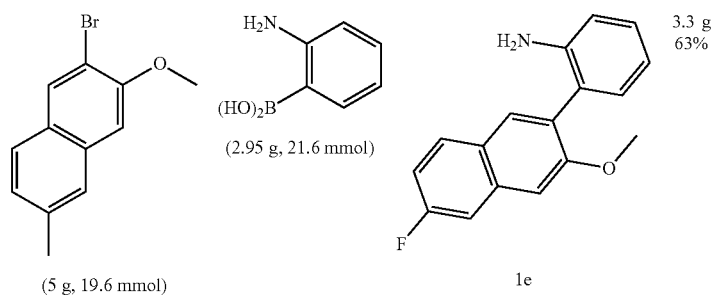 | | 3.3 g 63% |
| 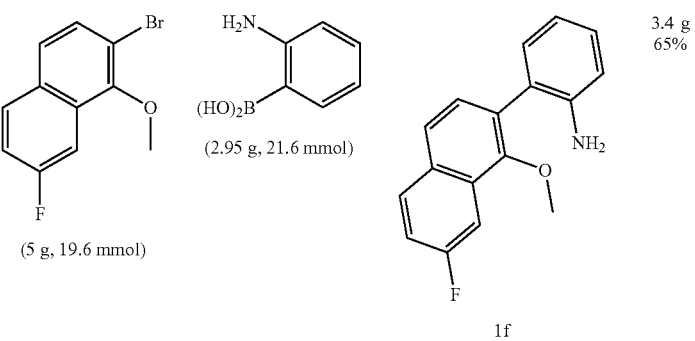 | | 3.4 g 65% |

Synthesis of Intermediate 2a

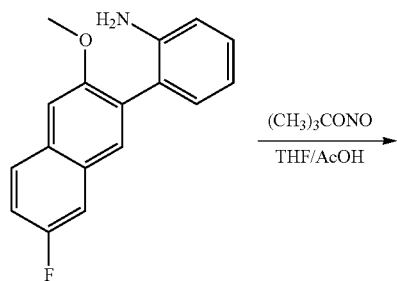

A mixture of Intermediate 1a (7 g, 26.2 mmol), 35 ml of tetrahydrofuran and 70 ml of glacial acetic acid was stirred at −10° C., and then tert-butyl nitrite (8.1 g, 78.6 mmol) was added over a period of 10 minutes. The reaction mixture was stirred at −10° C. for 2 hours, and then warmed to room temperature for 2 hours. The reaction was finished, and then diluted with 200 mL of water. The crude precipitate was purified by column chromatography on silica to afford Intermediate 2a (4 g, 65%) as a white solid.

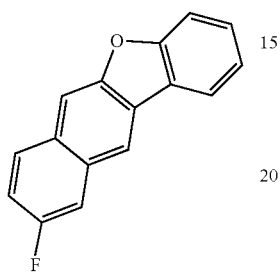

Synthesis of Intermediate 2b to 2f

Synthesis of Intermediate 2b to 2f were according to the synthesis method of Intermediate 2a.

| Reactant structure | Product structure | Weight Yield |
|---|---|---|
| 1b (7 g, 26.2 mmol) | 2b | 4 g 65% |
| 1c (7 g, 26.2 mmol) | 2c | 3.9 g 63% |
| 1d (7 g, 26.2 mmol) | 2d | 4.2 g 68% |

-continued

| Reactant structure | Product structure | Weight Yield |
|---|---|---|
| 1e (7 g, 26.2 mmol) | 2e | 4.2 g 68% |
| 1f | 2f | 4.2 g 65% |

Synthesis of C1

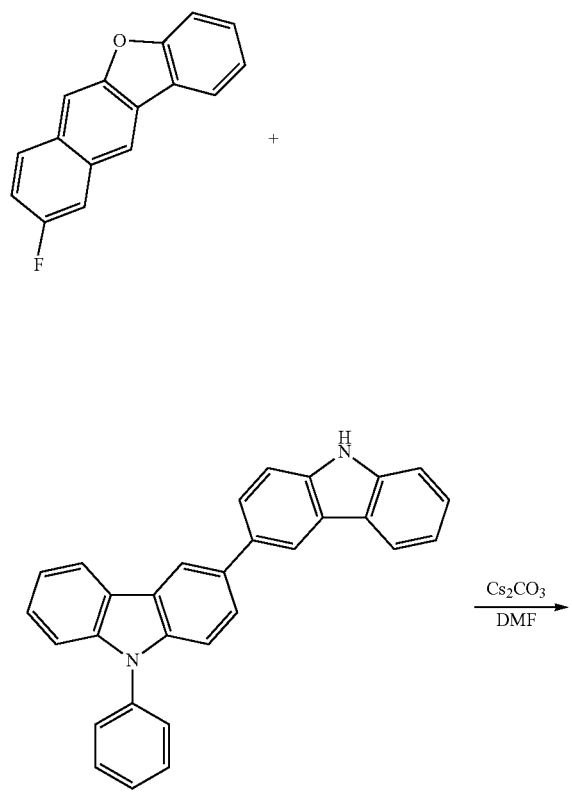

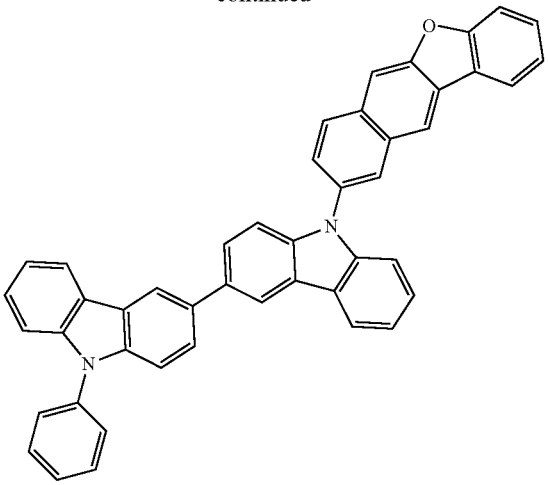

Intermediate 2a (3 g, 12.7 mmol), 9-phenyl-9H,9'H-3,3'-bicarbazole (7.78 g, 19 mmol), cesium carbonate (8.27 g, 25.4 mmol), were add to DMF (40 mL) in 100 mL flask, and the mixture was heated at 153° C. stirred 12 hrs. After cooling to room temperature, the mixture was added to 200 ml water and was filtered to give a solid. The solid was washed with water and MeOH, and then filtered to give compound C1 (5.71 g, 72%) as a yellow solid. MS (m/z, EI+): 624.74.

Example 2 to 12

Synthesis of Compound C2, C3, C7, C9, C17, C49, C51, C53, C57, C59 and C60.

Synthesis of Compound C2, C3, C7, C9, C17, C49, C51, C53, C57, C59 and C60 were prepared according to the synthesis method of Compound C1.
| Reactant structure | | Product structure | Weight Yield |
|---|---|---|---|
| 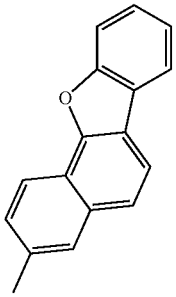 2b (3 g, 12.7 mmol) | 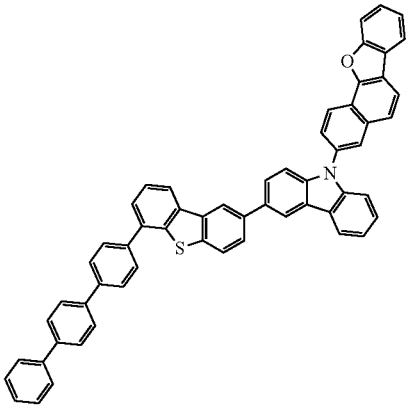 (11 g, 19 mmol) | 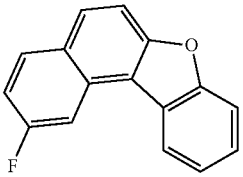 C2 MS (m/z, EI⁺):793.98 | 7.6 g 76% |
| 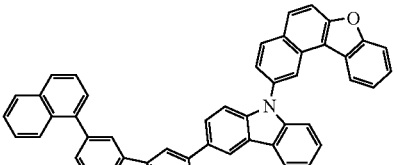 2c (3 g, 12.7 mmol) | (9.06 g, 19 mmol) | C3 MS (m/z, EI⁺):691.85 | 6.2 g 71% |
| 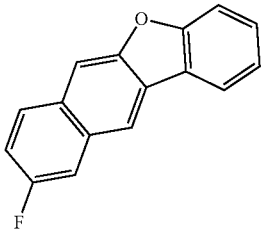 2a (3 g, 12.7 mmol) | 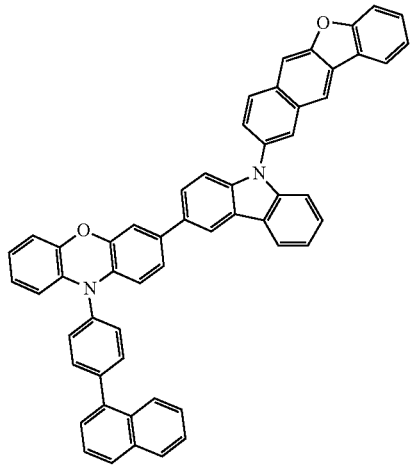 (10.5 g, 19 mmol) | C7 MS (m/z, EI⁺):766.9 | 7.2 g 74% |

-continued

| Reactant structure | Product structure | Weight Yield |
|---|---|---|
| 2c (3 g, 12.7 mmol) / (10.5 g, 19 mmol) | C9<br>MS (m/z, EI⁺):766.9 | 7.5 g<br>77% |
| 2b (3 g, 12.7 mmol) / (7.15 g, 19 mmol) | C17<br>MS (m/z, EI⁺):591.79 | 5.9 g<br>78% |
| 2e (3 g, 12.7 mmol) / (7.78 g, 19 mmol) | C49<br>MS (m/z, EI⁺):624.74 | 6 g<br>76% |

-continued
| Reactant structure | Product structure | Weight Yield |
|---|---|---|
| 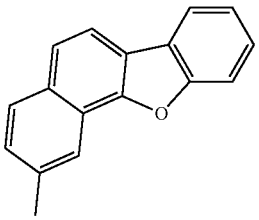<br>2f (3 g, 12.7 mmol)    (8.75 g, 19 mmol) | 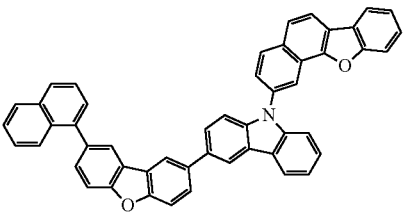<br>C51<br>MS (m/z, EI⁺):675.79 | 6.35 g<br>74% |
| 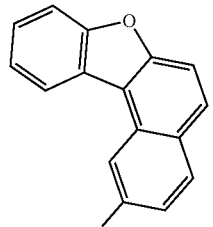<br>2d (3 g, 12.7 mmol)    (7.15 g, 19 mmol) | 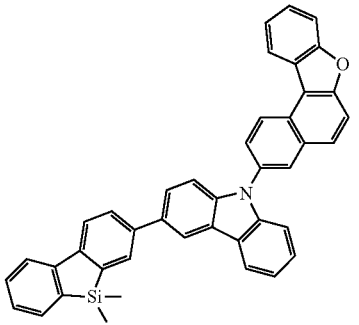<br>C53<br>MS (m/z, EI⁺):591.79 | 5.78 g<br>77% |
| 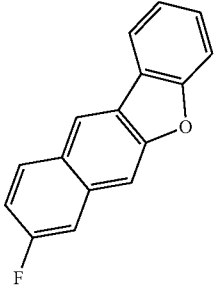<br>2e (3 g, 12.7 mmol)    (10.49 g, 19 mmol) | 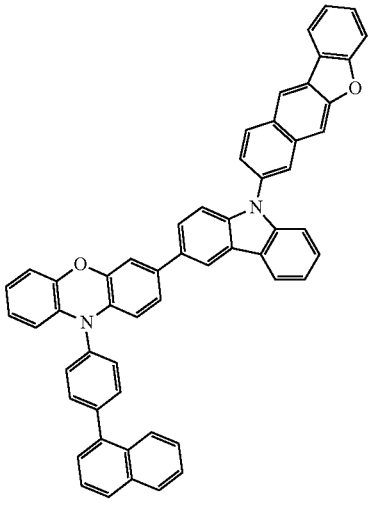<br>C57<br>MS (m/z, EI⁺):766.90 | 7.59 g<br>78% |

| Reactant structure | Product structure | Weight Yield |
|---|---|---|
| 2d (3 g, 12.7 mmol)   (12.22 g, 19 mmol) | C59<br>MS (m/z, EI⁺):858.09 | 8.28 g<br>76% |
| 2f (3 g, 12.7 mmol)   (12.22 g, 19 mmol) | C60<br>MS (m/z, EI⁺):858.09 | 7.84 g<br>72% |

Example 13

Synthesis of C97

Synthesis of Intermediate 3a

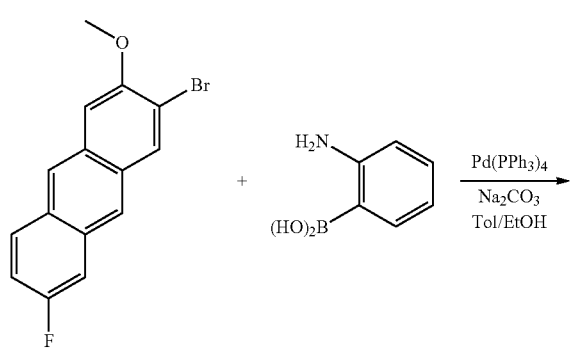

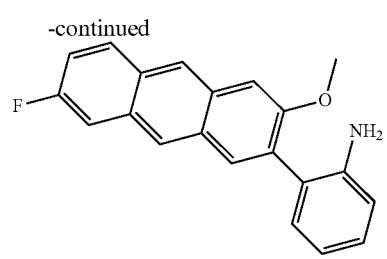

A mixture of 3-bromo-6-fluoro-2-methoxyanthracene (5 g, 16.4 mmol), (2-aminophenyl)boronic acid (2.46 g, 18 mmol), 30 ml of 2M Na₂CO₃₍aq₎, 30 ml of ethanol and 60 ml of toluene was degassed and placed under nitrogen condition, and then Pd(PPha)₄ (0.38 g, 0.33 mmol) was added and heated at 100° C. for 12 hours. After the reaction was finished, the mixture was cooled to room temperature, and then extracted with ethyl acetate and water. The organic layer dried with anhydrous MgSO₄, and then evaporated under reduced pressure. The residue was purified by column chromatography on silica to give Intermediate 1a (3.43 g, 66%) as an off-white solid.

Synthesis of Intermediate 3b to 3f

Synthesis of Intermediate 3b to 3f were according to the synthesis method of Intermediate 3a.

| Reactant structure | Product structure | Weight Yield |
|---|---|---|
| 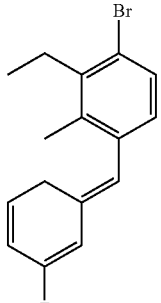<br>(5 g, 16.4 mmol) | 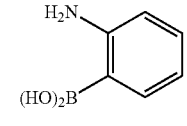 (2.46 g, 18 mmol) | 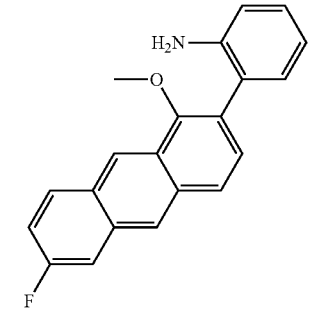<br>3b | 3.38 g<br>65% |
| 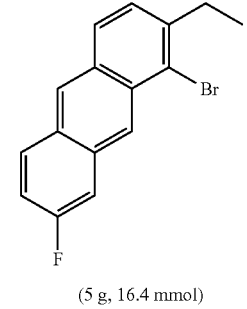 [SMILES: CCc1ccc2cc3ccc(F)cc3cc2c1Br]<br>(5 g, 16.4 mmol) | 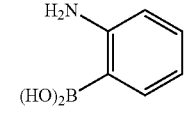 (2.46 g, 18 mmol) | 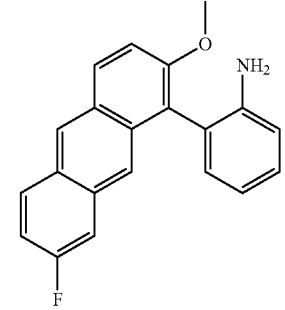<br>3c | 3.06 g<br>59% |
| 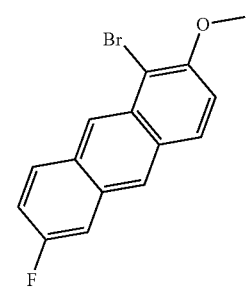<br>(5 g, 16.4 mmol) | 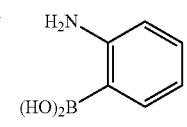 (2.46 g, 18 mmol) | 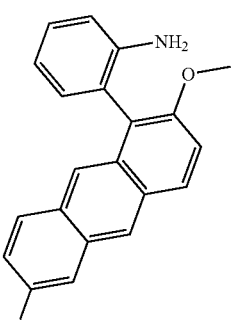<br>3d | 3.48 g<br>67% |
| 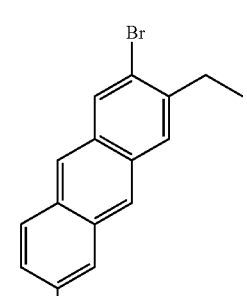<br>(5 g, 16.4 mmol) | 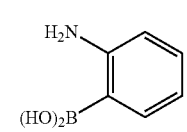 (2.46 g, 18 mmol) | 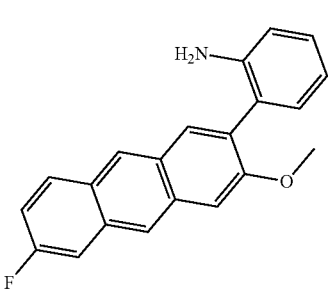<br>3e | 3.3 g<br>63% |

-continued

| Reactant structure | Product structure | Weight Yield |
|---|---|---|
| (5 g, 16.4 mmol) + (HO)₂B-phenyl-NH₂ (2.46 g, 18 mmol) | 3f | 3.32 g 64% |

Synthesis of Intermediate 4a

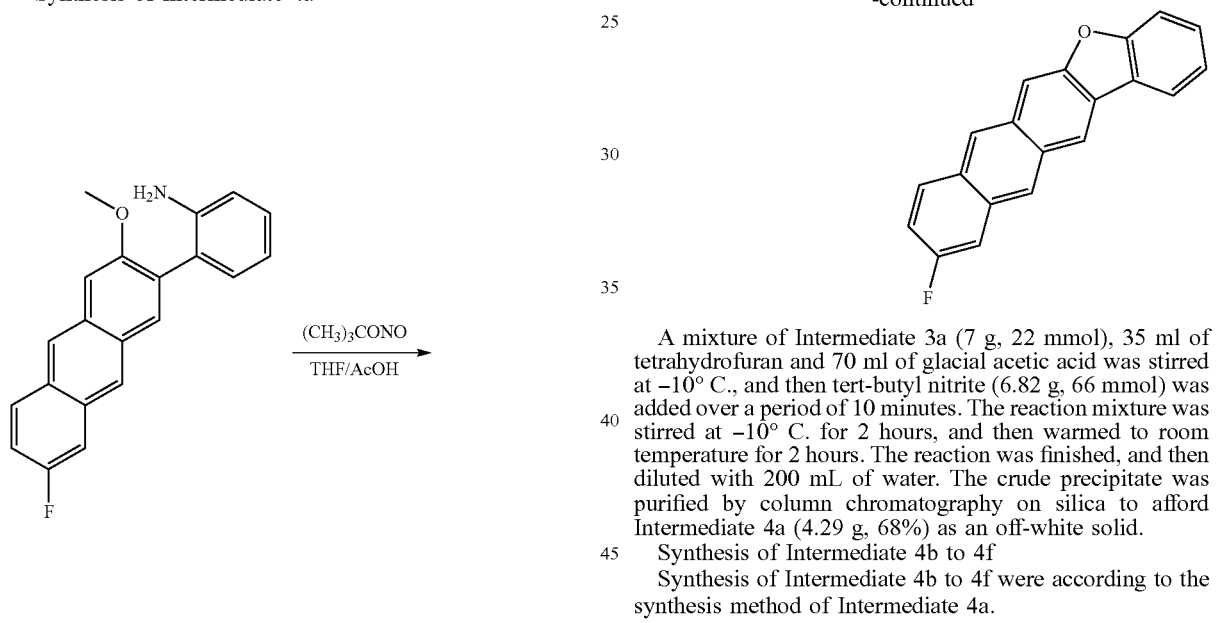

A mixture of Intermediate 3a (7 g, 22 mmol), 35 ml of tetrahydrofuran and 70 ml of glacial acetic acid was stirred at −10° C., and then tert-butyl nitrite (6.82 g, 66 mmol) was added over a period of 10 minutes. The reaction mixture was stirred at −10° C. for 2 hours, and then warmed to room temperature for 2 hours. The reaction was finished, and then diluted with 200 mL of water. The crude precipitate was purified by column chromatography on silica to afford Intermediate 4a (4.29 g, 68%) as an off-white solid.

Synthesis of Intermediate 4b to 4f

Synthesis of Intermediate 4b to 4f were according to the synthesis method of Intermediate 4a.

| Reactant structure | Product structure | Weight Yield |
|---|---|---|
| 3b (7 g, 22 mmol) | 4b | 4.23 g 67% |

-continued

| Reactant structure | Product structure | Weight Yield |
|---|---|---|
| 3C (7 g, 22 mmol) | 4c | 3.9 g 63% |
| 3d (7 g, 22 mmol) | 4d | 4.04 g 64% |
| 3e (7 g, 22 mmol) | 4e | 4 g 63% |
| 3f (7 g, 22 mmol) | 4f | 3.9 g 62% |

Synthesis of C97

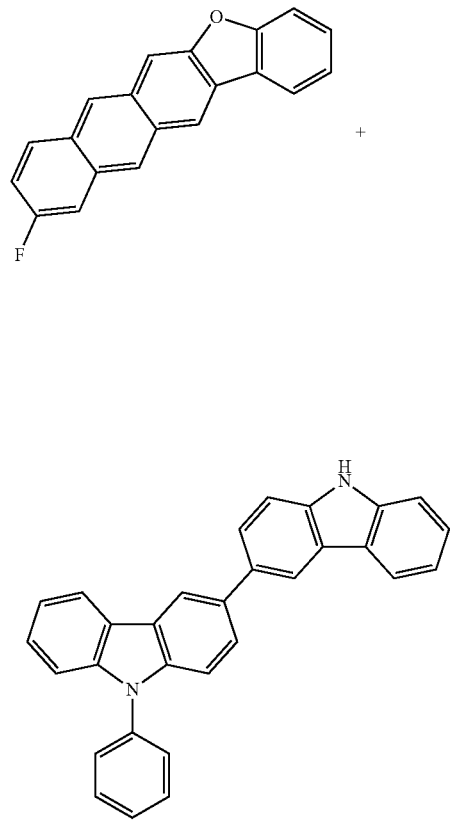

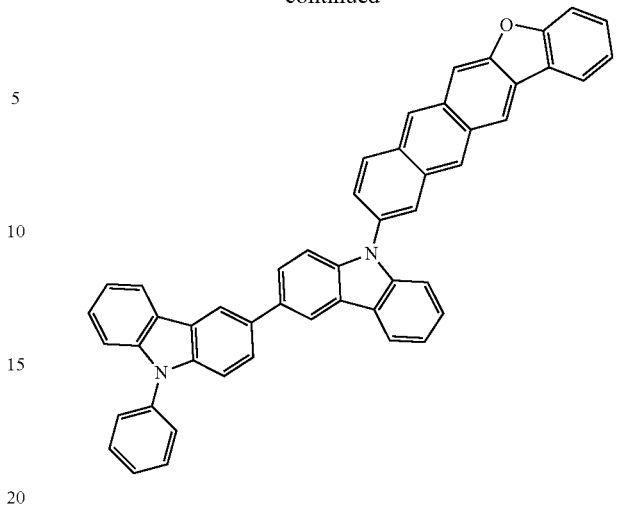

Intermediate 4a (3 g, 9.1 mmol), 9-phenyl-9H,9'H-3,3'-bicarbazole (7.78 g, 13.7 mmol), cesium carbonate (6.83 g, 21 mmol), were add to DMF (40 mL) in 100 mL flask, and the mixture was heated at 153° C. stirred 12 hrs. After cooling to room temperature, the mixture was added to 200 ml water and was filtered to give a solid. The solid was washed with water and MeOH, and then filtered to give compound C97 (4.8 g, 75%) as a yellow solid. MS (m/z, EI$^+$): 674.80.

Example 14 to 18

Synthesis of Compound C98, C105, C145, C147 and C149.

Synthesis of Compound C98, C105, C145, C147 and C149 were prepared according to the synthesis method of Compound C97.

| Reactant structure | Product structure | Weight Yield |
|---|---|---|
| 4b (3 g, 9.1 mmol) ; (7.9 g, 13.7 mmol) | C98  MS (m/z, EI$^+$):767.95 | 6 g 75% |

-continued
| Reactant structure | Product structure | Weight Yield |
|---|---|---|
| 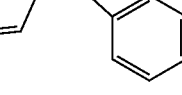 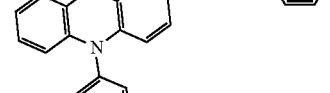 4c (3 g, 9.1 mmol)  (8.7 g, 13.7 mmol) | 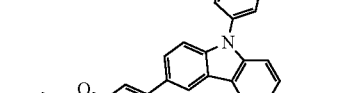 C105 MS (m/z, EI+):816.96 | 6 g 70% |
|  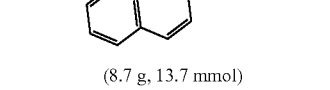 4e (3 g, 9.1 mmol)  (6.8 g, 13.7 mmol) |  C145 MS (m/z, EI+):674.8 | 4.87 g 69% |
| 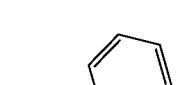  4f (3 g, 9.1 mmol)  (7.3 g, 13.7 mmol) |  C147 MS (m/z, EI+):725.85 | 5.5 g 73% |
| 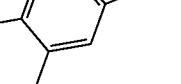 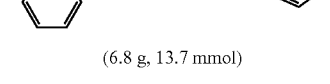 4d (3 g, 9.1 mmol)  (5.9 g, 13.7 mmol) | 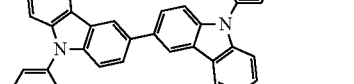 C149 MS (m/z, EI+):641.85 | 5 g 74% |

Example 19

Synthesis of C193

Synthesis of Intermediate 5a

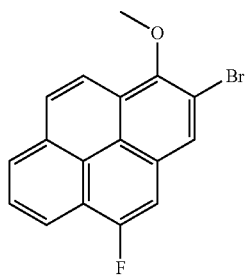

+

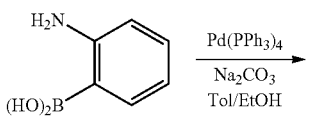

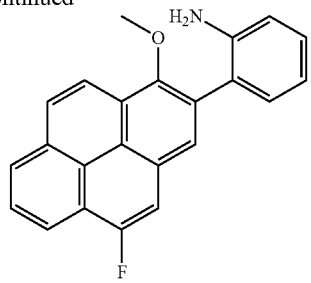

A mixture of 2-bromo-5-fluoro-1-methoxypyrene (5 g, 15.2 mmol), (2-aminophenyl)boronic acid (2.3 g, 16.7 mmol), 30 ml of 2M $Na_2CO_{3(aq)}$, 30 ml of ethanol and 60 ml of toluene was degassed and placed under nitrogen condition, and then $Pd(PPh_3)_4$ (0.35 g, 0.3 mmol) was added and heated at 100° C. for 12 hours. After the reaction was finished, the mixture was cooled to room temperature, and then extracted with ethyl acetate and water. The organic layer dried with anhydrous $MgSO_4$, and then evaporated under reduced pressure. The residue was purified by column chromatography on silica to give Intermediate 5a (3.47 g, 67%) as an off-white solid.

Synthesis of Intermediate 5b to 5g

Synthesis of Intermediate 5b to 5g were according to the synthesis method of Intermediate 5a.

| Reactant structure | | Product structure | Weight Yield |
|---|---|---|---|
| (5 g, 15.2 mmol) | (2.3 g, 16.7 mmol) | 5b | 3.22 g 62% |
| (5 g, 15.2 mmol) | (2.3 g, 16.7 mmol) | 5c | 3.53 g 68% |

-continued
| Reactant structure | | Product structure | Weight Yield |
|---|---|---|---|
| 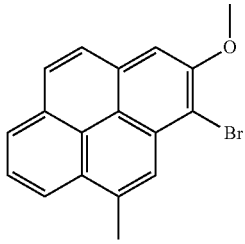 (5 g, 15.2 mmol) | 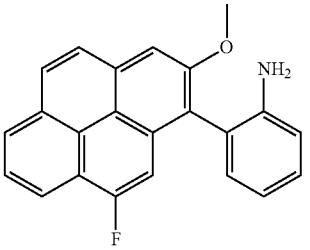 (2.3 g, 16.7 mmol) | 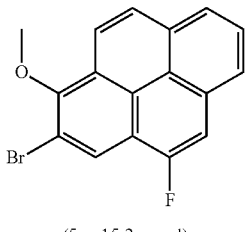 5d | 3.48 g 67% |
| 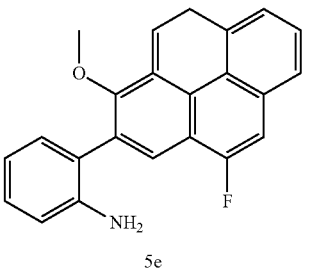 (5 g, 15.2 mmol) | (2.3 g, 16.7 mmol) | 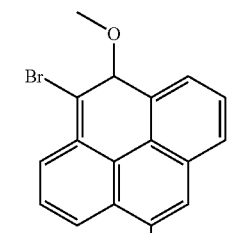 5e | 3.3 g 64% |
| 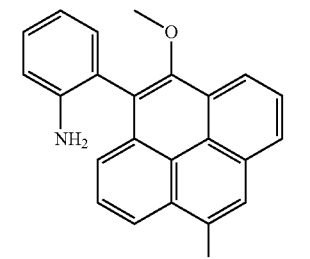 (5 g, 15.2 mmol) | (2.3 g, 16.7 mmol) | 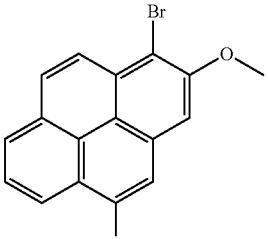 5f | 3.4 g 66% |
| 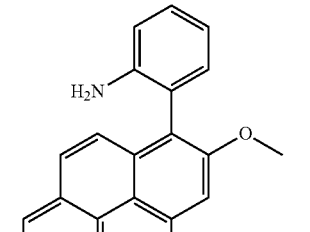 5 g, 15.2 mmol) | (2.3 g, 16.7 mmol) | 5g | 3.4 g 66% |

-continued

| Reactant structure | Product structure | Weight Yield |
|---|---|---|
| 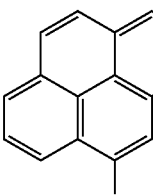 (5 g, 15.2 mmol) 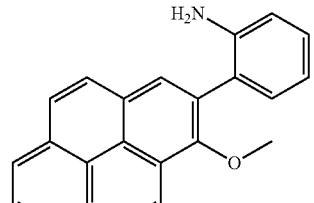 (2.3 g, 16.7 mmol) | 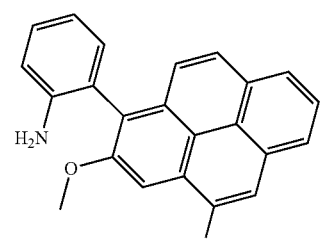 5h | 3.6 g 70% |

Synthesis of Intermediate 6a

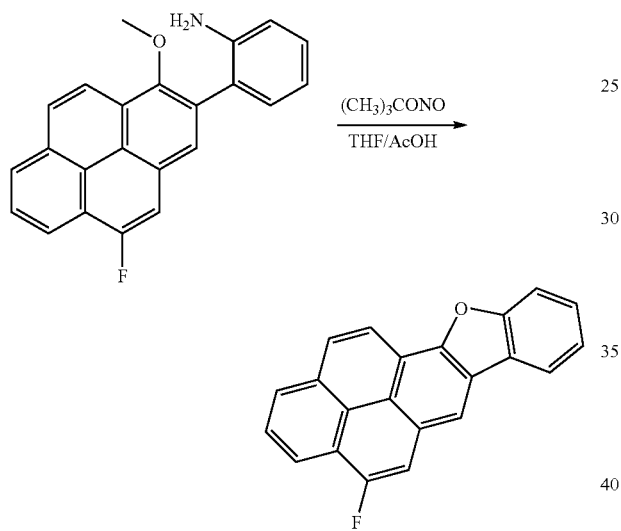

A mixture of Intermediate 5a (7 g, 20 mmol), 35 ml of tetrahydrofuran and 70 ml of glacial acetic acid was stirred at −10° C., and then tert-butyl nitrite (6.34 g, 60 mmol) was added over a period of 10 minutes. The reaction mixture was stirred at −10° C. for 2 hours, and then warmed to room temperature for 2 hours. The reaction was finished, and then diluted with 200 mL of water. The crude precipitate was purified by column chromatography on silica to afford Intermediate 6a (4.4 g, 69%) as an off-white solid.

Synthesis of Intermediate 6b to 6h

Synthesis of Intermediate 6b to 6h were according to the synthesis method of Intermediate 6a.

| Reactant structure | Product structure | Weight Yield |
|---|---|---|
| 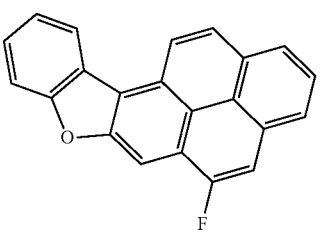 5b (7 g, 20 mmol) | 6b | 4.13 g 65% |

-continued
| Reactant structure | Product structure | Weight Yield |
|---|---|---|
| 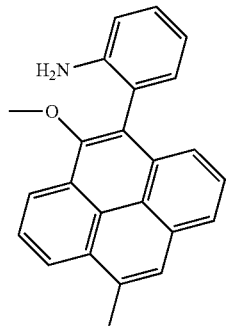<br>5c (7 g, 20 mmol) | 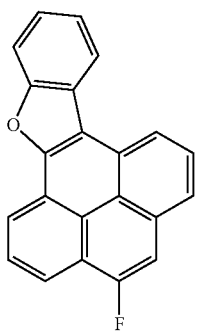<br>6c | 4 g<br>63% |
| 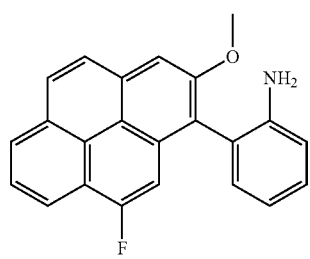<br>5d (7 g, 20 mmol) | 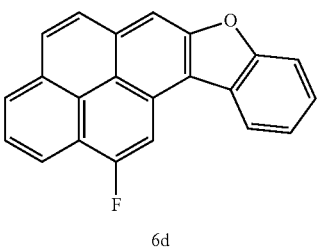 [SMILES: Fc1cc2c3c(cc4ccc5cccc1c5c42)oc1ccccc13]<br>6d | 3.9 g<br>62% |
| 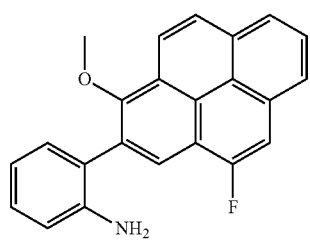<br>5e (7 g, 20 mmol) | 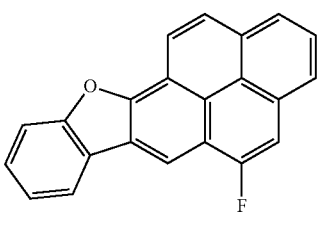<br>6e | 4.3 g<br>68% |
| 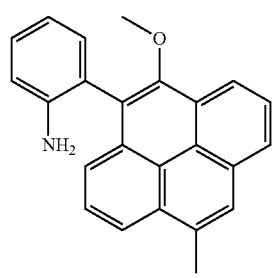<br>5f (7 g, 20 mmol) | 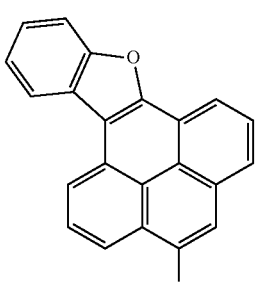<br>6f | 4.4 g<br>70% |

207

-continued

| Reactant structure | Product structure | Weight Yield |
|---|---|---|
| 5g (7 g, 20 mmol) | 6g | 3.9 g 61% |
| 5h (7 g, 20 mmol) | 6h | 4.3 g 68% |

Synthesis of C193

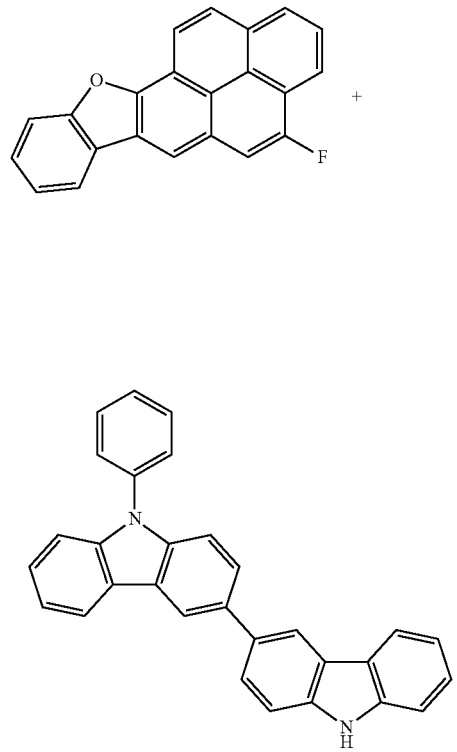

208

-continued

Intermediate 6a (3 g, 9.7 mmol), 9-phenyl-9H,9'H-3,3'-bicarbazole (5.9 g, 14.5 mmol), cesium carbonate (6.3 g, 19.3 mmol), were add to DMF (40 mL) in 100 mL flask, and the mixture was heated at 153° C. stirred 12 hrs. After cooling to room temperature, the mixture was added to 200 ml water and was filtered to give a solid. The solid was washed with water and MeOH, and then filtered to give compound C193 (5 g, 74%) as a yellow solid. MS (m/z, EI+): 698.83

Synthesis of Compound C193, C195, C197, C201, C241, C245, C246 and C251.
Synthesis of Compound C193, C195, C197, C201, C241, C245, C246 and C251 were prepared according to the synthesis method of Compound C193.
| Reactant structure | | Product structure | Weight Yield |
|---|---|---|---|
| 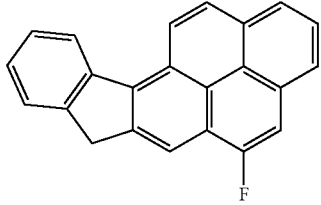<br>6b (3 g, 9.7 mmol) | 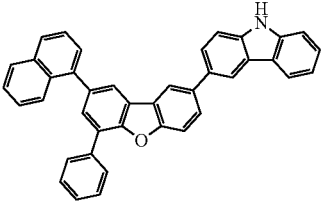<br>(7.8 g, 14.5 mmol) | 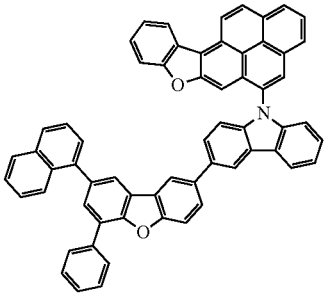<br>C195<br>MS (m/z, EI⁺):825.97 | 5.6 g<br>70% |
| 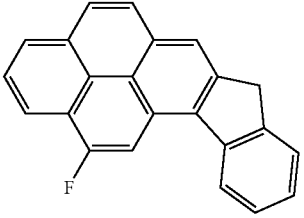<br>6d (3 g, 9.7 mmol) | 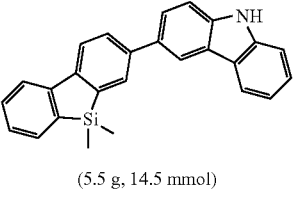<br>(5.5 g, 14.5 mmol) | 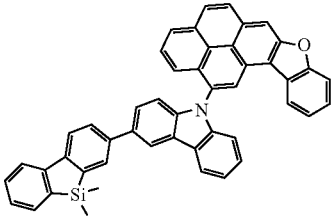<br>C197<br>MS (m/z, EI⁺):665.87 | 4.7 g<br>73% |
| 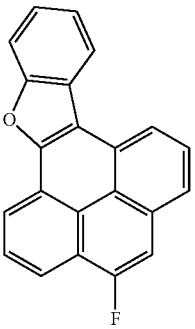<br>6c (3 g, 9.7 mmol) | 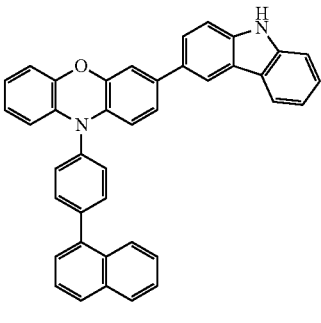<br>(8 g, 14.5 mmol) | 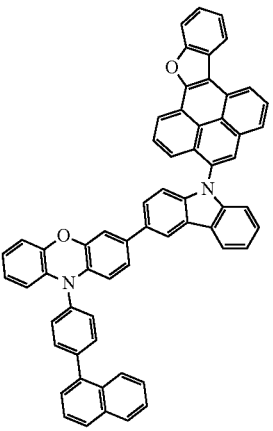<br>C201<br>MS (m/z, EI⁺):840.98 | 5.3 g<br>65% |

-continued
| Reactant structure | Product structure | Weight Yield |
|---|---|---|
| 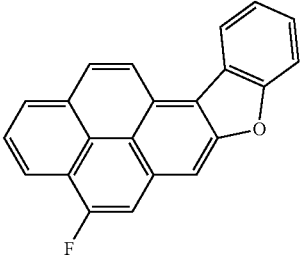 6g (3 g, 9.7 mmol)    (5.9 g, 14.5 mmol) | 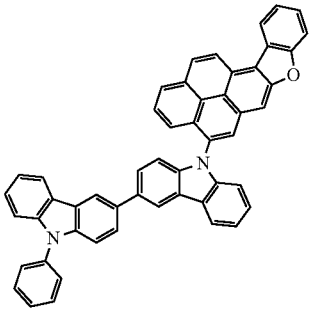 C241 MS (m/z, EI$^+$):698.83 | 4.8 g 71% |
| 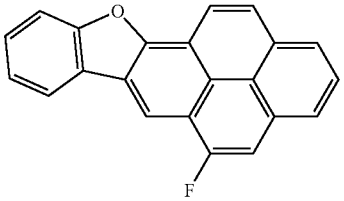 6e (3 g, 9.7 mmol)    (5.5 g, 14.5 mmol) | 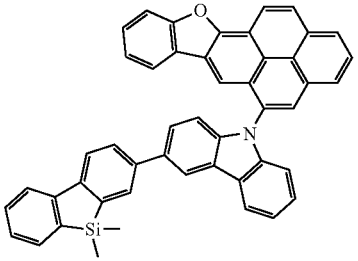 C245 MS (m/z, EI$^+$):665.87 | 4.7 g 73% |
| 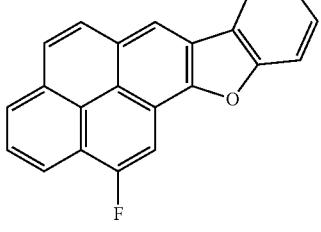 6h (3 g, 9.7 mmol)    (6.2 g, 14.5 mmol) | 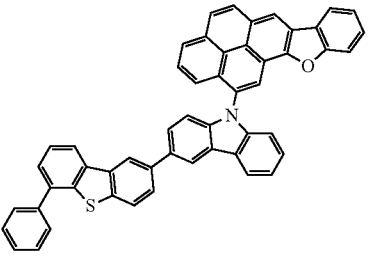 C246 MS (m/z, EI$^+$):715.87 | 4.5 g 65% |
| 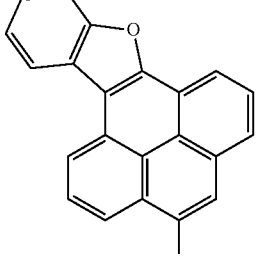 6f (3 g, 9.7 mmol)    (9.4 g, 14.5 mmol) | 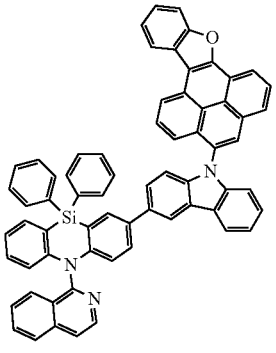 C251 MS (m/z, EI$^+$):932.17 | 56 g 66% |

It is understood that the various embodiments described herein are by way of example only, and are not intended to limit the scope of the invention.

For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. An organic compound represented by the following formula (1):

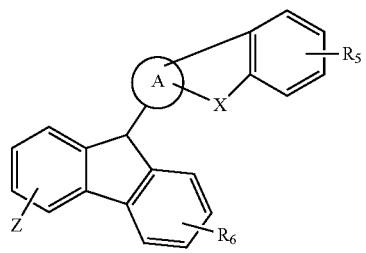

wherein X represents a divalent bridge selected from the group consisting of O, S, $NAr_1$, $CR_1R_2$ and $SiR_3R_4$; ring A represents a fused ring hydrocarbon unit with two to four rings; $R_1$ to $R_6$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms; $Ar_1$ represents a substituted or unsubstituted aryl group having 6 to 30 carbon atoms; Z is represented by the following formula:

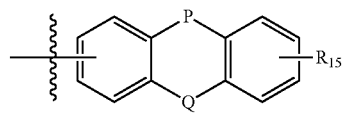

wherein Q represents a divalent bridge selected from the group consisting of O, S, $NAr_2$, $CR_7R_8$ and $SiR_9R_{10}$; P is a single bond or a divalent bridge selected from the group consisting of O, S, $NAr_3$, $CR_{11}R_{12}$, $SiR_{13}R_{14}$; wherein at least one of P and Q is $NAr_3$ if P is not a single bond; $Ar_2$ and $Ar_3$ independently represent a substituted or unsubstituted aryl group having 6 to 30 carbon atoms; $R_7$ to $R_{15}$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms.

2. The organic compound according to claim 1, wherein the organic compound is represented by one of the following formula (4) to formula (9):

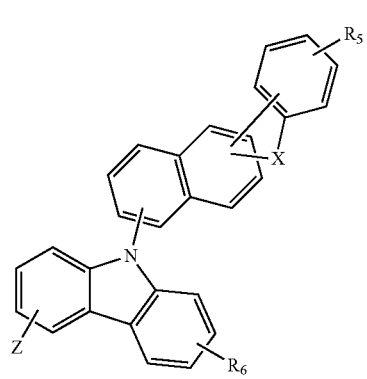
formula (4)

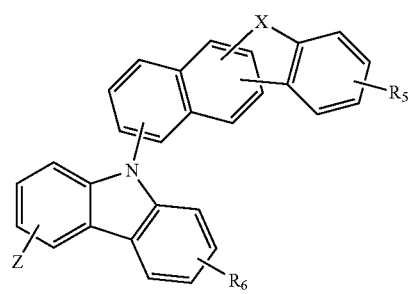
formula (5)

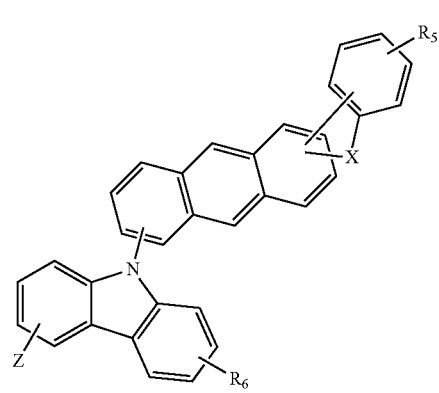
(formula 6)

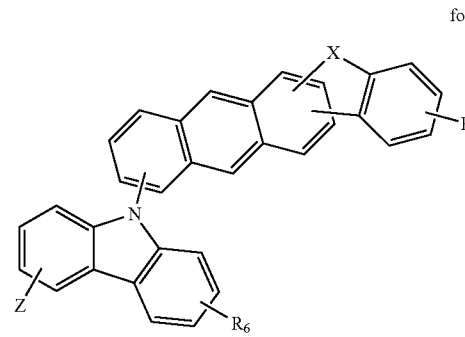
formula (7)

formula (8)
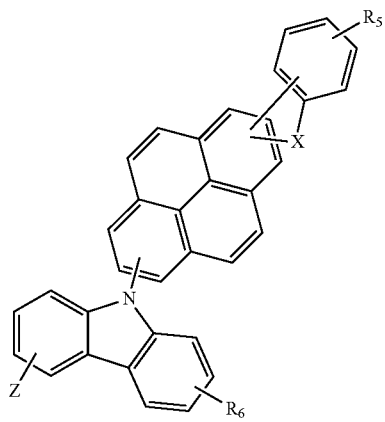
(formula 9)
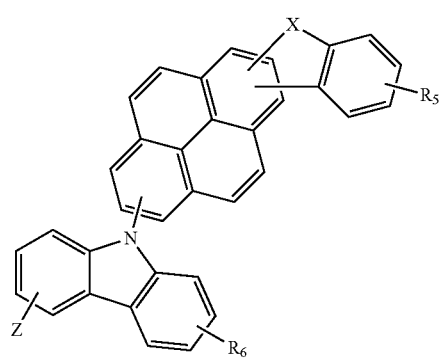
3. The organic compound according to claim 1, wherein the organic compound is represented by one of the following formula (10) to formula (29):
formula (10)
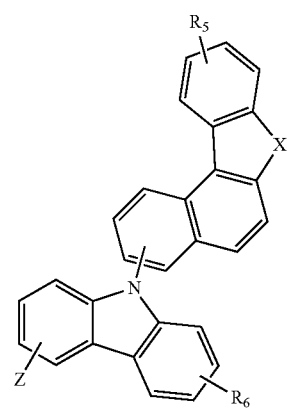
formula (11)
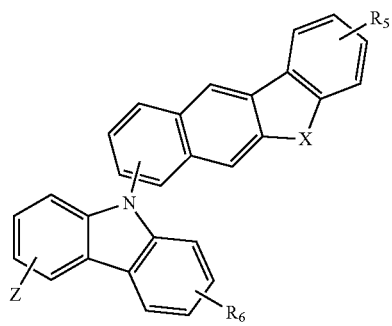
formula (12)
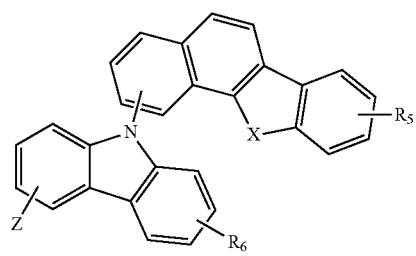
formula (13)
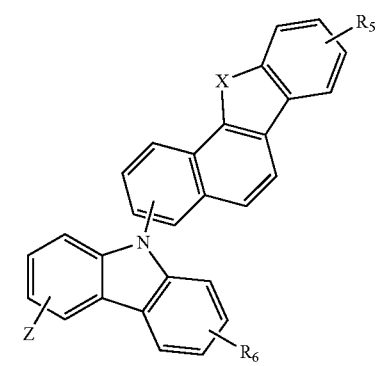
formula (14)
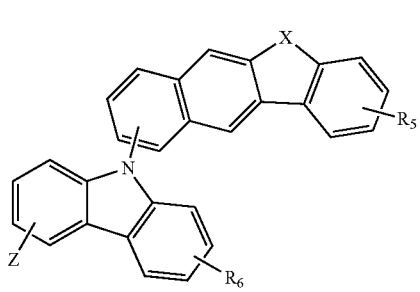
formula (15)
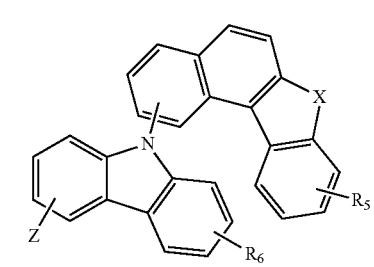

formula (16)
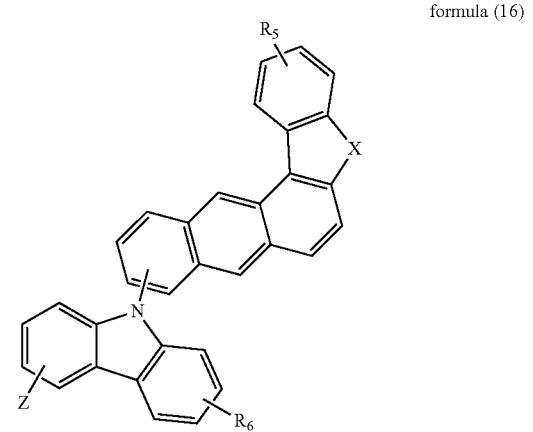
formula (17)
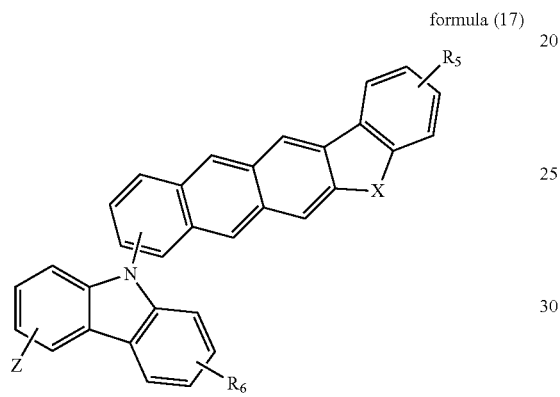
formula (18)
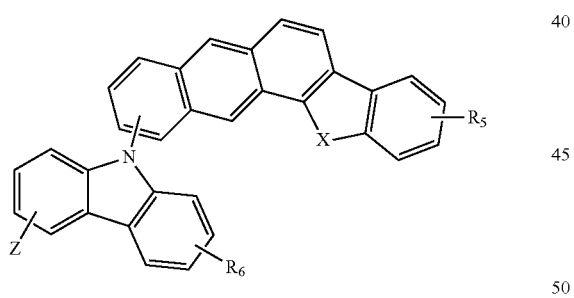
formula (19)
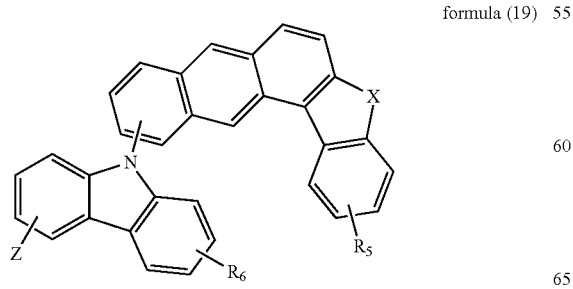
formula (20)
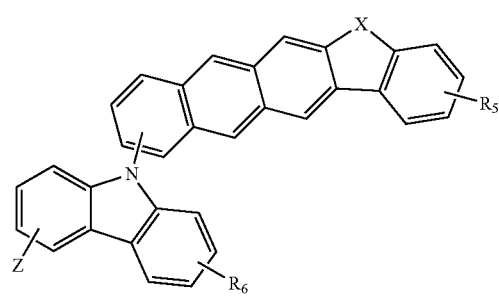
formula (21)
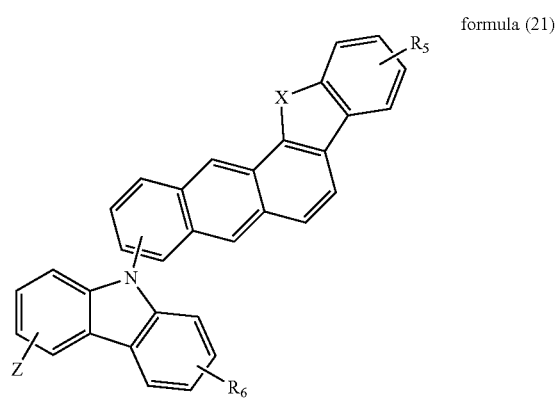
formula (22)
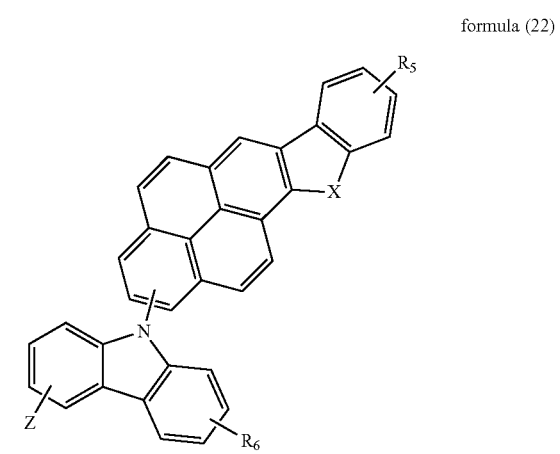
formula (23)
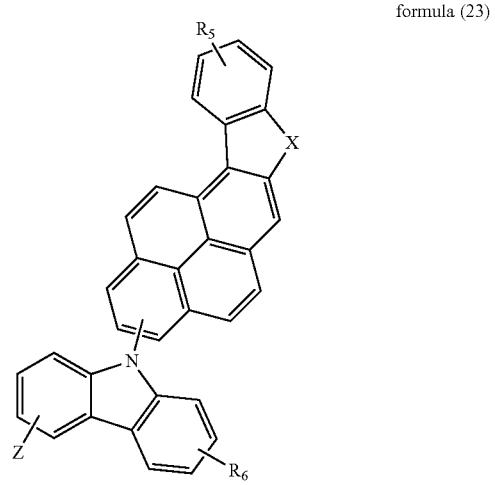

-continued formula (24)
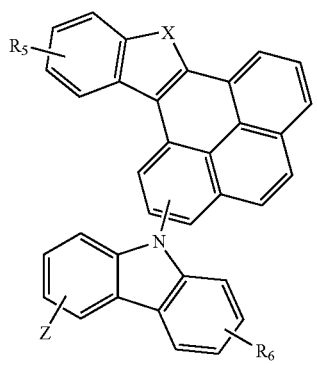

formula (25)
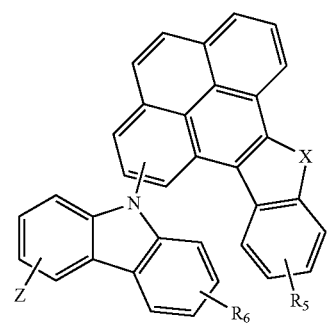

formula (26)
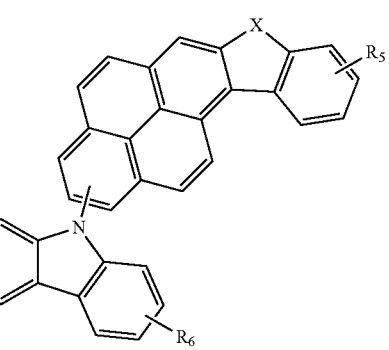

formula (27)
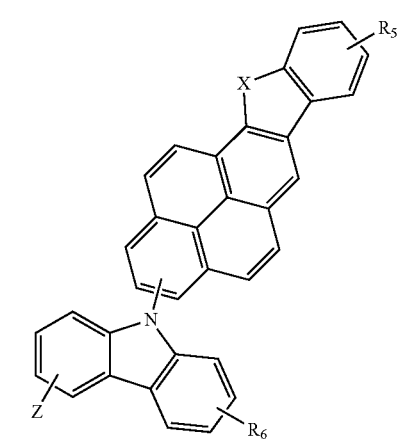

-continued formula (28)
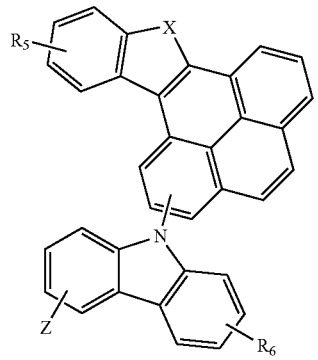

formula (29)
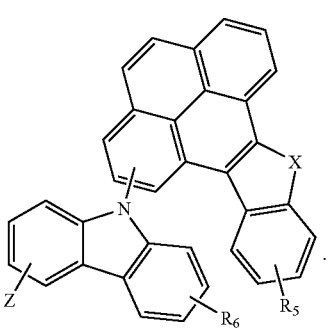

4. The organic compound according to claim 1, wherein the alkyl group, aralkyl group, the aryl group, the heteroaryl group, the arylamine group, or the heteroarylamine group is substituted by a halogen, an alkyl group, an aryl group, or a heteroaryl group.

5. The organic compound according to claim 1, wherein $Ar_1$ represents a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted triphenylenyl group.

6. The organic compound according to claim 1, wherein $Ar_1$ represents one of the following substituents:

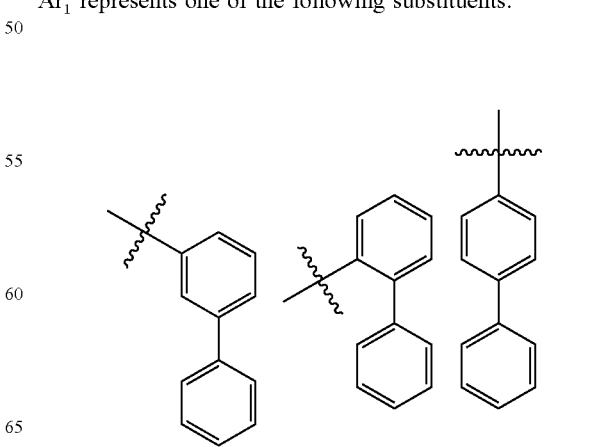

221
-continued
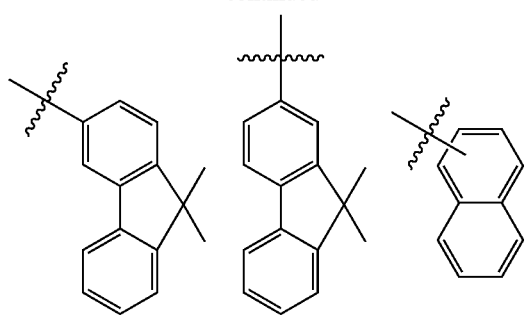
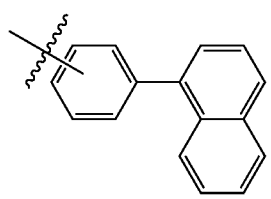
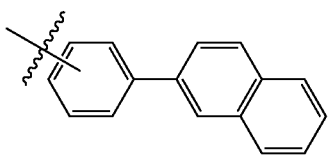
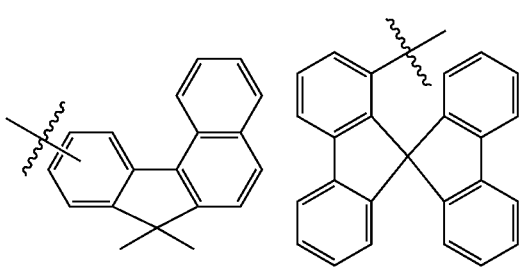
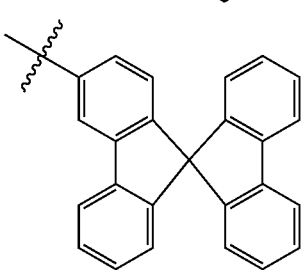
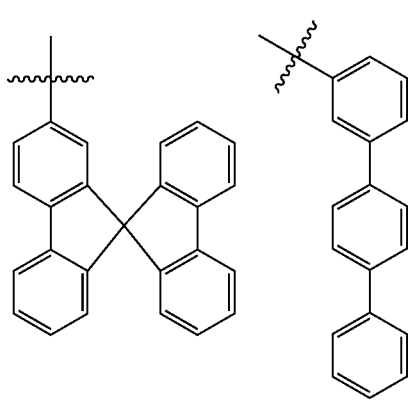
222
-continued
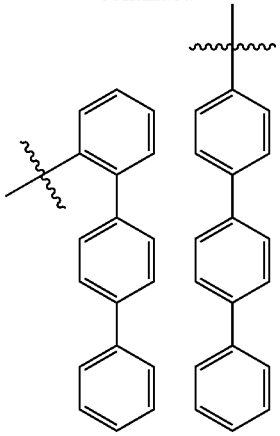
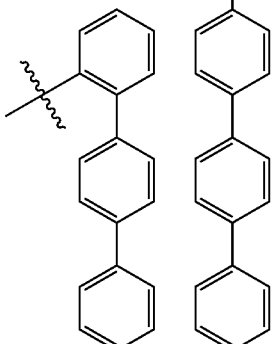
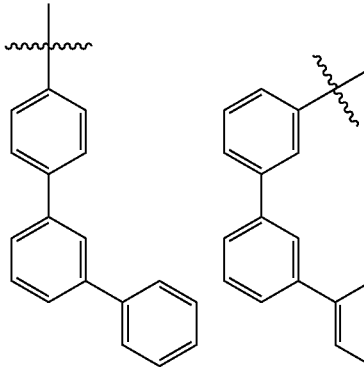
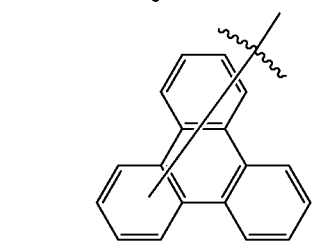
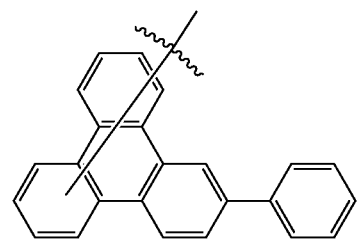
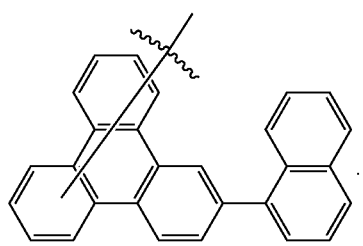
7. The organic compound according to claim 1, wherein the organic compound has one of the following formulas:

223 224
C1
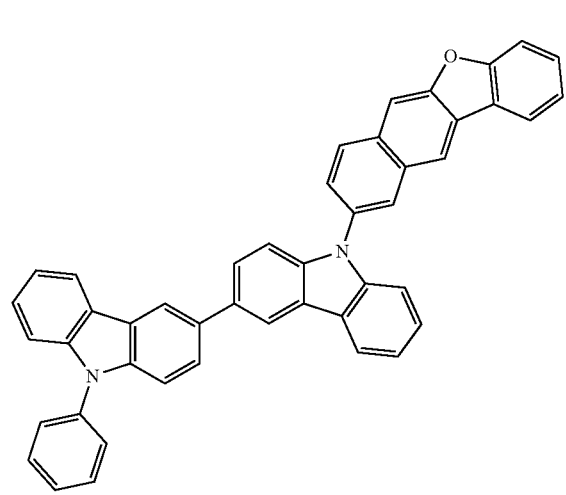
C2
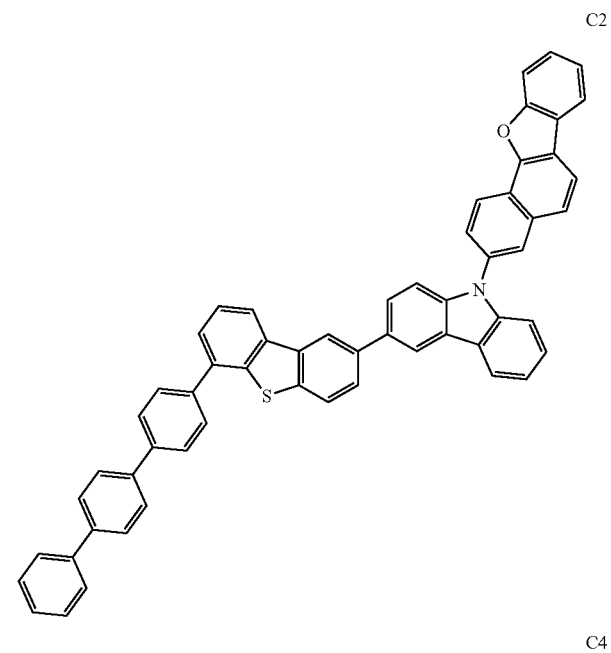
C3
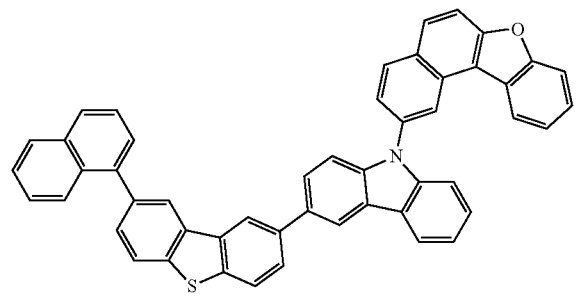
C4
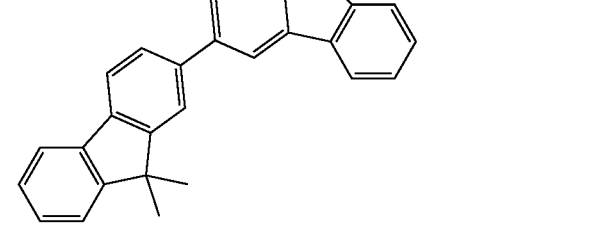
C5
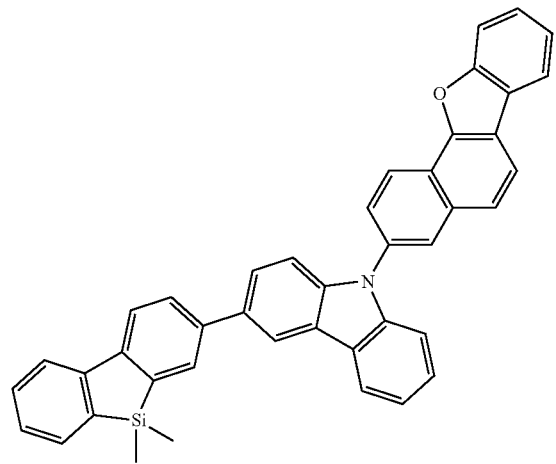
C6
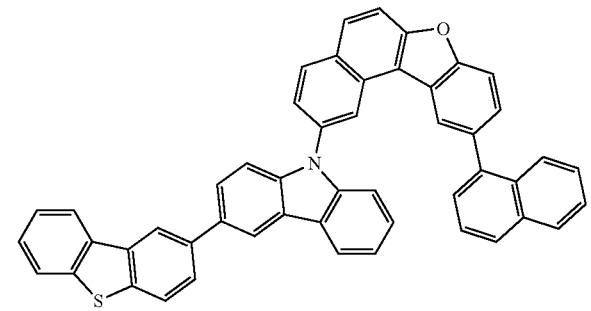

-continued
C7
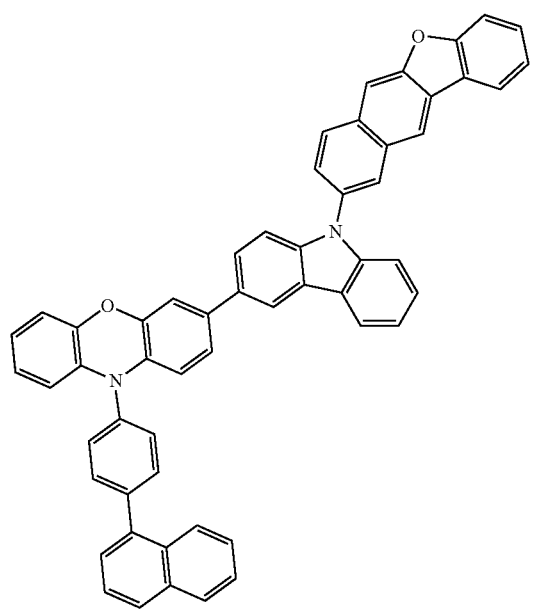
C8
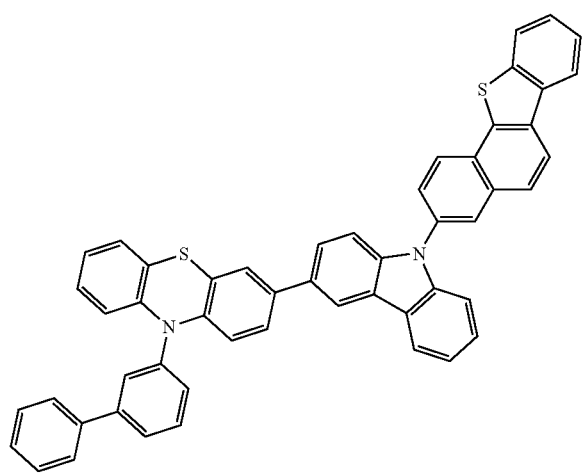
C9
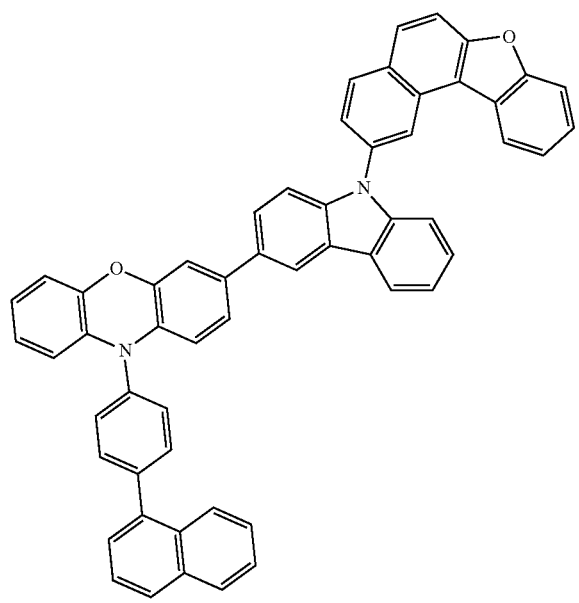
C10
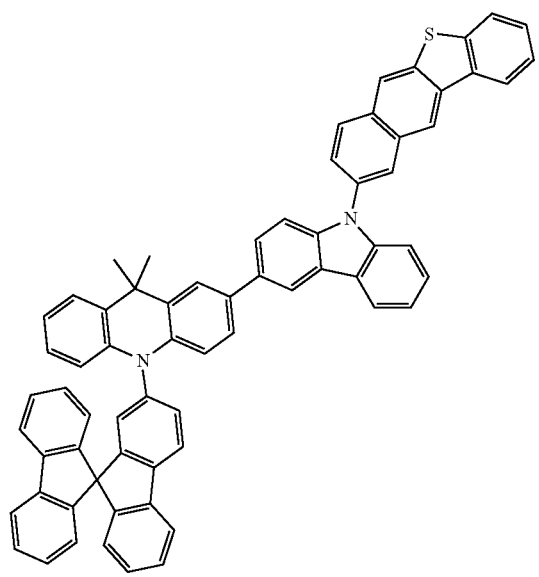

-continued
C11
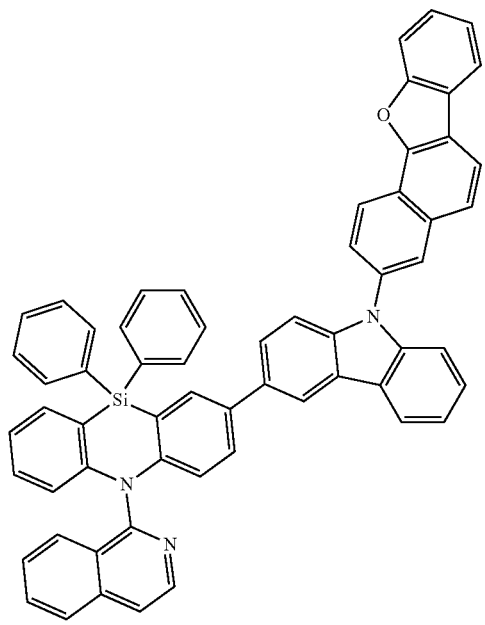
C12
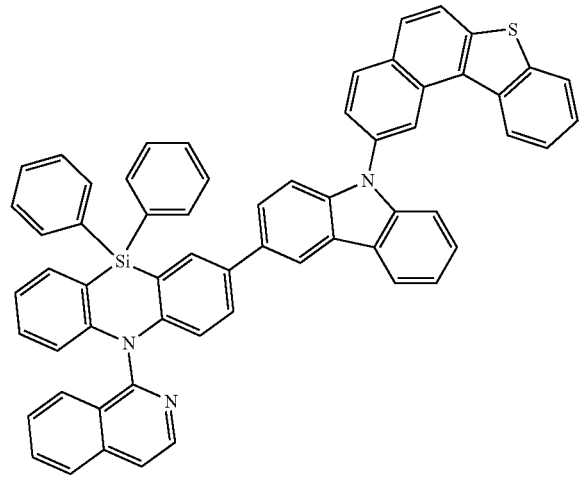
C13
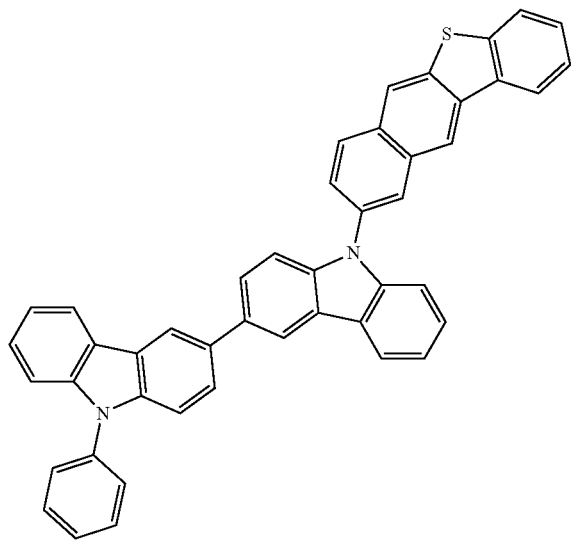
C14
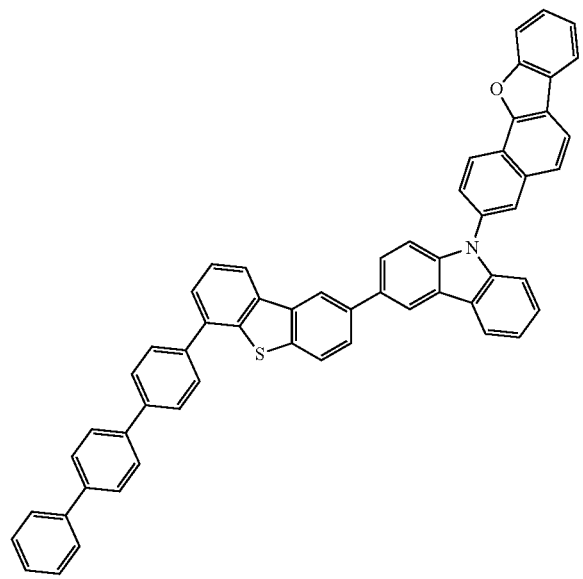

-continued
C15
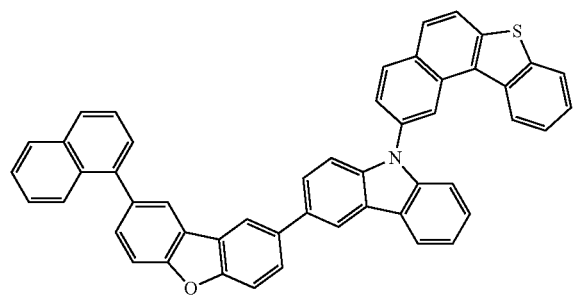
C16
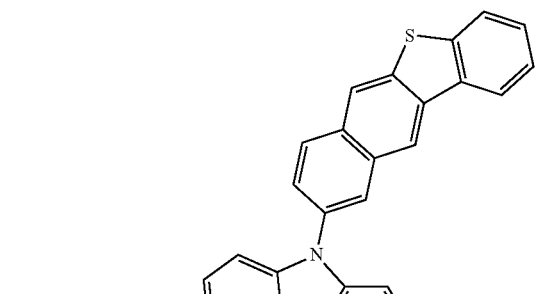
C17
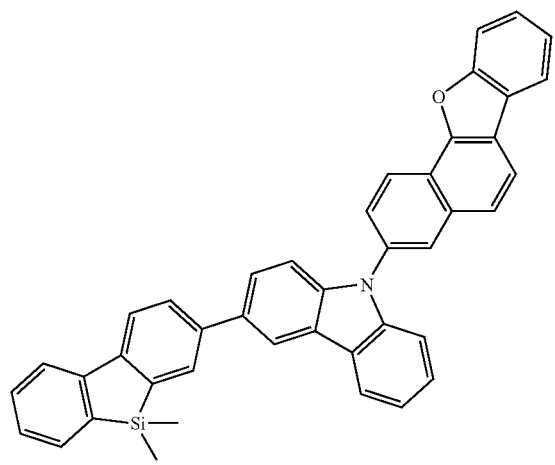
C18
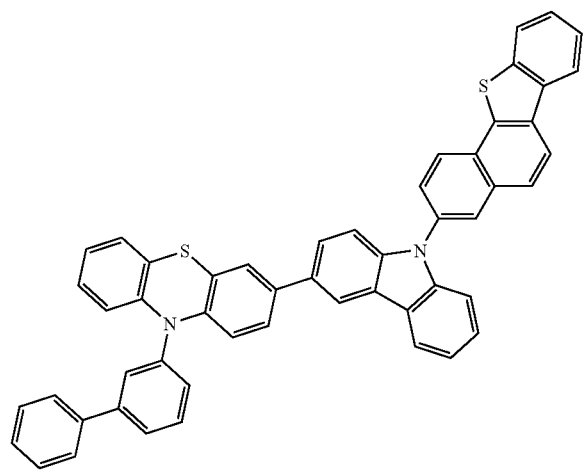
C19
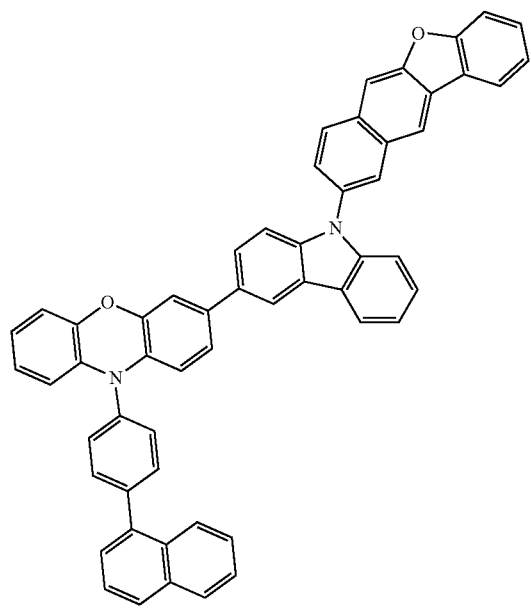
C20

-continued
C21
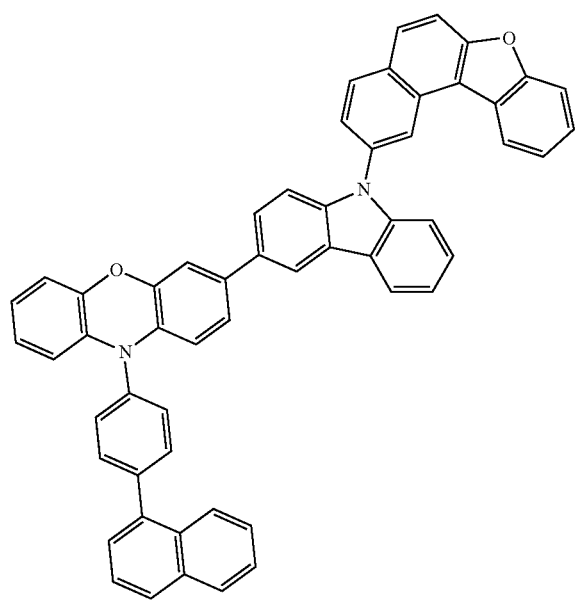
C22
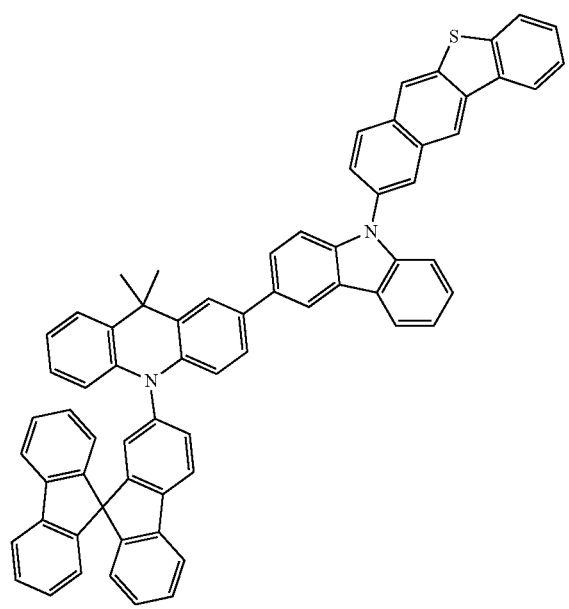
C23
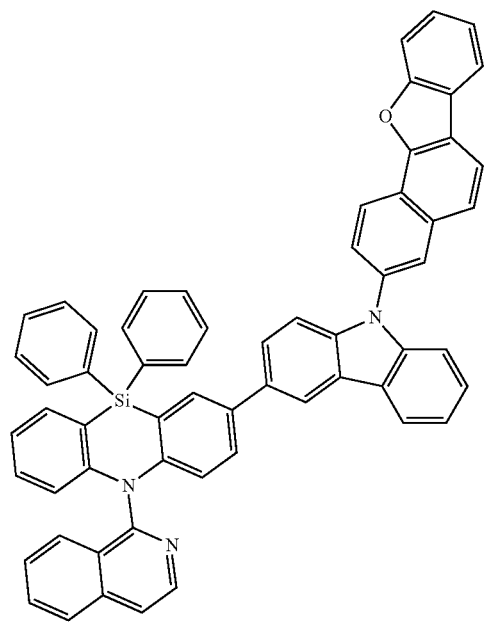
C24
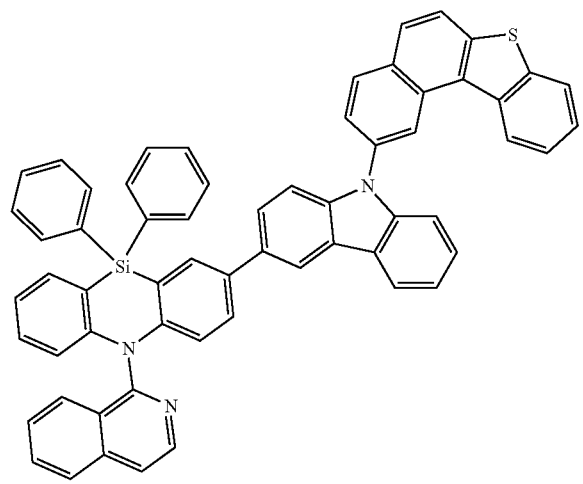

-continued
C25
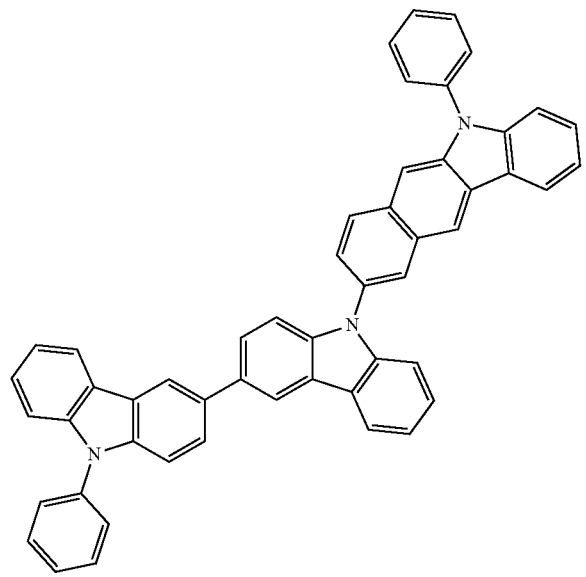
C26
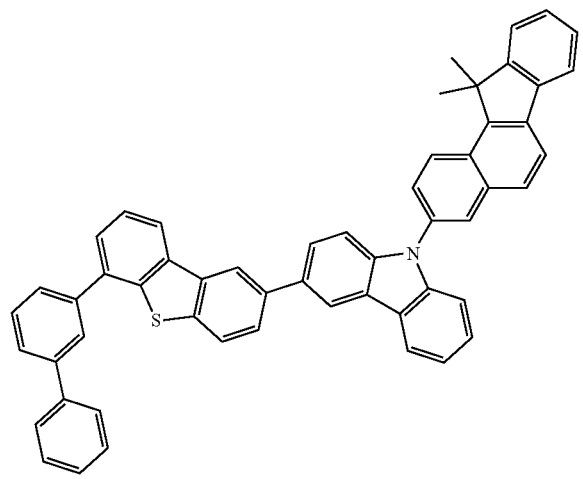
C27
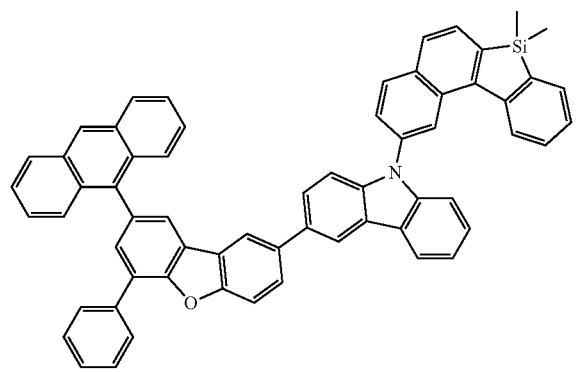
C28
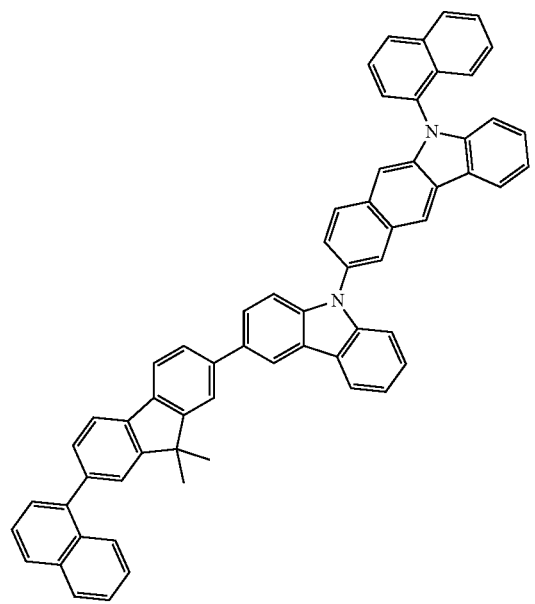

-continued
C29
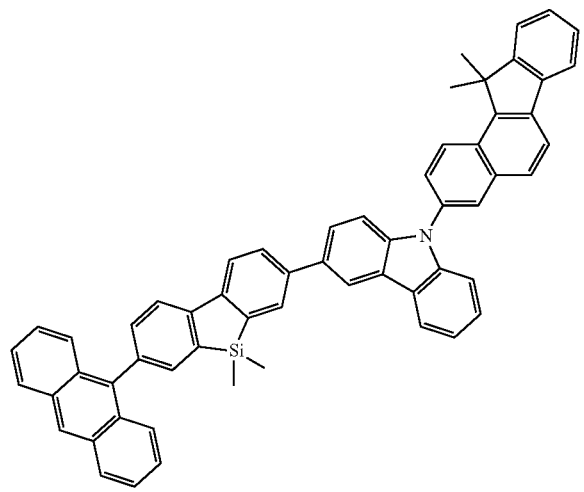
C30
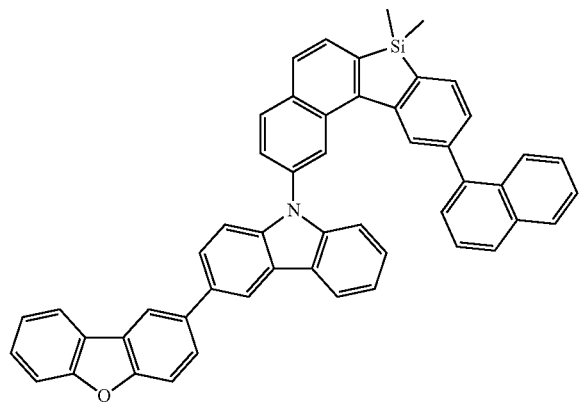
C31
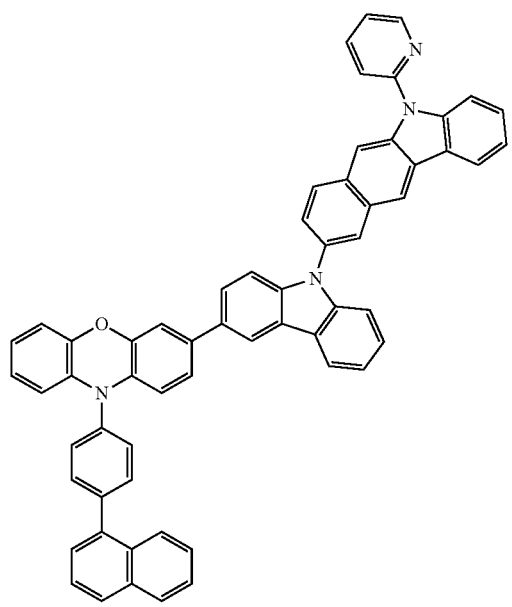
C32
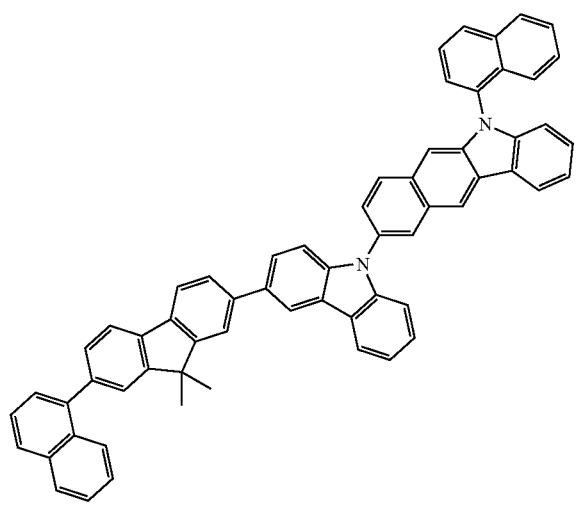

-continued
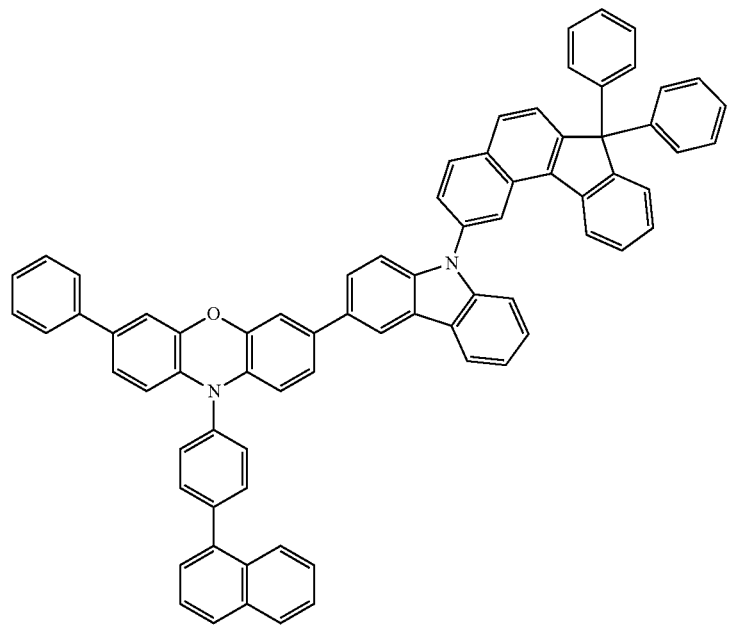
C33
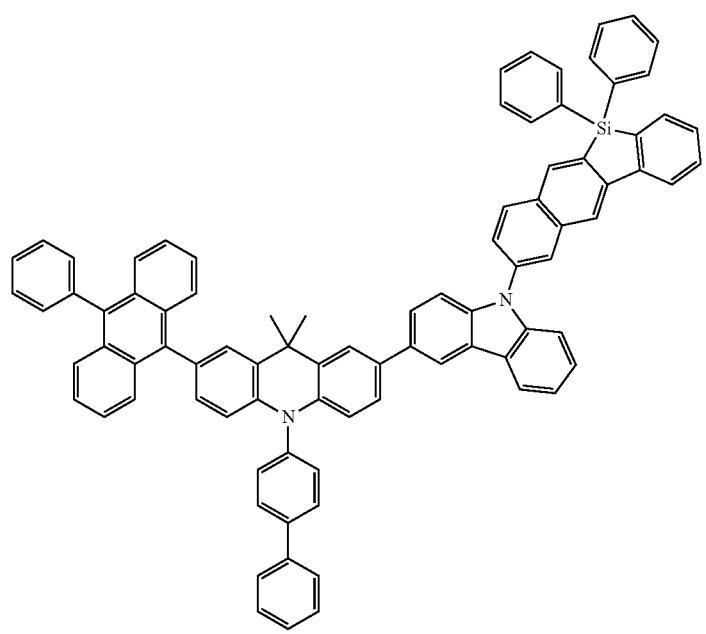
C34

-continued
C35
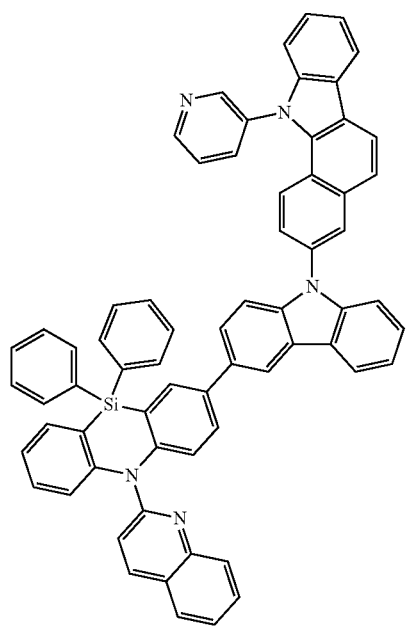
C36
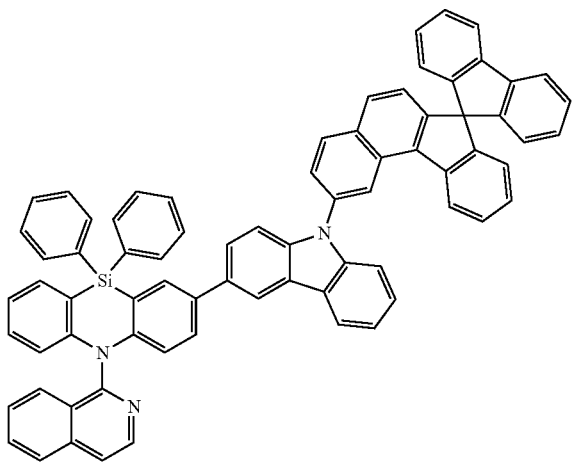
C37
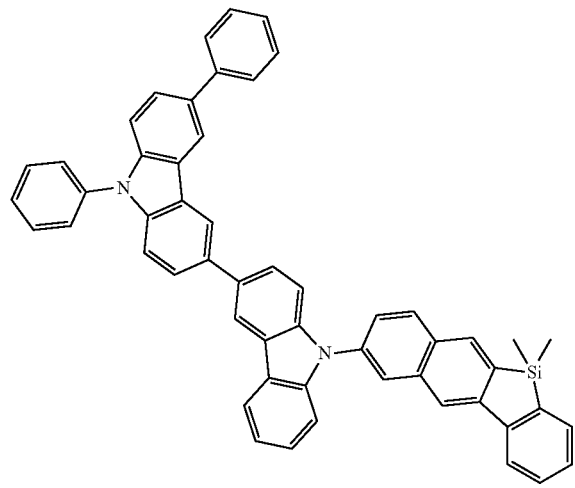
C38
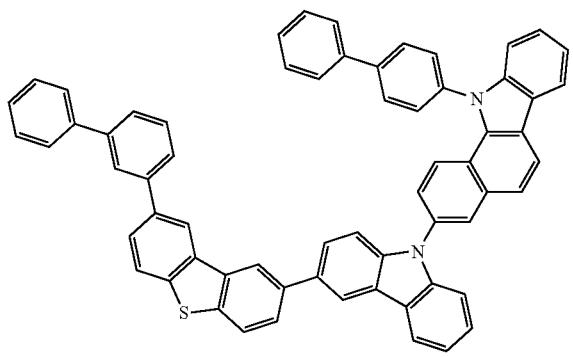

-continued

C39 C40

C41 C42

C43
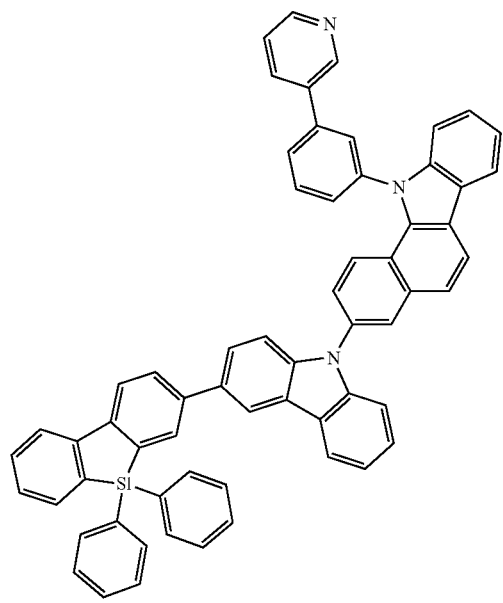
C44
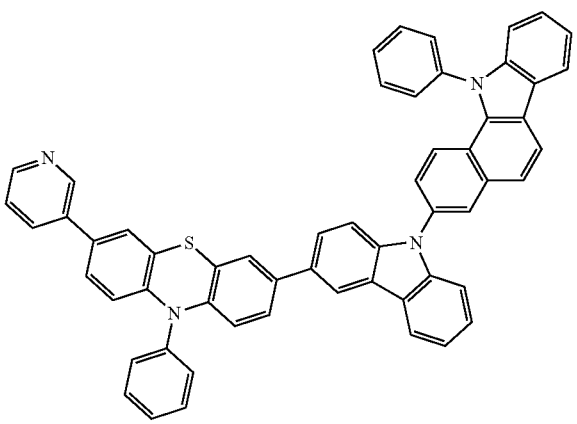
C45
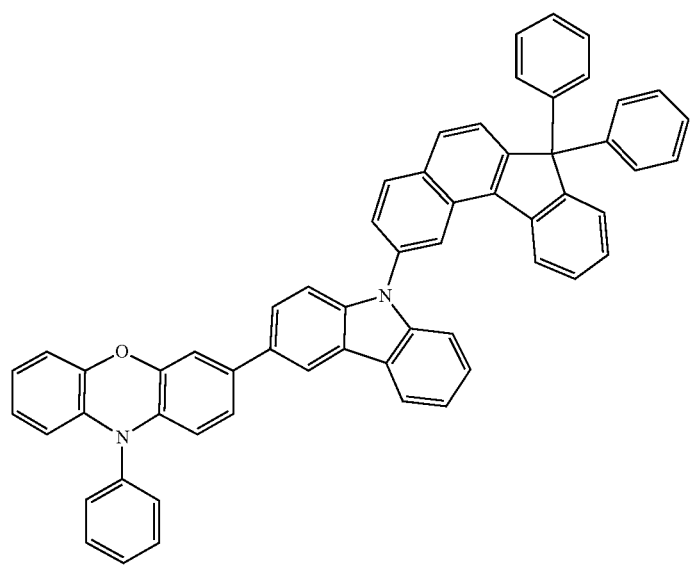

-continued
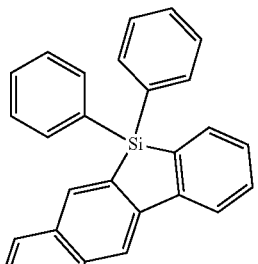
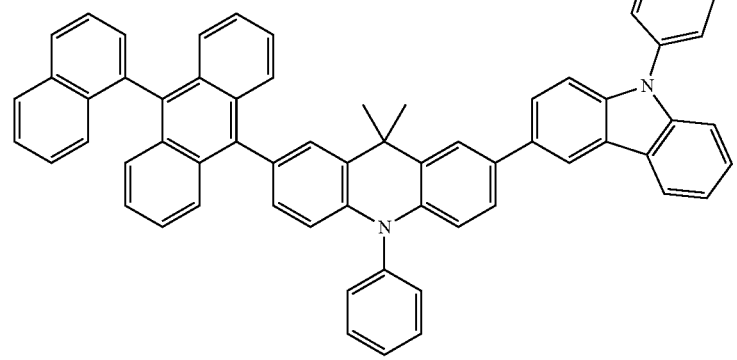
C46
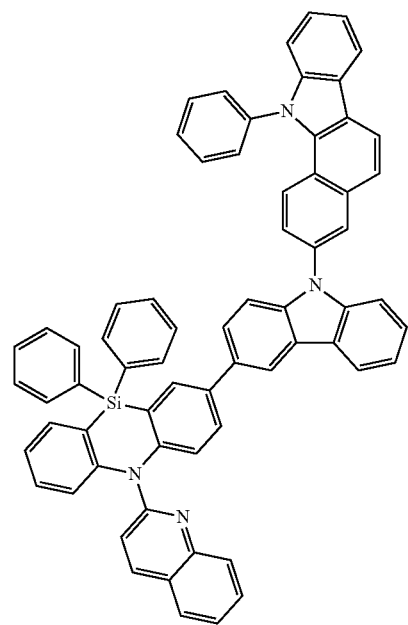
C47
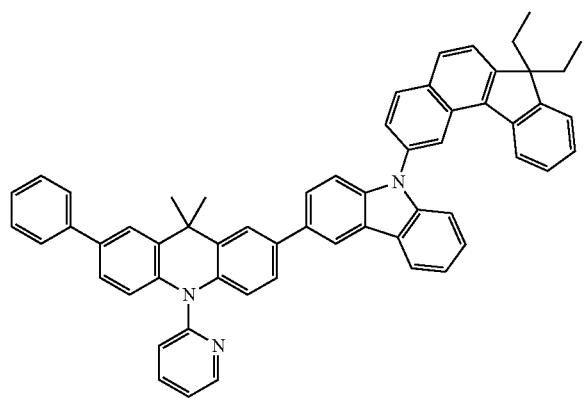
C48

-continued
C49
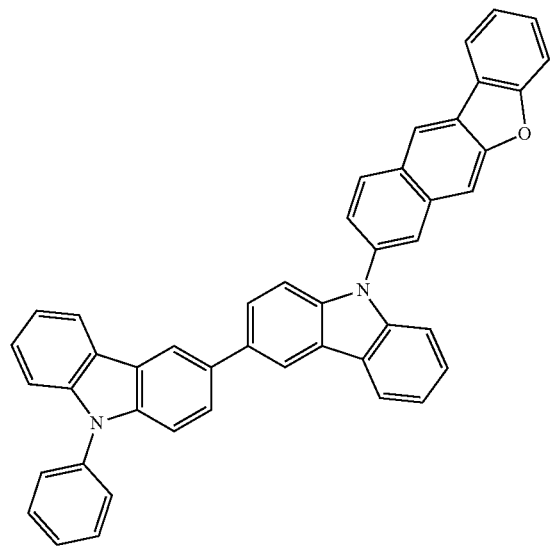
C50
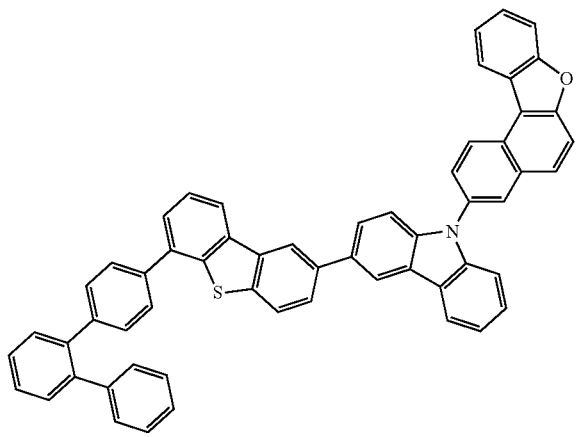
C51
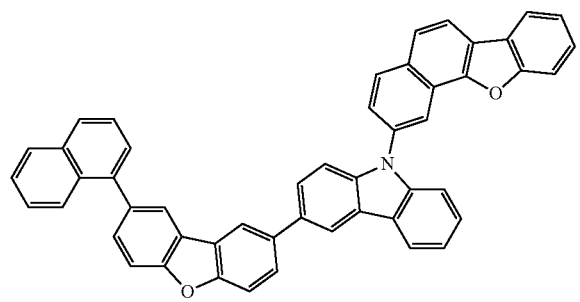
C52
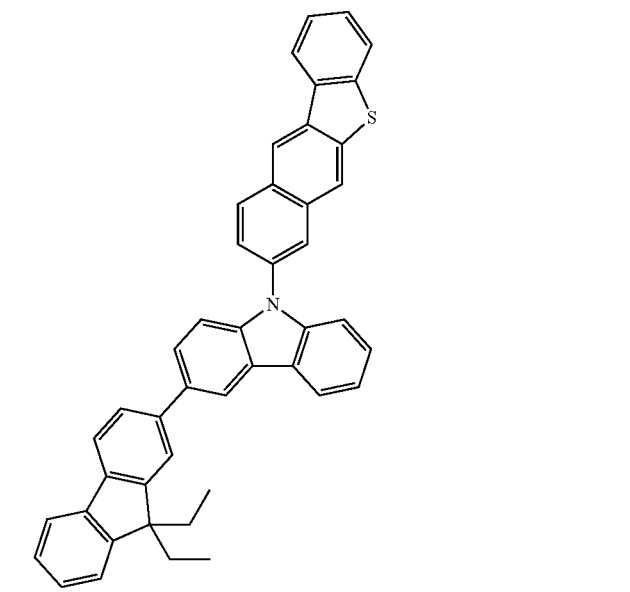
C53
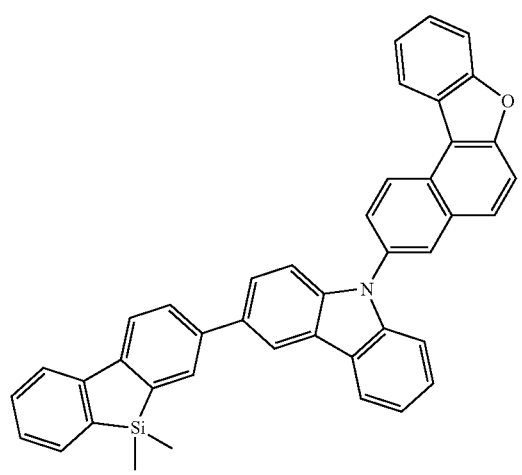
C54
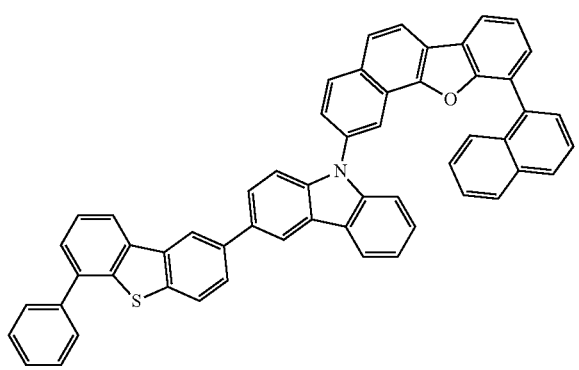

-continued
C55
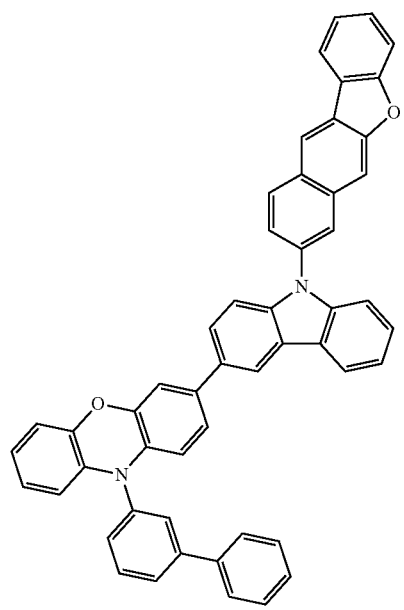
C56
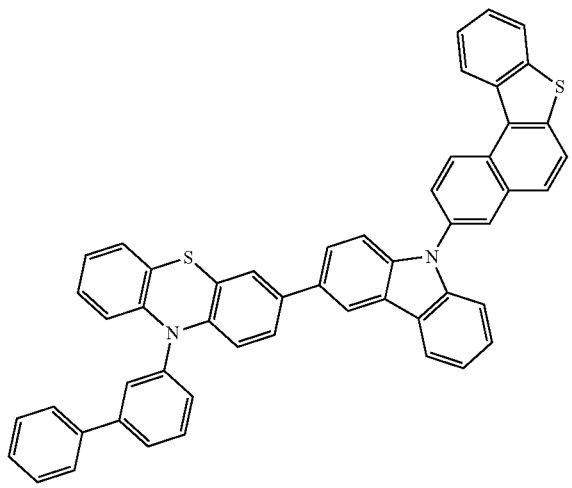
C57
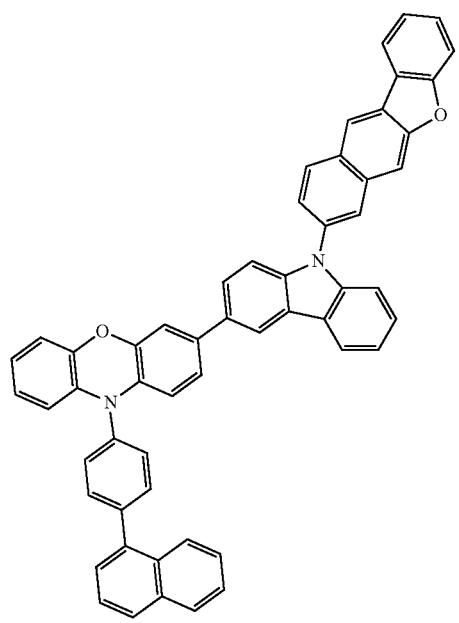
C58
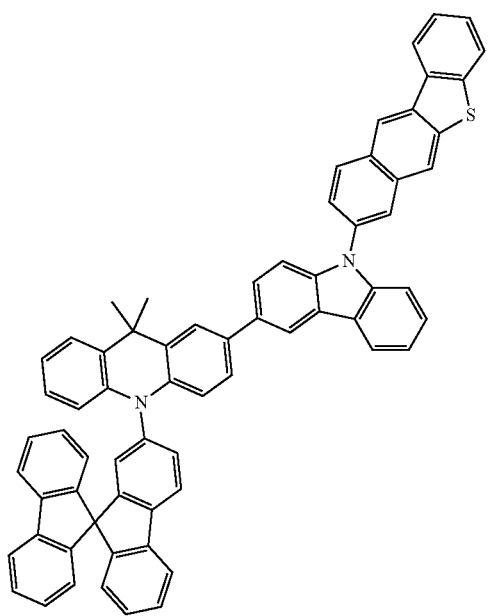

-continued
C59
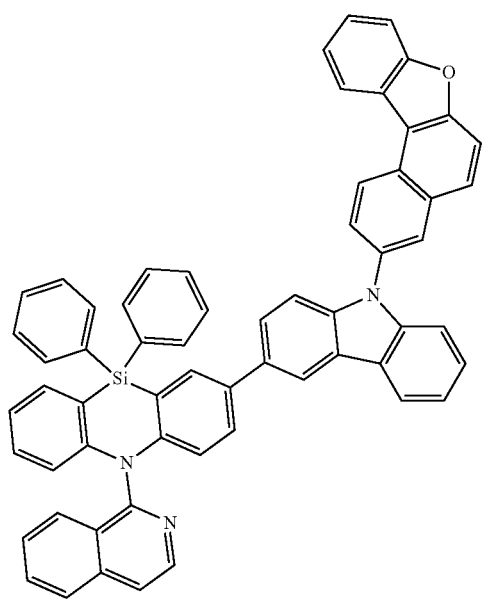
C60
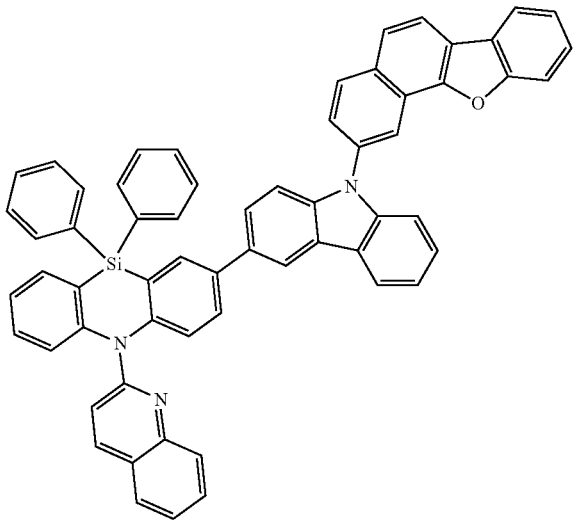
C61
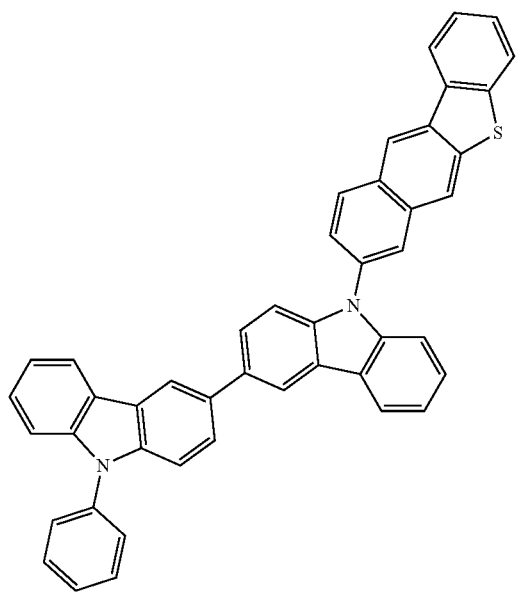
C62
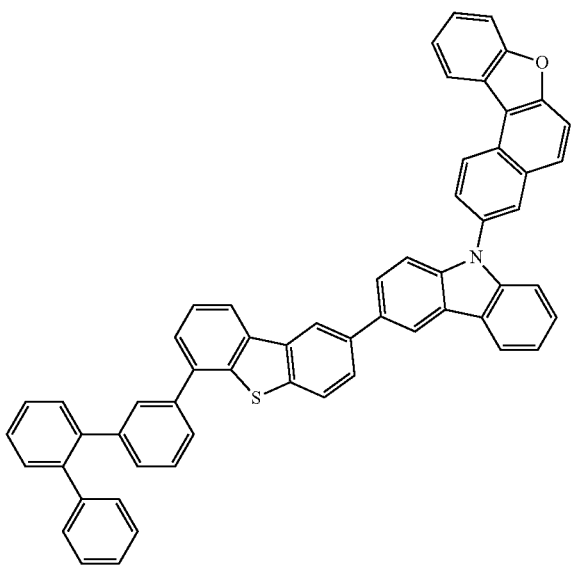

-continued
C63
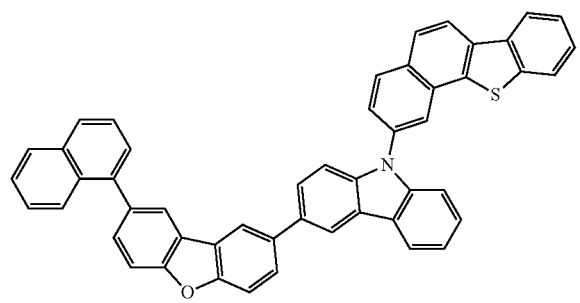
C64
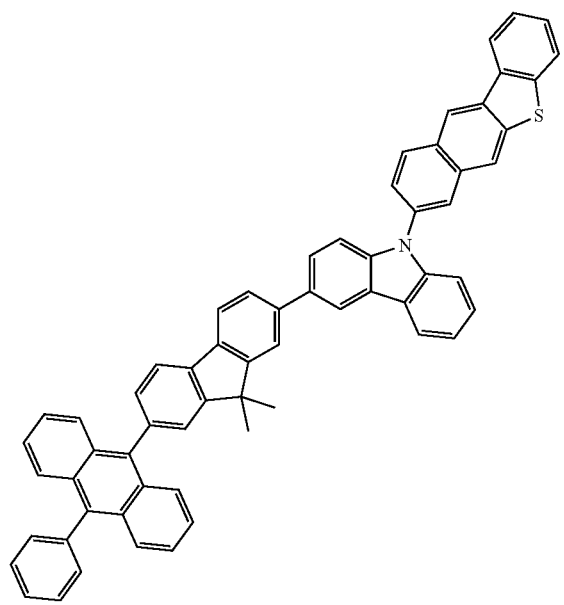
C65
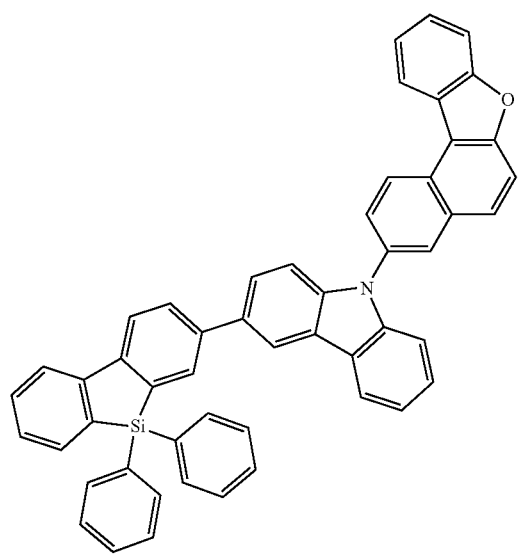
C66
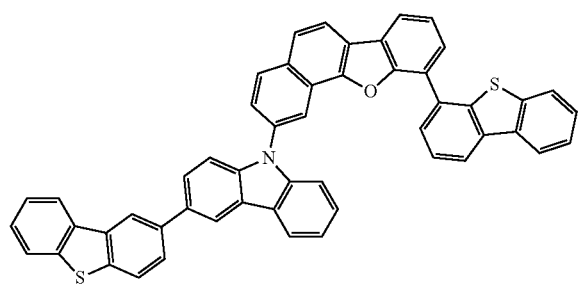

-continued
C67
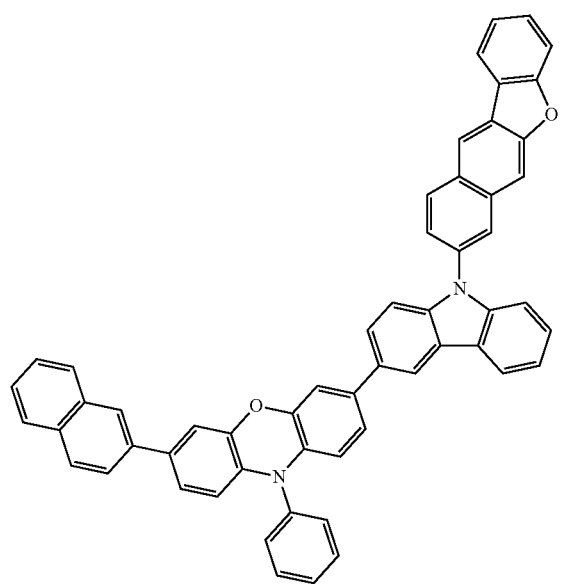
C68
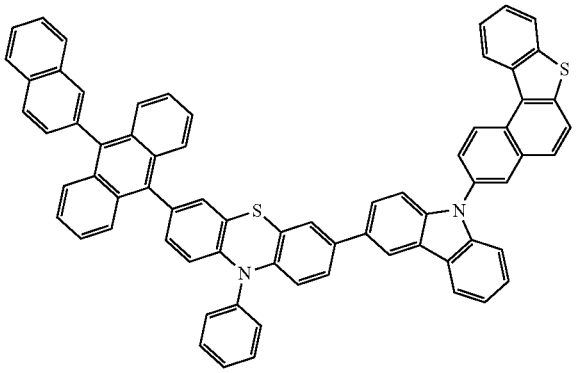
C69
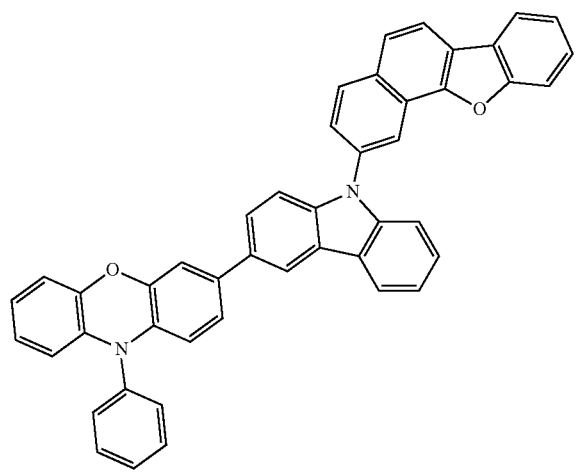
C70
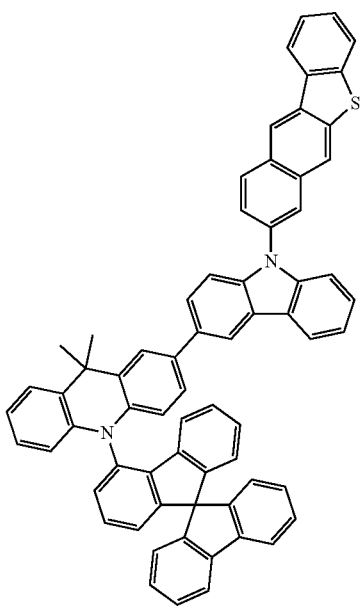

-continued
C71
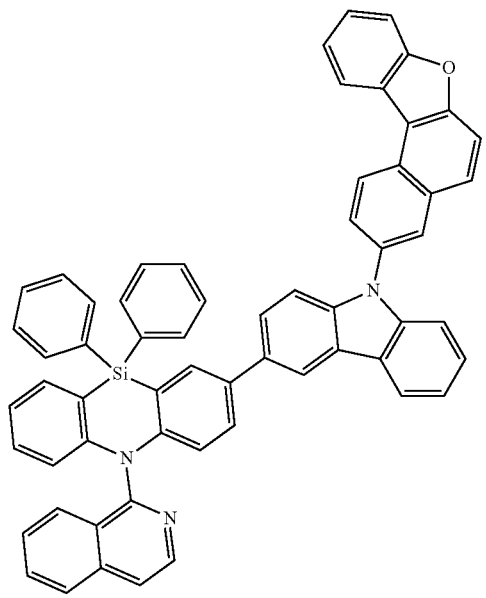
C72
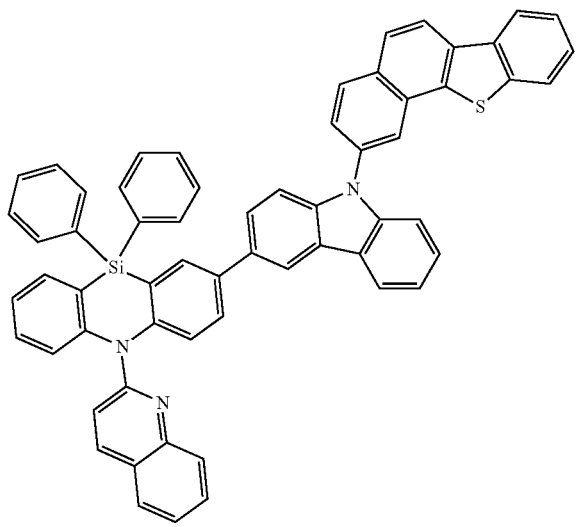
C73
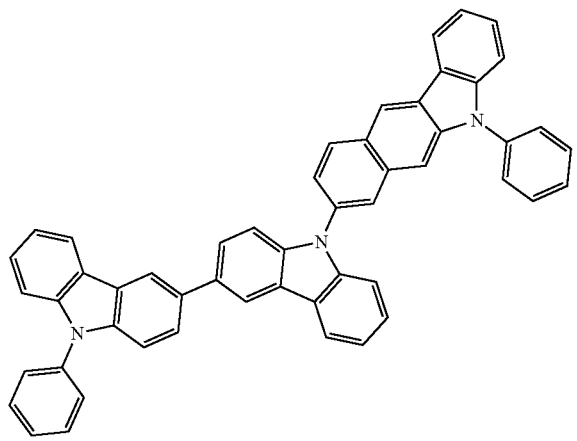
C74
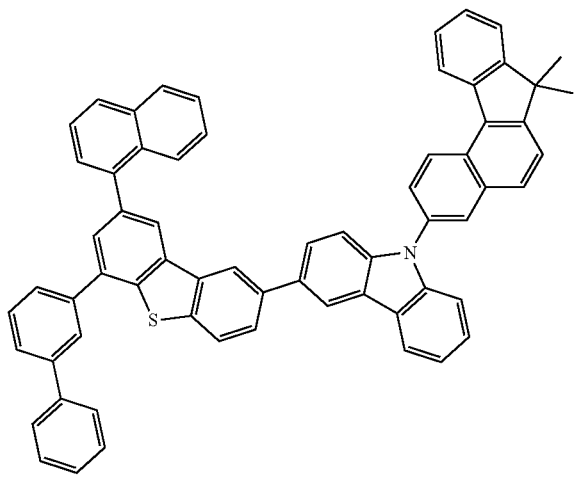
C75
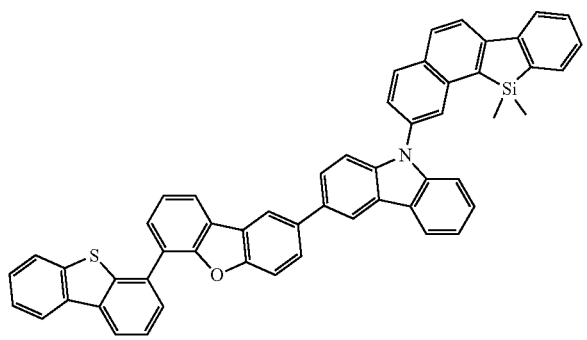
C76
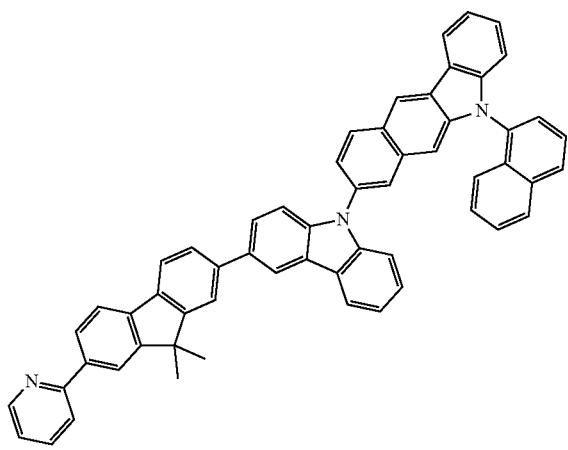

-continued
C77
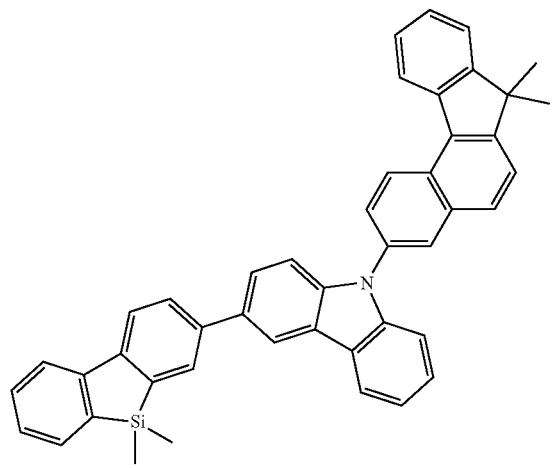
C78
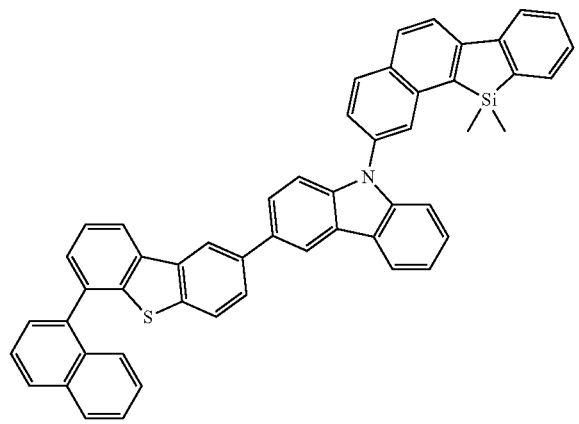
C79
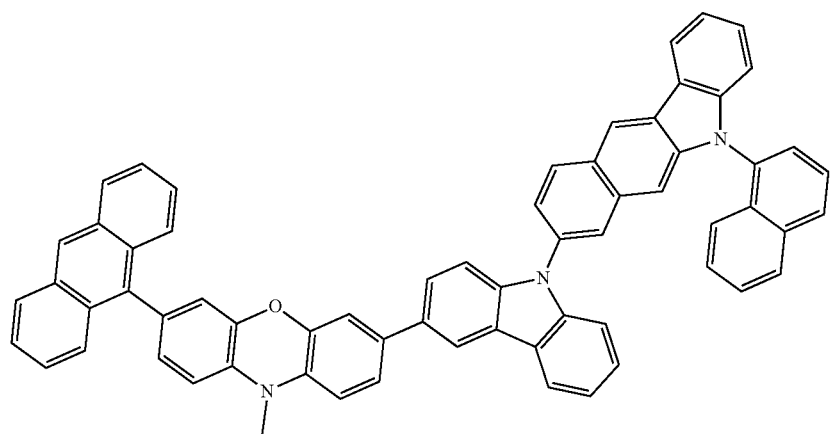
C80
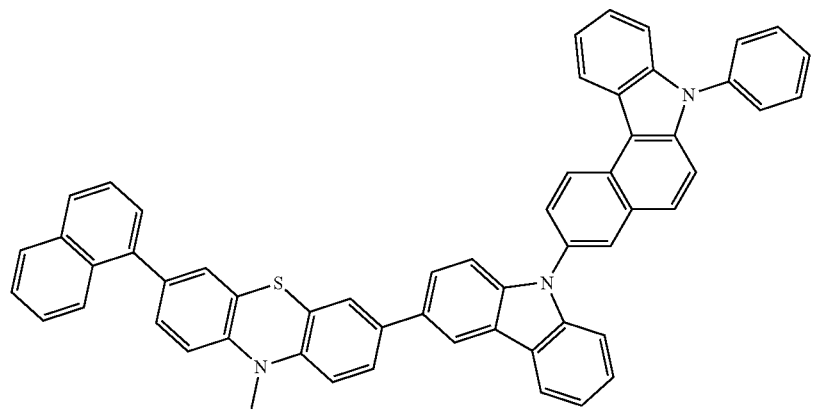

-continued
C81
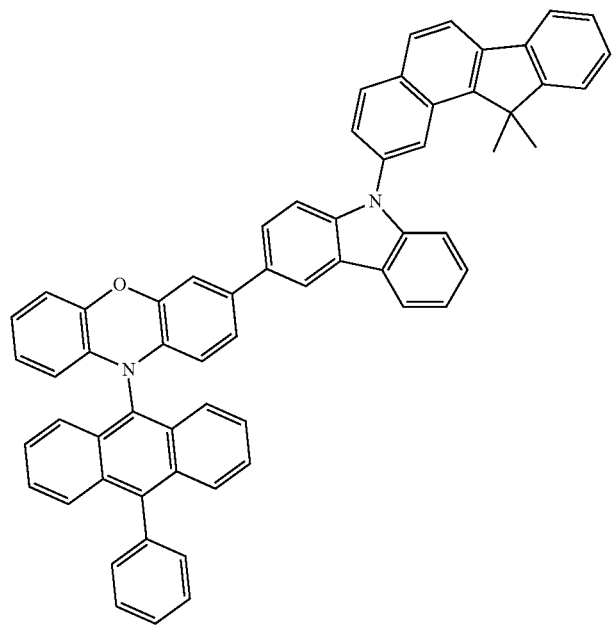
C82
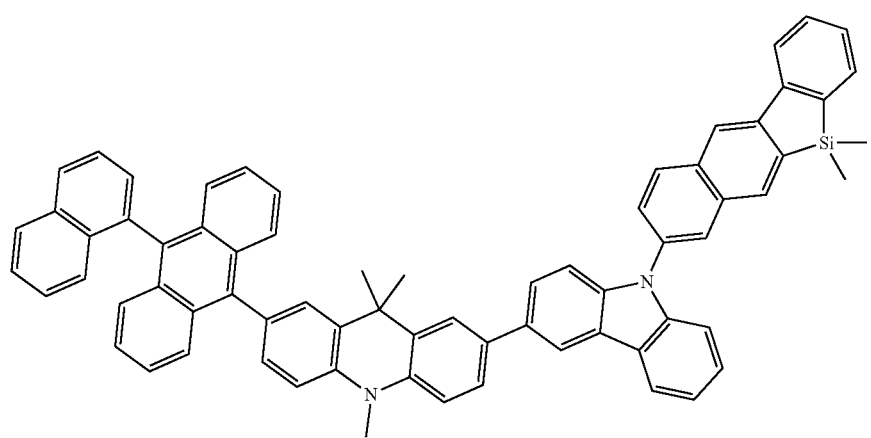

-continued
C83
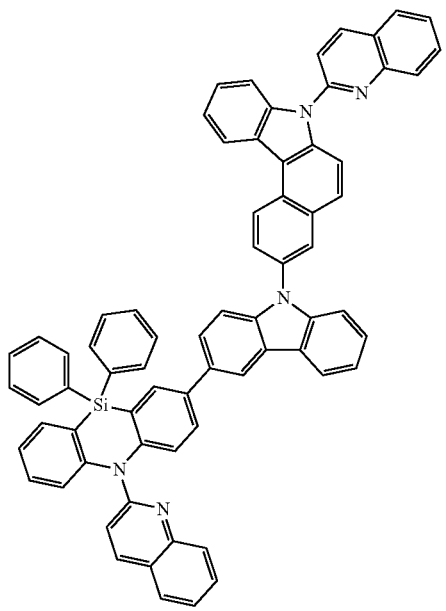
C84
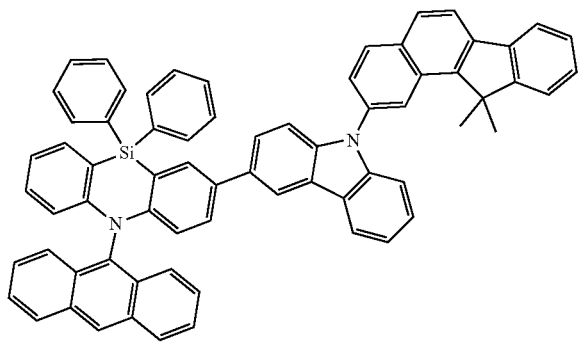
C85
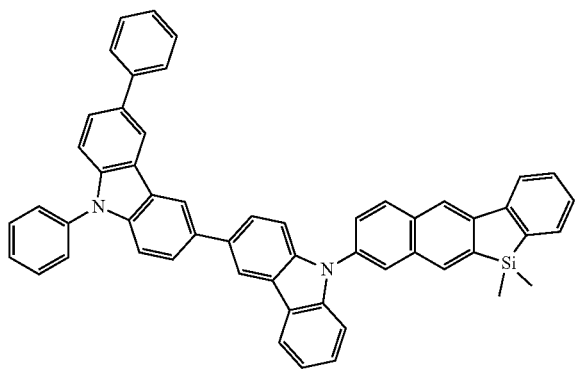
C86
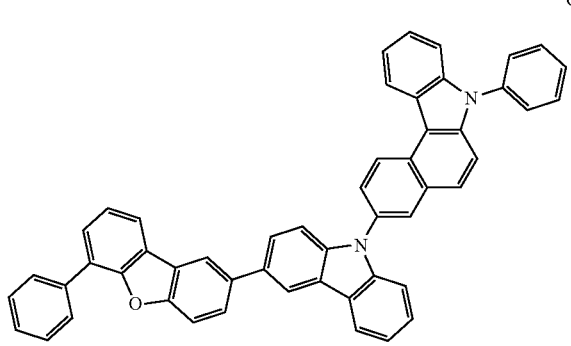
C87
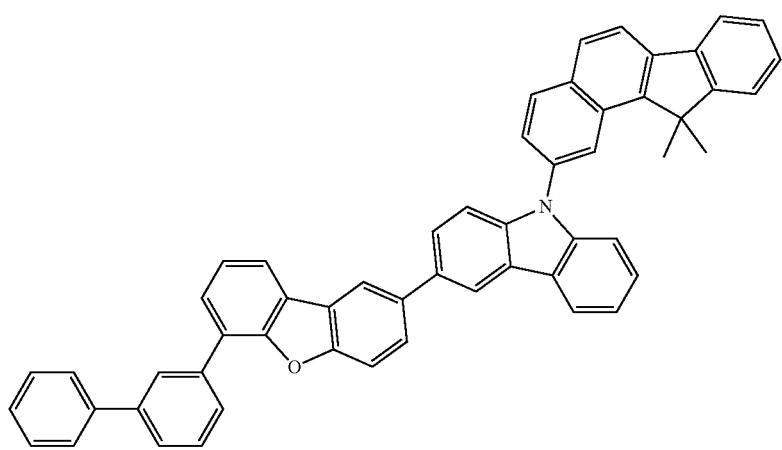

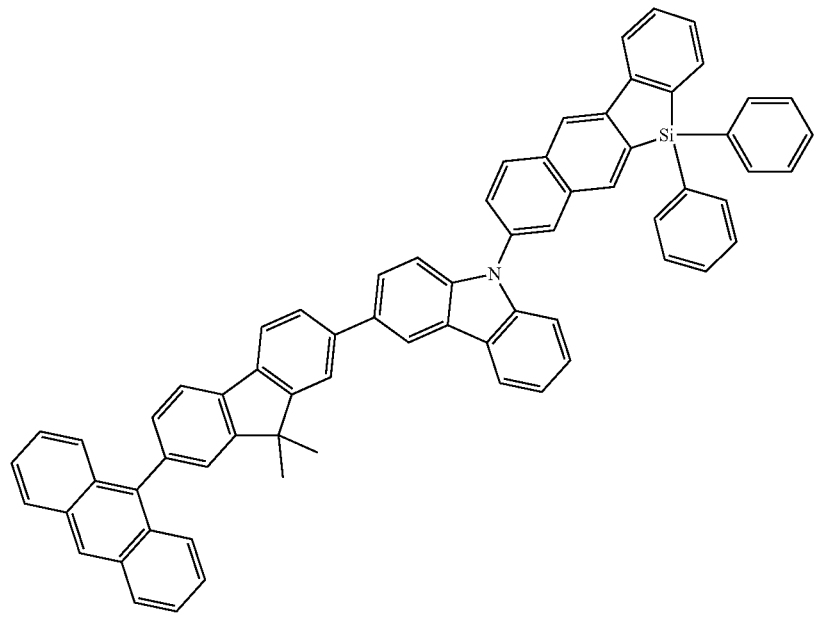
C88
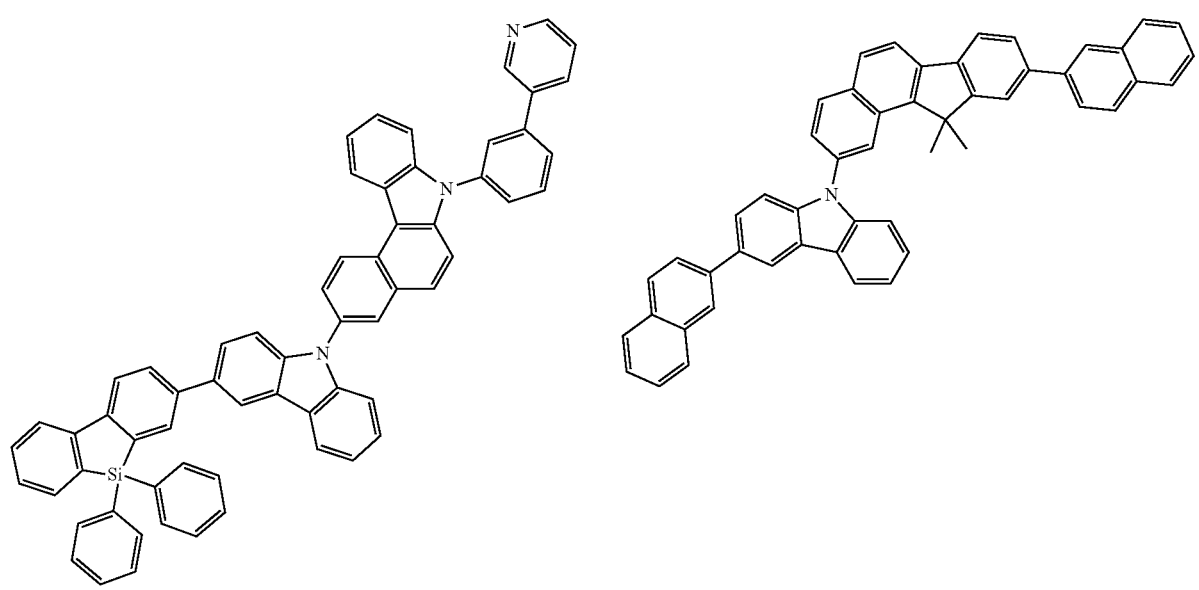
C89
C90

-continued
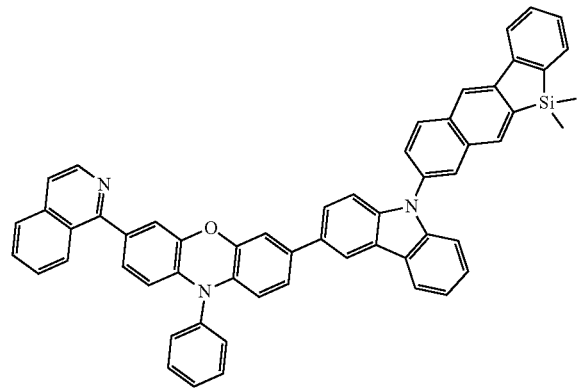
C91
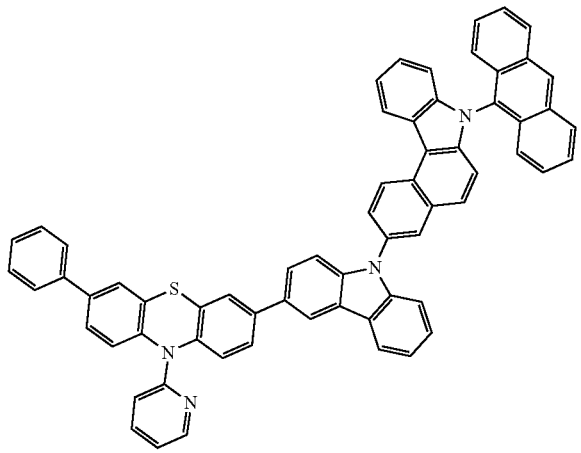
C92
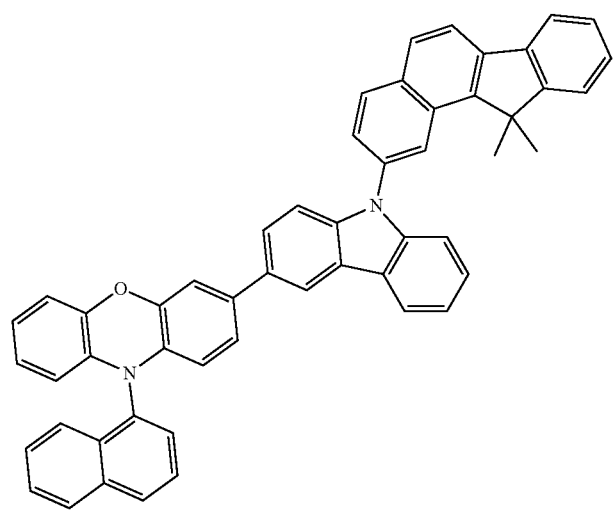
C93
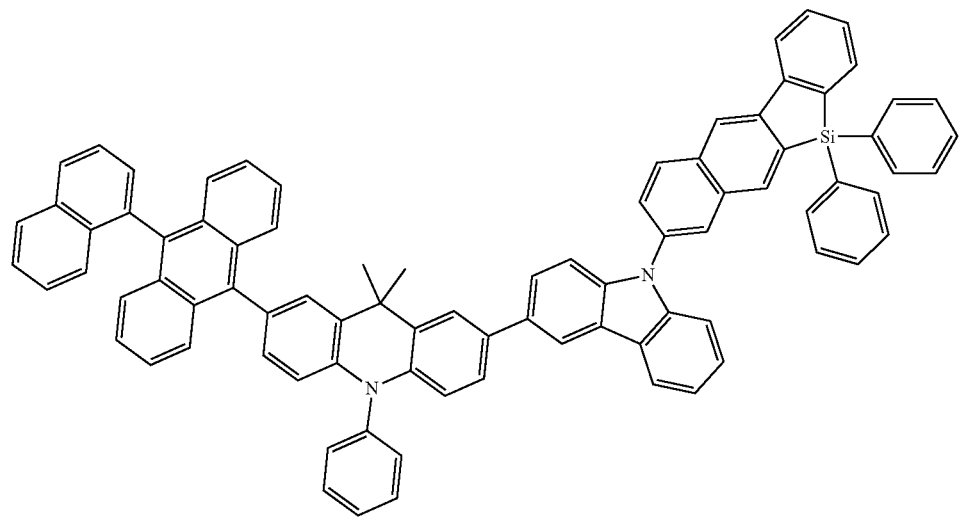
C94

-continued
269 C95
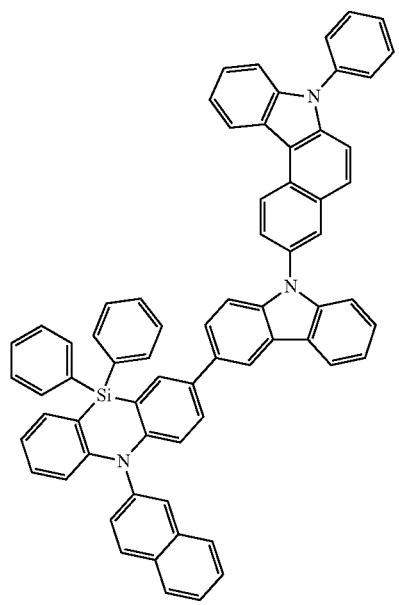
270 C96
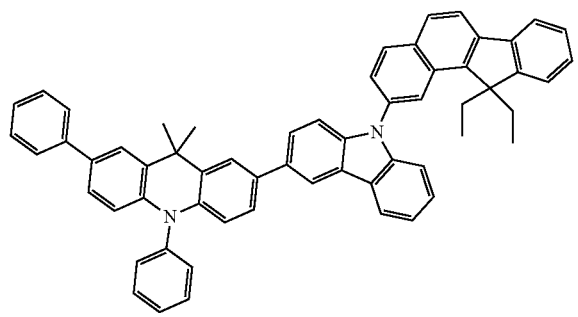
C97
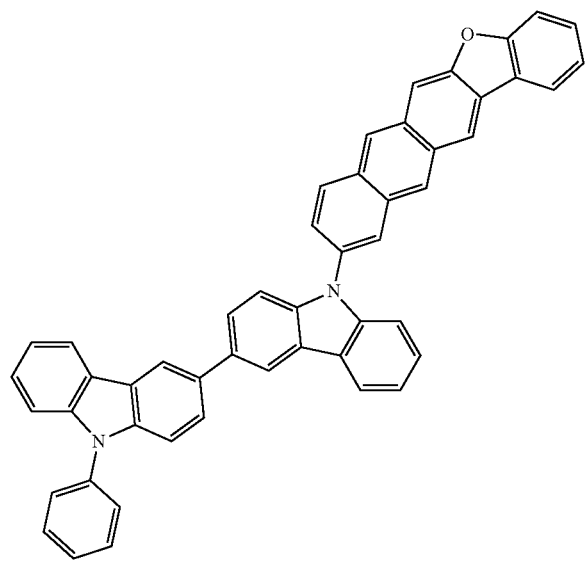
C98
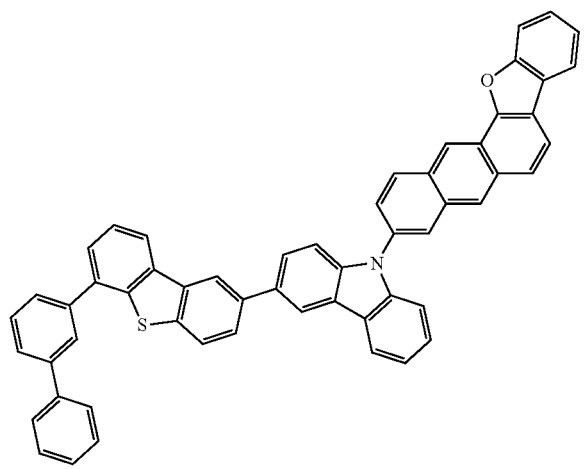

-continued
C99
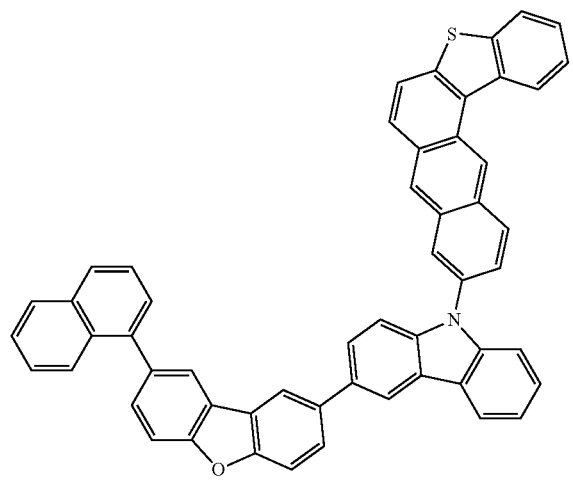
C100
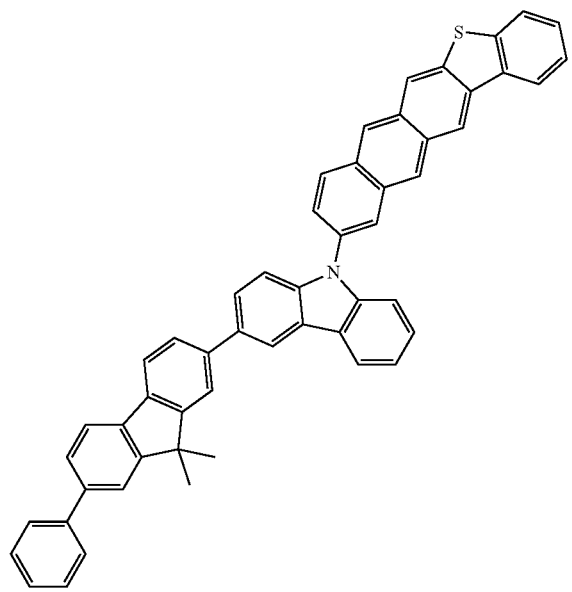
C101
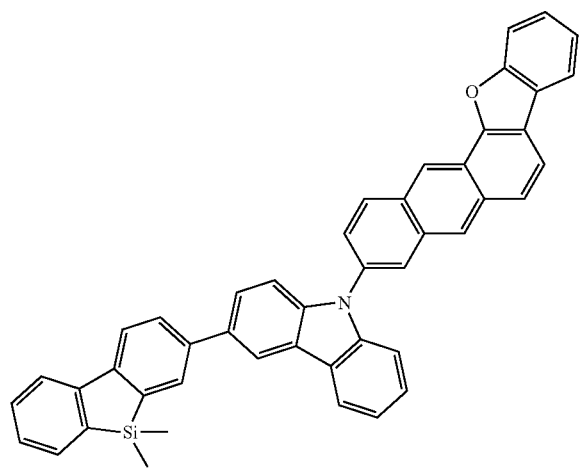
C102
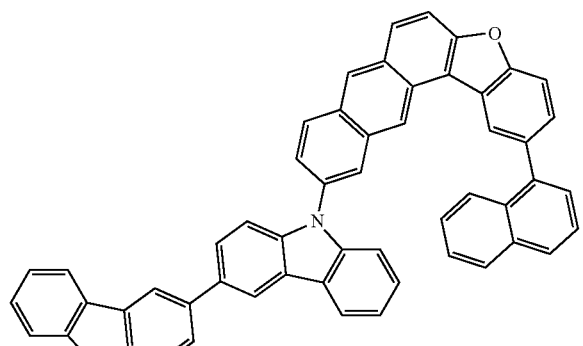

-continued
C103
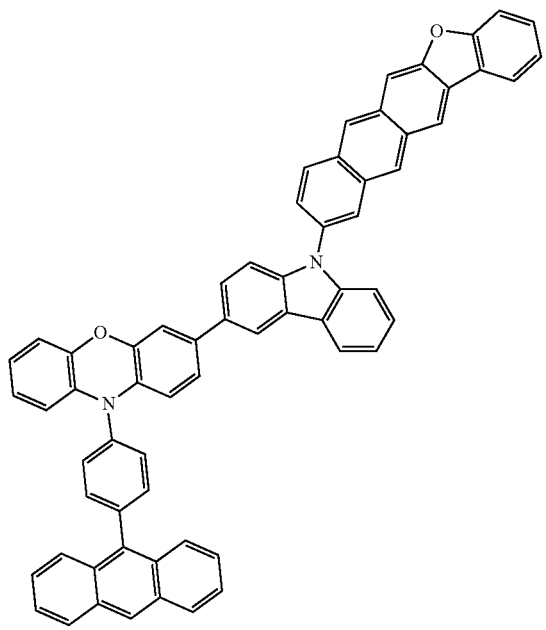
C104
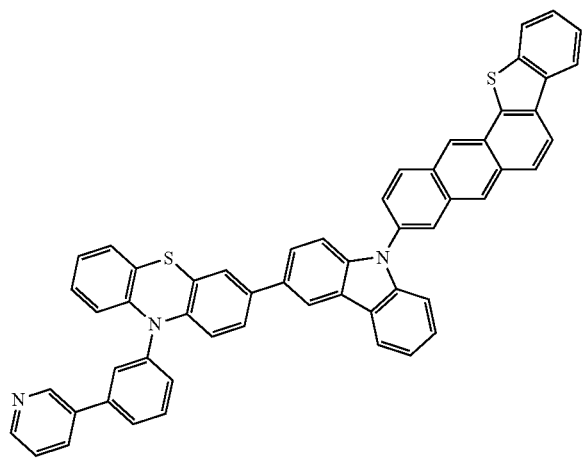
C105
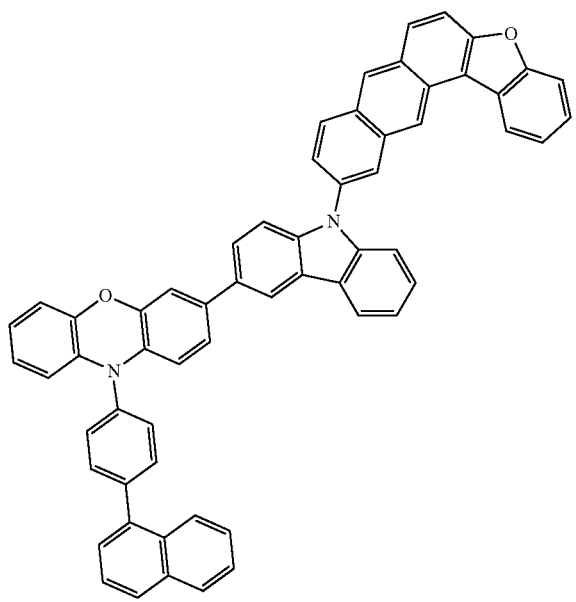
C106
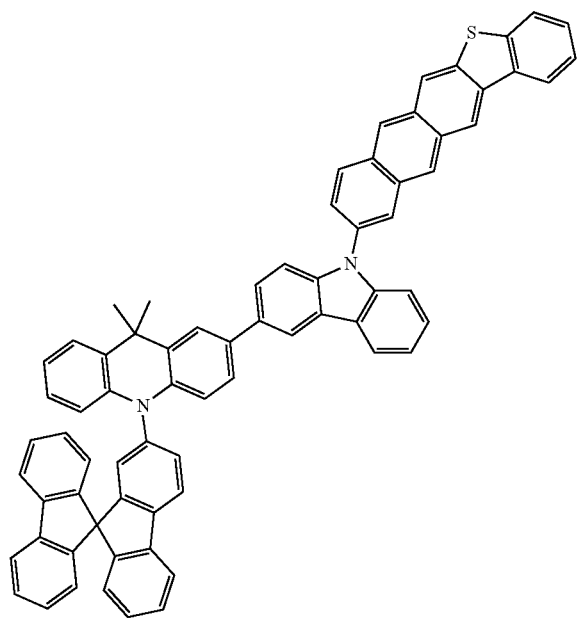

-continued
C110
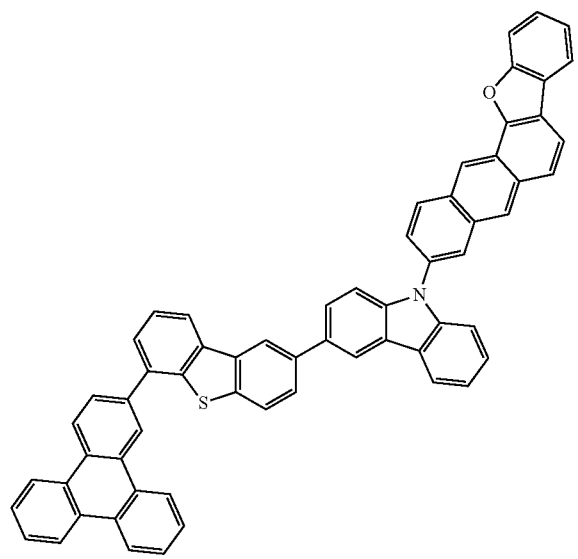
C111
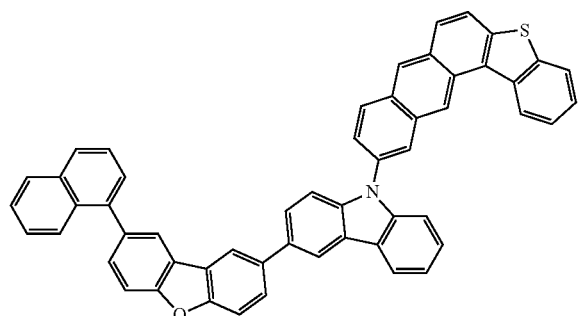
C112
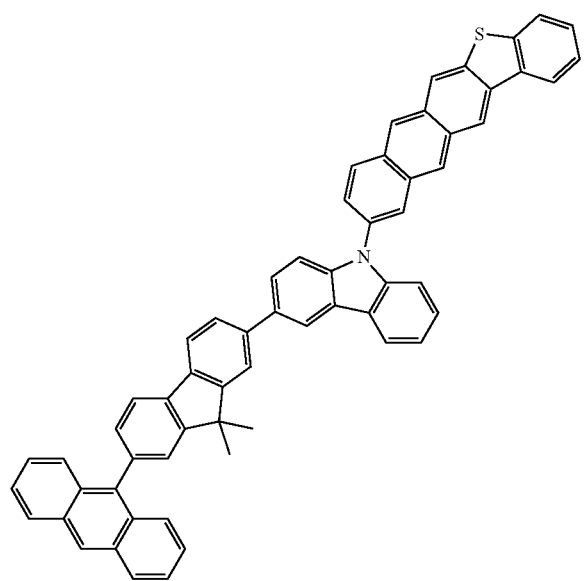
C113
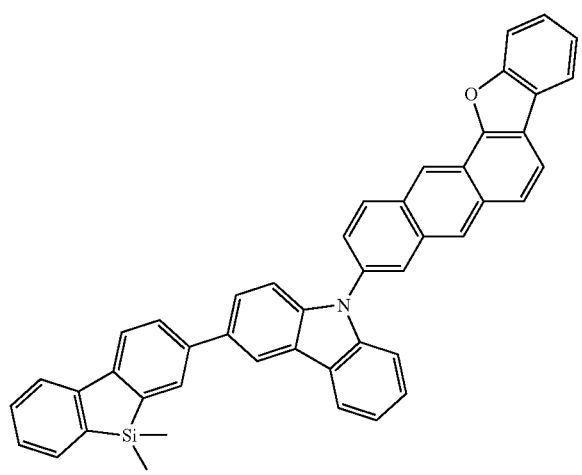

-continued
C114
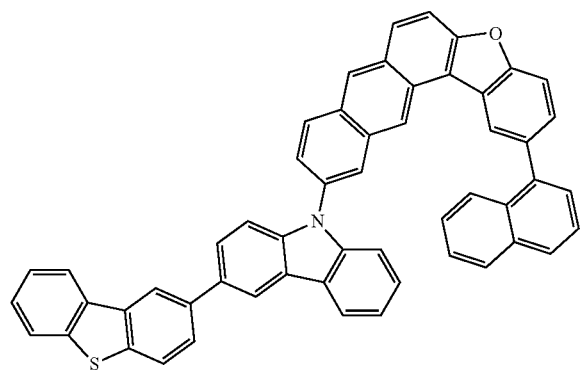
C115
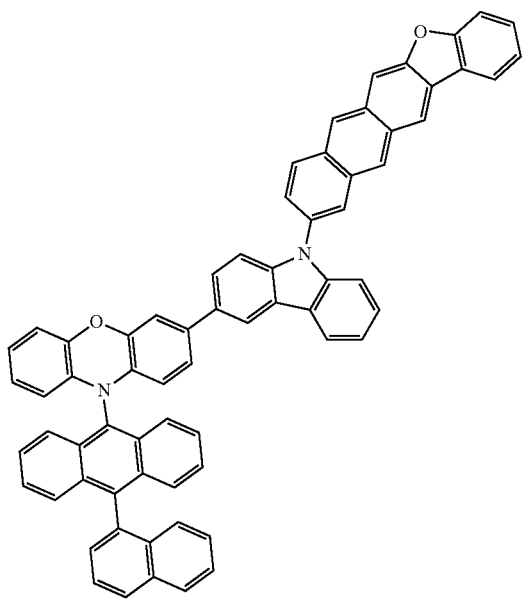
C116
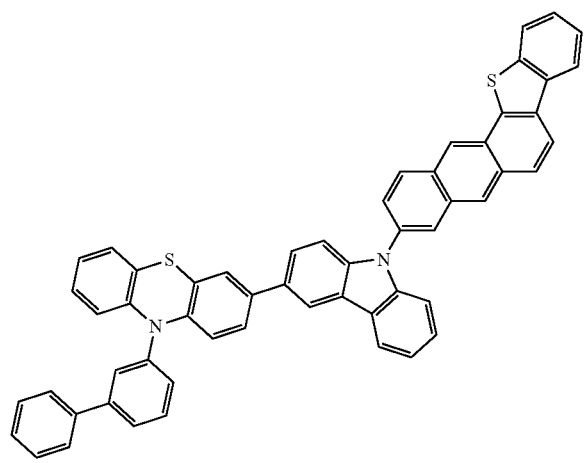
C117
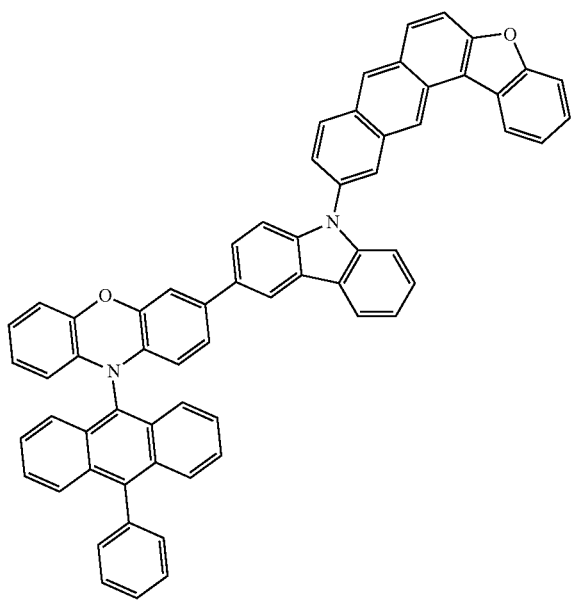

-continued
C118
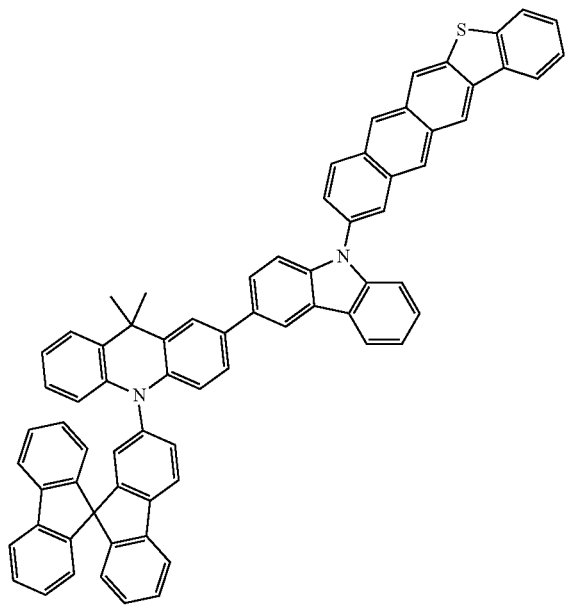
C119
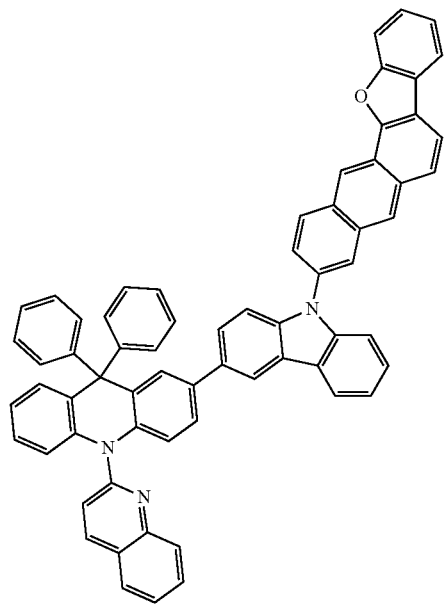
C120
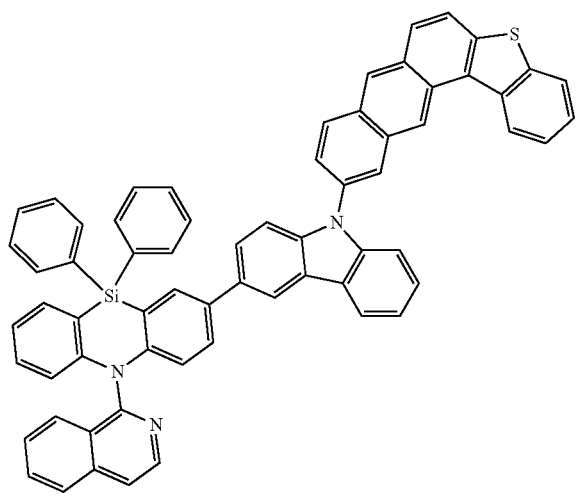
C121
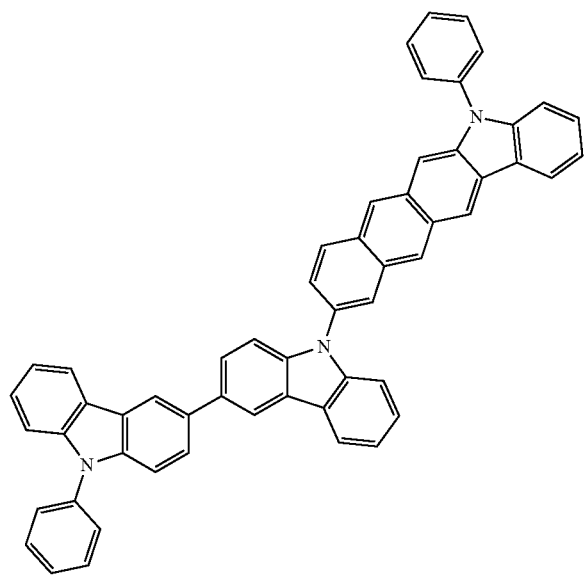

-continued
C122
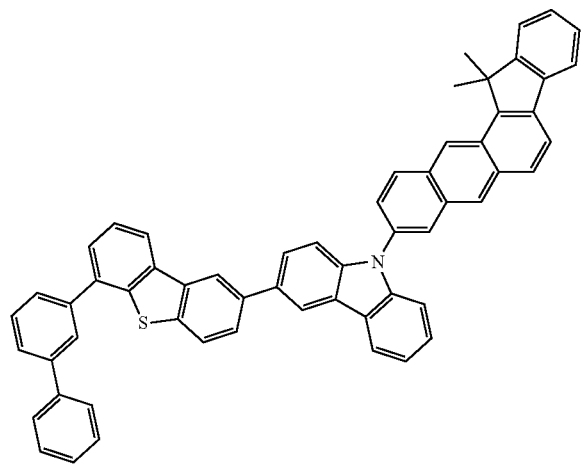
C123
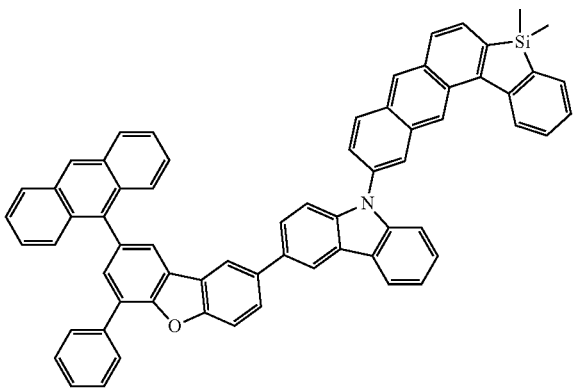
C124
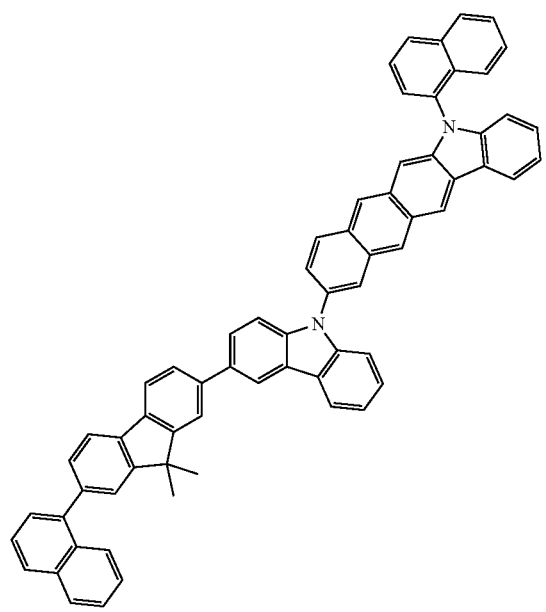
C125
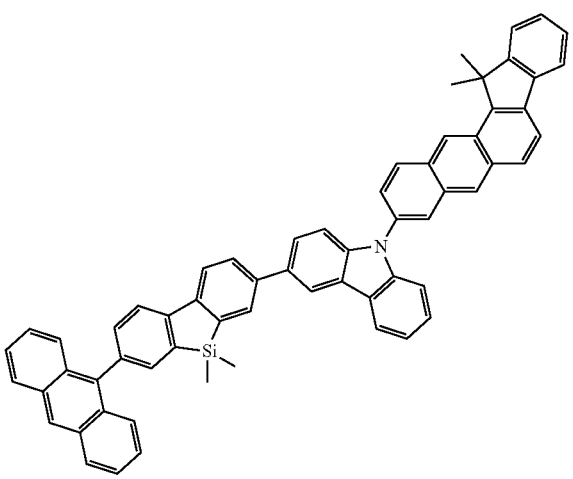

-continued
C126
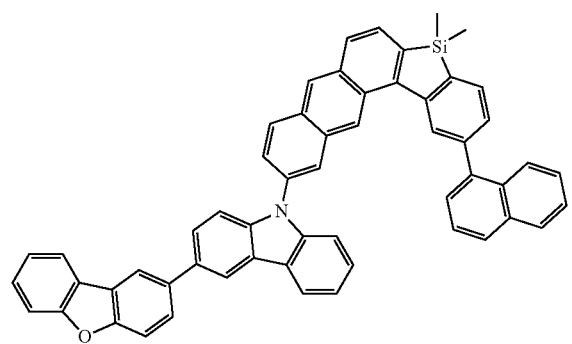
C127
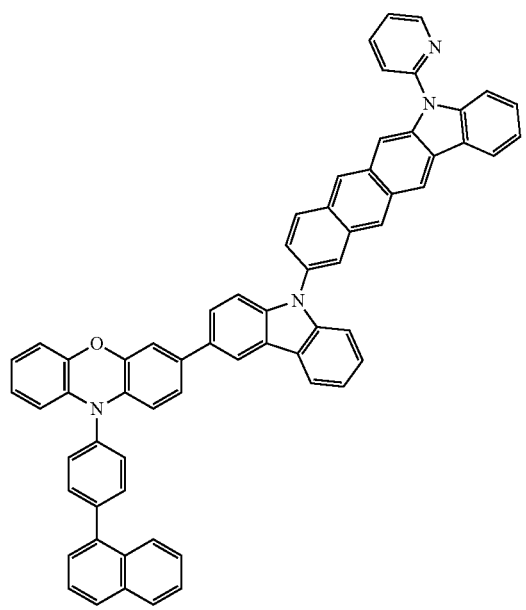
C128
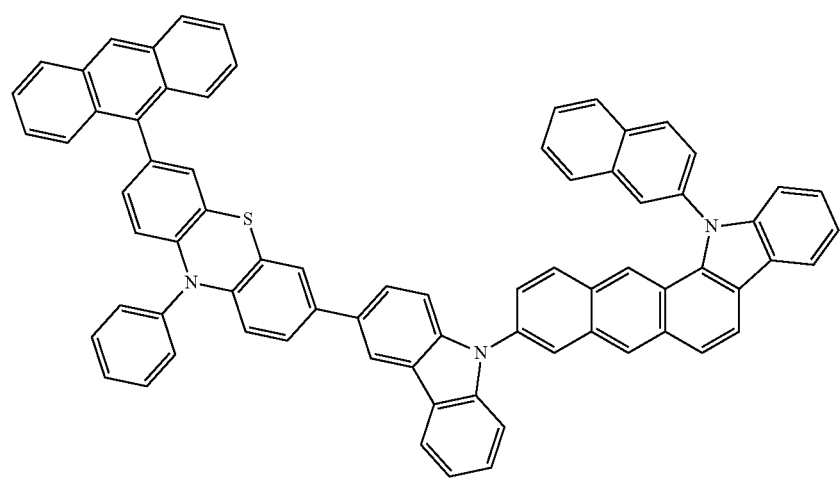

C129
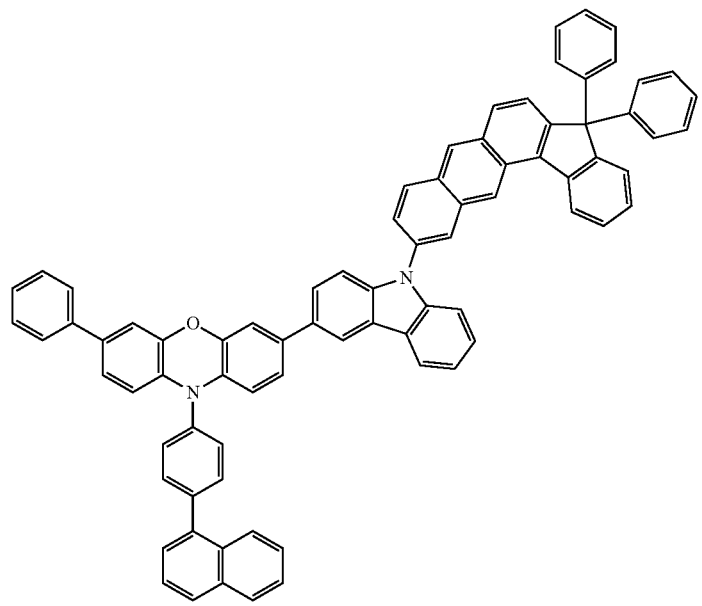
C130
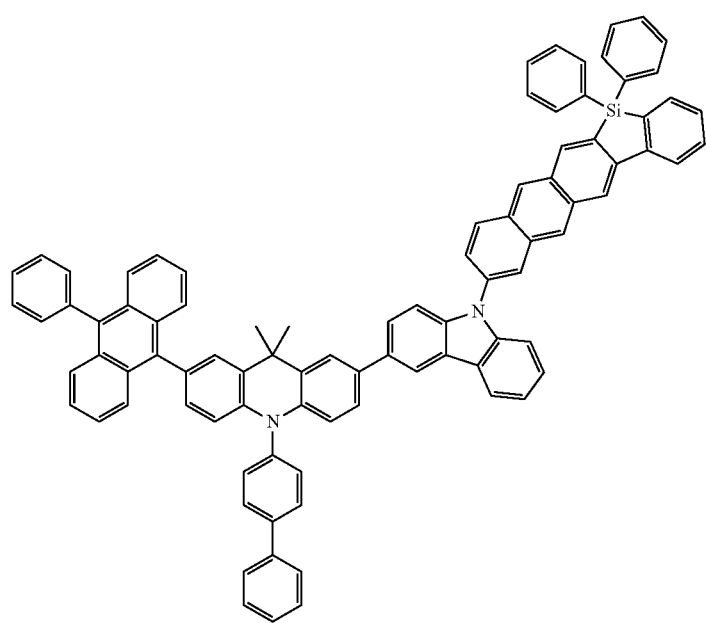

-continued
C131
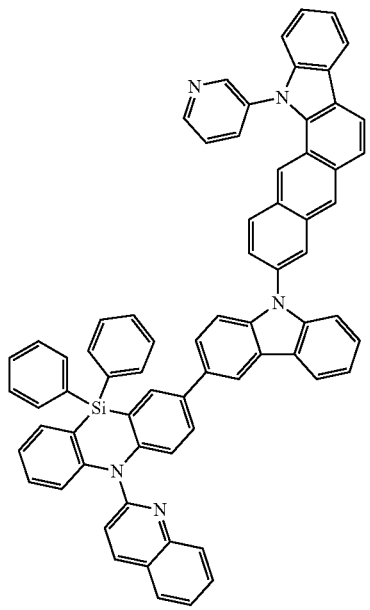
C132
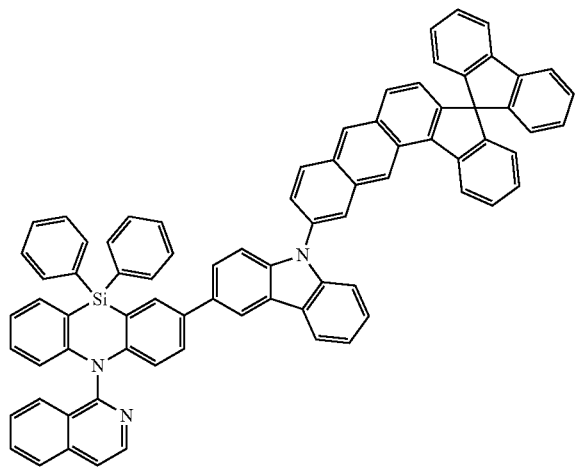
C133
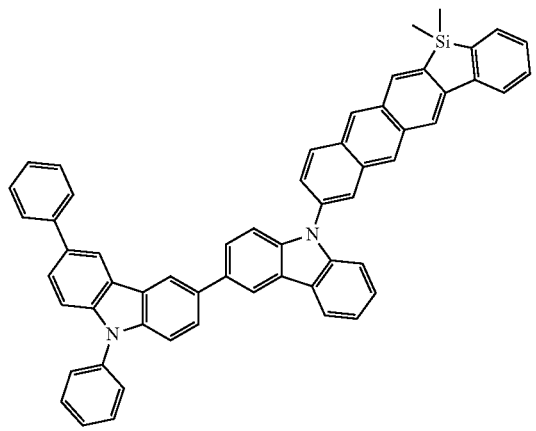
C134
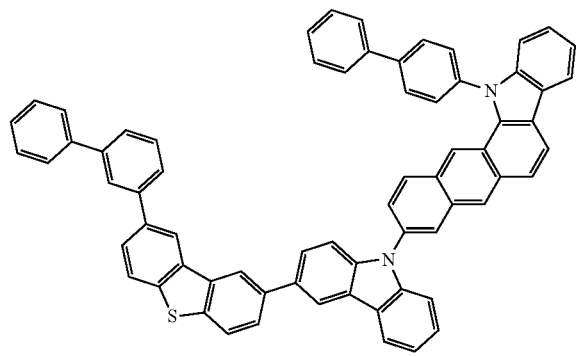
C135
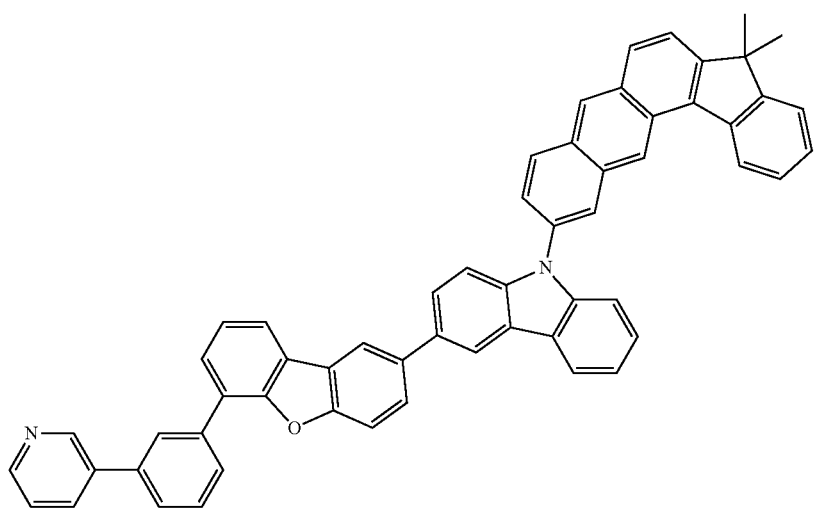

-continued
C136
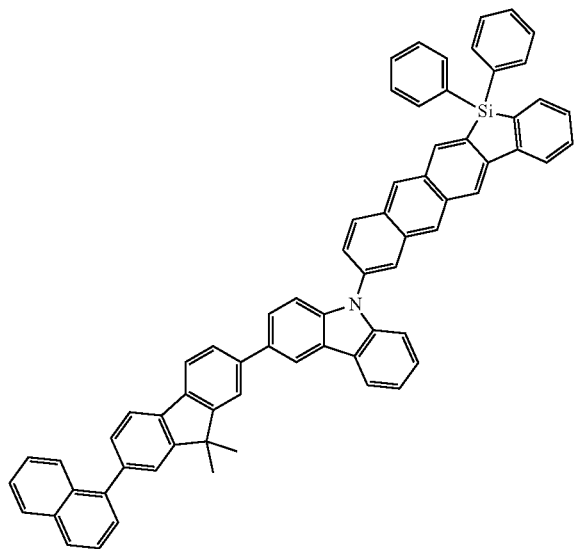
C137
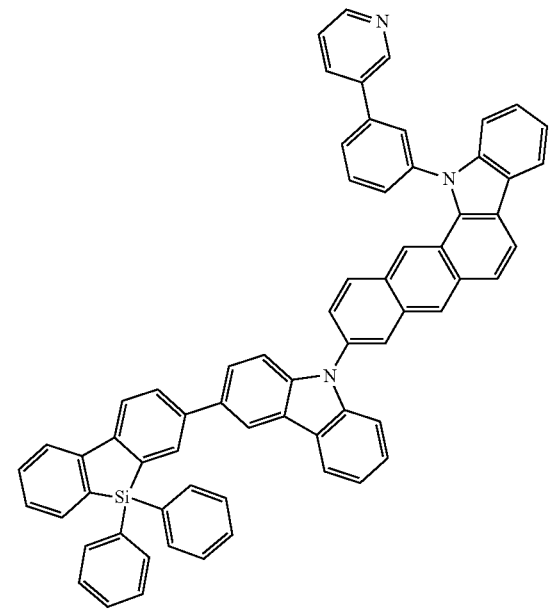
C138
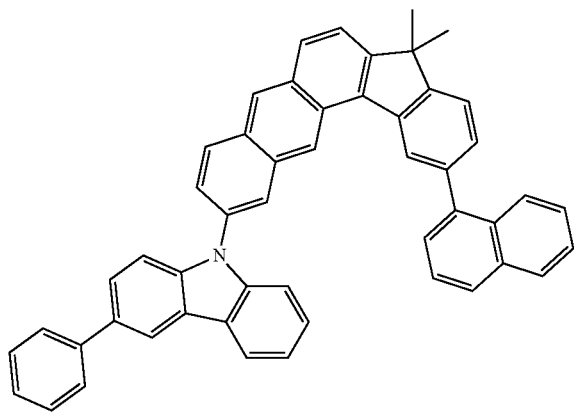
C139
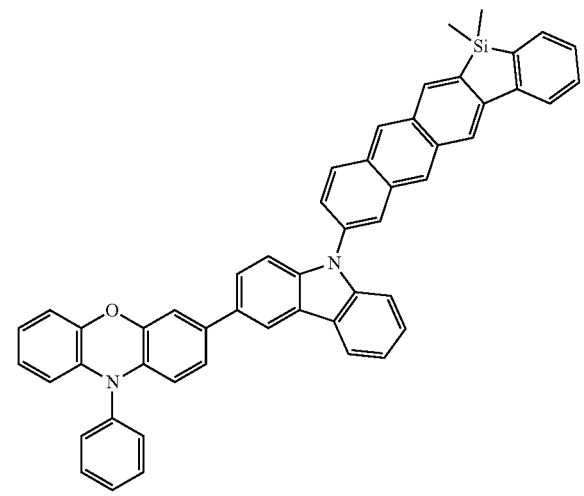
C140
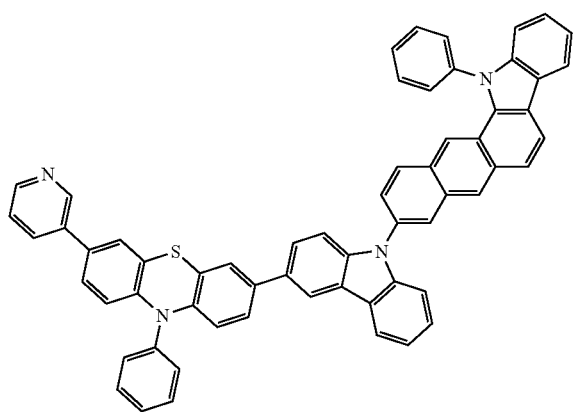
C141
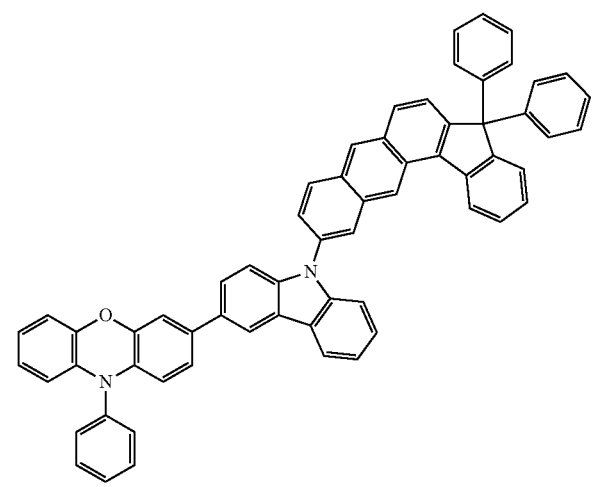

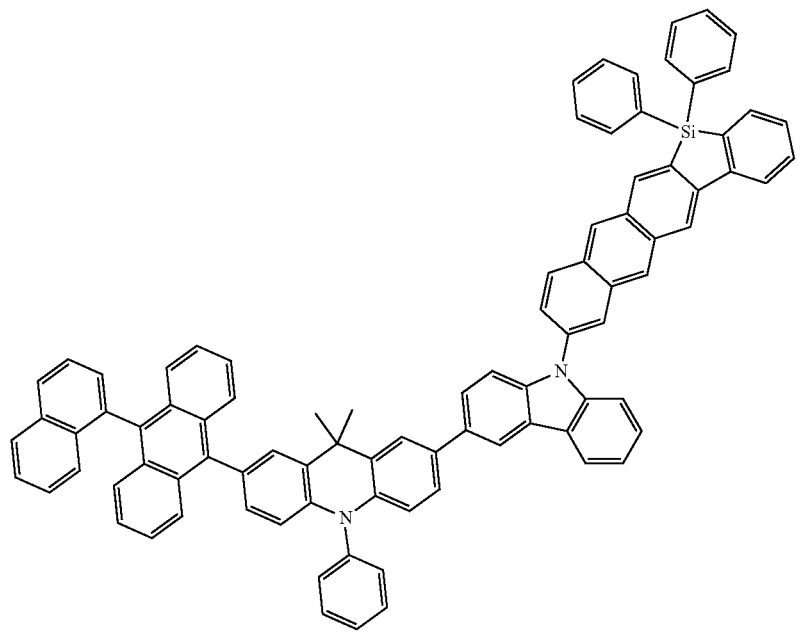
C142
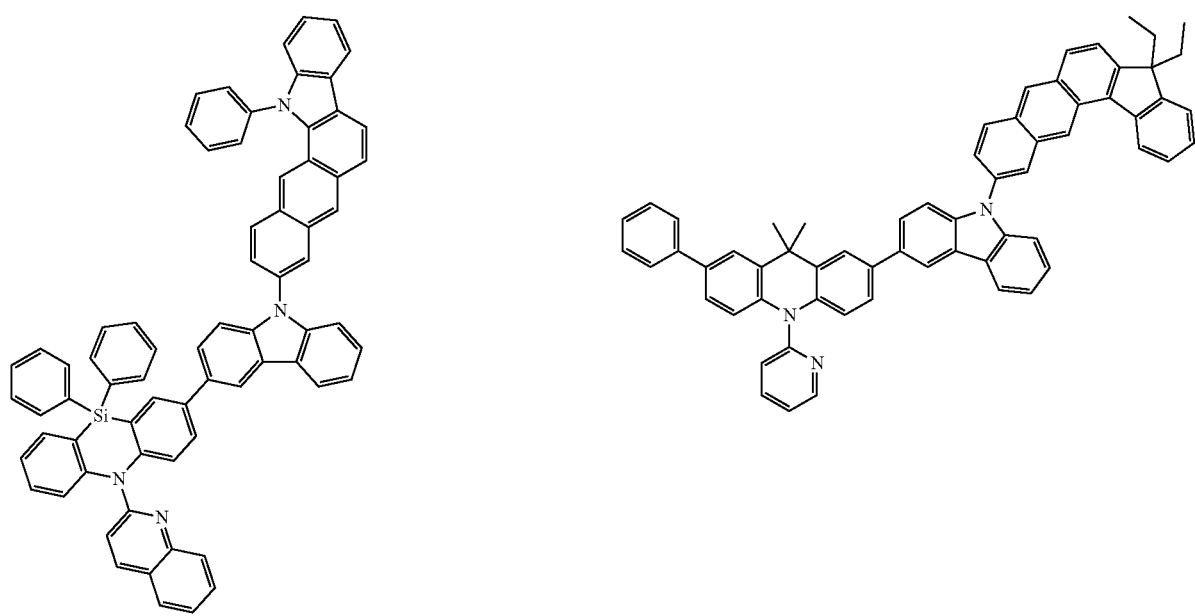
C143
C144

-continued
C145
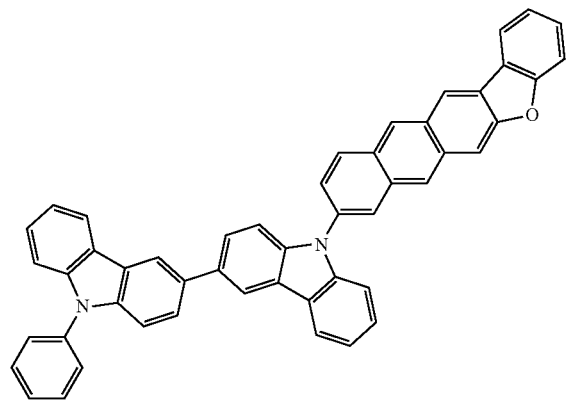
C146
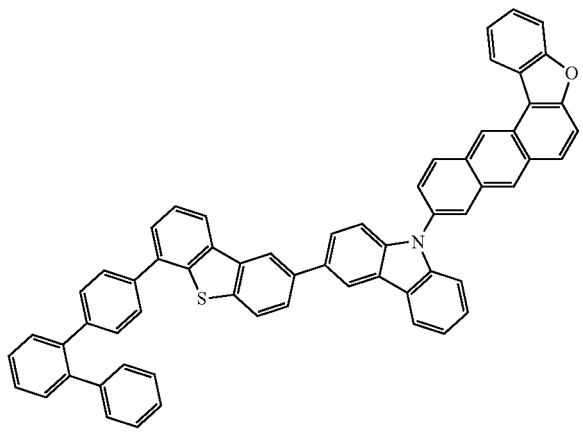
C147
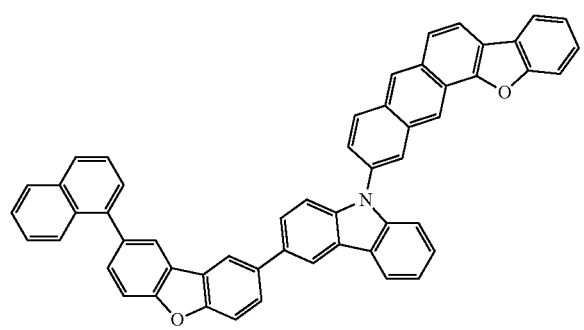
C148
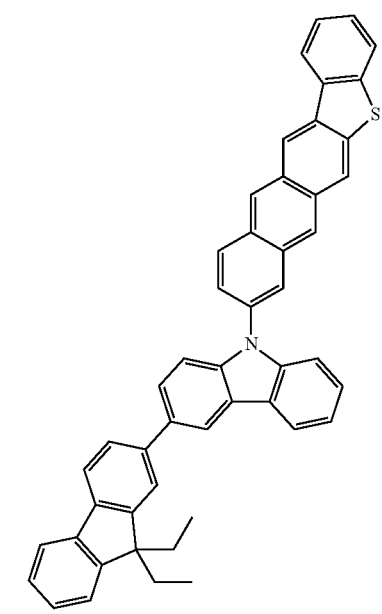
C149
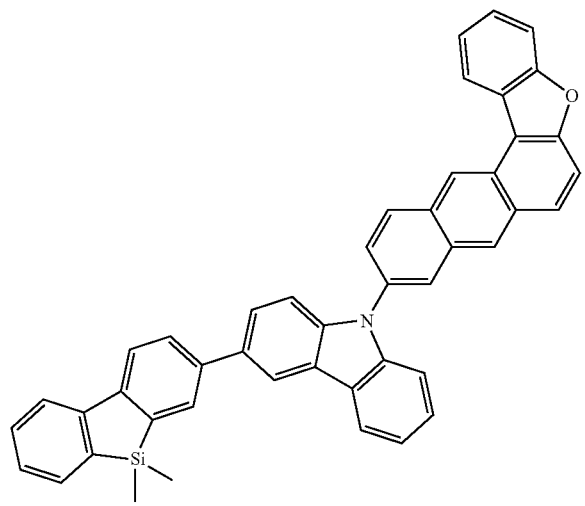
C150
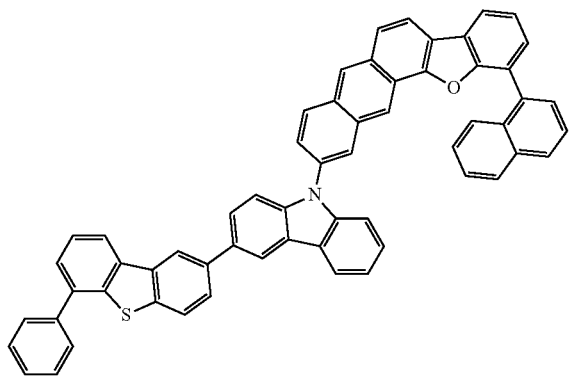

-continued
C151
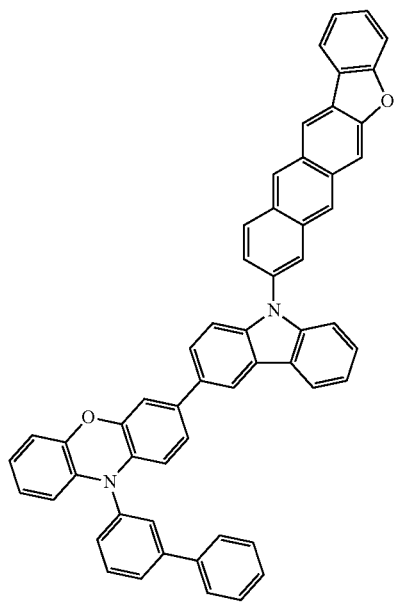
C152
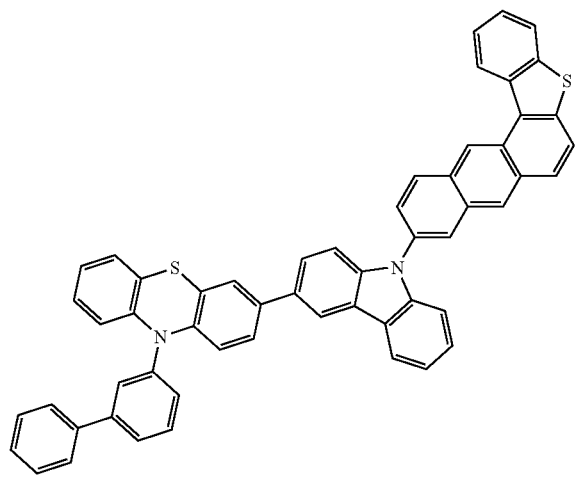
C153
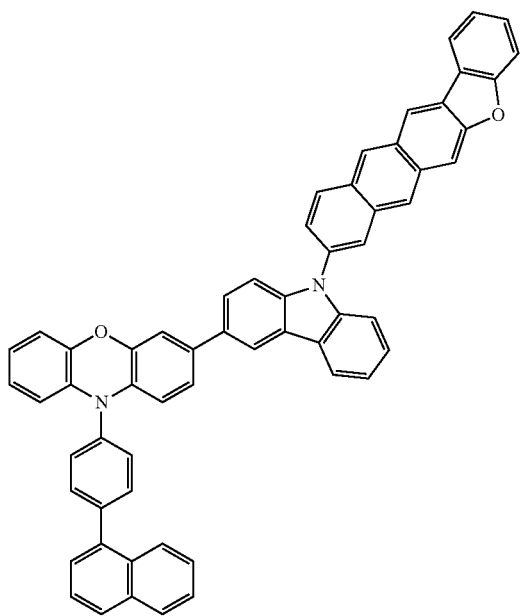
C154
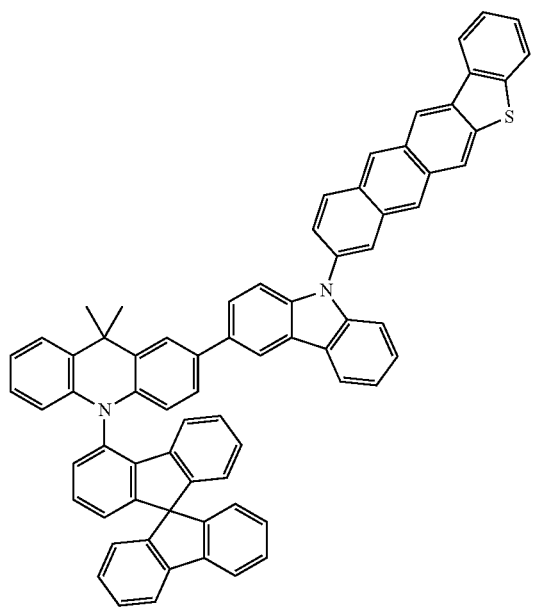

-continued
C158
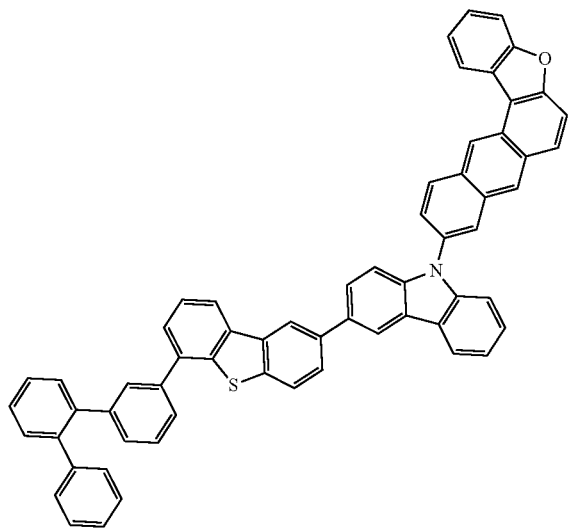
C159
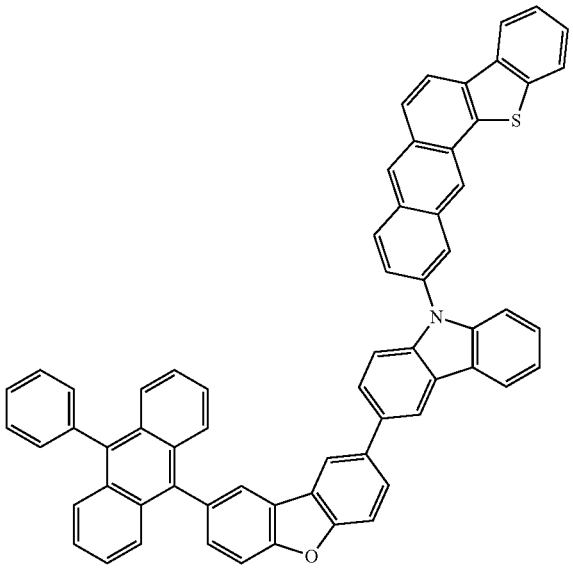
C160
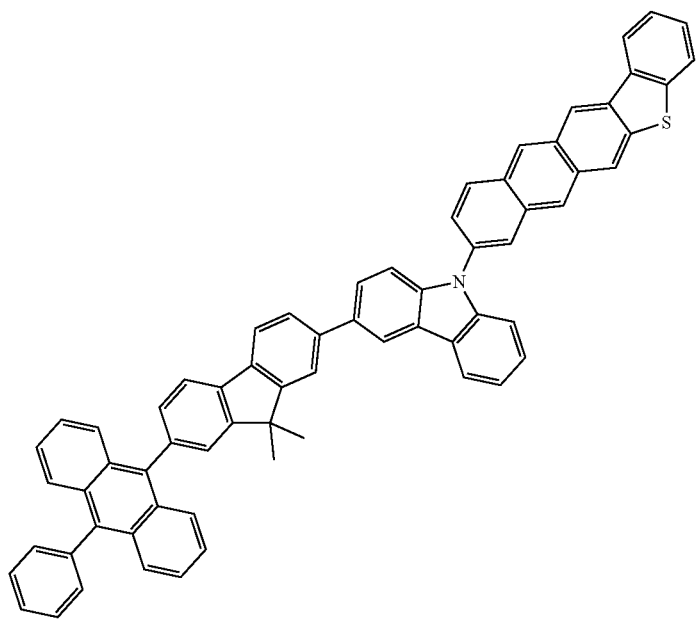

C161
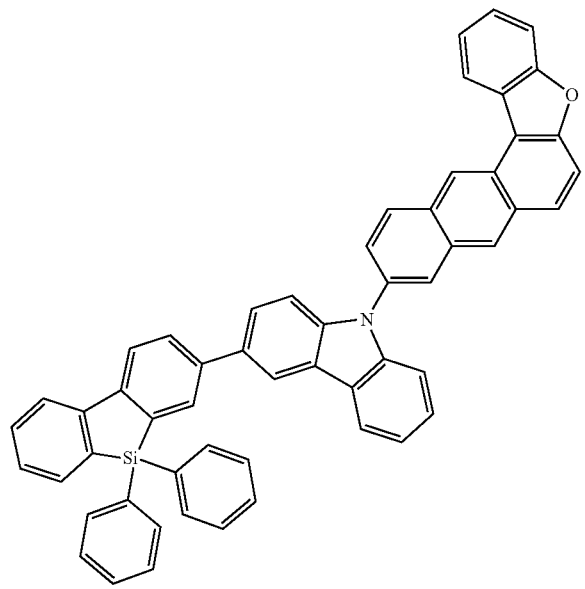
C162
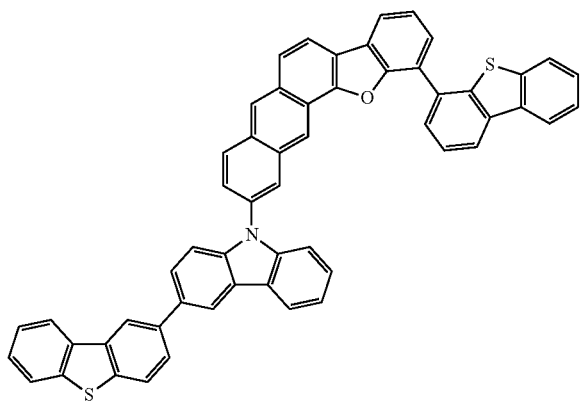
C163
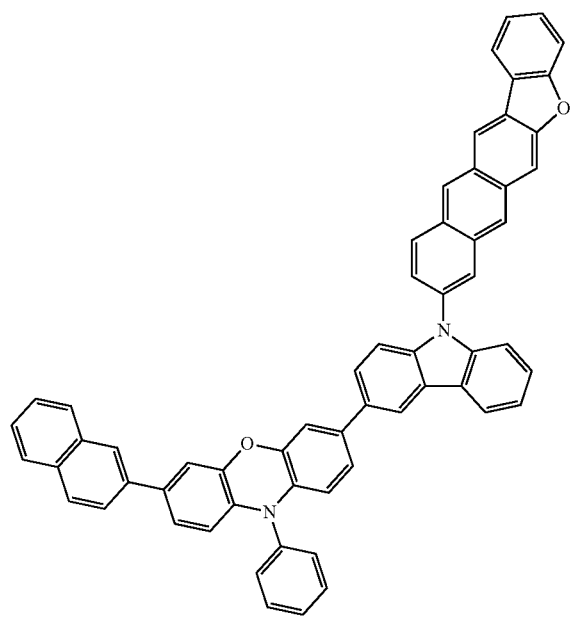

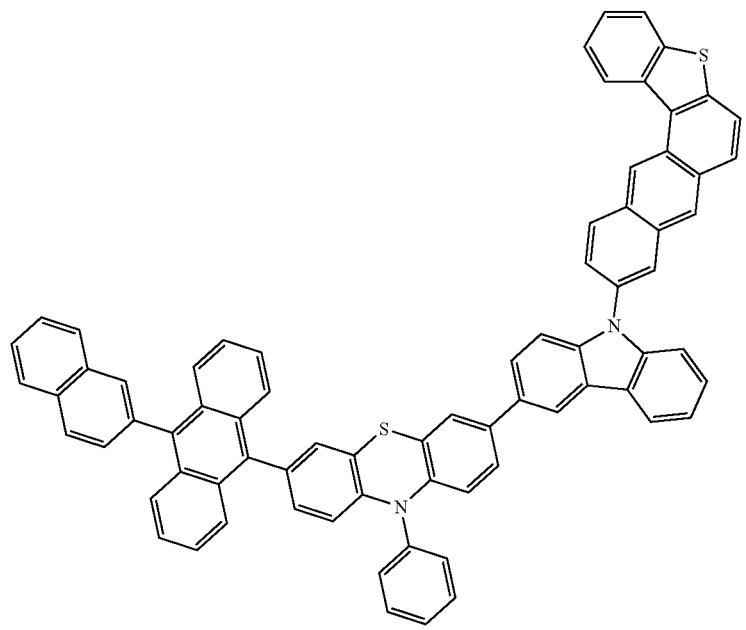
C164
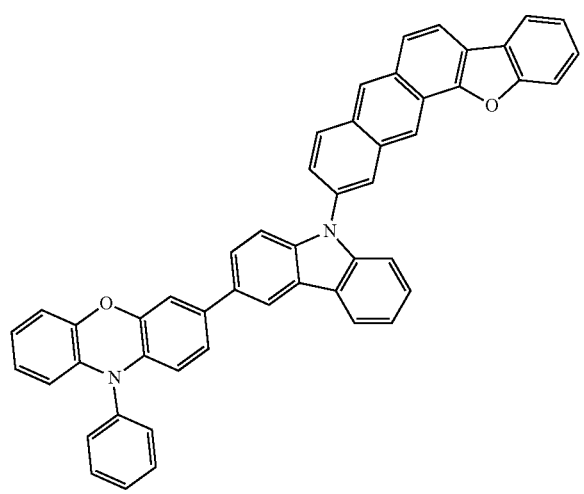
C165
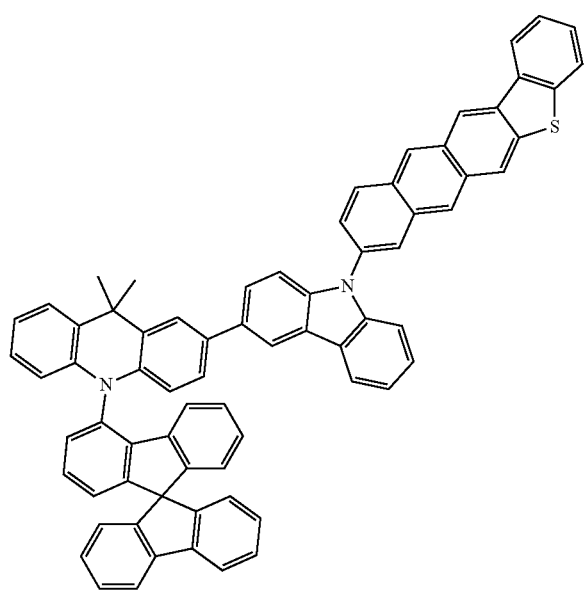
C166

-continued
C167
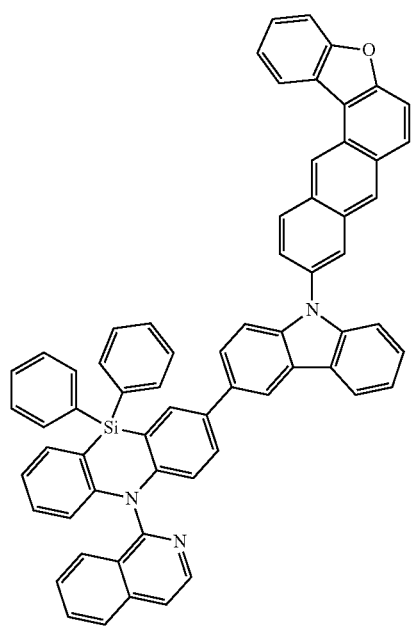
C168
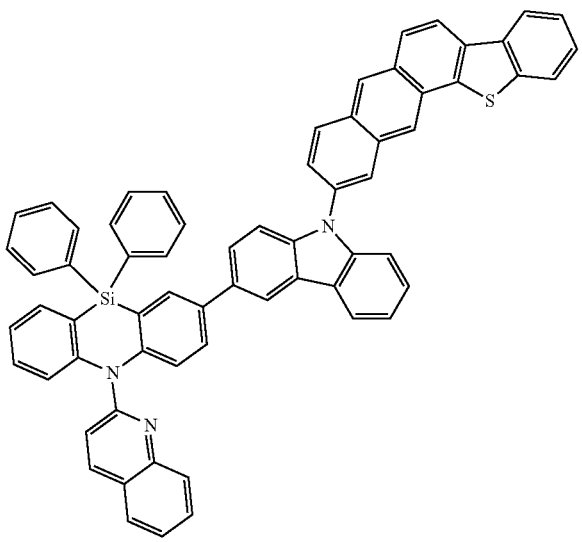
C169
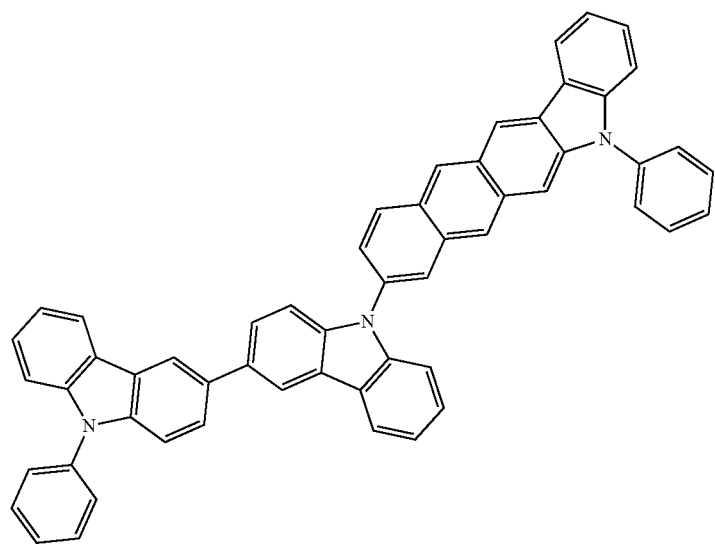
C170
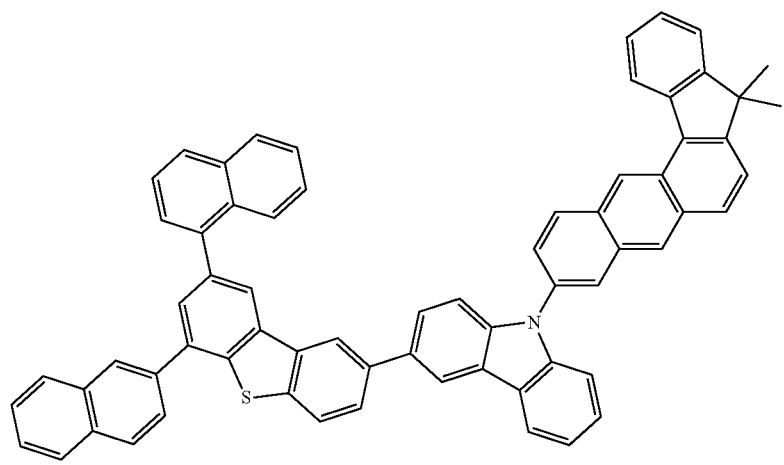

-continued
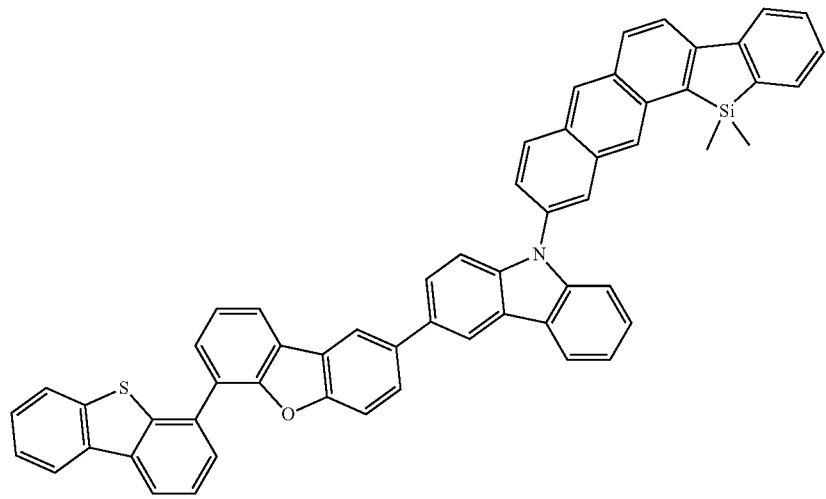
C171
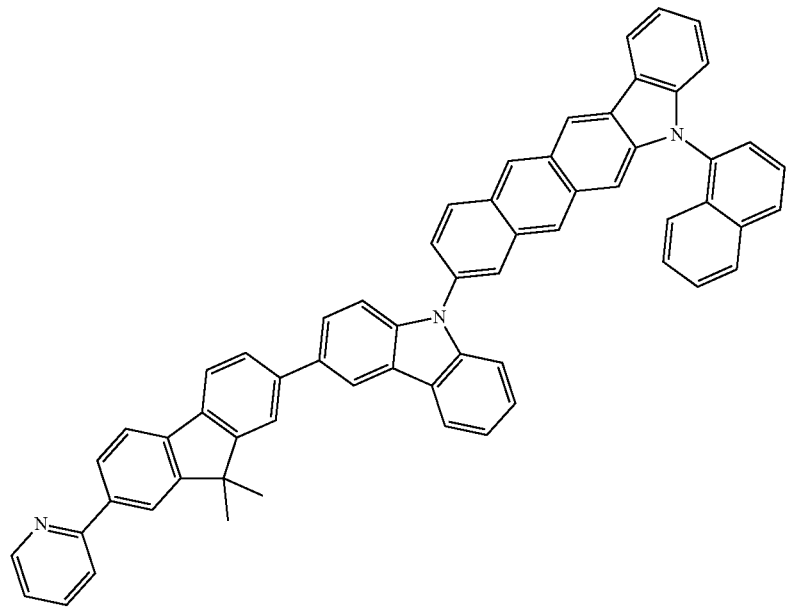
C172
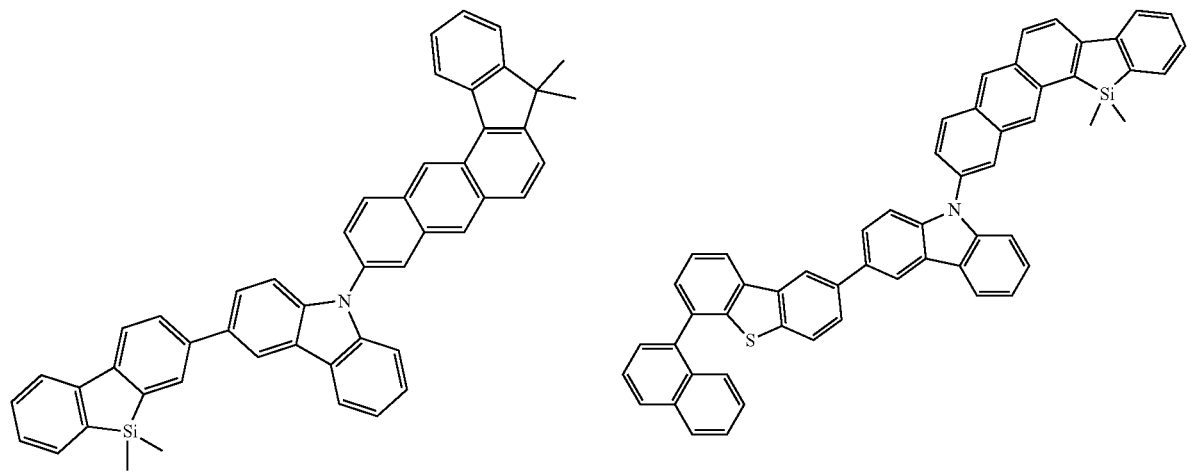
C173    C174

-continued
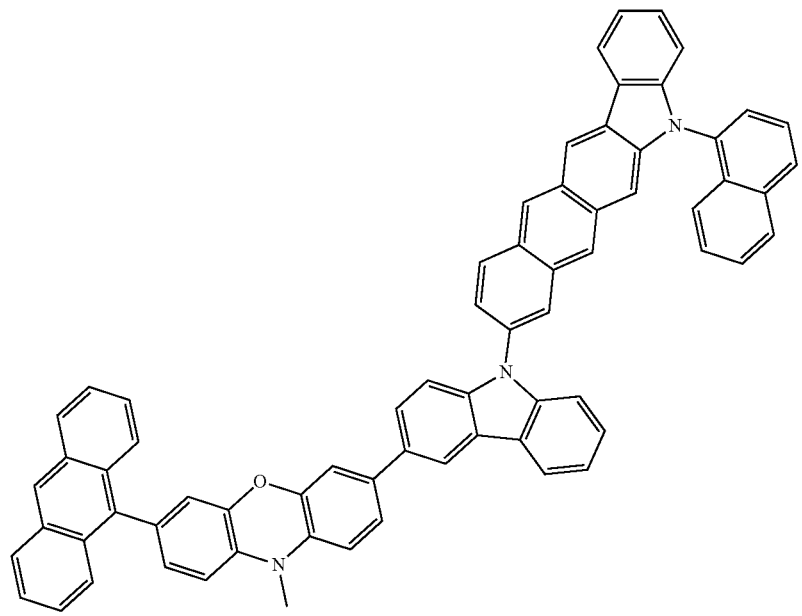
C175
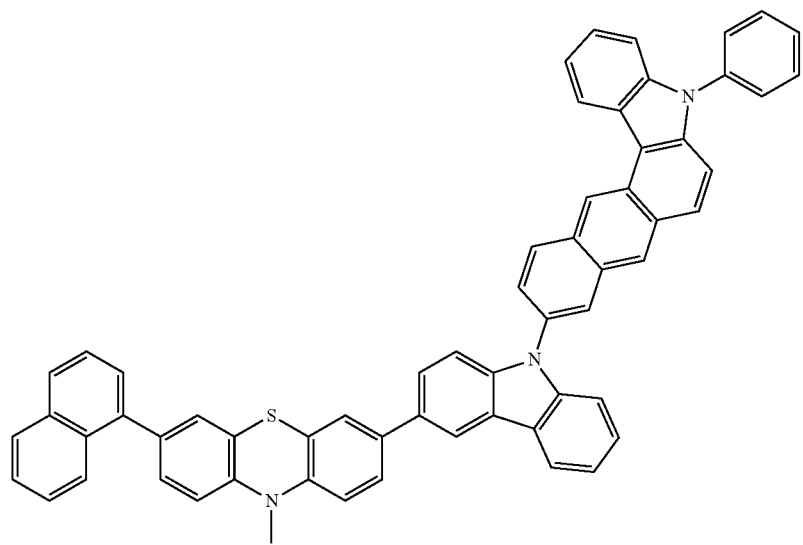
C176

-continued
C177
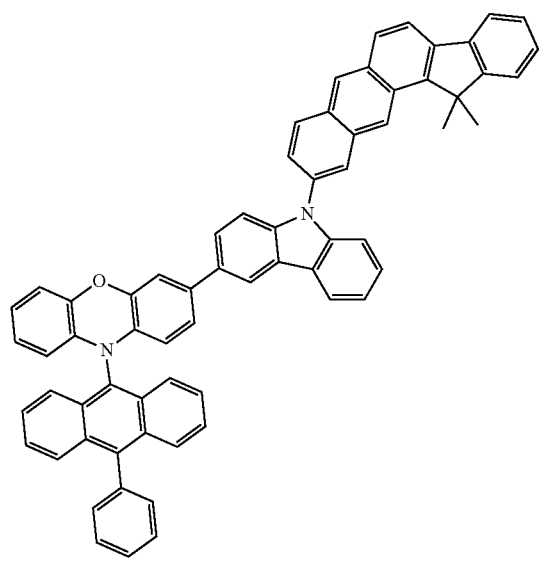
C178
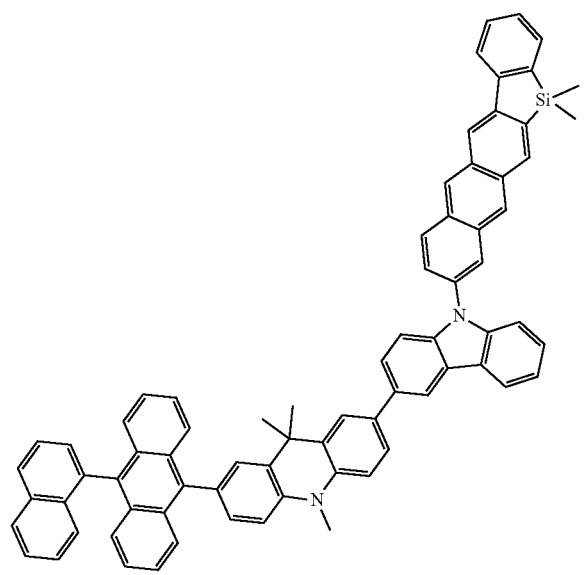
C179
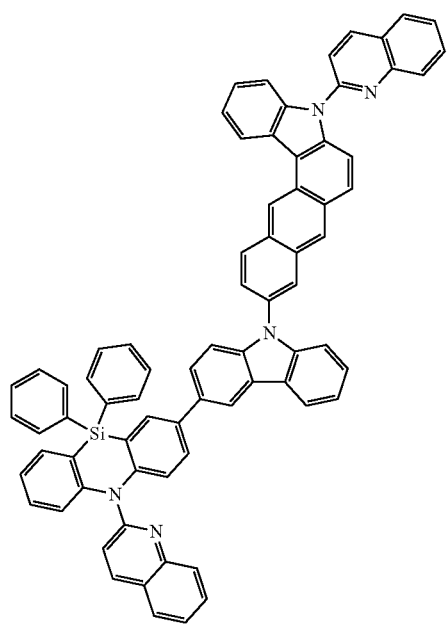
C180
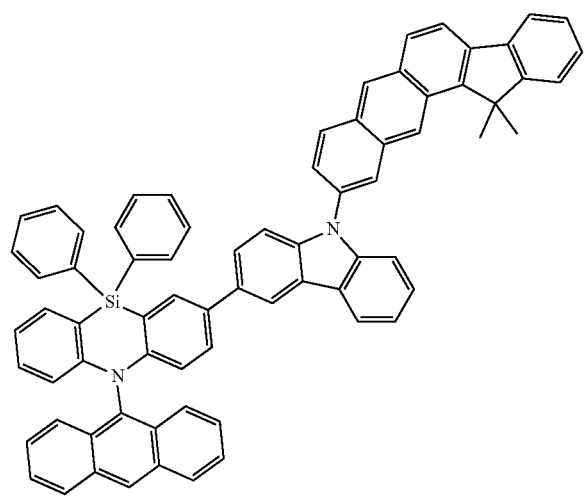

-continued
C181
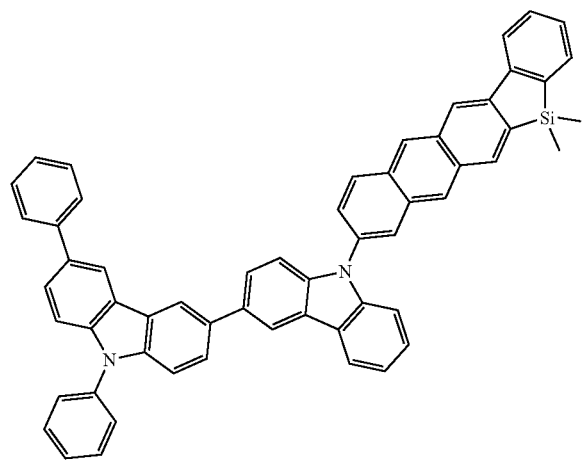
C182
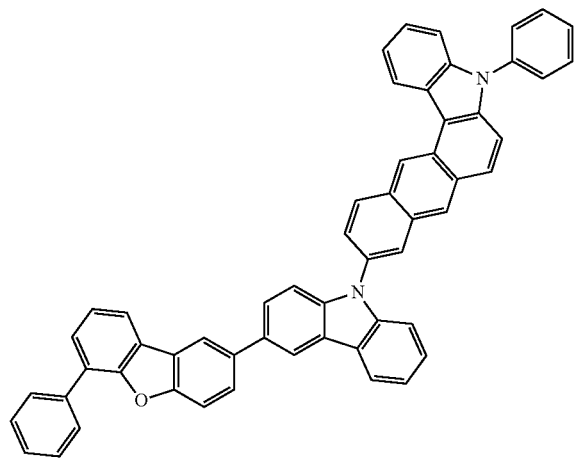
C183
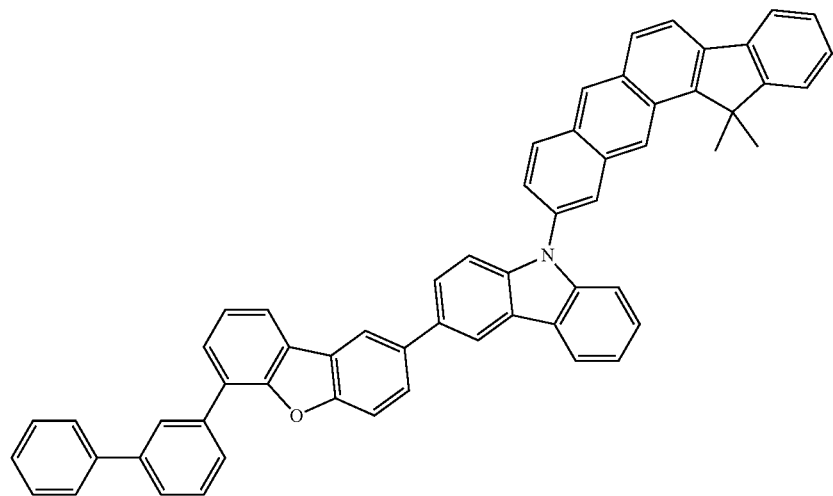
C184
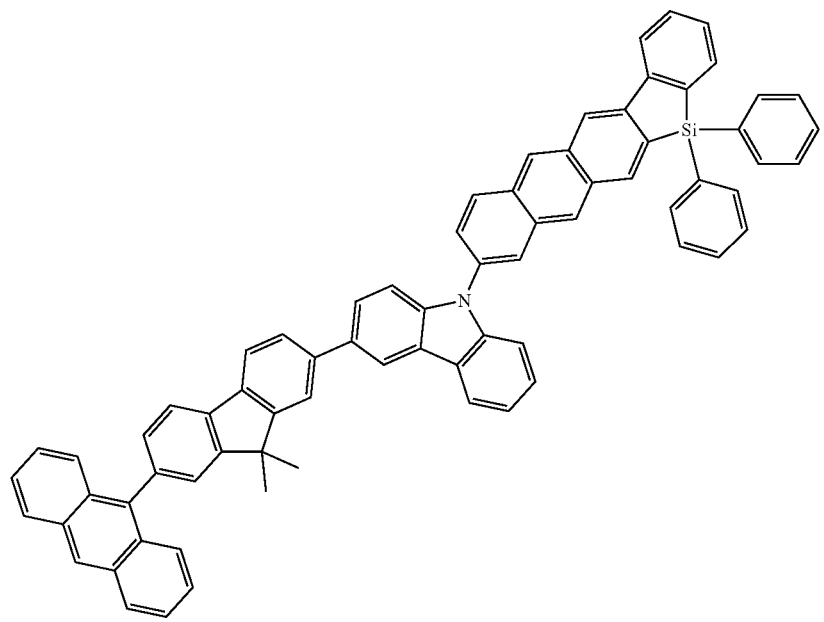

-continued
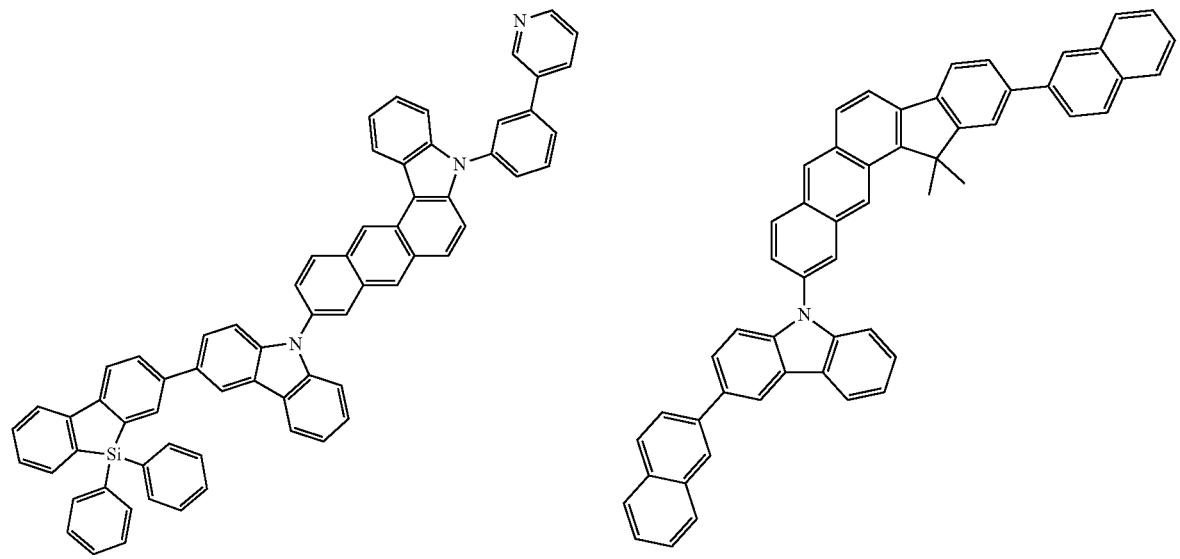
C185
C186
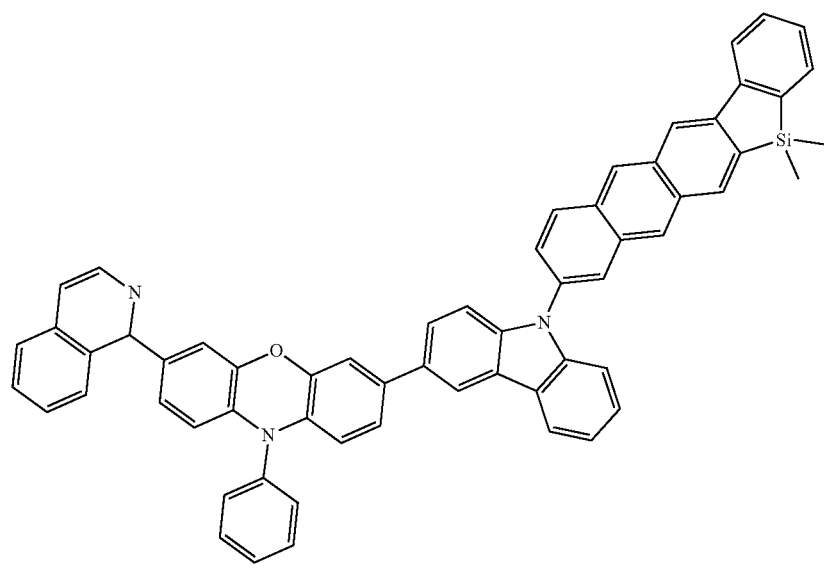
C187

-continued
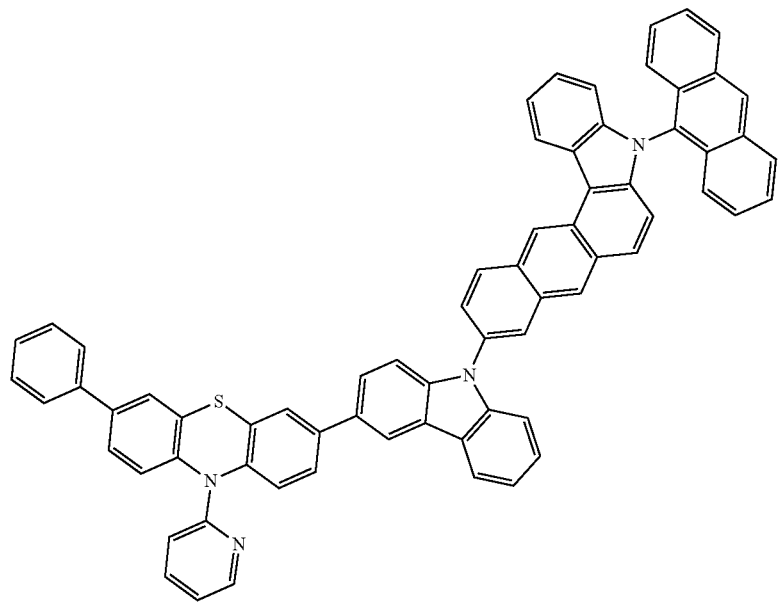
C188
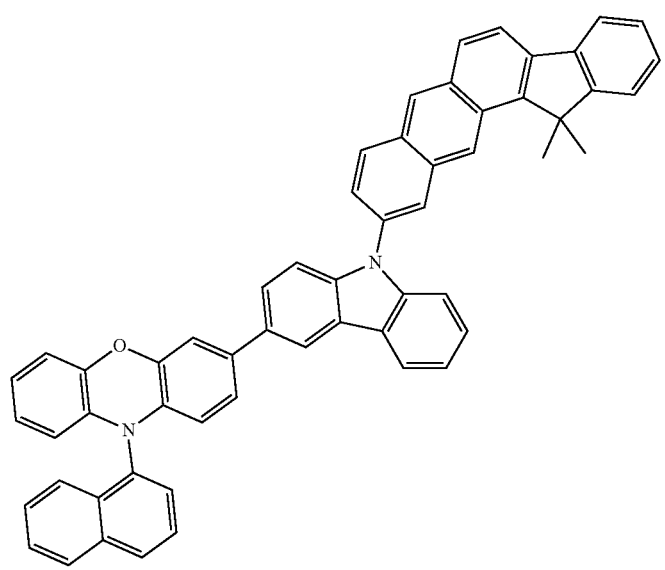
C189

C190
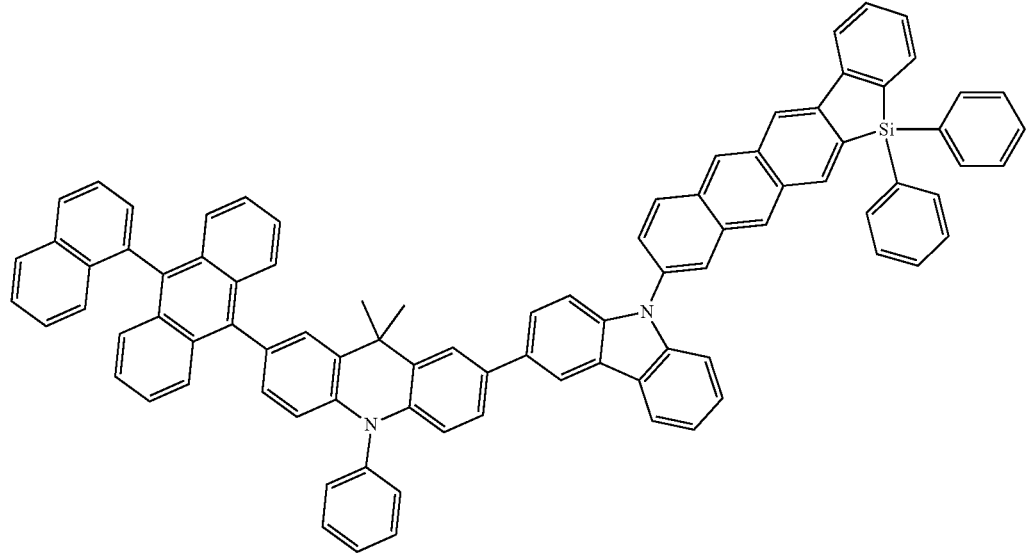
C191
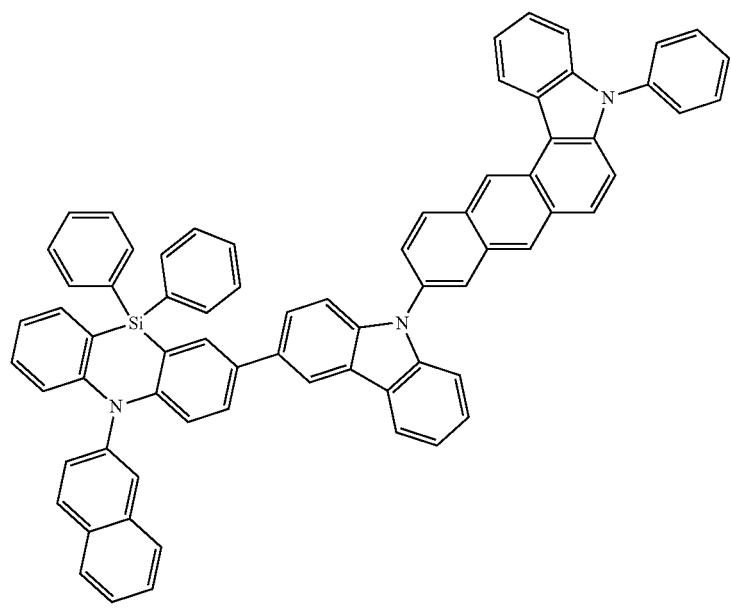
C192
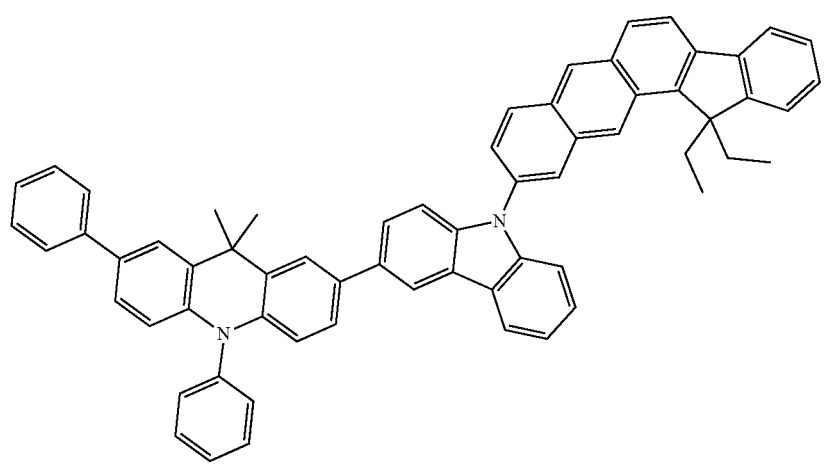

-continued
C193
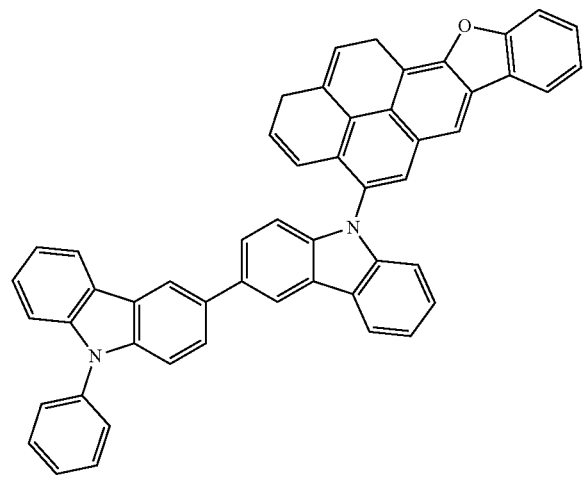
C194
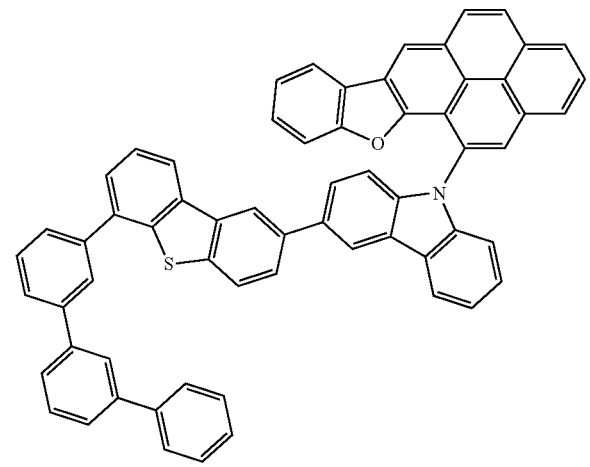
C195
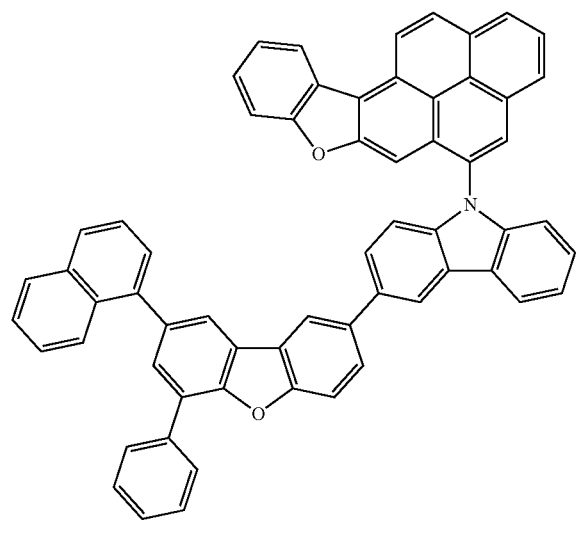
C196
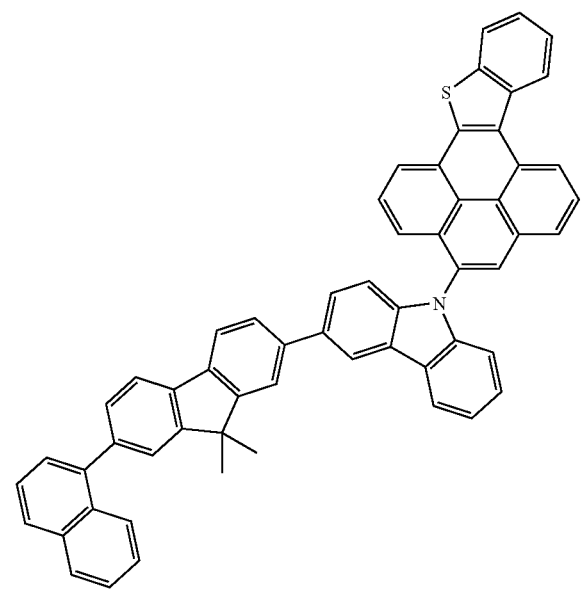
C197
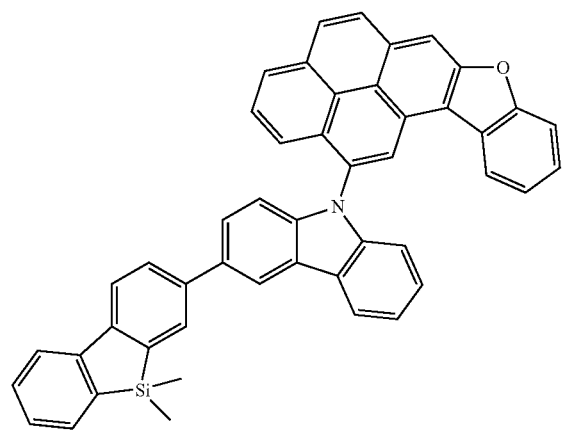
C198
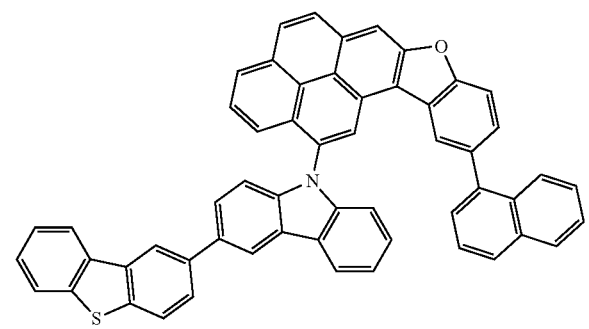

-continued
C199
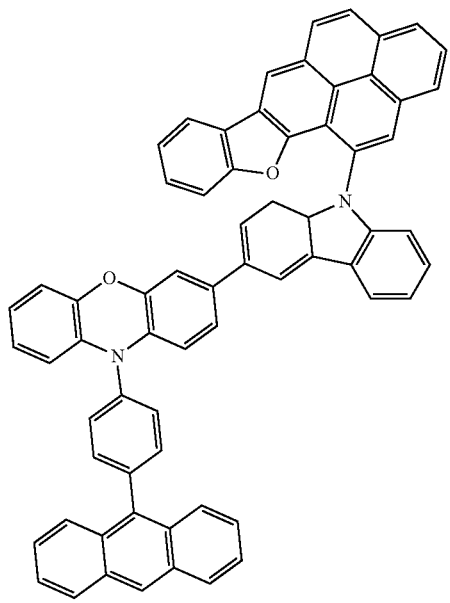
C200
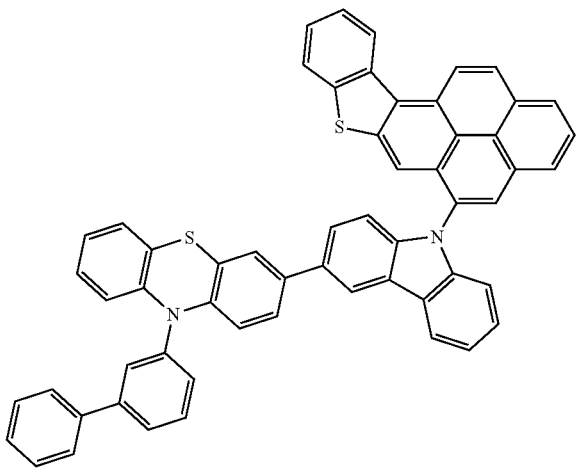
C201
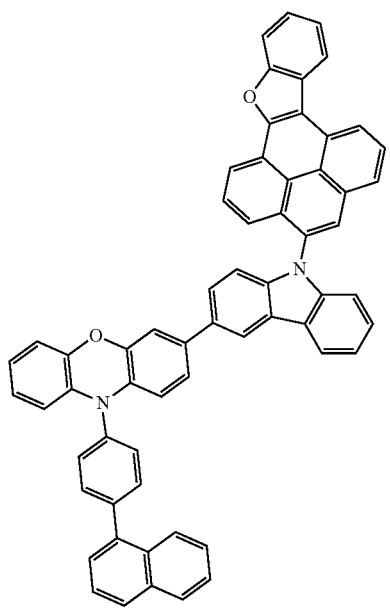
C202
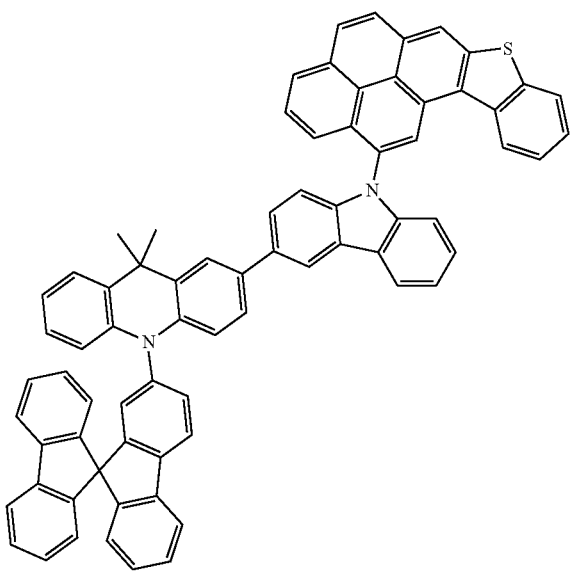
C206
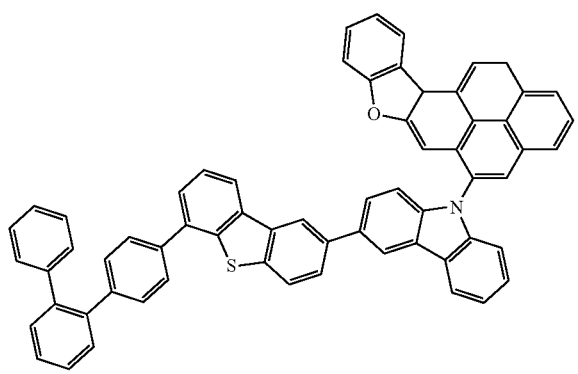
C207
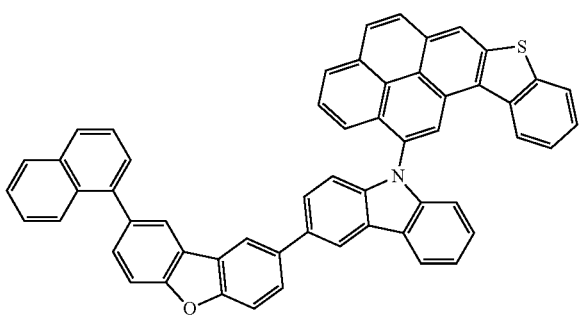

-continued
C208
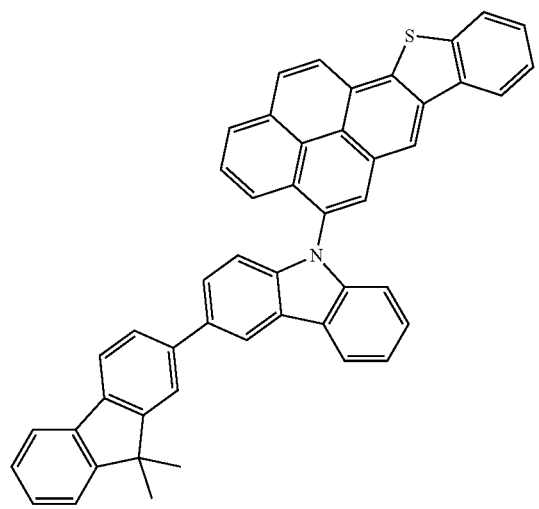
C209
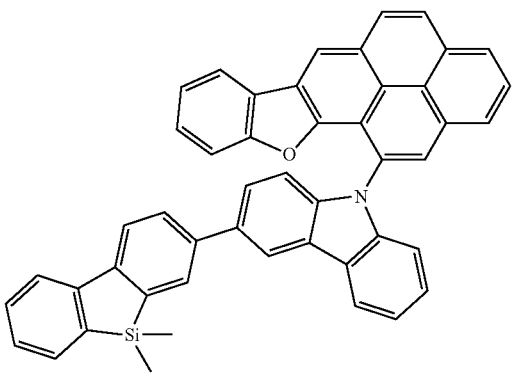
C210
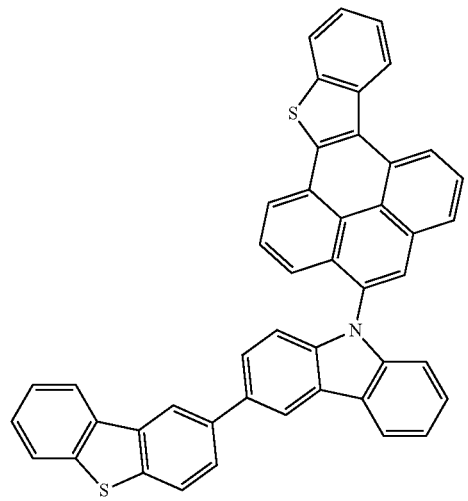
C211
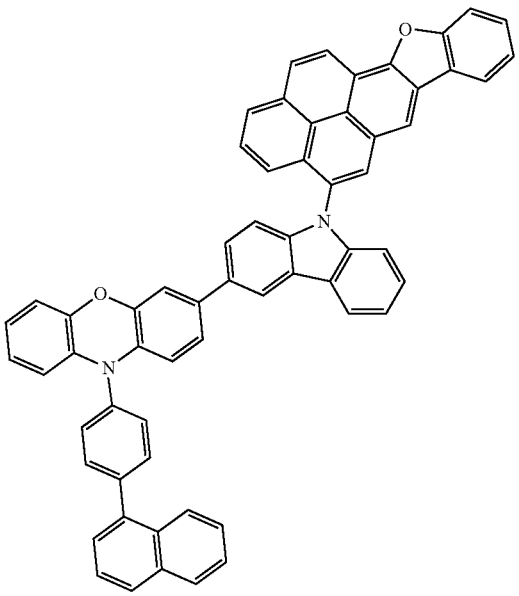

-continued
C212
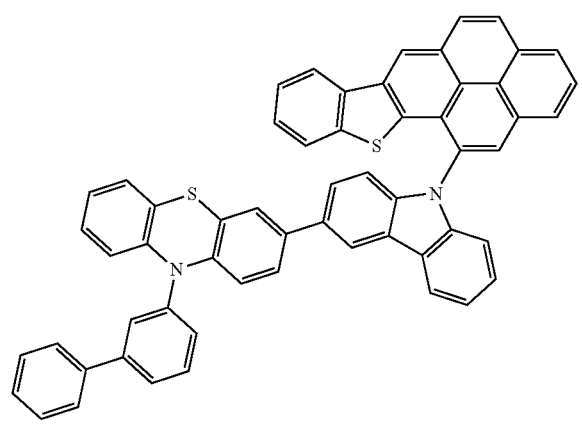
C213
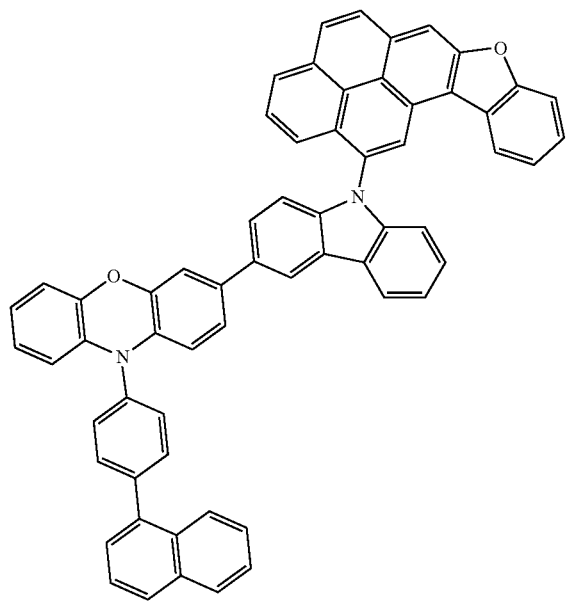
C214
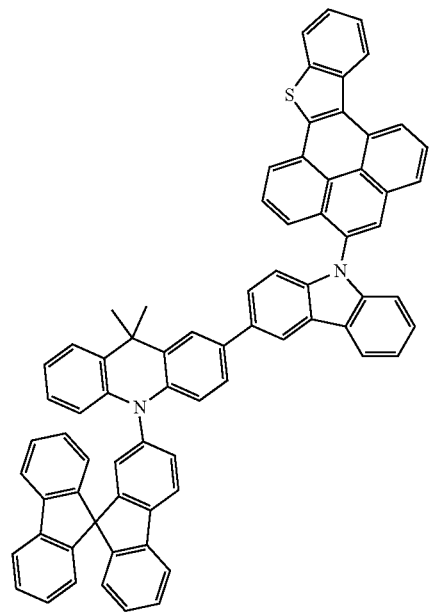
C215
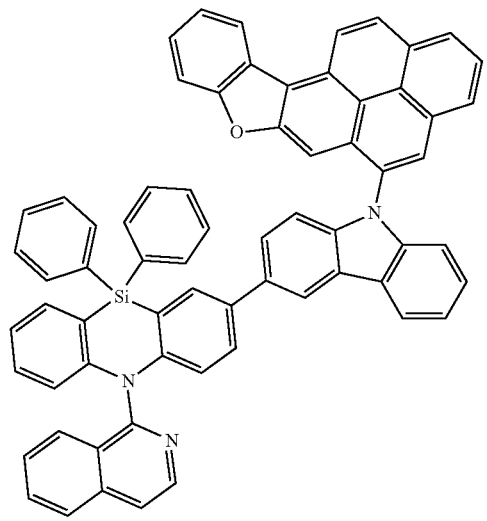

-continued
C216
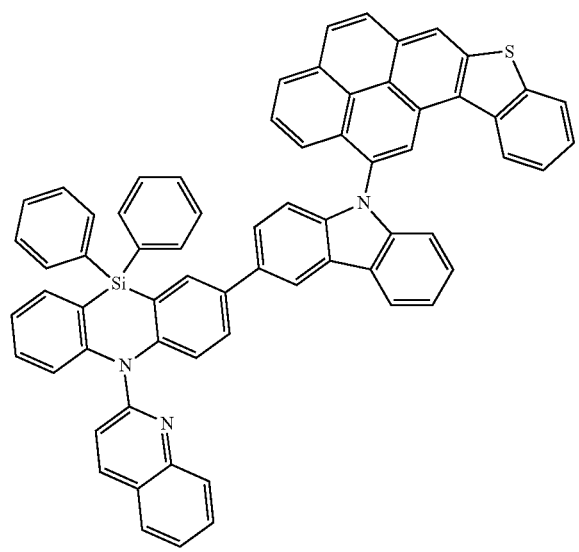
C217
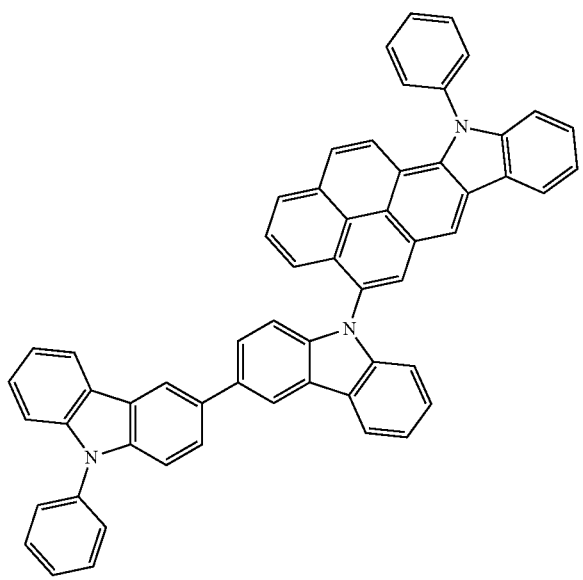
C218
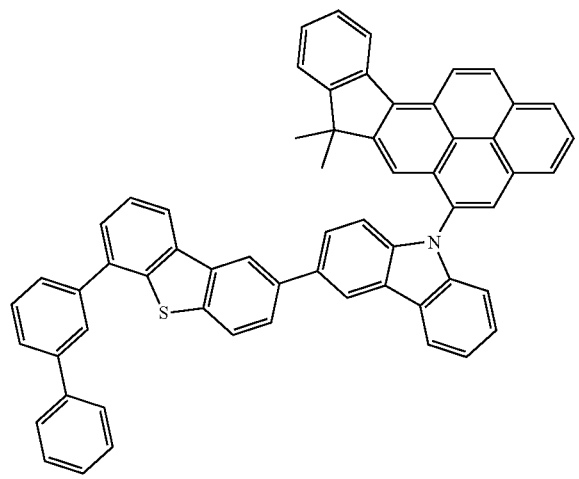
C219
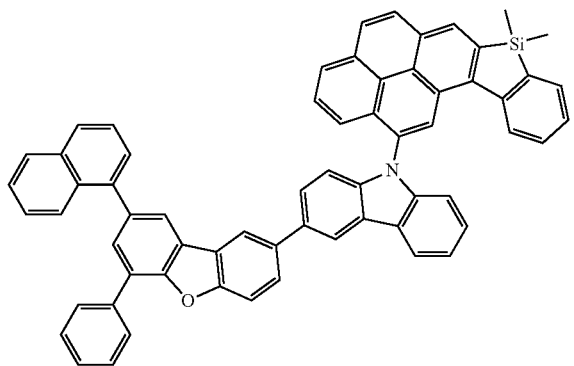

-continued
C220
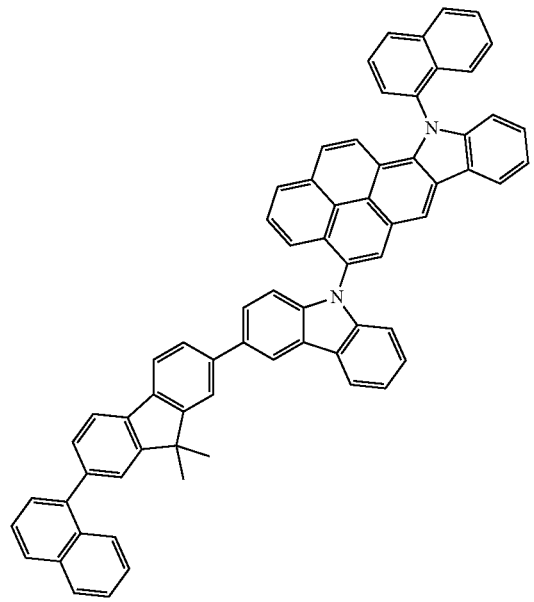
C221
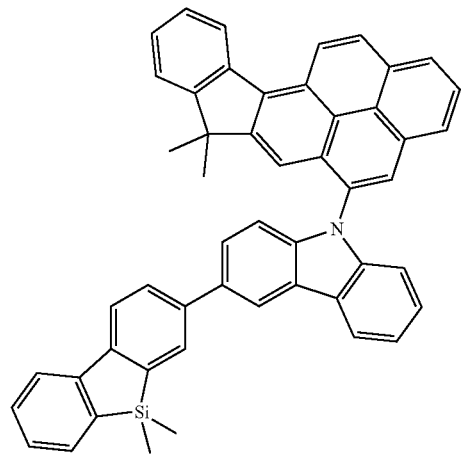
C222
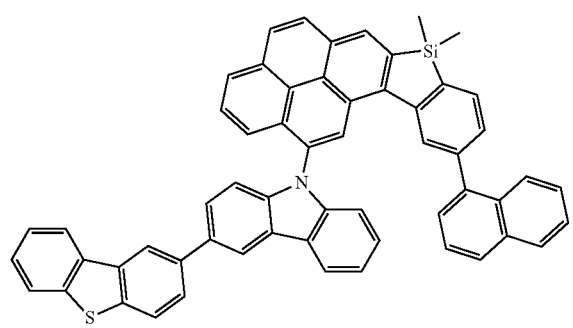
C223
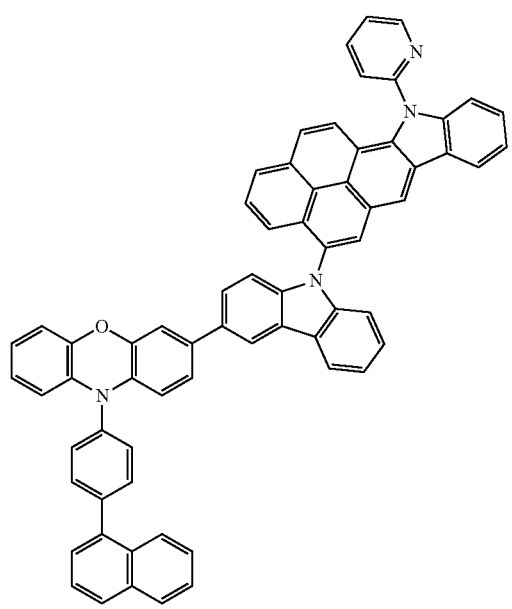

331 332
-continued
C224
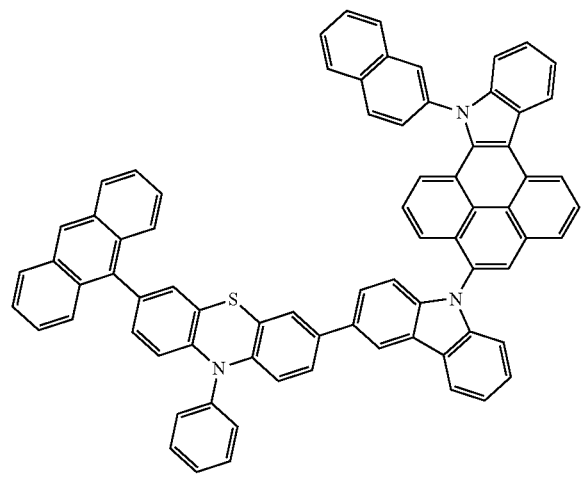
C225
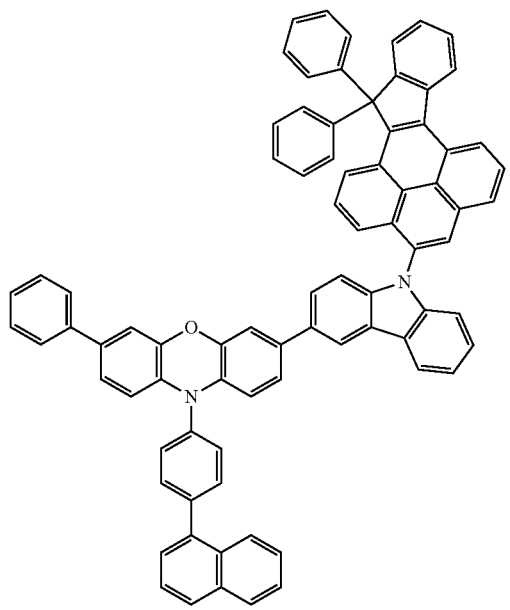
C226
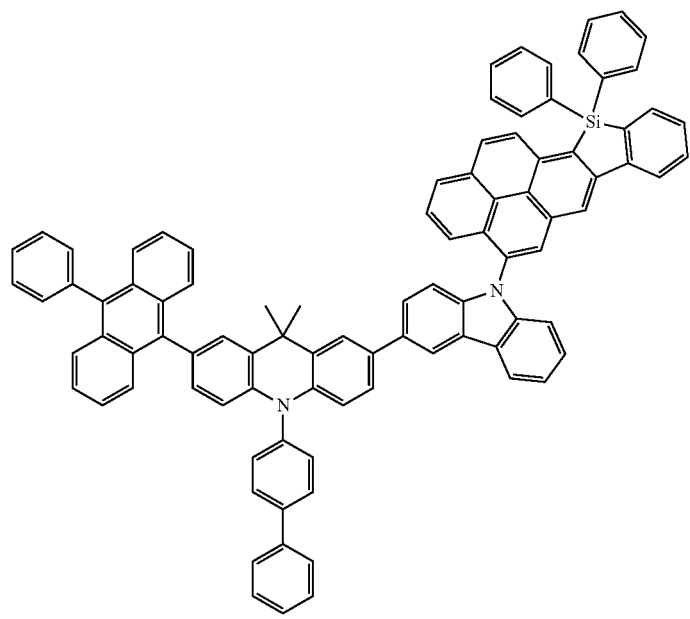

-continued
C227
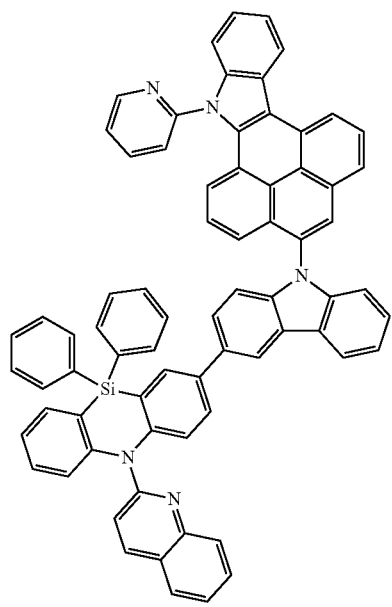
C228
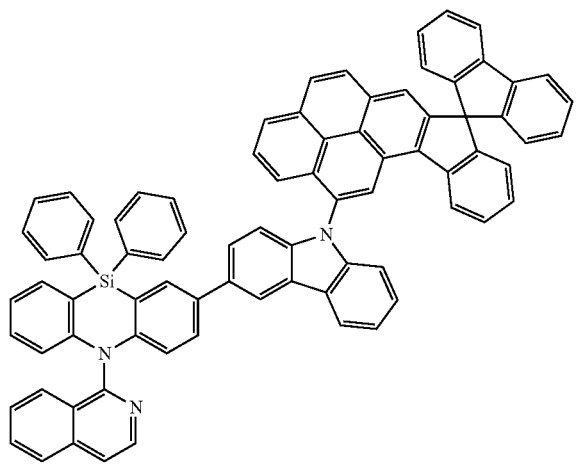
C229
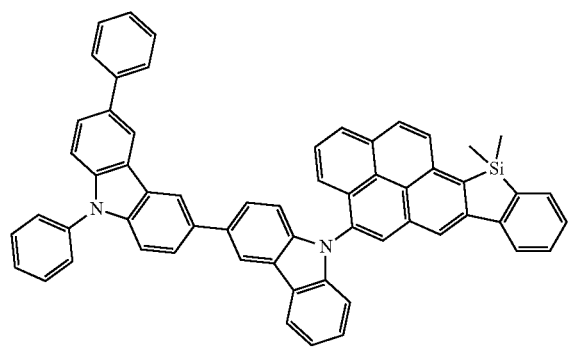
C230
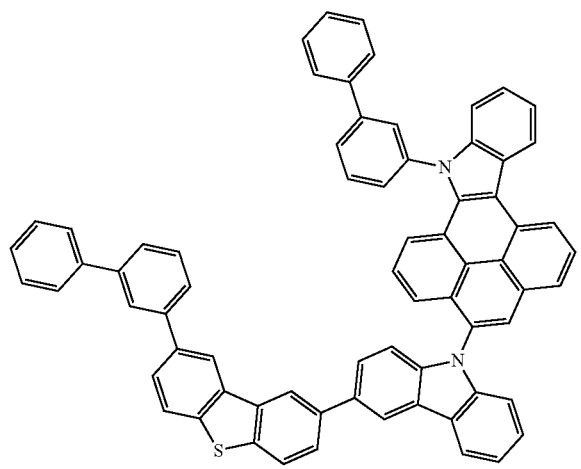

-continued
C231
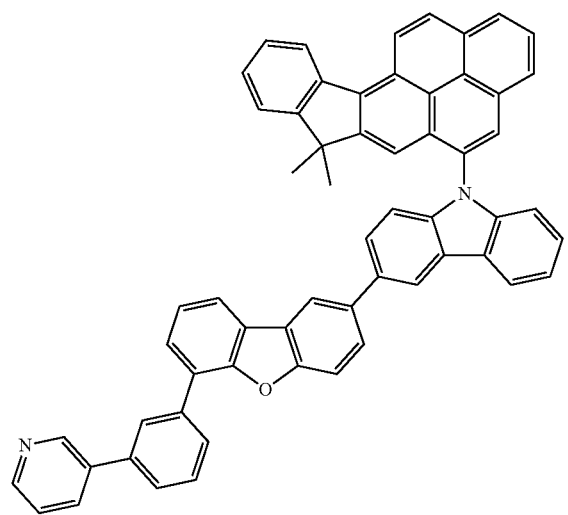
C232
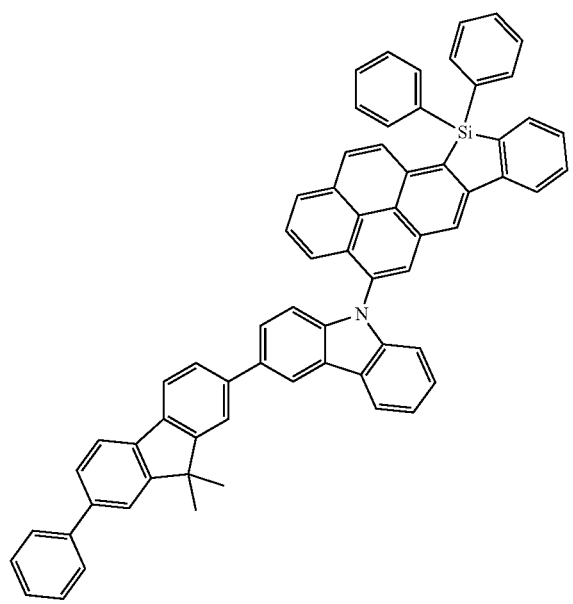
C233
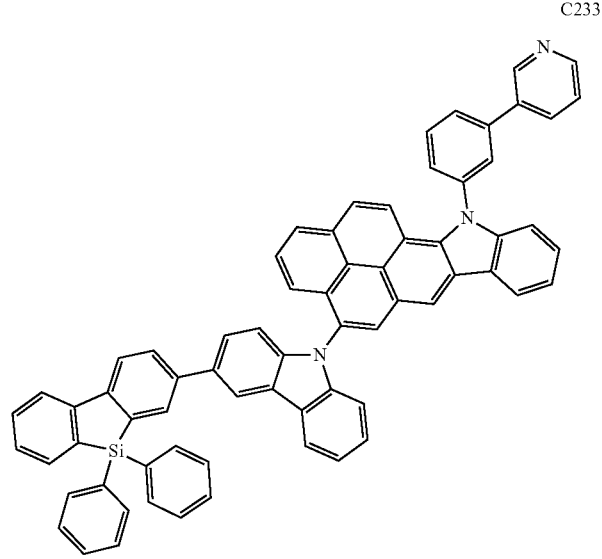
C234

-continued
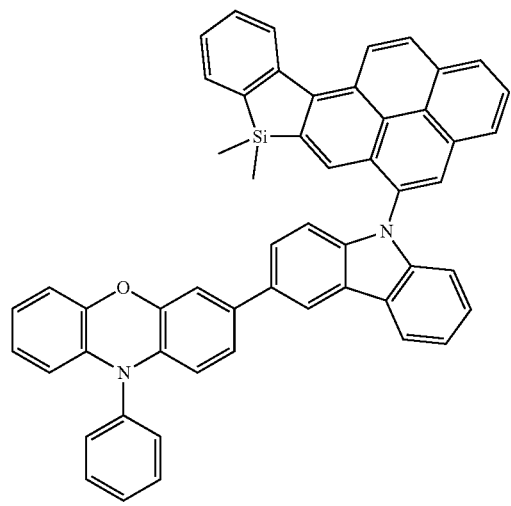
C235
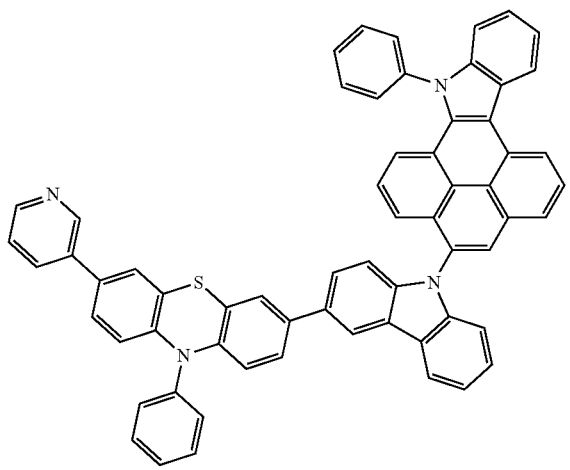
C236
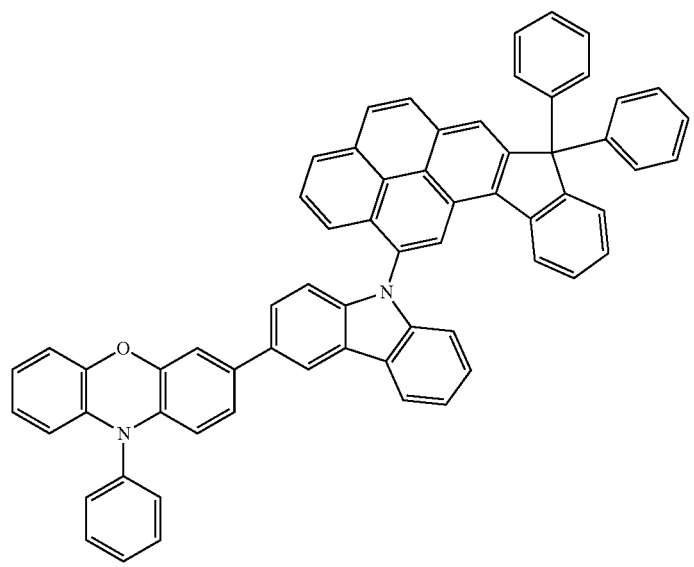
C237

-continued
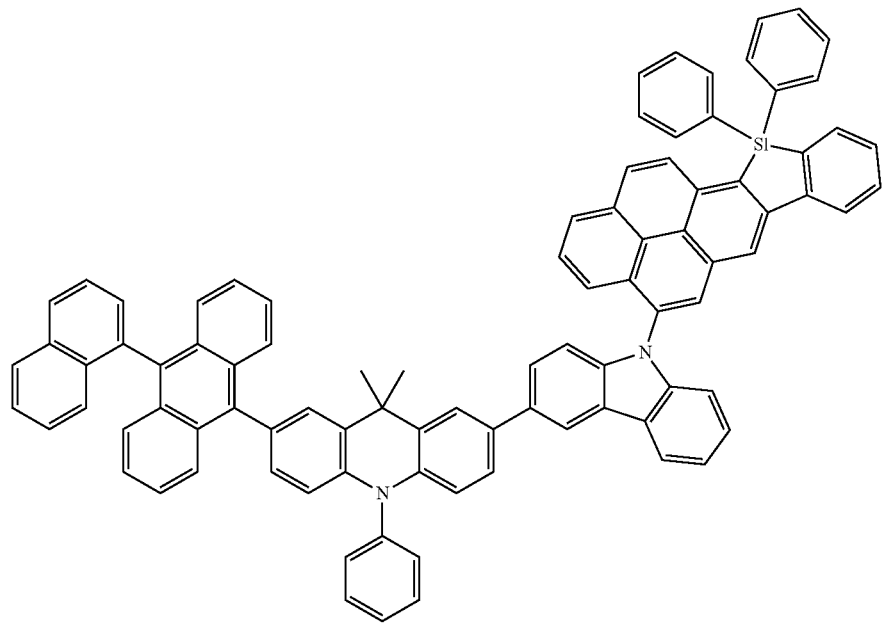
C238
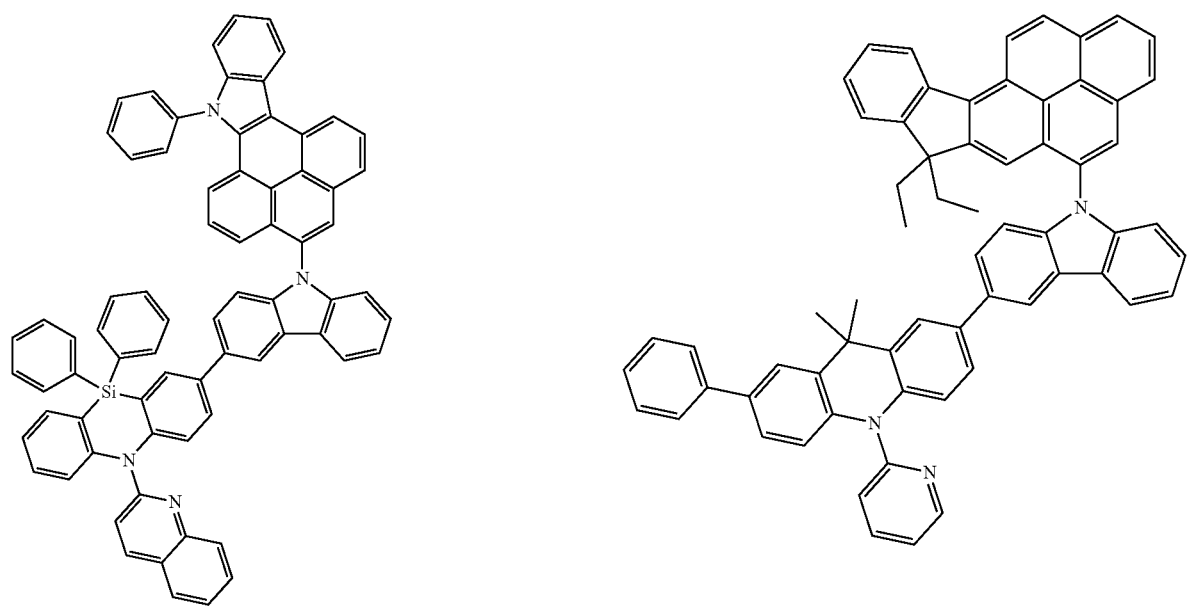
C239  C240

-continued
C241
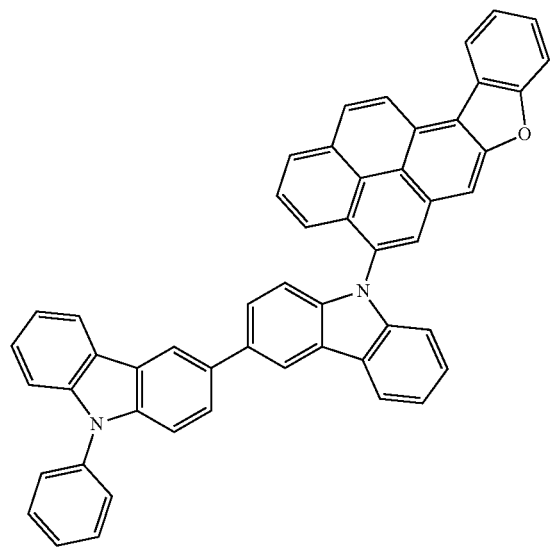
C242
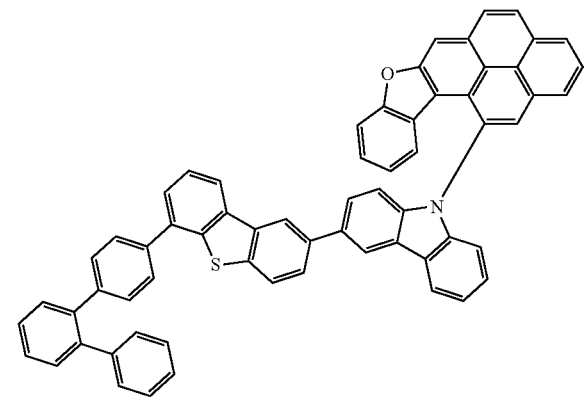
C243
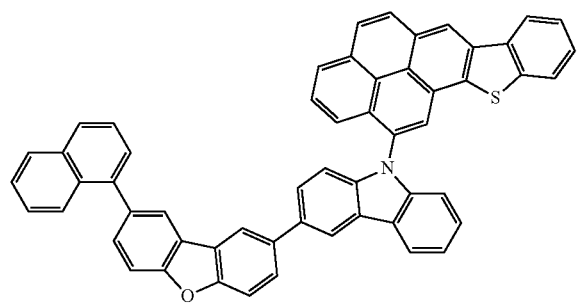
C244
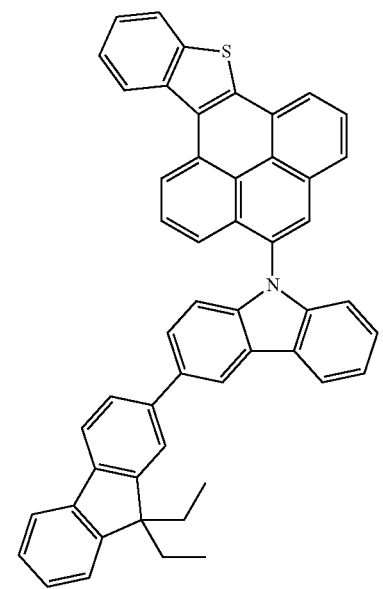
C245
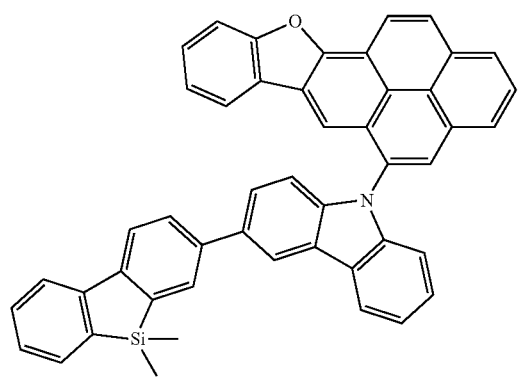
C246
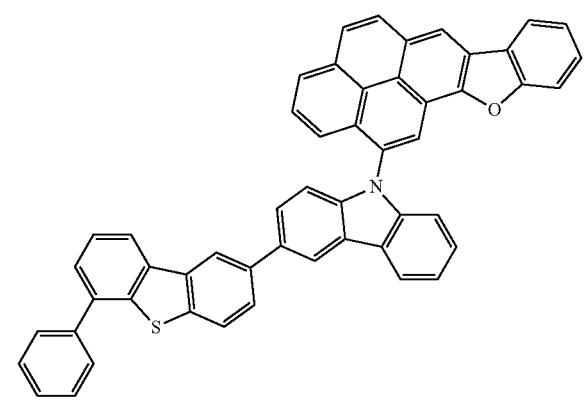

-continued
C247
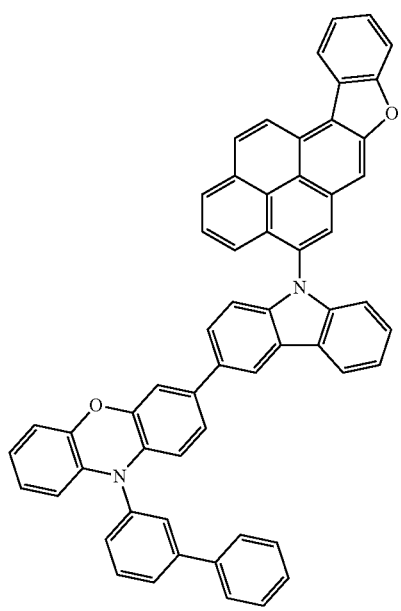
C248
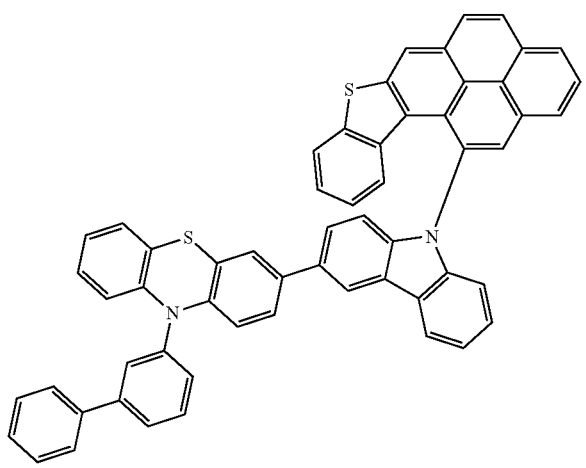
C249
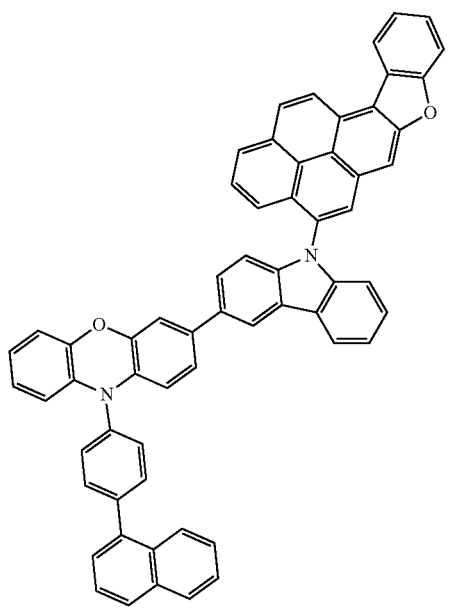
C250
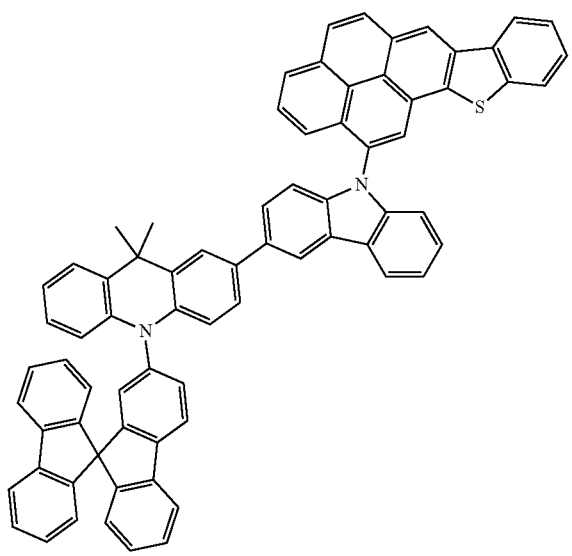

-continued
C251 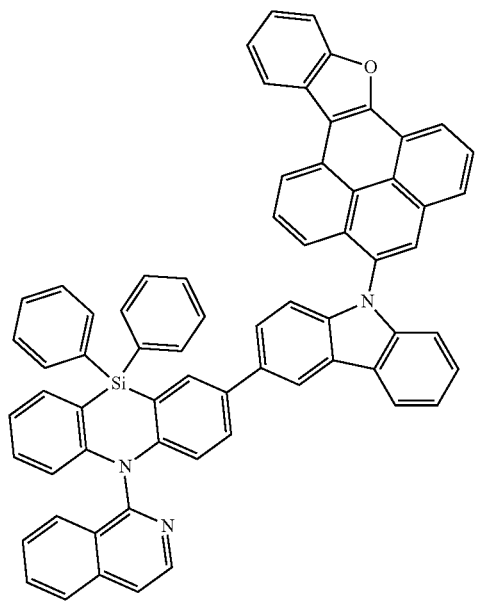
C252 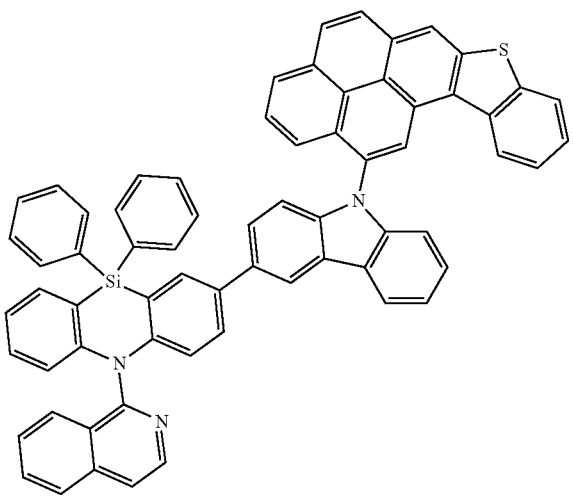
C253 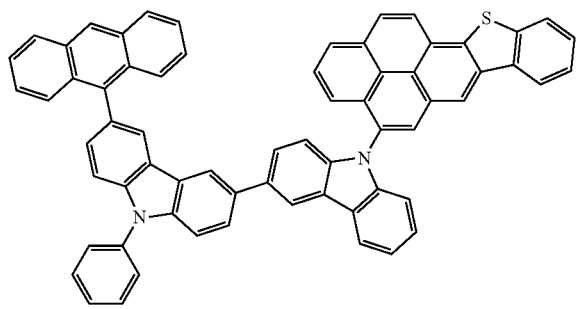
C254 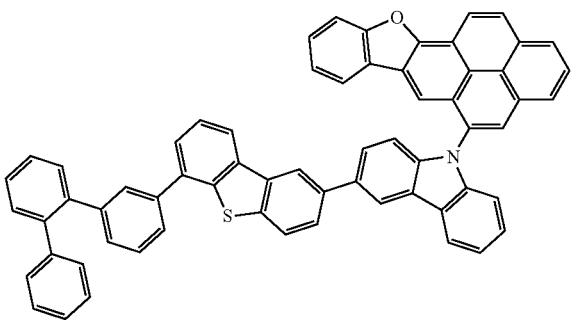
C255 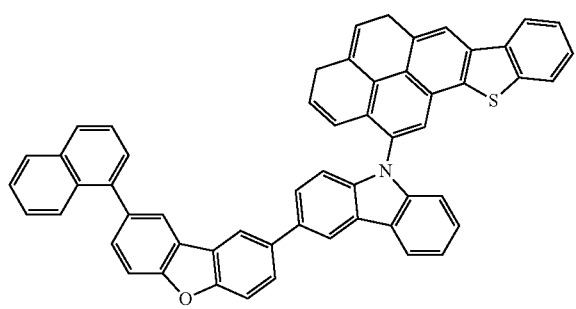
C256 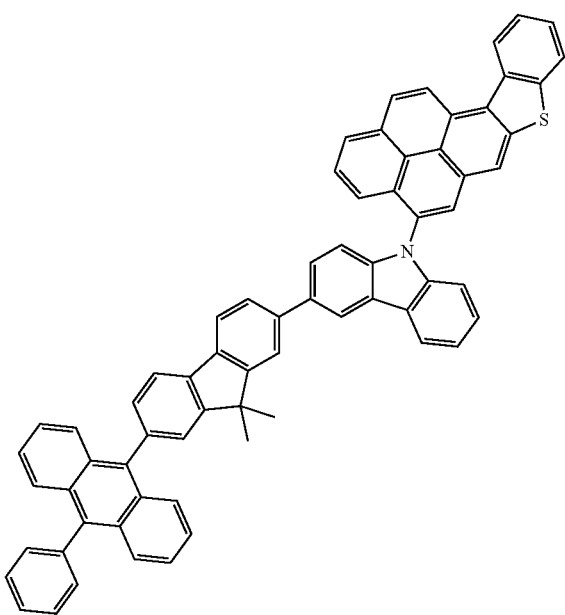

-continued
C257
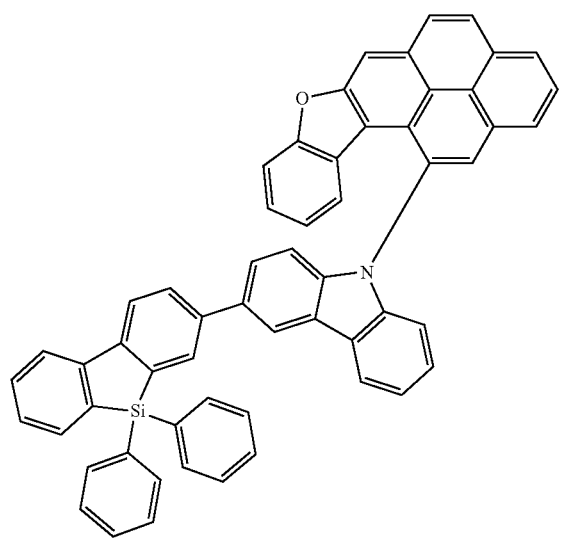
C258
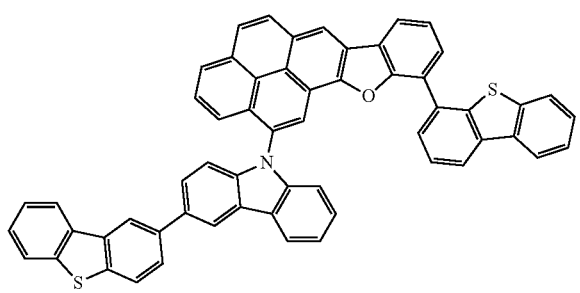
C259
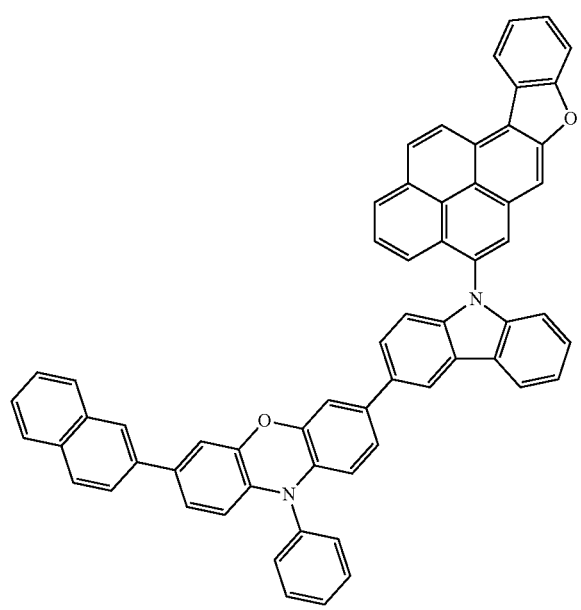
C260
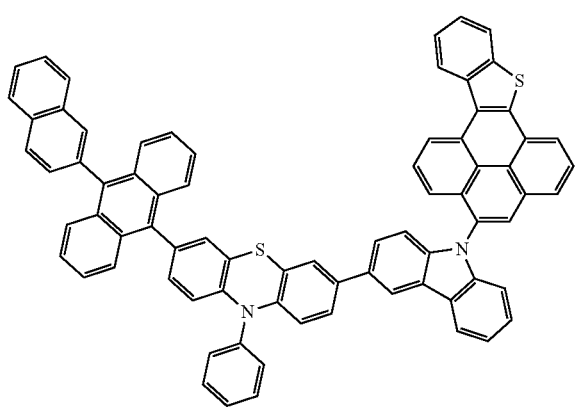

-continued
C261
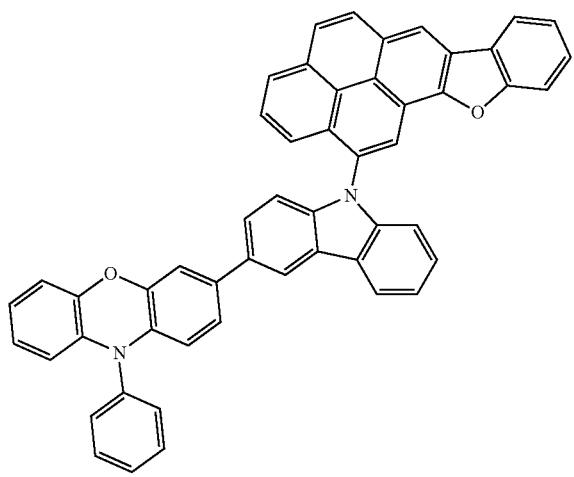
C262
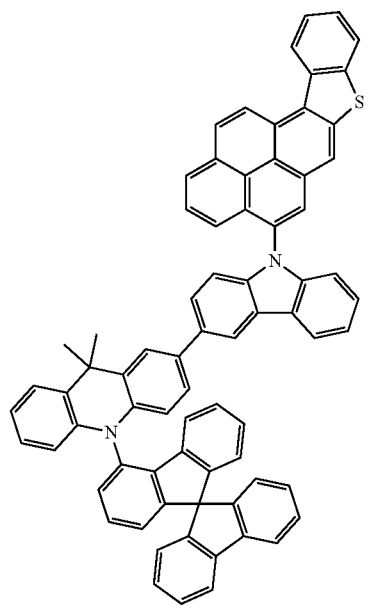
C263
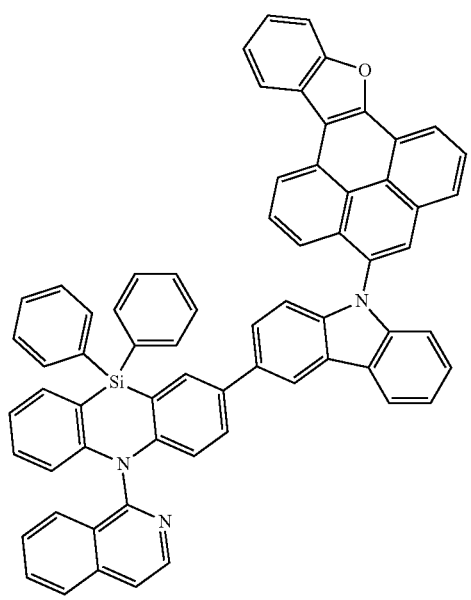
C264
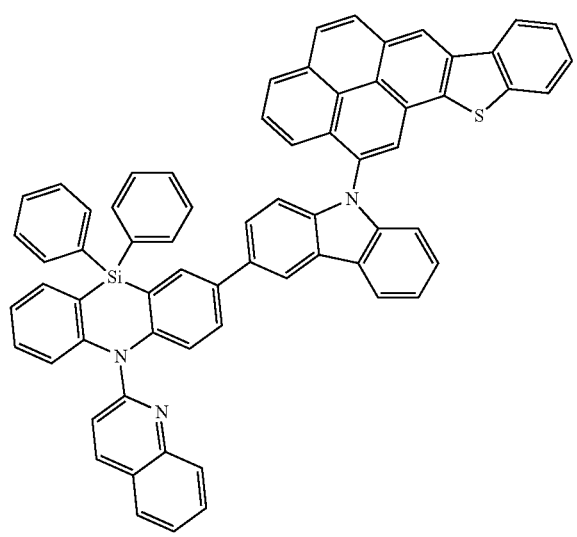

-continued
C265
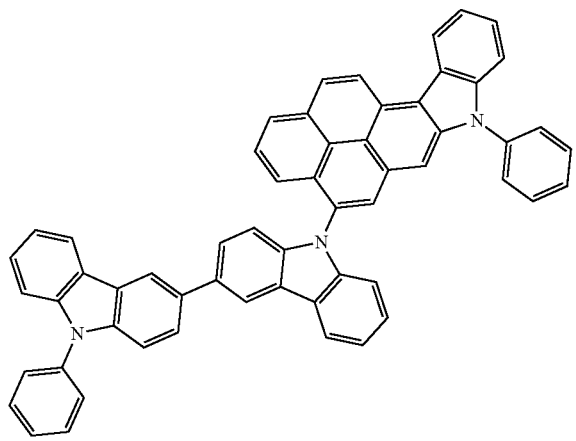
C266
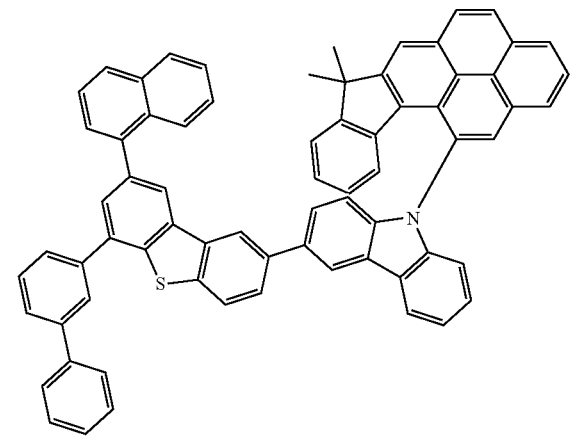
C267
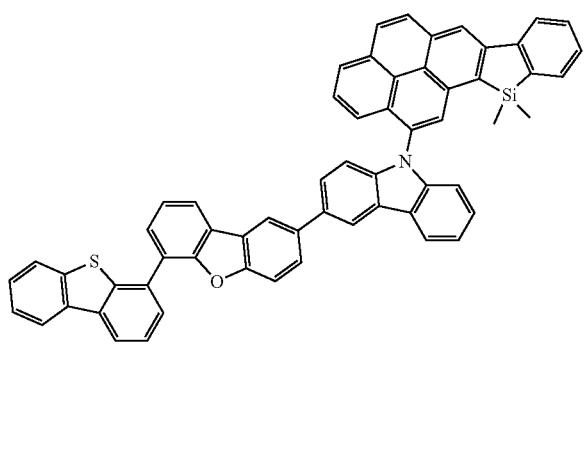
C268
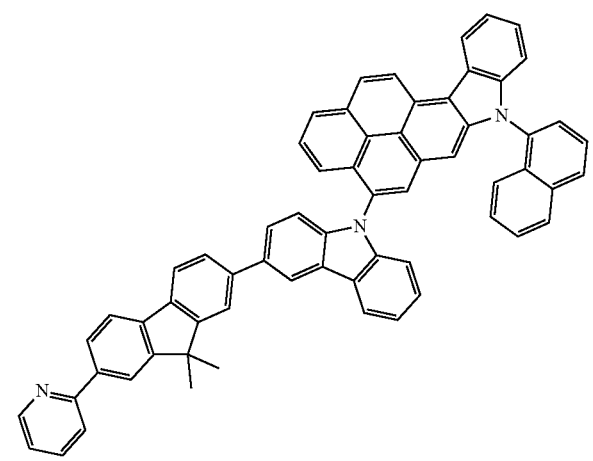
C269
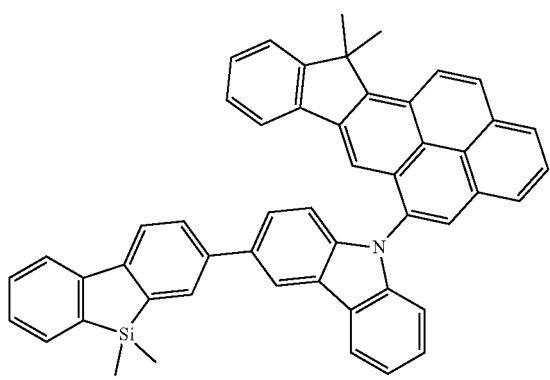
C270
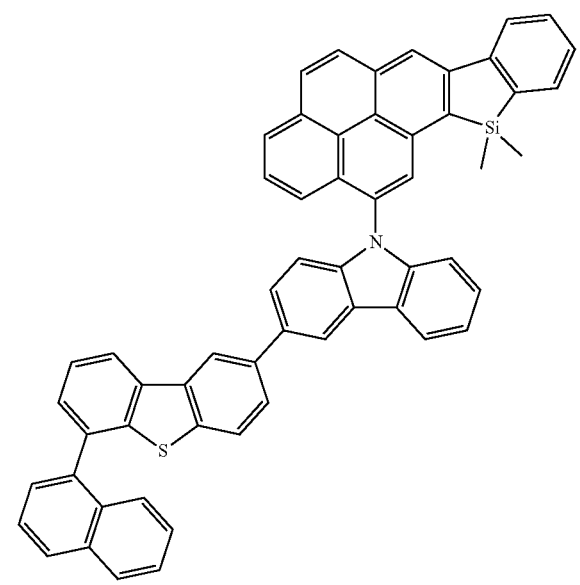

-continued
C271
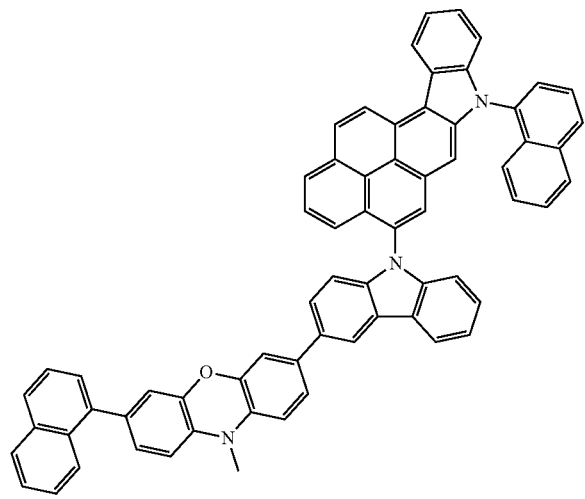
C272
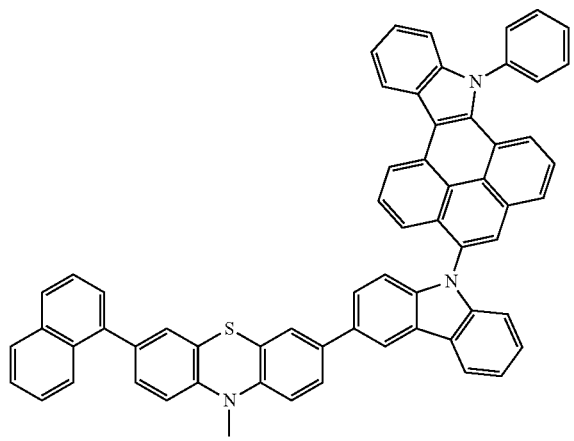
C273
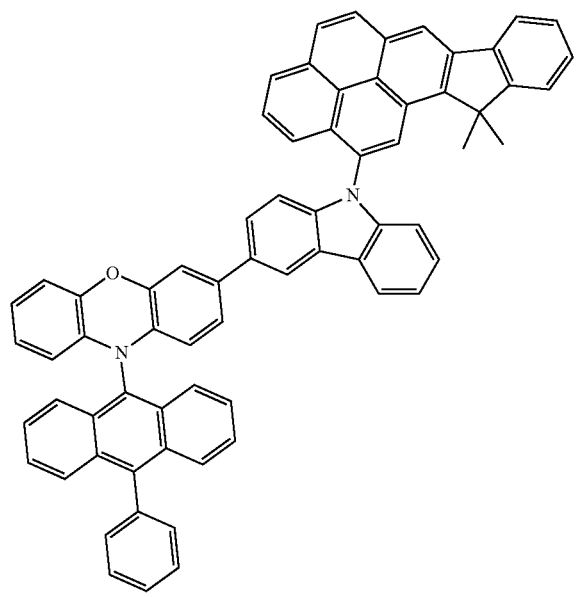
C274
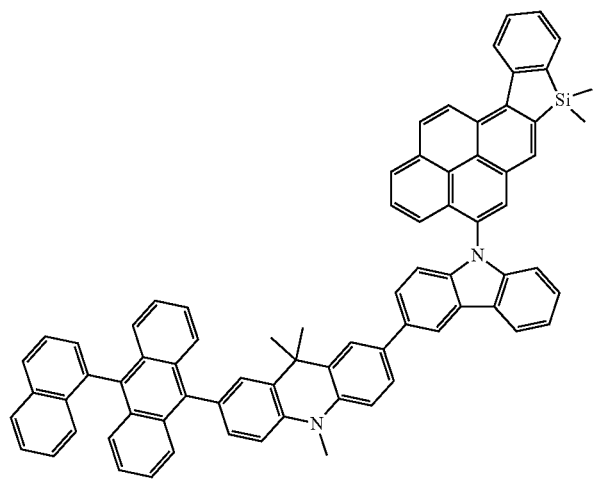

-continued
| C275 | C276 |
|---|---|
| 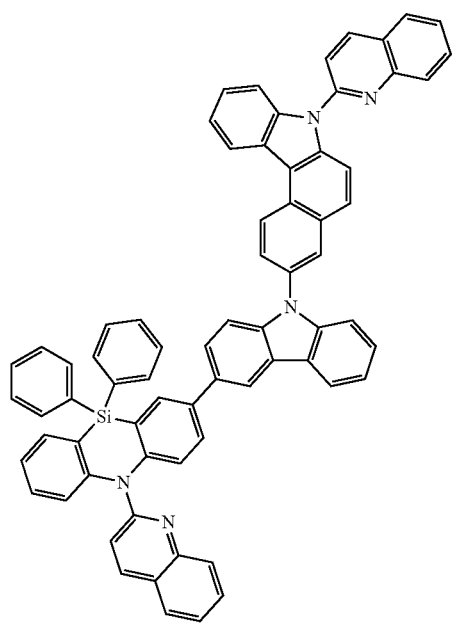 | 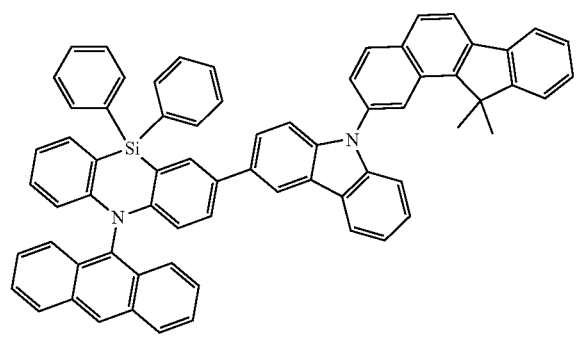 |
| C277 | C278 |
|---|---|
| 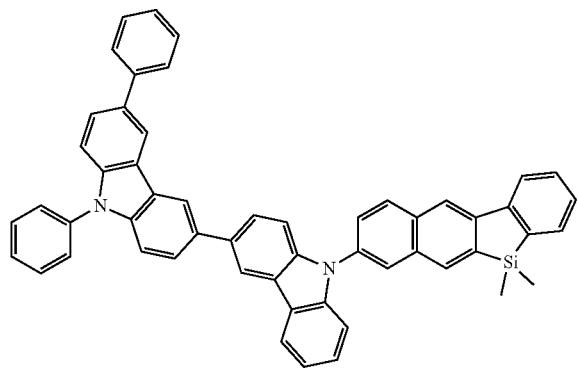 | 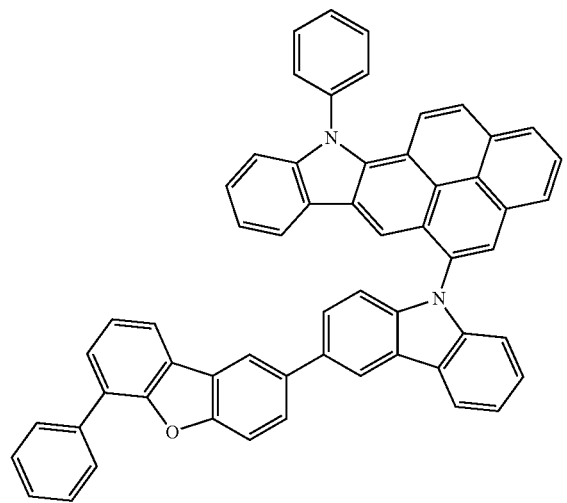 |

-continued
C279
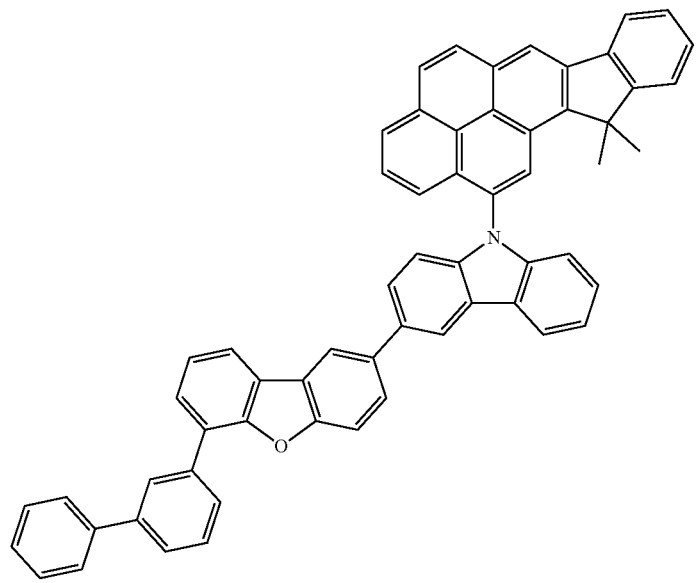
C280
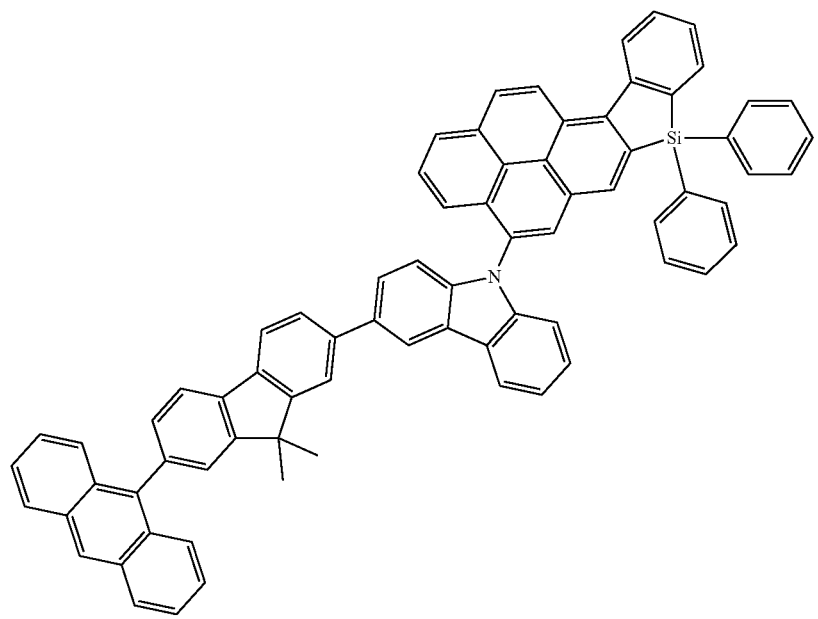
C281 C282
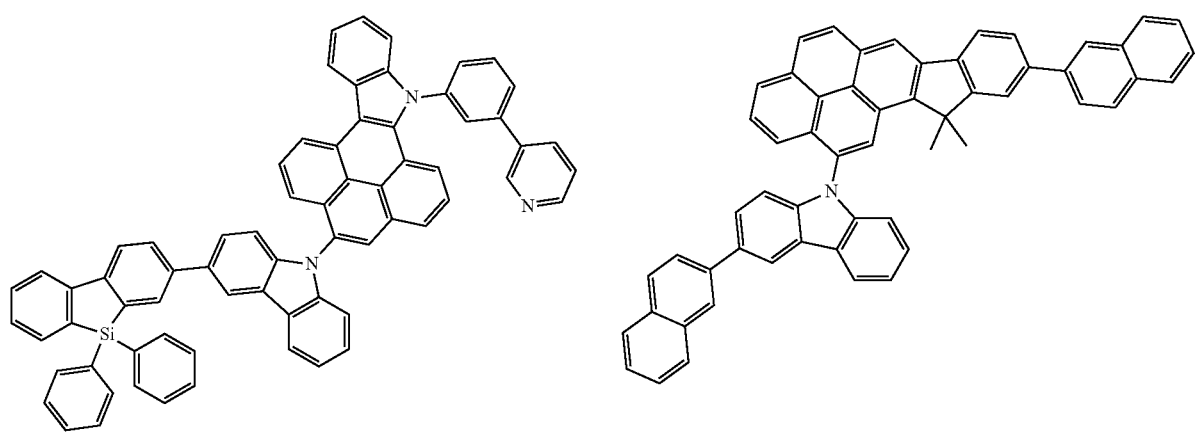

-continued
C283
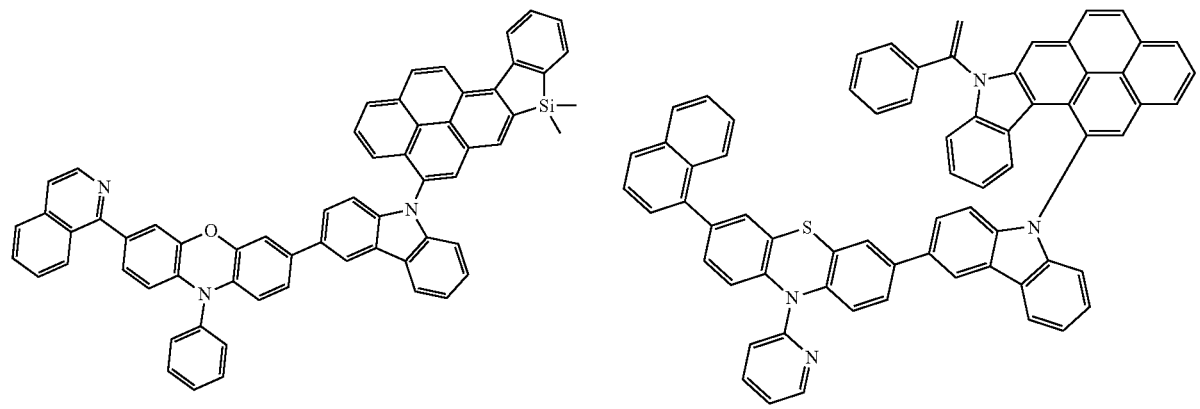
C284
C285
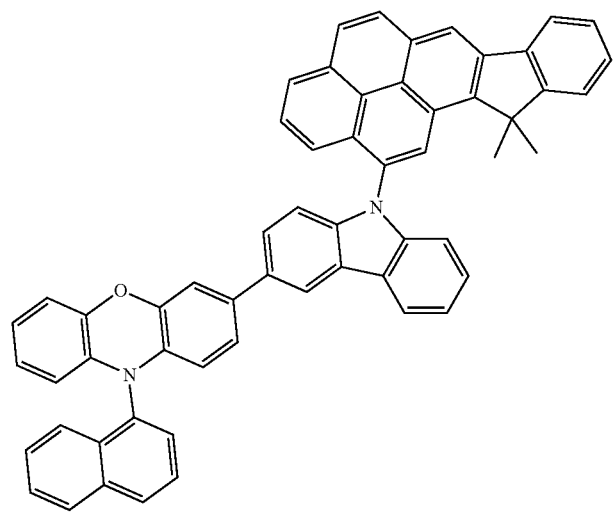
C286
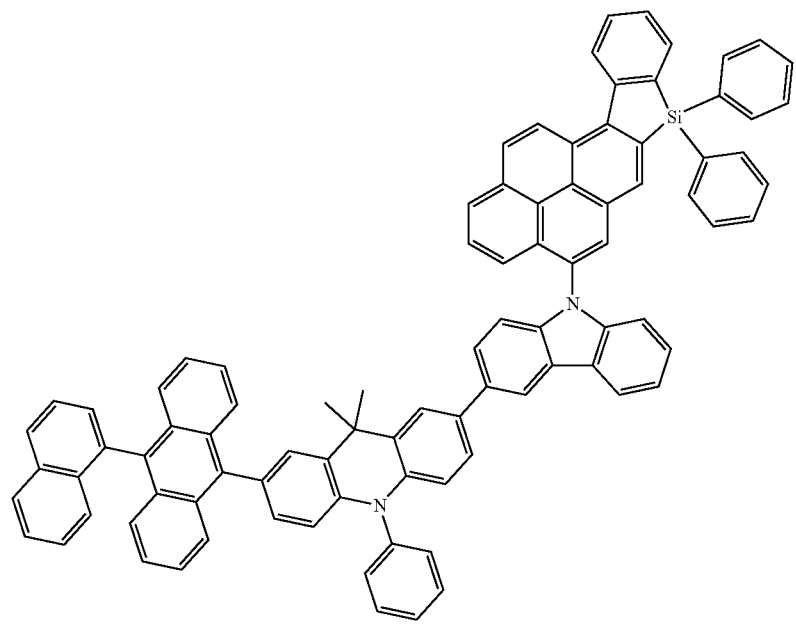

-continued

C287

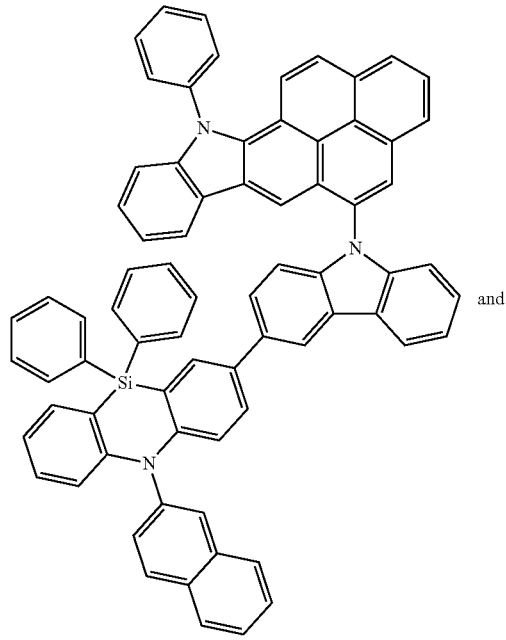

and

C288

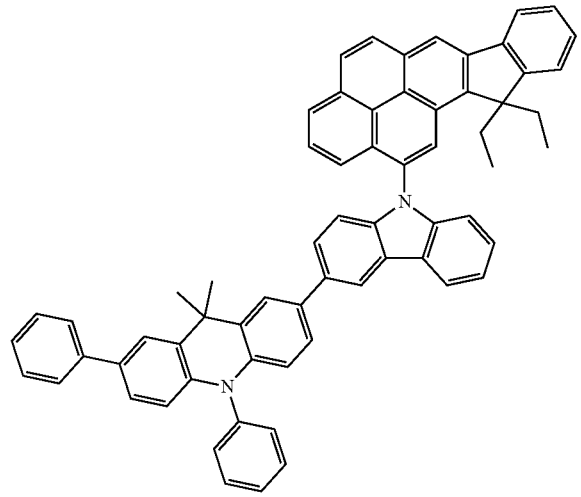

8. An organic electroluminescence device comprising an anode, a cathode and one or more organic layers formed between the anode and the cathode, wherein at least one of the organic layers comprises the organic compound according to claim 1.

9. The organic electroluminescence device of claim 8, wherein the organic layers comprise an emissive layer having a host, and wherein the organic compound is comprised as the host.

10. The organic electroluminescence device of claim 8, wherein the organic layers comprise a hole transporting layer, and wherein the organic compound of claim 1 is comprised as the hole transporting layer.

11. The organic electroluminescence device of claim 8, wherein the organic layers comprise a electron transporting layer, and wherein the organic compound of claim 1 is comprised as the electron transporting layer.

12. The organic electroluminescence device of claim 8, wherein the organic layers comprise an electron blocking layer, and wherein the organic compound of claim 1 is comprised as the electron blocking layer.

13. The organic electroluminescence device of claim 8, wherein the organic layers comprise a hole blocking layer, and wherein the organic compound of claim 1 is comprised as the hole blocking layer.

14. The organic electroluminescence device of claim 8, wherein the organic electroluminescence device is a lighting panel.

15. The organic electroluminescence device of claim 8, wherein the organic electroluminescence device is a backlight panel.

* * * * *